US012152257B2

(12) United States Patent
Stella et al.

(10) Patent No.: US 12,152,257 B2
(45) Date of Patent: Nov. 26, 2024

(54) MUTANT CPF1 ENDONUCLEASES

(71) Applicant: University of Copenhagen, Copenhagen K (DK)

(72) Inventors: Stefano Stella, Copenhagen K (DK); Guillermo Montoya, Frederiksberg (DK)

(73) Assignee: University of Copenhagen, Copenhagen K (DK)

( * ) Notice: Subject to any disclaimer, the term of this patent is extended or adjusted under 35 U.S.C. 154(b) by 948 days.

(21) Appl. No.: 15/734,839

(22) PCT Filed: Jun. 4, 2019

(86) PCT No.: PCT/EP2019/064444
§ 371 (c)(1),
(2) Date: Dec. 3, 2020

(87) PCT Pub. No.: WO2019/233990
PCT Pub. Date: Dec. 12, 2019

(65) Prior Publication Data
US 2021/0230567 A1     Jul. 29, 2021

(30) Foreign Application Priority Data

Jun. 4, 2018 (EP) .................................. 18175707
Aug. 27, 2018 (EP) .................................. 18190950

(51) Int. Cl.
*C12N 9/22* (2006.01)
*C12Q 1/6806* (2018.01)

(52) U.S. Cl.
CPC ............ *C12N 9/22* (2013.01); *C12Q 1/6806* (2013.01)

(58) Field of Classification Search
CPC ....... C12N 9/22; C12N 15/907; C12Q 1/6806
See application file for complete search history.

(56) References Cited

U.S. PATENT DOCUMENTS

| | | | |
|---|---|---|---|
| 9,790,490 B2 | 10/2017 | Zhang et al. | |
| 10,648,020 B2 | 5/2020 | Zhang et al. | |
| 10,669,540 B2 | 6/2020 | Zhang et al. | |
| 10,947,530 B2 | 3/2021 | Liu et al. | |
| 11,041,169 B2 | 6/2021 | Keiji | |
| 11,091,798 B2 | 8/2021 | Zhang et al. | |
| 11,214,780 B2 | 1/2022 | Liu et al. | |
| 11,268,082 B2 | 3/2022 | Liu et al. | |
| 11,286,478 B2 | 3/2022 | Zhang et al. | |
| 11,306,324 B2 | 4/2022 | Liu et al. | |
| 11,434,491 B2 | 9/2022 | Chen et al. | |
| 11,634,755 B2 | 4/2023 | Zhang et al. | |
| 11,649,443 B2 | 5/2023 | Halperin | |
| 11,667,677 B2 | 6/2023 | Tak et al. | |
| 11,725,228 B2 | 8/2023 | Joung et al. | |
| 11,773,432 B2 | 10/2023 | Zhang et al. | |
| 11,781,172 B2 | 10/2023 | Zhang et al. | |
| 11,834,665 B2 | 12/2023 | Smanski et al. | |
| 11,840,694 B2 | 12/2023 | Tan et al. | |
| 11,866,697 B2 | 1/2024 | Zhang et al. | |
| 11,884,947 B2 | 1/2024 | Chen et al. | |
| 2020/0172931 A1 | 6/2020 | Liu et al. | |
| 2021/0155911 A1 | 5/2021 | Zhang et al. | |
| 2021/0269788 A1 | 9/2021 | Joung et al. | |
| 2022/0025347 A1 | 1/2022 | Joung et al. | |
| 2023/0348883 A1 | 11/2023 | Liu et al. | |

FOREIGN PATENT DOCUMENTS

| | | |
|---|---|---|
| CN | 106244591 A | 12/2016 |
| EP | 3009511 A2 | 4/2016 |
| EP | 3310917 B1 | 2/2020 |
| EP | 3470519 B1 | 2/2020 |
| EP | 3502253 B1 | 5/2020 |
| EP | 3009511 B2 | 1/2021 |
| EP | 3428274 B1 | 10/2021 |
| EP | 3625342 B1 | 8/2022 |
| EP | 3365356 B1 | 6/2023 |
| EP | 4269577 A2 | 11/2023 |
| EP | 3365357 B1 | 2/2024 |
| WO | 2017/064546 A1 | 4/2017 |
| WO | 2017/106657 A1 | 6/2017 |
| WO | 2018/027078 A1 | 2/2018 |
| WO | WO2018074979 A1 | 4/2018 |
| WO | WO2018176009 A1 | 9/2018 |
| WO | WO2019023680 A1 | 1/2019 |
| WO | WO2019126762 A2 | 6/2019 |
| WO | WO2019161783 A1 | 8/2019 |

OTHER PUBLICATIONS

Stella Stefano et al: "Structure of the Cpf1 endonuclease R-loop complex after target DNA cleavage", Nature, vol. 546, No. 7659, Jun. 22, 2017 (Jun. 22, 2017). (Year: 2017).*
International Search Report and Written Opinion for Application No. PCT/EP2019/064444 mailed Oct. 15, 2019.
International Preliminary Report on Patentability for Application No. PCT/EP2019/064444 mailed Dec. 8, 2020.
Alcon et al., Assembly of Francisella novicida Cpf1 endonuclease in complex with guide RNA and target DNA. Acta Crystallogr F Struct Biol Commun. Jul. 1, 2017;73(Pt 7):409-415.
Chen et al., CRISPR-Cas12a target binding unleashes indiscriminate single-stranded DNase activity. Science. Apr. 27, 2018;360(6387):436-439. doi: 10.1126/science.aar6245. Epub Feb. 15, 2018.

(Continued)

*Primary Examiner* — Tekchand Saidha

(74) *Attorney, Agent, or Firm* — Steptoe LLP; Z. Ying Li; Debashree Chatterjee

(57) ABSTRACT

The present invention relates to mutant Cpf1 endonucleases having altered activity compared to the wild type Cpf1, and their use to introduce single strand breaks in nucleic acid sequences. Methods for detection and quantification of a nucleic acid sequence are also disclosed. Methods for diagnosis of an infectious disease are also disclosed.

16 Claims, 9 Drawing Sheets
Specification includes a Sequence Listing.

(56) References Cited

OTHER PUBLICATIONS

Dong et al., The crystal structure of Cpf1 in complex with CRISPR RNA. Nature. Apr. 28, 2016;532(7600):522-6. doi: 10.1038/nature17944. Epub Apr. 20, 2016.

Li et al., Design and assessment of engineered CRISPR-Cpf1 and its use for genome editing. Nat Protoc. May 2018;13(5):899-914. doi: 10.1038/nprot.2018.004. Epub Apr. 5, 2018.

Singh et al., Real-time observation of DNA target interrogation and product release by the RNA-guided endonuclease CRISPR Cpf1 (Cas12a). Proc Natl Acad Sci U S A. May 22, 2018;115(21):5444-5449. doi: 10.1073/pnas.1718686115.

Stella et al., Class 2 CRISPR-Cas RNA-guided endonucleases: Swiss Army knives of genome editing. Nat Struct Mol Biol. Nov. 2017;24(11):882-892. doi: 10.1038/nsmb.3486.

Stella et al., Conformational Activation Promotes CRISPR-Cas12a Catalysis and Resetting of the Endonuclease Activity. Cell. Dec. 13, 2018;175(7):1856-1871.e21. doi: 10.1016/j.cell.2018.10.045. Epub Nov. 29, 2018.

Stella et al., Structure of the Cpf1 endonuclease R-loop complex after target DNA cleavage. Nature. Jun. 22, 2017;546(7659):559-563. doi: 10.1038/nature22398. Epub May 31, 2017.

Yamano et al., Crystal structure of Cpf1 in complex with guide RNA and target DNA. Cell. May 5, 2016; 165(4): 949-962.

Zetsche et al., Cpf1 is a single RNA-guided endonuclease of a class 2 CRISPR-Cas system. Cell. Oct. 22, 2015;163(3):759-71. doi: 10.1016/j.cell.2015.09.038. Epub Sep. 25, 2015.

PCT/EP2019/064444, Oct. 15, 2019, International Search Report and Written Opinion.

PCT/EP2019/064444, Dec. 8, 2020, International Preliminary Report on Patentability.

GenBank: EOS46485.1.

Makarova et al., "Unification of Cas Protein Families and a Simple Scenario for the Origin and Evolution of CRISPR-Cas Systems," (2011) Biology Direct 6:38.

Makarova et al., "Annotation and Classification of CRISPR-Cas Systems," (2015) Methods Mol Biol. 1311:47-75.

Mojica et al., "Intervening Sequences of Regularly Spaced Prokaryotic Repeats Derive From Foreign Genetic Elements," (2005) J Mol Evol. 60:174-82.

Vestergaard et al., "Adaptive Immune Systems of Archaea," (2014) RNA Biology 11(2):156-67.

\* cited by examiner

A

|  | Expression in E.Coli | Soluble protein |
|---|---|---|
| Fn-Cpf1-wt | + | + |
| Finger-Deletion | + | - |
| Finger-Substitution | + | - |
| Fn-Cpf1-wt | + | + |
| REC-linker-Deletion | + | + |
| REC-linker-Substitution | + | + |
| Fn-Cpf1-wt | + | + |
| Lid-Deletion | + | - |
| Lid-Substitution | + | +/- |

FIG. 5

MUTANT CPF1 ENDONUCLEASES

RELATED APPLICATIONS

This application is a national stage filing under 35 U.S.C. § 371 of international application number PCT/EP2019/064444, filed Jun. 4, 2019, which claims the benefit of European application number EP 18175707.1, filed Jun. 4, 2018 and EP 18190950.8, filed Aug. 27, 2018, each of which is herein incorporated by reference in its entirety.

TECHNICAL FIELD

The present invention relates to mutant Cpf1 (also known as Cas12a) endonucleases having altered activity compared to the wild type Cpf1, and their use to both introduce single strand breaks or double strand breaks in nucleic acid target sequences which are either single stranded or double stranded and single strand DNA breaks upon binding (but not cleavage) on the DNA-target either single stranded or double stranded non-specific manner. Methods for detection and quantification of a nucleic acid sequence are also disclosed. Methods for diagnosis of an infectious disease are also disclosed.

BACKGROUND

Cpf1 is a DNA endonuclease, belonging to the CRISPR-Cas (Clustered regularly interspaced short palindromic repeats) class 2 type V-B adaptive immune system, that the bacteria and archaea use to protect the cells against the invasion of potential dangerous DNA molecules (Makarova et al., 2011; Makarova and Koonin, 2015; Vestergaard et al., 2014). Cpf1 forms with a relatively small (between 40 to 45 bases) crRNA (CRISPR-RNA) molecule, a ribonucleoprotein complex that is able to recognize, unwind and cut with high specificity the DNA-target complementary to the crRNA. The Cpf1 DNA-target sequences are stored in the CRISPR-array that is a region of DNA containing repetitive sequences adjacent to unique sequences (spacers) that are the record of the potential dangerous DNA previously encountered by the cell (Zetsche et al., 2015). The CRISPR array is transcribed as single pre-crRNA that is then processed by Cpf1 to produce mature crRNAs (Fonfara et al., 2016). These RNAs thus contain a conserved part, identical for all the crRNAs, which folds in a pseudoknot structure recognized by Cpf1, and a variable region that is complementary to the target DNAs. To maintain the integrity of the CRISPR-array the cleavage of the DNA-target is bound to the recognition of a short PAM sequence (protospacer adjacent motif) usually 3 or 4 nucleotides length upstream of the target site. The PAM sequence that is recognized by Cpf1 is present in the invading DNA molecules but not in the CRISPR-array thus protecting this DNA region from cleavage (Mojica et al., 2005).

Some CRISPR endonucleases such as Cas9, Cpf1, and Cas13 have been used to modify the genomes of several organisms as well as diagnostic molecules to identify infections and also as potential tools for gene therapy (Chen et al., 2018; Gootenberg, 2018).

However, CRISPR endonucleases have so far being used in the same way as they act in nature. There is a need to discover the full potential of these enzymes and optimize them for use in known as well as new applications.

SUMMARY

The present disclosure relates to mutant Cpf1 endonucleases that are capable of introducing single strand breaks or double strand breaks in nucleic acid target sequences which are either single stranded or double stranded. Furthermore, mutant Cpf1 endonucleases of the present disclosure are able to bind (without cutting) the DNA-target either single stranded or double stranded, and to cleave in a non-specific manner single stranded DNA. Moreover, mutant Cpf1 endonucleases, and the complexes they form with crRNAs, capable of introducing one or more single strand or double strand breaks in a nucleic acid sequence, which is different from the nucleic acid sequence recognized and hybridized by the crRNA are disclosed.

The new mutantCpf1 endonucleases disclosed herein present several advantages over wild type Cpf1 endonucleases and can be favourably used for detection and quantification of target nucleic acid sequences in a specific or non-specific manner, even at very low concentrations, such as at concentrations below the picomolar range.

The new mutantCpf1 endonucleases disclosed herein present several advantages over wild type Cpf1 endonucleases and can be favourably used for cutting target nucleic acid sequences both double stranded and single stranded. Furthermore, in the double stranded target the cut can be on both strands or on one strand only.

Finally, the new mutant Cpf1 endonucleases disclosed herein may also be used for diagnosis of an infectious disease, by detection of genetic material deriving from the infectious agent causing the disease.

One aspect of the present disclosure relates to a mutant Cpf1 endonuclease or orthologue thereof comprising a polypeptide sequence having at least 95% sequence identity to:
  i) the sequence corresponding to residues 1 to 323, 337 to 1005, and 1019 to 1329 of SEQ ID NO: 2, wherein said polypeptide sequence further comprises:
     a. at least two amino acid mutations in, the REC domain (residues 324 to 336; SEQ ID NO: 16) compared to SEQ ID NO: 2, wherein each mutation independently is an amino acid substitution or deletion; and/or
     b. at least two amino acid substitutions in the Lid domain (residues 1006 to 1018; SEQ ID NO: 20) compared to SEQ ID NO: 2, wherein at least one of the residues at positions 917 and 1006 is a glutamic acid (E) or an aspartic acid (D);
  and/or
  ii) SEQ ID NO: 2, wherein said polypeptide sequence comprises at least two amino acid substitutions in two positions independently selected from the positions corresponding to residues 918, 1013, 1014, 1025 and 1028 of SEQ ID NO: 2.

Another aspect of the present disclosure relates to a polynucleotide encoding the mutant Cpf1 endonuclease or orthologue thereof as disclosed herein.

Another aspect of the present disclosure relates to a recombinant vector comprising a polynucleotide or a nucleic acid sequence encoding a mutant Cpf1 endonuclease or orthologue thereof as disclosed herein, said polynucleotide or nucleic acid sequence being optionally linked to a promoter.

A further aspect of the present disclosure relates to a cell expressing the mutant Cpf1 or orthologue thereof, or the polynucleotide, nucleic acid or recombinant vector as disclosed herein.

An even further aspect of the present disclosure relates to a system for expression of a crRNA-Cpf1 complex comprising a. a polynucleotide or a recombinant vector comprising a polynucleotide encoding a mutant Cpf1 endonuclease or orthologue thereof, or a nucleic acid as disclosed herein; and
b. a polynucleotide or a recombinant vector comprising a polynucleotide encoding a guide RNA (crRNA) operably linked to a promoter.

Another aspect of the present disclosure relates to a use of a crRNA-Cpf1 complex for introducing a single strand break in a first target nucleic acid, wherein:
a. a Cpf1 endonuclease or orthologue thereof is contacted with a guide RNA (crRNA), thereby obtaining a crRNA-Cpf1 complex capable of recognising a second target nucleic acid, the second target nucleic acid comprising a protospacer adjacent motif (PAM), and
b. the crRNA-Cpf1 complex is contacted with the first target nucleic acid; whereby a single strand break is made in the first target sequence.

Another aspect of the present disclosure relates to a method of introducing a single strand break in a first target nucleic acid, comprising the steps of:
a. designing a guide-RNA (crRNA) capable of recognising a second target nucleic acid comprising a protospacer adjacent motif (PAM);
b. contacting the crRNA of step a. with a Cpf1 endonuclease or orthologue thereof, thereby obtaining a crRNA-Cpf1 complex capable of binding to said second target nucleic acid, and
c. contacting the crRNA and the Cpf1 with said first target nucleic acid, thereby introducing one or more single strand breaks in the first target nucleic acid.

A further aspect of the present disclosure relates to an in vitro method of introducing a site-specific, double-stranded break at a second target nucleic acid in a mammalian cell, the method comprising introducing into the mammalian cell a crRNA-Cpf1 complex, wherein the Cpf1 is a mutant Cpf1 endonuclease or orthologue as disclosed herein, and wherein the crRNA is specific for the second target nucleic acid.

A further aspect of the present disclosure relates to a method for detection of a second target nucleic acid in a sample, the method comprising:
a. Providing a crRNA-Cpf1 complex, wherein the Cpf1 is a Cpf1 endonuclease or orthologue thereof as disclosed herein, and wherein the crRNA is specific for the second target nucleic acid;
b. Providing a labelled ssDNA, wherein the ssDNA is labelled with at least one set of interactive labels comprising at least one dye and at least one quencher;
c. Contacting the crRNA-Cpf1 complex and the ssDNA with the sample, wherein the sample comprises at least one second target nucleic acid; and
d. Detecting cleavage of the ssDNA by detecting a fluorescent signal from the fluorophore, thereby detecting the presence of the second target nucleic acid in the sample.

Another aspect of the present disclosure relates to an in vitro method for diagnosis of an infectious disease in a subject, the method comprising:
a. Providing a crRNA-Cpf1 complex, wherein the Cpf1 is a Cpf1 endonuclease or orthologue thereof as disclosed herein, and wherein the crRNA is specific for a second target nucleic acid;
b. Providing a labelled ssDNA, wherein the ssDNA is labelled with at least one set of interactive labels comprising at least one dye and at least one quencher;
c. Providing a sample from the subject, wherein said sample comprises or is suspected of comprising the second target nucleic acid; and
d. Determining the level and/or concentration of the second target nucleic acid according to the methods disclosed herein,
wherein the second target nucleic acid is a nucleic acid of the genome of an infectious agent causing the disease or a fragment thereof, thereby diagnosing an infectious disease in a subject.

DESCRIPTION OF THE DRAWINGS

FIG. 5 Protein expression and purification profiles mutant Cpf1 with deletions or substitutions in the REC-linker, lid and finger regions.

DETAILED DESCRIPTION

Figure 1:
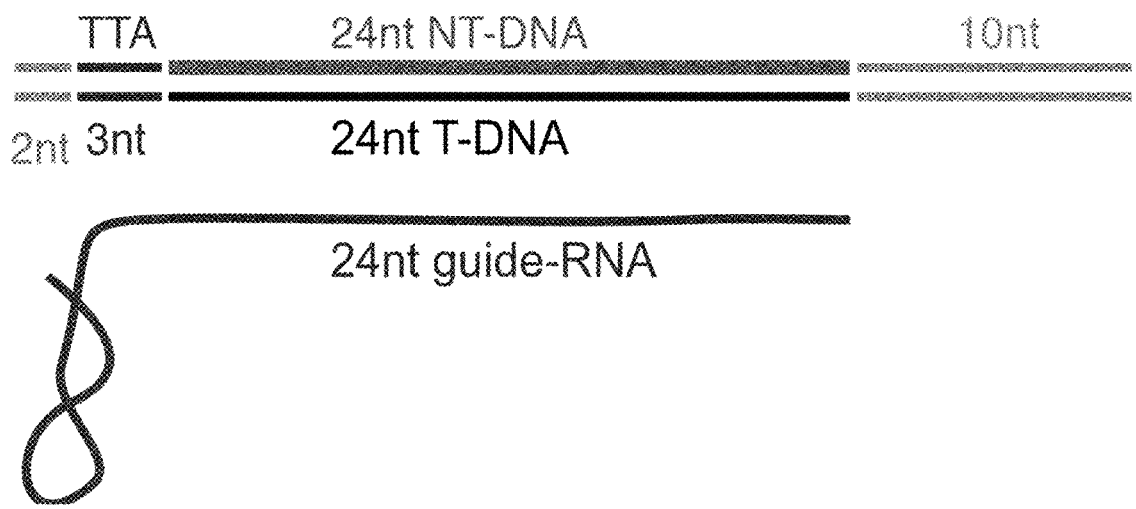
FIG. 1. Representation of the crRNA and the double strand DNA target.

The invention is as defined in the claims.

The present disclosure relates to mutant Cpf1 endonucleases or orthologues thereof and their use to introduce single strand breaks or double strand breaks in nucleic acid target sequences which are either single stranded or double stranded in a specific or non-specific manner. Throughout the present disclosure a "mutant Cpf1 endonuclease" may be a naturally occurring mutant, for example a mutant encoded by a Cpf1 gene carrying one or more single nucleotide polymorphisms (SNPs), or a non-naturally occurring mutant, for example a mutant obtained by direct mutagenesis or random mutagenesis of the Cpf1 gene.

The inventors have identified mutants of Cpf1 with modified activities. Some of the mutants disclosed herein are able to function as a nickase, thus recognizing and introducing a single strand break at a specific target DNA sequence. The inventors have also identified mutants of Cpf1 that recognize a target DNA sequence and, following binding to said target nucleic acid, introduce a single strand break at non-target DNA sequences. Some mutants can cleave the DNA in a single stranded sequence, others in a double stranded sequence. The cleavage may be specific or non-specific. The cleavage may be activated by double stranded target DNA, by single stranded target DNA or both.

The inventors also provide methods for detecting and quantifying a target DNA sequence using a mutant Cpf1 endonuclease. The inventors also provide methods for diagnosing an infectious disease by detecting and quantifying a target DNA sequence using a mutant Cpf1 endonuclease.

Definitions

Codon The term "codon" as used herein refers to a triplet of adjacent nucleotides coding for a specific amino acid.

CRISPR-Cas system The term refers to members of the CRISPR-Cas family. The prokaryotic adaptive immune system CRISPR-Cas (clustered regularly interspaced short palindromic repeats and CRISPR-associated proteins) can bind and cleave a target DNA sequence through RNA-guided recognition. According to their molecular architecture, the different members of the CRISPR-Cas system have been classified in two classes: class 1 encompasses several effector proteins, whereas class 2 systems use a single element (Makarova et al., 2015). Cpf1 ("CRISPR from *Prevotella* and *Francisella*") has been described as a new member of class 2 type V CRISPR-Cas endonucleases present in a number of bacterial genomes (Zetsche et al., 2015).

Endonuclease The term refers to an enzyme capable of cleaving the phosphodiester bond within a polynucleotide chain. Some endonucleases are specific, i.e. they recognise a given nucleotide sequence which directs the site of cleavage, some are non-specific. The present disclosure is directed to both specific and non-specific endonucleases. One example of endonucleases is nicking endonucleases. A nicking endonuclease as used herein is referred to an enzyme that cuts one strand of a double-stranded DNA to produce a "nicked" DNA molecule. A nicking endonuclease as used herein refers also to an endonuclease that cuts one strand of a single stranded DNA.

Fragment The term is used to indicate a non full-length part of a nucleic acid or polypeptide. Thus, a fragment is itself also a nucleic acid or polypeptide, respectively. DNA fragments are designated starting from the 5'-end throughout the present disclosure.

Gene editing The term refers to the use of genetic engineering procedures to insert, delete or replace one or more nucleotides in a nucleotide sequence.

Guide RNA The term will herein be used interchangeably with "crRNA" and refers to the RNA molecule which is required for recognition of a target nucleic acid sequence by CRISPR-Cas proteins, in particular Cpf1.

Homologue A homologue or functional homologue may be any polypeptide that exhibits at least some sequence identity with a reference polypeptide and has retained at least one aspect of the original functionality. Herein a functional homologue of Cpf1 is a polypeptide sharing at least some sequence identity with Cpf1 or a fragment thereof which has the capability to function as an endonuclease similarly to Cpf1, i.e. it is capable of specifically binding a crRNA, and of specifically recognising, binding and cleaving a target nucleic acid.

Protospacer adjacent motif (PAM) The term refers to the DNA sequence immediately downstream the DNA sequence targeted by a CRISPR-Cas system such as Cpf1. The crRNA of a crRNA-Cpf1 complex is capable of recognizing and hybridizing only a target DNA sequence comprising a PAM.

Recognition The term "recognition" as understood herein refers to the ability of a molecule to identify a nucleotide sequence. For example, an enzyme or a DNA binding domain may recognise a nucleic acid sequence as a potential substrate and bind to it. Preferably, the recognition is specific.

Sequence identity As used herein, the term refers to two polynucleotide sequences that are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

As applied to polypeptides, peptides or proteins, a degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences.

The global percentage of sequence identity is determined with the algorithm GAP, BESTFIT, or FASTA in the Wisconsin Genetics Software Package Release 7.0, using default gap weights.

The term "interactive labels" or "set of interactive labels" as used herein refers to at least one fluorophore and at least one quencher which can interact when they are located adjacently. When the interactive labels are located adjacently the quencher can quench the fluorophore signal. The interaction may be mediated by fluorescence resonance energy transfer (FRET).

The term "located adjacently" as used herein refers to the physical distance between two objects. If a fluorophore and a quencher are located adjacently, the quencher is able to partly or fully quench the fluorophore signal. FRET quenching may typically occur over distances up to about 100 Å. Located adjacently as used herein may refer to distances below and/or around 100 Å.

The term "fluorescent label" or "fluorophore" as used herein refers to a fluorescent chemical compound that can re-emit light upon light excitation. The fluorophore absorbs light energy of a specific wavelength and re-emits light at a longer wavelength.

The absorbed wavelengths, energy transfer efficiency, and time before emission depend on both the fluorophore structure and its chemical environment, as the molecule in its excited state interacts with surrounding molecules. Wavelengths of maximum absorption (≈excitation) and emission (for example, Absorption/Emission=485 nm/517 nm) are the typical terms used to refer to a given fluorophore, but the whole spectrum may be important to consider.

The term "quench" or "quenching" as used herein refers to any process which decreases the fluorescence intensity of a given substance such as a fluorophore. Quenching may be mediated by fluorescence resonance energy transfer (FRET). FRET is based on classical dipole-dipole interactions between the transition dipoles of the donor (e.g. fluorophore)

and acceptor (e.g. quencher) and is dependent on the donor-acceptor distance. FRET can typically occur over distances up to 100 Å. FRET also depends on the donor-acceptor spectral overlap and the relative orientation of the donor and acceptor transition dipole moments. Quenching of a fluorophore can also occur as a result of the formation of a non-fluorescent complex between a fluorophore and another fluorophore or non-fluorescent molecule. This mechanism is known as 'contact quenching,' 'static quenching,' or 'ground-state complex formation The term "quencher" as used herein refers to a chemical compound which is able to quench a given substance such as a fluorophore.

Target strand and non-target strand The target strand refers to the nucleic acid strand which interacts with the crRNA to form a crRNA-DNA hybrid. The non-target strand is complementary to the target strand, and is displaced to the RuvC/NuC pocket of the Cpf1 endonuclease.

The term "orthologue" as used herein refers to genes (and proteins encoded by said genes) inferred to be descended from the same ancestral sequence separated by a speciation event: when a species diverges into two separate species, the copies of a single gene in the two resulting species are said to be orthologous. Orthologs, or orthologous genes, are genes in different species that originated by vertical descent from a single gene of the last common ancestor. Cpf1 orthologues can be identified and characterized based on sequence similarities to the present system, as has been described with type II systems for example. For example, orthologues of Cpf1 include *F. novicida* U1 12, *Prevotella albensis*, *Acidaminococcus* sp. BV3L6, *Eubacterium eligens* CAG:72, *Butyrivibrio fibrisolvens*, *Smithella* sp. SCADC, *Flavobacterium* sp. 316, *Porphyromonas crevioricanis*, Bacteroidetes oral taxon 274, and Lachnospiraceae bacterium ND2006.

Mutant Cpf1

The inventors have identified three domains of Cpf1 which appear to be involved in different activities of the enzyme. These three domains are:

The REC domain
The Lid domain
The finger domain.

In FnCpf1 (SEQ ID NO: 2), these three domains are defined as follows:

REC domain: from residue 324 to residue 336;
Lid domain: from residue 1006 to 1018;
Finger domain: from residue 298 to 309.

Substitution or deletion of amino acids in any of these three domains results in modified enzyme activity, as will be detailed herein below. In addition, five residues were identified which appear important for enzymatic activity, i.e. mutations or deletions of any of these three residues also modifies enzyme activity. These residues are at position 918, 1013, 1014, 1025 and 1028, of which 1013 and 1014 are part of the Lid region. The present disclosure thus relates to modified Cpf1 proteins having altered activities.

One aspect of the present disclosure thus relates to a mutant Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to:

i) the sequence corresponding to residues 1 to 297, 310 to 323, 337 to 1005, and 1019 to 1329 of SEQ ID NO: 2, wherein said polypeptide sequence further comprises at least one amino acid substitution or deletion in the finger domain (residues 298 to 309; SEQ ID NO: 12), the REC domain (residues 324 to 336; SEQ ID NO: 16) or the Lid domain (residues 1006 to 1018; SEQ ID NO: 20) compared to SEQ ID NO: 2; and/or ii) SEQ ID NO: 2, wherein said polypeptide sequence comprises at least one amino acid substitution in position 918, 1013, 1014, 1025 or 1028 of SEQ ID NO: 2.

One aspect of the present disclosure thus relates to a mutant Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to:

i) the sequence corresponding to residues 1 to 323, 337 to 1005, and 1019 to 1329 of SEQ ID NO: 2, wherein said polypeptide sequence further comprises:

a. at least two amino acid mutations in the REC domain (residues 324 to 336; SEQ ID NO: 16) compared to SEQ ID NO: 2, wherein each mutation independently is an amino acid substitution or deletion; and/or b. at least two amino acid substitutions in the Lid domain (residues 1006 to 1018; SEQ ID NO: 20) compared to SEQ ID NO: 2, wherein at least one of the residues at positions 917 and 1006 is a glutamic acid (E) or an aspartic acid (D);

and/or ii) SEQ ID NO: 2, wherein said polypeptide sequence comprises at least two amino acid substitutions in two positions independently selected from the positions corresponding to residues position 918, 1013, 1014, 1025 and 1028 of SEQ ID NO: 2.

One aspect of the present disclosure relates to a mutant Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 2, wherein said polypeptide sequence comprises at least one amino acid substitution in position 918, 1013, or 1014 of SEQ ID NO: 2.

One aspect of the present disclosure relates to a mutant Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 2, wherein said polypeptide sequence comprises at least two amino acid substitutions in two positions independently selected from the positions corresponding to residues 918, 1013, 1014, 1025 and 1028 of SEQ ID NO: 2.

In one embodiment the Cpf1 endonuclease is derived from *Francisella novicida*.

In some embodiments, the mutant Cpf1 comprises a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity, such as 100% identity to the sequence corresponding to residues 1 to 323 and 337 to 1329 of SEQ ID NO: 2, wherein said polypeptide sequence further comprises at least one amino acid substitution or deletion in the finger domain (residues 298 to 309; SEQ ID NO: 12), the REC domain (residues 324 to 336; SEQ ID NO: 16) or Lid finger domain (residues 1006 to 1018; SEQ ID NO: 20) compared to SEQ ID NO: 2. The mutant Cpf1 may further comprise at least one amino acid substitution in position 918, 1013, 1014, 1025 or 1028 of SEQ ID NO: 2.

In some embodiments, the mutant Cpf1 comprises a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity, such as 100% identity to the sequence corresponding to residues 1 to 323 and 337 to 1329 of SEQ ID NO: 2, wherein said polypeptide sequence further comprises at least two mutations in the REC domain (residues 324 to 336; SEQ ID NO: 16), wherein each mutation independently is an amino acid substitution or deletion, or at least two amino acid substitutions in the Lid domain (residues 1006 to 1018; SEQ ID NO: 20), compared to SEQ ID NO: 2. The mutant Cpf1 comprising mutations in the REC and/or Lid domain may further comprise at least one amino acid substitution in position 918, 1013, 1014, 1025 or 1028 of SEQ ID NO: 2.

In one embodiment, the mutant Cpf1 has at least one amino acid substitution or deletion in the finger domain. The at least one amino acid substitution or deletion may be substitution or deletion of 1, 2, 3, 4, 5, 6, 7, 8, 9, 10, 11 or 12 contiguous or non-contiguous amino acids of the finger domain defined as residues 298 to 309 of SEQ ID NO: 2. Accordingly, the mutant Cpf1 may comprise a sequence having at least 80%, such as at least 85%, at least 90%, at least 95%, at least 96%, at least 97%, at least 98%, at least 99% or 100% sequence identity to the sequence corresponding to residues 1 to 297 and 310 to 1329 of SEQ ID NO: 2. The mutant Cpf1 may further comprise at least one amino acid substitution in position 918, 1013, 1014, 1025 or 1028 of SEQ ID NO: 2.

In another embodiment, the mutant Cpf1 has at least one amino acid substitution or deletion in the REC domain. The at least one amino acid substitution or deletion may be substitution or deletion of 1, 2, 3, 4, 5, 6, 7, 8, 9, 10, 11, 12 or 13 contiguous or non-contiguous amino acids of the REC domain defined as residues 324 to 336 of SEQ ID NO: 2. Accordingly, the mutant Cpf1 may comprise a sequence having at least 80%, such as at least 85%, at least 90%, at least 95%, at least 96%, at least 97%, at least 98%, at least 99% or 100% sequence identity to the sequence corresponding to residues 1 to 323 and 337 to 1329 of SEQ ID NO: 2. The mutant Cpf1 may further comprise at least one amino acid substitution in position 918, 1013, 1014, 1025 or 1028 of SEQ ID NO: 2.

In another embodiment, the mutant Cpf1 has at least two amino acid mutations in the REC domain, wherein each mutation independently is an amino acid substitution or deletion. The at least two amino acid mutations may be substitutions and/or deletions of 1, 2, 3, 4, 5, 6, 7, 8, 9, 10, 11, 12 or 13 contiguous or non-contiguous amino acids of the REC domain defined as residues 324 to 336 of SEQ ID NO: 2. Accordingly, the mutant Cpf1 may comprise a sequence having at least 80%, such as at least 85%, at least 90%, at least 95%, at least 96%, at least 97%, at least 98%, at least 99% or 100% sequence identity to the sequence corresponding to residues 1 to 323 and 337 to 1329 of SEQ ID NO: 2. The mutant Cpf1 comprising at least two mutations in the REC domain may further comprise at least one amino acid substitution in position 918, 1013, 1014, 1025 or 1028 of SEQ ID NO: 2.

In another embodiment, the mutant Cpf1 has at least one amino acid substitution or deletion in the lid domain. The at least one amino acid substitution or deletion may be substitution or deletion of 1, 2, 3, 4, 5, 6, 7, 8, 9, 10, 11, 12 or 13 contiguous or non-contiguous amino acids of the Lid domain defined as residues 1006 to 1013 of SEQ ID NO: 2. Accordingly, the mutant Cpf1 may comprise a sequence having at least 80%, such as at least 85%, at least 90%, at least 95%, at least 96%, at least 97%, at least 98%, at least 99% or 100% sequence identity to the sequence corresponding to residues 1 to 1005 and 1019 to 1329 of SEQ ID NO: 2. The mutant Cpf1 may further comprise at least one amino acid substitution in position 918, 1013, 1014, 1025 or 1028 of SEQ ID NO: 2.

In another embodiment, the mutant Cpf1 has at least two amino acid substitutions in the Lid domain. The at least two amino acid substitutions may be substitutions of 1, 2, 3, 4, 5, 6, 7, 8, 9, 10, 11, 12 or 13 contiguous or non-contiguous amino acids of the Lid domain defined as residues 1006 to 1013 of SEQ ID NO: 2. Accordingly, the mutant Cpf1 may comprise a sequence having at least 80%, such as at least 85%, at least 90%, at least 95%, at least 96%, at least 97%, at least 98%, at least 99% or 100% sequence identity to the sequence corresponding to residues 1 to 1005 and 1019 to 1329 of SEQ ID NO: 2. The mutant Cpf1 comprising at least two substitutions in the Lid domain may further comprise at least one amino acid substitution in position 918, 1013, 1014, 1025 or 1028 of SEQ ID NO: 2

In another embodiment, Cpf1 has at least one amino acid substitution or deletion in the finger domain and in the REC domain, where the at least one amino acid substitution or deletion is as defined above. Accordingly, the mutant Cpf1 may comprise a sequence having at least 80%, such as at least 85%, at least 90%, at least 95%, at least 96%, at least 97%, at least 98%, at least 99% or 100% sequence identity to the sequence corresponding to residues 1 to 297, 310 to 323 and 337 to 1329 of SEQ ID NO: 2. The mutant Cpf1 may further comprise at least one amino acid substitution in position 918, 1013, 1014, 1025 or 1028 of SEQ ID NO: 2.

In another embodiment, Cpf1 has at least two amino acid mutations in the Lid domain and in the REC domain, wherein each mutation independently is an amino acid substitution or deletion as defined above. Accordingly, the mutant Cpf1 may comprise a sequence having at least 80%, such as at least 85%, at least 90%, at least 95%, at least 96%, at least 97%, at least 98%, at least 99% or 100% sequence identity to the sequence corresponding to residues 1 to 297, 310 to 323 and 337 to 1329 of SEQ ID NO: 2. The mutant Cpf1 comprising at least two amino acid mutations in the Lid domain and in the REC domain may further comprise at least one amino acid substitution in position 918, 1013, 1014, 1025 or 1028 of SEQ ID NO: 2.

In another embodiment, Cpf1 has at least one amino acid substitution or deletion in the finger domain and in the lid domain, where the at least one amino acid substitution or deletion is as defined above. Accordingly, the mutant Cpf1 may comprise a sequence having at least 80%, such as at least 85%, at least 90%, at least 95%, at least 96%, at least 97%, at least 98%, at least 99% or 100% sequence identity to the sequence corresponding to residues 1 to 297, 310 to 1005 and 1019 to 1329 of SEQ ID NO: 2. The mutant Cpf1 may further comprise at least one amino acid substitution in position 918, 1013, 1014, 1025 or 1028 of SEQ ID NO: 2.

In another embodiment, Cpf1 has at least one amino acid substitution or deletion in the REC domain and in the lid domain, where the at least one amino acid substitution or deletion is as defined above. Accordingly, the mutant Cpf1 may comprise a sequence having at least 80%, such as at least 85%, at least 90%, at least 95%, at least 96%, at least 97%, at least 98%, at least 99% or 100% sequence identity to the sequence corresponding to residues 1 to 323, 336 to 1005 and 1019 to 1329 of SEQ ID NO: 2. The mutant Cpf1 may further comprise at least one amino acid substitution in position 918, 1013, 1014, 1025 or 1028 of SEQ ID NO: 2.

In another embodiment, Cpf1 has at least one amino acid substitution or deletion in the finger domain, in the REC domain and in the lid domain, where the at least one amino acid substitution or deletion is as defined above. Accordingly, the mutant Cpf1 may comprise a sequence having at least 80%, such as at least 85%, at least 90%, at least 95%, at least 96%, at least 97%, at least 98%, at least 99% or 100% sequence identity to the sequence corresponding to residues 1 to 297, 310 to 323, 337 to 1005 and 1019 to 1329 of SEQ ID NO: 2. The mutant Cpf1 may further comprise at least one amino acid substitution in position 918, 1013, 1014, 1025 or 1028 of SEQ ID NO: 2.

In a specific embodiment, the Cpf1 mutant is as set forth in SEQ ID NO: 42, i.e. the finger domain is deleted. In another embodiment, the Cpf1 mutant is as set forth in SEQ ID NO: 34, i.e. the REC domain is deleted. In another embodiment, the Cpf1 mutant is as set forth in SEQ ID NO: 36, i.e. the REC domain is substituted. In another embodiment, the Cpf1 mutant is as set forth in SEQ ID NO: 40, i.e. the Lid domain is deleted. In another embodiment, the Cpf1 mutant is as set forth in SEQ ID NO: 38, i.e. the Lid domain is substituted.

It will be understood that the at least one amino acid substitution or deletion as defined above may refer to deletion of some amino acids in a domain, while other amino acids may be substituted.

All of the above mutants may further comprise at least one amino acid substitution and/or deletion in one or more of positions 918, 1013, 1014, 1025 or 1028 of SEQ ID NO: 2, as further detailed herein below. In one embodiment, the mutant further comprises at least one amino acid substitution at one of positions 918, 1013, 1014, 1025 or 1028 of SEQ ID NO: 2, the other positions remaining unmodified. In one embodiment, the mutant thus further comprises one substitution at one of positions 918, 1013, 1014, 1025 or 1028 of SEQ ID NO: 2. For example, the mutant further comprises one substitution at position 918, or at position 1013, or at position 1014, or at position 1025, or at position 1028.

In another embodiment, the mutant further comprises amino acid substitutions and/or deletions at two of positions 918, 1013, 1014, 1025 or 1028 of SEQ ID NO: 2. For example, the mutant further comprises substitutions at positions 918 and 1013; or at positions 918 and 1014; or at positions 918 and 1025; or at positions 918 and 1028; or at positions 1013 and 1014; or at positions 1013 and 1025; or at positions 1013 and 1028; or at positions 1014 and 1025; or at positions 1014 and 1028; or at positions 1025 and 1028.

In another embodiment, the mutant further comprises amino acid substitutions and/or deletions at three of positions 918, 1013, 1014, 1025 or 1028 of SEQ ID NO: 2. For example, the mutant further comprises substitutions at positions 918, 1013 and 1014; or at positions 918, 1013 and 1025; or at positions 918, 1013 and 1028; or at positions 918, 1014 and 1025; or at positions 918, 1014 and 1028; or at positions 918 and 1025 and 1028; or at positions 1013, 1014 and 1025; or at positions 1013, 1014 and 1028; or at positions 1014, 1025 and 1028.

In another embodiment, the mutant further comprises amino acid substitutions and/or deletions at four of positions 918, 1013, 1014, 1025 and 1028 of SEQ ID NO: 2. For example, the mutant further comprises substitutions at positions 918, 1013, 1014 and 1025; or at positions 918, 1013, 1025 and 1028; or at positions 1013, 1014, 1025 and 1028; or at positions 918, 1014, 1025 and 1028.

In another embodiment, the mutant further comprises amino acid substitutions and/or deletions at five of positions 918, 1013, 1014, 1025 and 1028 of SEQ ID NO: 2.

The at least one amino acid substitution, whether in the finger, REC or Lid domain or at one or more of positions 918, 1013, 1014, 1025 and 1028 of SEQ ID NO: 2, may in some embodiments be a substitution of an amino acid having a charged side chain to an amino acid having an uncharged side chain or a non-polar side chain. In some embodiments, the amino acid is substituted to an amino acid selected from the group consisting of glycine, alanine, valine, leucine, isoleucine, serine or threonine. In some embodiments, the amino acid is substituted to a glycine.

The at least two amino acid substitutions, whether in the finger, REC or Lid domain or at one or more of positions 918, 1013, 1014, 1025 and 1028 of SEQ ID NO: 2, may in some embodiments be a substitution of an amino acid having a charged side chain to an amino acid having an uncharged side chain or a non-polar side chain. In some embodiments, the amino acid is substituted to an amino acid selected from the group consisting of glycine, alanine, valine, leucine, isoleucine, serine or threonine. In some embodiments, the amino acid is substituted to a glycine.

For example, the finger domain of SEQ ID NO: 2, KGINEYINLY SQ (SEQ ID NO: 20), may be mutated to GGGAGAAGGA SG (SEQ ID NO: 22). The REC domain of SEQ ID NO: 2, LFKQILSDTE SKS (SEQ ID NO: 12) may be mutated to GGGAGASAGG SGS (SEQ ID NO: 14). The Lid domain of SEQ ID NO: 2, EDLNFGFKRG RFK (SEQ ID NO: 16) may be mutated to GGGAGGAAGG GAG (SEQ ID NO: 18).

In one embodiment of the present disclosure, the mutant Cpf1 endonuclease or orthologue thereof comprises a polypeptide sequence orthologue thereof comprising a polypeptide sequence having at least 95% sequence identity to SEQ ID NO: 2, such as at least 96% sequence identity to SEQ ID NO: 2, such as at least 97% sequence identity to SEQ ID NO: 2, such as at least 98% sequence identity to SEQ ID NO: 2, such as at least 99% sequence identity to SEQ ID NO: 2, such as about 100% sequence identity to SEQ ID NO: 2, wherein said polypeptide sequence comprises at least one amino acid substitution of an amino acid having a charged side chain to an amino acid residue having an uncharged side chain in position 918, 1013, or 1014 of SEQ ID NO: 2.

In one embodiment of the present disclosure, the mutant Cpf1 endonuclease or orthologue thereof comprises a polypeptide sequence orthologue thereof comprising a polypeptide sequence having at least 95% sequence identity to SEQ ID NO: 2, such as at least 96% sequence identity to SEQ ID NO: 2, such as at least 97% sequence identity to SEQ ID NO: 2, such as at least 98% sequence identity to SEQ ID NO: 2, such as at least 99% sequence identity to SEQ ID NO: 2, such as about 100% sequence identity to SEQ ID NO: 2, wherein said polypeptide sequence comprises at least two amino acid substitutions of two amino acids having a charged side chain to two amino acid residues having an uncharged side chain in two positions independently selected from the positions corresponding to residues 918, 1013, or 1014 of SEQ ID NO: 2.

In one embodiment of the present disclosure, the mutant Cpf1 endonuclease or orthologue thereof comprises a polypeptide sequence orthologue thereof comprising a polypeptide sequence having at least 95% sequence identity to SEQ ID NO: 2, such as at least 96% sequence identity to SEQ ID NO: 2, such as at least 97% sequence identity to SEQ ID NO: 2, such as at least 98% sequence identity to SEQ ID NO: 2, such as at least 99% sequence identity to SEQ ID NO: 2, such as about 100% sequence identity to SEQ ID NO: 2, wherein said polypeptide sequence comprises at least one amino acid substitution of an amino acid having a charged side chain to an amino acid residue having a non-polar side chain in position 918, 1013, or 1014 of SEQ ID NO: 2.

In one embodiment of the present disclosure, the mutant Cpf1 endonuclease or orthologue thereof comprises a polypeptide sequence orthologue thereof comprising a polypeptide sequence having at least 95% sequence identity to SEQ ID NO: 2, such as at least 96% sequence identity to SEQ ID NO: 2, such as at least 97% sequence identity to SEQ ID NO: 2, such as at least 98% sequence identity to SEQ ID NO: 2, such as at least 99% sequence identity to SEQ ID NO: 2, such as about 100% sequence identity to SEQ ID NO: 2, wherein said polypeptide sequence comprises at least one amino acid substitution of an amino acid having a charged side chain to an amino acid residue selected from the group consisting of glycine, alanine, valine, leucine, isoleucine, serine or threonine, in position 918, 1013, or 1014 of SEQ ID NO: 2.

In one embodiment of the present disclosure, the mutant Cpf1 endonuclease or orthologue thereof comprises a polypeptide sequence orthologue thereof comprising a polypeptide sequence having at least 95% sequence identity to SEQ ID NO: 2, such as at least 96% sequence identity to SEQ ID NO: 2, such as at least 97% sequence identity to SEQ ID NO: 2, such as at least 98% sequence identity to SEQ ID NO: 2, such as at least 99% sequence identity to SEQ ID NO: 2, such as about 100% sequence identity to SEQ ID NO: 2, wherein said polypeptide sequence comprises at least one amino acid substitution of an amino acid having a charged side chain to a glycine in position 918, 1013, or 1014 of SEQ ID NO: 2.

In one embodiment of the present disclosure, the mutant Cpf1 endonuclease or orthologue thereof comprises a polypeptide sequence orthologue thereof comprising a polypeptide sequence having at least 95% sequence identity to SEQ ID NO: 2, such as at least 96% sequence identity to SEQ ID NO: 2, such as at least 97% sequence identity to SEQ ID NO: 2, such as at least 98% sequence identity to SEQ ID NO: 2, such as at least 99% sequence identity to SEQ ID NO: 2, such as about 100% sequence identity to SEQ ID NO: 2, wherein said polypeptide sequence comprises at least one amino acid substitution selected from R918G, K1013G, R1014G, Q1025G or E1028G.

In one embodiment of the present disclosure, the mutant Cpf1 endonuclease or orthologue thereof comprises a polypeptide sequence orthologue thereof comprising a polypeptide sequence having at least 95% sequence identity to SEQ ID NO: 2, such as at least 96% sequence identity to SEQ ID NO: 2, such as at least 97% sequence identity to SEQ ID NO: 2, such as at least 98% sequence identity to SEQ ID NO: 2, such as at least 99% sequence identity to SEQ ID NO: 2, such as about 100% sequence identity to SEQ ID NO: 2, wherein said polypeptide sequence comprises at least two amino acid substitutions selected from R918G, K1013G, R1014G, Q1025G or E1028G.

In one embodiment of the present disclosure, the mutant Cpf1 endonuclease or orthologue thereof comprises a polypeptide sequence having at least 95% sequence identity to SEQ ID NO: 2, wherein said polypeptide sequence comprises an amino acid substitution at residue K1013.

In one embodiment of the present disclosure, the mutant Cpf1 endonuclease or orthologue thereof comprises a polypeptide sequence having at least 95% sequence identity to SEQ ID NO: 2, such as at least 96% sequence identity to SEQ ID NO: 2, such as at least 97% sequence identity to SEQ ID NO: 2, such as at least 98% sequence identity to SEQ ID NO: 2, such as at least 99% sequence identity to SEQ ID NO: 2, such as about 100% sequence identity to SEQ ID NO: 2, wherein said polypeptide sequence comprises an amino acid substitution at residues R918 and K1013.

In one embodiment of the present disclosure, the mutant Cpf1 endonuclease or orthologue thereof comprises a polypeptide sequence having at least 95% sequence identity to SEQ ID NO: 2, such as at least 96% sequence identity to SEQ ID NO: 2, such as at least 97% sequence identity to SEQ ID NO: 2, such as at least 98% sequence identity to SEQ ID NO: 2, such as at least 99% sequence identity to SEQ ID NO: 2, such as about 100% sequence identity to SEQ ID NO: 2, wherein said polypeptide sequence an amino acid substitution at residues K1013 and R1014.

In one embodiment of the present disclosure, the mutant Cpf1 endonuclease or orthologue thereof comprises a polypeptide sequence having at least 95% sequence identity to SEQ ID NO: 2, such as at least 96% sequence identity to SEQ ID NO: 2, such as at least 97% sequence identity to SEQ ID NO: 2, such as at least 98% sequence identity to SEQ ID NO: 2, such as at least 99% sequence identity to SEQ ID NO: 2, such as about 100% sequence identity to SEQ ID NO: 2, wherein said polypeptide sequence comprises the amino acid substitution K1013G.

In one embodiment of the present disclosure, the mutant Cpf1 endonuclease or orthologue thereof comprises a polypeptide sequence having at least 95% sequence identity to SEQ ID NO: 2, such as at least 96% sequence identity to SEQ ID NO: 2, such as at least 97% sequence identity to SEQ ID NO: 2, such as at least 98% sequence identity to SEQ ID NO: 2, such as at least 99% sequence identity to SEQ ID NO: 2, such as about 100% sequence identity to SEQ ID NO: 2, wherein said polypeptide sequence comprises the amino acid substitutions R918G and K1013G.

In one embodiment of the present disclosure, the mutant Cpf1 endonuclease or orthologue thereof comprises a polypeptide sequence having at least 95% sequence identity to SEQ ID NO: 2, such as at least 96% sequence identity to SEQ ID NO: 2, such as at least 97% sequence identity to SEQ ID NO: 2, such as at least 98% sequence identity to SEQ ID NO: 2, such as at least 99% sequence identity to SEQ ID NO: 2, such as about 100% sequence identity to SEQ ID NO: 2, wherein said polypeptide sequence comprises the amino acid substitutions K1013G and R1014G.

In some embodiments of the present disclosure the mutant Cpf1 endonuclease or orthologue thereof comprises a polypeptide sequence having at least 95% sequence identity to SEQ ID NO: 2, such as at least 96% sequence identity to SEQ ID NO: 2, such as at least 97% sequence identity to SEQ ID NO: 2, such as at least 98% sequence identity to SEQ ID NO: 2, such as at least 99% sequence identity to SEQ ID NO: 2, such as about 100% sequence identity to SEQ ID NO: 2, wherein said Cpf1 polypeptide comprises an amino acid substitution at residues K1013 and R1014 as defined in the embodiments above and is a nickase that is capable of introducing a single strand break in a target nucleic acid, such as in the first target nucleic acid, wherein the first target nucleic acid and the second target nucleic acid are identical.

In some embodiments of the present disclosure the mutant Cpf1 endonuclease or orthologue thereof comprises a polypeptide sequence having at least 95% sequence identity to SEQ ID NO: 2, such as at least 96% sequence identity to SEQ ID NO: 2, such as at least 97% sequence identity to SEQ ID NO: 2, such as at least 98% sequence identity to SEQ ID NO: 2, such as at least 99% sequence identity to SEQ ID NO: 2, such as about 100% sequence identity to SEQ ID NO: 2, wherein said Cpf1 polypeptide comprises an amino acid substitution at residues R918 and K1013 as defined in the embodiments above and is a non-specific endonuclease that is capable of introducing single strand break at non-specific sites of a nucleic acid, such as at non-specific sites of the first target nucleic acid. In some embodiments of the present disclosure the mutant Cpf1 endonuclease or orthologue thereof is a non-specific endonuclease that recognizes a target DNA sequence, but introduces a single strand break only at non-specific sites of a nucleic acid sequences. In some embodiments of the present disclosure, the mutated, non-specific Cpf1 endonuclease remains active for an extended period of time and introduces single strand breaks in several non-specific single-stranded nucleic acid sequences prior to returning into the inactive state.

In some embodiments the mutant Cpf1 endonuclease or orthologue thereof comprises a polypeptide sequence having at least 95% sequence identity to SEQ ID NO: 3 or SEQ ID NO: 4, such as at least 96% sequence identity to SEQ ID NO: 3 or SEQ ID NO: 4, for example at least 97% sequence identity to SEQ ID NO: 3 or SEQ ID NO: 4, such as at least 98% sequence identity to SEQ ID NO: 3 or SEQ ID NO: 4, for example at least 99% sequence identity to SEQ ID NO: 3 or SEQ ID NO: 4, such as 100% sequence identity to SEQ ID NO: 3 or SEQ ID NO: 4.

In some embodiments the mutant Cpf1 endonuclease or orthologue thereof comprises SEQ ID NO: 3 or SEQ ID NO: 4.

In some embodiments the mutant Cpf1 endonuclease or orthologue thereof consists of SEQ ID NO: 3 or SEQ ID NO: 4.

In one embodiment of the present disclosure, the mutant Cpf1 endonuclease or orthologue thereof comprises a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 2, wherein said polypeptide sequence comprises an amino acid substitution at residue Q1025.

In another embodiment of the present disclosure, the mutant Cpf1 endonuclease or orthologue thereof comprises a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 2, wherein said polypeptide sequence comprises an amino acid substitution at residue E1028.

In one embodiment of the present disclosure, the mutant Cpf1 endonuclease or orthologue thereof comprises a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 2, wherein said polypeptide sequence comprises an amino acid substitution at residues Q1025 and E1028.

The substitution at position 1025 or 1028 may be as described herein. In some embodiments, position 1025 is substituted by a glycine. In some embodiments, position 1028 is substituted by a glycine. In some embodiments, positions 1025 and 1028 are both substituted by a glycine.

Cpf1 contains an RNAse active site, which is used to process its own pre-crRNA to assemble an active ribonucleoprotein to achieve interference.

The modification of the finger domain, of the REC domain and of the Lid domain of Cpf1, results in altered properties of Cpf1. The mutant proteins may thus have altered properties compared to the wild type protein, in particular the mutant Cpf1 may be able to:

Cleave a double stranded target nucleic acid;
Cleave a double stranded non-target nucleic acid;
Cleave a single stranded target nucleic acid;
Cleave a single stranded non-target nucleic acid;
Cleave single stranded DNA in a non-specific manner, optionally enhanced by double stranded target DNA;
Cleave single stranded DNA in a non-specific manner, optionally enhanced by single stranded target DNA;
Cleave only one strand of the double stranded nucleic acid target;
Cleave only the target double stranded nucleic acid; and/or
Cleave only the target single stranded nucleic acid.

The mutant Cpf1 may have one or more of the above activities. In some embodiments, the mutant Cpf1 displays improved activities compared to the wild type Cpf1.

The mutants disclosed herein may thus have different applications. For instance, mutants cleaving the target and/or non-target nucleic acid, whether single-stranded or double-stranded, in a more efficient manner than the wild-type Cpf1 from which they are derived, may be generally more useful to efficient gene editing. Mutants cleaving preferentially a double-stranded target and/or non-target nucleic acid may exhibit higher specificity than the wild-type Cpf1 from which they are derived. Mutants able to cleave single-stranded DNA non-specifically, but unable to cleave the target or non-target strand, may retain activity longer than the wild-type protein.

The mutants disclosed herein may thus have different applications. For instance, mutants cleaving the target and but not non-target single stranded nucleic acid, whether the target is single-stranded or double-stranded, in a more efficient manner than the wild type Cpf1 from which they are derived, may be generally more useful to efficient gene editing. Mutants cleaving preferentially a double-stranded target and/or non-target nucleic acid may exhibit higher specificity than the wild type Cpf1 from which they are derived. Mutants able to cleave single-stranded DNA non-specifically, but unable to cleave the target nucleic acid, may retain activity longer than the wild type protein and may be more efficient in detection of a target.

In one embodiment the Cpf1 endonuclease is a nicking endonuclease.

Polynucleotides and nucleic acid sequences encoding the mutant Cpf1 disclosed herein are also provided. The skilled person knows how to design such nucleic acid sequences encoding the desired Cpf1 mutant.

In some embodiments, the present disclosure provides a nucleic acid encoding a mutant Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to:
  i) the sequence corresponding to residues 1 to 297, 310 to 323, 337 to 1005, and 1019 to 1329 of SEQ ID NO: 2, wherein said polypeptide sequence further comprises at least one amino acid substitution or deletion in the finger domain (residues 298 to 309; SEQ ID NO: 12), the REC domain (residues 324 to 336; SEQ ID NO: 16) or the Lid domain (residues 1006 to 1018; SEQ ID NO: 20) compared to SEQ ID NO: 2; and/or
  ii) SEQ ID NO: 2, wherein said polypeptide sequence comprises at least one amino acid substitution in position 918, 1013, 1014, 1025 or 1028 of SEQ ID NO: 2.

In some embodiments, the present disclosure provides a nucleic acid encoding a mutant Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to:
  i) the sequence corresponding to residues 1 to 323, 337 to 1005, and 1019 to 1329 of SEQ ID NO: 2, wherein said polypeptide sequence further comprises:
    a. at least two amino acid mutations in the REC domain (residues 324 to 336; SEQ ID NO: 16) compared to SEQ ID NO: 2, wherein each mutation independently is an amino acid substitution or deletion; and/or
    b. at least two amino acid substitutions in the Lid domain (residues 1006 to 1018; SEQ ID NO: 20) compared to SEQ ID NO: 2, wherein at least one of the residues at positions 917 and 1006 is a glutamic acid (E) or an aspartic acid (D);
and/or
  ii) SEQ ID NO: 2, wherein said polypeptide sequence comprises at least two amino acid substitutions in two positions independently selected from the positions corresponding to residues 918, 1013, 1014, 1025 and 1028 of SEQ ID NO: 2.

The nucleic acid sequence encoding FnCpf1 is set out in SEQ ID NO: 1.

In some embodiments, the nucleic acid sequence encodes a Cpf1 mutant wherein the finger domain has been deleted. In a particular embodiment, the nucleic acid sequence is as set out in SEQ ID NO: 41, and encodes the mutant Cpf1 of SEQ ID NO: 42.

In other embodiments, the nucleic acid sequence encodes a Cpf1 mutant wherein the REC domain has been deleted. In a particular embodiment, the nucleic acid sequence is as set out in SEQ ID NO: 33, and encodes the mutant Cpf1 of SEQ ID NO: 34.

In other embodiments, the nucleic acid sequence encodes a Cpf1 mutant wherein the amino acid residues of the REC domain have been substituted. In a particular embodiment, the nucleic acid sequence is as set out in SEQ ID NO: 35, and encodes the mutant Cpf1 of SEQ ID NO: 36.

In other embodiments, the nucleic acid sequence encodes a Cpf1 mutant wherein the lid domain has been deleted. In a particular embodiment, the nucleic acid is as set out in SEQ ID NO: 39, and encodes the mutant Cpf1 of SEQ ID NO: 40.

In other embodiments, the nucleic acid sequence encodes a Cpf1 mutant wherein the amino acid residues of the lid domain have been substituted. In a particular embodiment, the nucleic acid sequence is as set out in SEQ ID NO: 37, and encodes the mutant Cpf1 of SEQ ID NO: 38.

In some embodiments, the Cpf1 endonuclease or orthologue thereof is encoded by a nucleic acid sequence comprising or consisting of a sequence which is at least 70% identical, such as at least 75% identical, such as at least 80% identical, such as at least 85% identical, such as at least 86% identical, such as at least 87% identical, such as at least 88% identical, such as at least 89% identical, such as at least 90% identical, such as at least 91% identical, such as at least 92% identical, such as at least 93% identical, such as at least 94% identical, such as at least 95% identical, such as at least 96% identical, such as at least 97% identical, such as at least 98% identical, such as at least 99% identical to the sequence encoding the parent Cpf1, i.e. the parent sequence. In one embodiment, the parent sequence is the sequence encoding FnCpf1, as set out in SEQ ID NO: 1.

One aspect of the present disclosure relates to a vector comprising a polynucleotide or a nucleic acid sequence encoding a mutant Cpf1 endonuclease or orthologue thereof as defined above in operable combination with a promoter, wherein the Cpf1 endonuclease or orthologue thereof has at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to a polypeptide of SEQ ID NO: 2 and said polypeptide sequence comprises at least one amino acid substitution in position 918, 1013, or 1014 of SEQ ID NO: 2.

One aspect of the present disclosure relates to a vector comprising a polynucleotide or a nucleic acid sequence encoding a mutant Cpf1 endonuclease or orthologue thereof as defined above in operable combination with a promoter, wherein the Cpf1 endonuclease or orthologue thereof has at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to a polypeptide of SEQ ID NO: 2 and said polypeptide sequence comprises at least two amino acid substitution in position 918, 1013, or 1014 of SEQ ID NO: 2.

One aspect of the present disclosure relates to a vector comprising a polynucleotide or a nucleic acid sequence encoding a mutant Cpf1 endonuclease or orthologue thereof as defined above in operable combination with a promoter, wherein the Cpf1 endonuclease or orthologue thereof has at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to a polypeptide of SEQ ID NO: 2 and said polypeptide sequence comprises at least two amino acid substitution in position 1025 and 1028 of SEQ ID NO: 2.

In one embodiment, the vector further comprises a nucleic acid sequence encoding a guide RNA (crRNA) in operable combination with a promoter, wherein the crRNA binds the encoded Cpf1 endonuclease and a segment with sufficient base pairs to hybridize to a target nucleic acid. The crRNA is further described in the section below "Guide RNA (crRNA)".

One aspect of the present disclosure relates to a system for expression of a crRNA-Cpf1 complex comprising
  a. a polynucleotide as disclosed herein, or a recombinant vector as disclosed herein comprising a polynucleotide encoding a mutant Cpf1 endonuclease or orthologue thereof;
  b. a polynucleotide or a recombinant vector comprising a polynucleotide encoding a guide RNA (crRNA) operably linked to a promoter.

One aspect of the present disclosure relates to a cell expressing the polynucleotide or the recombinant vector as described herein above. The Cpf1 may be expressed from a cell, in particular suitable expression hosts as are known to the skilled person. In one embodiment, Cpf1 is expressed from *Escherichia coli*. This can be done as is known in the art, for example by introducing a vector comprising the nucleic acid sequence encoding the desired Cpf1 effector protein or homologue as described herein above in an *E. coli* cell. The protein can be purified as is known in the art. In one embodiment, said polynucleotide is codon-optimized for expression in a host cell.

Without being bound by theory, the finger domain, the REC domain and the Lid domain appear to be conserved. Accordingly, the Cpf1 mutant may be a mutant of Cpf1 from *Francisella novicida, Acidaminococcus* sp. BV3L6, Lachnospiraceae bacterium COE1, *Succiniclasticum ruminis, Candidatus Methanoplasma termitum*, uncultured *Clostridium* sp. or *Butyrivibrio fibrisolvens*.

In one embodiment, the Cpf1 is FnCpf1 from *Francisella novicida*, and the domains are as defined herein above.

In another embodiment, the Cpf1 is derived from *Acidaminococcus* sp. BV3L6, as set out in SEQ ID NO: 24. The finger domain is defined by residues 275 to 285 of SEQ ID NO: 24. The REC domain is defined by residues 305 to 317 of SEQ ID NO: 24. The Lid domain is defined by residues 993 to 1005 of SEQ ID NO: 24. Position 918 of SEQ ID NO: 2 corresponds to position 909 of SEQ ID NO: 24. Position 1013 of SEQ ID NO: 2 corresponds to position 1000 of SEQ ID NO: 24. Position 1014 of SEQ ID NO: 2 corresponds to position 1001 of SEQ ID NO: 24. Position 1025 of SEQ ID NO: 2 corresponds to position 1013 of SEQ ID NO: 24. Position 1028 of SEQ ID NO: 2 corresponds to position 1016 of SEQ ID NO: 24.

In another embodiment, the Cpf1 is derived from Lachnospiraceae bacterium COE1 as set out in SEQ ID NO: 25. The finger domain is defined by residues 260 to 270 of SEQ ID NO: 25. The REC domain is defined by residues 283 to 295 of SEQ ID NO: 25. The Lid domain is defined by residues 936 to 948 of SEQ ID NO: 25. Position 918 of SEQ ID NO: 2 corresponds to position 843 of SEQ ID NO: 25. Position 1013 of SEQ ID NO: 2 corresponds to position 943 of SEQ ID NO: 25. Position 1014 of SEQ ID NO: 2 corresponds to position 944 of SEQ ID NO: 25. Position 1025 of SEQ ID NO: 2 corresponds to position 955 of SEQ ID NO: 25. Position 1028 of SEQ ID NO: 2 corresponds to position 958 of SEQ ID NO: 25.

In another embodiment, the Cpf1 is derived from *Succiniclasticum ruminis*, as set out in SEQ ID NO: 26. The finger domain is defined by residues 279 to 289 of SEQ ID NO: 26. The REC domain is defined by residues 309 to 321 of SEQ ID NO: 26. The Lid domain is defined by residues 997 to 1009 of SEQ ID NO: 26. Position 918 of SEQ ID NO: 2 corresponds to position 913 of SEQ ID NO: 26. Position 1013 of SEQ ID NO: 2 corresponds to position 1004 of SEQ ID NO: 26. Position 1014 of SEQ ID NO: 2 corresponds to position 1005 of SEQ ID NO: 26. Position 1025 of SEQ ID NO: 2 corresponds to position 1017 of SEQ ID NO: 26. Position 1028 of SEQ ID NO: 2 corresponds to position 1020 of SEQ ID NO: 26.

In another embodiment, the Cpf1 is derived from *Candidatus Methanoplasma termitum*, as set out in SEQ ID NO: 43. The finger domain is defined by residues 256 to 266 of SEQ ID NO: 43. The REC domain is defined by residues 281 to 293 of SEQ ID NO: 43. The Lid domain is defined by residues 944 to 956 of SEQ ID NO: 43. Position 918 of SEQ ID NO: 2 corresponds to position 860 of SEQ ID NO: 43. Position 1013 of SEQ ID NO: 2 corresponds to position 951 of SEQ ID NO: 43. Position 1014 of SEQ ID NO: 2 corresponds to position 952 of SEQ ID NO: 43. Position 1025 of SEQ ID NO: 2 corresponds to position 963 of SEQ ID NO: 43. Position 1028 of SEQ ID NO: 2 corresponds to position 966 of SEQ ID NO: 43.

In another embodiment, the Cpf1 is derived from uncultured *Clostridium* sp, as set out in SEQ ID NO: 44. The finger domain is defined by residues 266 to 270 of SEQ ID NO: 44. The REC domain is defined by residues 285 to 297 of SEQ ID NO: 44. The Lid domain is defined by residues 959 to 971 of SEQ ID NO: 44. Position 918 of SEQ ID NO: 2 corresponds to position 8776 of SEQ ID NO: 44. Position 1013 of SEQ ID NO: 2 corresponds to position 966 of SEQ ID NO: 44. Position 1014 of SEQ ID NO: 2 corresponds to position 967 of SEQ ID NO: 44. Position 1025 of SEQ ID NO: 2 corresponds to position 979 of SEQ ID NO: 44. Position 1028 of SEQ ID NO: 2 corresponds to position 982 of SEQ ID NO: 44.

In another embodiment, the Cpf1 is derived from *Butyrivibrio fibrisolvens*, as set out in SEQ ID NO: 27. The finger domain is defined by residues 234 to 242 of SEQ ID NO: 27. The REC domain is defined by residues 260 to 264 of SEQ ID NO: 27. The Lid domain is defined by residues 925 to 937 of SEQ ID NO: 27. Position 918 of SEQ ID NO: 2 corresponds to position 835 of SEQ ID NO: 27. Position 1013 of SEQ ID NO: 2 corresponds to position 932 of SEQ ID NO: 27. Position 1014 of SEQ ID NO: 2 corresponds to position 933 of SEQ ID NO: 27. Position 1025 of SEQ ID NO: 2 corresponds to position 944 of SEQ ID NO: 27. Position 1028 of SEQ ID NO: 2 corresponds to position 947 of SEQ ID NO: 27.

Guide RNA (crRNA)

In order to function as an endonuclease, the crRNA-Cpf1 complex requires not only the Cpf1 effector protein, but also a guide RNA (crRNA), which is responsible for recognition of the target nucleic acid to be cleaved.

The crRNA comprises or consists of a constant region and of a variable region. The constant region consists of 19-20 nucleotides and is constant for all complexes derived from a given organism. For optimal activity of the crRNA-Cpf1 complex, it may be important to design the crRNA based on the constant region specific for the organism from which Cpf1 or its homologue is derived.

The constant region may be specific for *Francisella novicida* and have the sequence set out in SEQ ID NO: 5.

The variable region consists of between 12 and 24 nucleotides, such as 13, 14, 15, 16, 17, 18, 19, 20, 21, 22, 23 or 24 nucleic acids. The variable region is the region of the crRNA which is thought to be responsible for target recognition. Modifying the sequence of the variable region can thus be taken advantage of in order for the crRNA-Cpf1 complex to be able to specifically cleave different target nucleic acids. In contrast to the constant region, the variable region is not organism-specific.

Accordingly, in one embodiment the crRNA consists of a constant region of 19 nucleotides and a variable region of 12 nucleotides, and the crRNA has a total length of 31 nucleotides. In another embodiment the crRNA consists of a constant region of 20 nucleotides and a variable region of 12 nucleotides, and the crRNA has a total length of 32 nucleotides. In another embodiment the crRNA consists of a constant region of 19 nucleotides and a variable region of 13 nucleotides, and the crRNA has a total length of 32 nucleotides. In another embodiment the crRNA consists of a constant region of 20 nucleotides and a variable region of 13 nucleotides, and the crRNA has a total length of 33 nucleotides. In another embodiment the crRNA consists of a constant region of 19 nucleotides and a variable region of 14 nucleotides, and the crRNA has a total length of 33 nucleotides. In another embodiment the crRNA consists of a constant region of 20 nucleotides and a variable region of 14 nucleotides, and the crRNA has a total length of 34 nucleotides. In another embodiment the crRNA consists of a constant region of 19 nucleotides and a variable region of 15 nucleotides, and the crRNA has a total length of 34 nucleotides. In another embodiment the crRNA consists of a constant region of 20 nucleotides and a variable region of 15 nucleotides, and the crRNA has a total length of 35 nucleotides. In another embodiment the crRNA consists of a constant region of 19 nucleotides and a variable region of 16 nucleotides, and the crRNA has a total length of 35 nucleotides. In another embodiment the crRNA consists of a constant region of 20 nucleotides and a variable region of 16 nucleotides, and the crRNA has a total length of 36 nucleotides. In another embodiment the crRNA consists of a constant region of 19 nucleotides and a variable region of 17 nucleotides, and the crRNA has a total length of 36 nucleotides. In another embodiment the crRNA consists of a constant region of 20 nucleotides and a variable region of 17 nucleotides, and the crRNA has a total length of 37 nucleotides. In another embodiment the crRNA consists of a constant region of 19 nucleotides and a variable region of 18 nucleotides, and the crRNA has a total length of 37 nucleotides. In another embodiment the crRNA consists of a constant region of 20 nucleotides and a variable region of 18 nucleotides, and the crRNA has a total length of 38 nucleotides. In another embodiment the crRNA consists of a constant region of 19 nucleotides and a variable region of 19 nucleotides, and the crRNA has a total length of 38 nucleotides. In another embodiment the crRNA consists of a constant region of 20 nucleotides and a variable region of 19 nucleotides, and the crRNA has a total length of 39 nucleotides. In another embodiment the crRNA consists of a constant region of 19 nucleotides and a variable region of 20 nucleotides, and the crRNA has a total length of 39 nucleotides. In another embodiment the crRNA consists of a constant region of 20 nucleotides and a variable region of 20 nucleotides, and the crRNA has a total length of 40 nucleotides. In another embodiment the crRNA consists of a constant region of 19 nucleotides and a variable region of 21 nucleotides, and the crRNA has a total length of 40 nucleotides. In another embodiment the crRNA consists of a constant region of 20 nucleotides and a variable region of 21 nucleotides, and the crRNA has a total length of 41 nucleotides. In another embodiment the crRNA consists of a constant region of 19 nucleotides and a variable region of 22 nucleotides, and the crRNA has a total length of 41 nucleotides. In another embodiment the crRNA consists of a constant region of 20 nucleotides and a variable region of 22 nucleotides, and the crRNA has a total length of 42 nucleotides. In another embodiment the crRNA consists of a constant region of 19 nucleotides and a variable region of 23 nucleotides, and the crRNA has a total length of 42 nucleotides. In another embodiment the crRNA consists of a constant region of 20 nucleotides and a variable region of 23 nucleotides, and the crRNA has a total length of 43 nucleotides. In another embodiment the crRNA consists of a constant region of 19 nucleotides and a variable region of 24 nucleotides, and the crRNA has a total length of 43 nucleotides. In another embodiment the crRNA consists of a constant region of 20 nucleotides and a variable region of 24 nucleotides, and the crRNA has a total length of 44 nucleotides.

The skilled person will have no difficulty in designing a variable region capable of binding the desired target nucleic acid. The variable region has a sequence which is the reverse complement of the target nucleic acid.

The crRNA thus consists of a constant region of 19 or 20 nucleotides, and of a variable region consisting of between 12 and 24 nucleotides, such that said crRNA is 31 nucleotides in length, 32 nucleotides in length, 33 nucleotides in length, 34 nucleotides in length, 35 nucleotides in length, 36 nucleotides in length, 37 nucleotides in length, 38 nucleotides in length, 39 nucleotides in length, 40 nucleotides in length, 41 nucleotides in length, 42 nucleotides in length, 43 nucleotides in length, 44 nucleotides in length, with the proviso that the 5'-terminal nucleotides consist of a PAM as described in the sections "First target nucleic acid" and "Second target nucleic acid".

Once a guide RNA sequence has been designed, the guide RNA can be synthesised by known methods. For example, DNA oligonucleotides corresponding to the reverse complemented sequence of the target site may be ordered from a company selling oligonucleotides. These oligonucleotides may contain a 24 base long T7 priming sequence. These DNA duplexes may then be used as template in a transcription reaction carried with T7 RNA polymerase. For example, the reaction may consist of incubation at 37° C. for at least 1 hour. The reaction may be stopped using 2× stop solution, for example 50 mM EDTA, 20 mM Tris-HCl PH 8.0 and 8 M Urea. The RNA may be purified by methods known in the art such as LiCl precipitation.

crRNA-Cpf1 Complex

When associated with the appropriate crRNA, Cpf1 forms a crRNA-Cpf1 complex. The crRNA-Cpf1 complexes formed by some Cpf1 mutants of the present disclosure is capable of introducing single strand breaks in a first target nucleic acid, and specifically recognizing a second target nucleic acid.

This is in contrast to a crRNA-Cpf1 complex formed with a wild type Cpf1 endonuclease, and which is capable of recognizing a specific nucleic acid and cleaving both strands of said specific nucleic acid in a staggered manner.

The crRNA may be modified in order for the crRNA-Cpf1 complex to be able to recognise different target nucleic acids. In particular, the variable region of the crRNA can be designed in order to recognise different targets. The sequence of the variable region of the crRNA needs to be complementary to the target nucleic acid.

It will be understood that a Cpf1 or homologue thereof derived from a given organism is preferably to be used in combination with a crRNA having a constant region as naturally found in the same organism. Thus, FnCpf1 or a homologue thereof is preferably assembled with a crRNA having a constant region as set out in SEQ ID NO: 5.

In order for the crRNA-Cpf1 complex to function efficiently as an endonuclease or restriction enzyme, the ratio of Cpf1 to crRNA is preferably adjusted. Preferably, the molar ratio of Cpf1 to crRNA is between 0.5:3.0 and 1.0:1.0, such as 0.7:2.5, such as 0.8:2.0, such as 0.9:1.75, such as 0.95:1.5, such as 1.0:1.4, such as 1.0:1.3, such as 1.1:1.2.

In some embodiments, the Cpf1 mutant which is capable of forming a crRNA-Cpf1 complex having the ability to introduce single strand breaks in a first target nucleic acid, and specifically recognize and optionally cleave a second target nucleic acid as described herein is a Cpf1 mutant having comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to:
  i) the sequence corresponding to residues 1 to 297, 310 to 323, 337 to 1005, and 1019 to 1329 of SEQ ID NO: 2, wherein said polypeptide sequence further comprises at least one amino acid substitution or deletion in the finger domain (residues 298 to 309; SEQ ID NO: 12), the REC domain (residues 324 to 336; SEQ ID NO: 16) or the Lid domain (residues 1006 to 1018; SEQ ID NO: 20) compared to SEQ ID NO: 2; and/or
  ii) SEQ ID NO: 2, wherein the polypeptide sequence comprises at least one amino acid substitution in position 918, 1013, 1014, 1025 or 1028 of SEQ ID NO: 2.

In some embodiments, the cleavage of the second target nucleic acid is single-stranded cleavage. In other embodiments, the cleavage of the second target nucleic acid is double-stranded cleavage. Preferably, cleavage of the second target nucleic acid is single-stranded cleavage. The cleavage may be further enhanced by the presence of an activator DNA, which may be single-stranded or double-stranded.

As can be seen in the examples, a mutant Cpf1 having a Q1025E substitution is capable of such non-specific DNA cleavage of a single stranded DNA. The cleavage is enhanced by the presence of single stranded target DNA or double stranded target DNA. Likewise, a mutant Cpf1 deleted for the REC domain as set out in SEQ ID NO: 34 and a mutant Cpf1 wherein the REC domain has been entirely substituted (SEQ ID NO: 36) are also capable of such non-specific DNA cleavage of a single stranded DNA. The cleavage is enhanced by the presence of single stranded target DNA or double stranded target DNA. A Cpf1 mutant in which the Lid domain has been entirely substituted is capable of such non-specific DNA cleavage of a single stranded DNA, albeit to a lesser extent than the above mutants; however in this case cleavage appears to be enhanced by the presence of single stranded target DNA only. A K1013G, R1014G mutant is also capable of such non-specific cleavage.

Herein are thus provided Cpf1 mutants which, when in complex with a crRNA, cleave a nucleic acid sequence more efficiently than the wild type Cpf1 endonuclease they are derived from. In some embodiments, the mutant Cpf1 endonuclease cuts both the target strand and the non-target strand more efficiently than the wild type Cpf1 endonuclease. In other embodiments, the mutant Cpf1 endonuclease alternatively or additionally cuts only one of the target strand and non-target strand more efficiently than the wild type Cpf1 endonuclease. In other embodiments, the mutant Cpf1 endonuclease alternatively or additionally is capable of introducing single-stranded breaks in a non-specific manner, as detailed herein below.

For example, a Cpf1 mutant comprising a mutation or a substitution at position 1025 of SEQ ID NO: 2 may cleave a nucleic acid sequence more efficiently than the wild type Cpf1 endonuclease of SEQ ID NO: 2.

A Cpf1 mutant comprising a mutation or a substitution at positions 1025 and 1028 of SEQ ID NO: 2 may cleave a nucleic acid sequence more efficiently than the wild type Cpf1 endonuclease of SEQ ID NO: 2.

A Cpf1 mutant comprising at least one mutation or substitution in the finger domain defined by residues 298 to 309 of SEQ ID NO: 2 may cleave a nucleic acid sequence more efficiently than the wild type Cpf1 endonuclease of SEQ ID NO: 2.

A Cpf1 mutant comprising at least one mutation or substitution in the REC domain defined by residues 324 to 336 of SEQ ID NO: 2 may cleave a nucleic acid sequence more efficiently than the wild type Cpf1 endonuclease of SEQ ID NO: 2.

A Cpf1 mutant comprising a mutation or a substitution in the Lid domain defined by residues 1006 to 1018 of SEQ ID NO: 2 may cleave a nucleic acid sequence more efficiently than the wild type Cpf1 endonuclease of SEQ ID NO: 2.

First Target Nucleic Acid

The mutant Cpf1 endonuclease of the present disclosure, after forming a crRNA-Cpf1 complex, is capable to introduce a single strand break in the first target nucleic acid. The first target nucleic acid is a nucleic acid sequence which may not be specifically recognized by the crRNA-Cpf1 complex of the present disclosure, but nevertheless cleaved.

In some embodiments, the first target nucleic acid is identical to the second target nucleic acid and it is recognized and cleaved by the crRNA-Cpf1 complex. Hence, the first target nucleic acid may be as defined in the section below "Second target nucleic acid".

In some embodiments, the first target nucleic acid is different from the second target nucleic acid and it is cleaved by the crRNA-Cpf1 complex only after hybridization of the crRNA-Cpf1 complex to the second target nucleic acid. Hence, in some embodiments the first target nucleic acid does not comprise a protospacer adjacent motif (PAM).

Second target nucleic acid Recognition and binding of the crRNA-Cpf1 complex to a second target nucleic acid relies on the crRNA binding to the second target nucleic acid. This is dependent on the presence of a PAM (protospacer adjacent motif) in the target nucleic acid. In some embodiments, Cpf1 is FnCpf1 and the PAM sequence is 5'-YRN-3' or 5'-RYN-3', where Y is a pyrimidine such as A or G, R is a purine such as T, U or C, and N is any nucleotide. Preferably, R is T or C.

In one embodiment, the PAM consists of the sequence 5'-TTN-3'. In another embodiment, the PAM consists of the sequence 5'-CCN-3'. In another embodiment, the PAM consists of the sequence 5'-TAN-3'. In another embodiment, the PAM consists of the sequence 5'-TCN-3'. In another embodiment, the PAM consists of the sequence 5'-TGN-3'. In another embodiment, the PAM consists of the sequence 5'-CTN-3'. In another embodiment, the PAM consists of the sequence 5'-CAN-3'. In another embodiment, the PAM consists of the sequence 5'-CGN-3'. In another embodiment, the PAM consists of the sequence 5'-ATN-3'. In another embodiment, the PAM consists of the sequence 5'-AAN-3'. In another embodiment, the PAM consists of the sequence 5'-ACN-3'. In another embodiment, the PAM consists of the sequence 5'-AGN-3'. In another embodiment, the PAM consists of the sequence 5'-TTN-3'. In another embodiment, the PAM consists of the sequence 5'-TAN-3'. In another embodiment, the PAM consists of the sequence 5'-TCN-3'. In another embodiment, the PAM consists of the sequence 5'-TGN-3'.

The crRNA preferably does not hybridize to the PAM itself. The choice of the PAM sequence may be dictated by the organism from which the Cpf1 to be used to cleave the target nucleic acid is derived.

The second target nucleic acid may comprise or consist of a recognition sequence comprising a sequence of at least 15 consecutive nucleotides, such as at least 16 consecutive nucleotides, such as at least 17 consecutive nucleotides, such as at least 18 consecutive nucleotides, such as at least 19 consecutive nucleotides, such as at least 20 consecutive nucleotides, such as at least 21 consecutive nucleotides, such as at least 22 consecutive nucleotides, such as at least 23 consecutive nucleotides, such as at least 24 consecutive nucleotides, such as at least 25 consecutive nucleotides, such as at least 26 consecutive nucleotides, such as at least 27 consecutive nucleotides, with the proviso that the 3 nucleic acids at the 5'-end consist of a PAM sequence.

The second target nucleic acid sequence is DNA or RNA. The second target nucleic acid sequence may be DNA selected from the group consisting of genomic DNA, chromatin, nucleosomes, plasmid DNA, methylated DNA, synthetic DNA, and DNA fragments, for example PCR products.

In some embodiments, the second target nucleic acid is RNA.

In some embodiments, the second target nucleic acid is preferably DNA.

The second target nucleic acid may be any nucleic acid which it may be desirable to cleave specifically. The second target nucleic acid may be purified prior to contacting it with the crRNA-Cpf1 complex, by methods known in the art.

In some embodiments, the second target nucleic acid may be in recognized and hybridized in vivo.

Use of a crRNA-Cpf1 endonuclease complex for introducing a single strand break One aspect of the present disclosure relates to use of a crRNA-Cpf1 complex for introducing a single strand break in a first target nucleic acid, wherein:
  a. a Cpf1 endonuclease or orthologue thereof is contacted with a guide RNA (crRNA), thereby obtaining a crRNA-Cpf1 complex capable of recognising a second target nucleic acid, the second target nucleic acid comprising a protospacer adjacent motif (PAM), and
  b. the crRNA-Cpf1 complex is contacted with the first target nucleic acid; whereby a single strand break is made in the first target sequence.

The crRNA-Cpf1 complex comprises a mutant Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to:
  i) the sequence corresponding to residues 1 to 297, 310 to 323, 337 to 1005, and 1019 to 1329 of SEQ ID NO: 2, wherein said polypeptide sequence further comprises at least one amino acid substitution or deletion in the finger domain (residues 298 to 309; SEQ ID NO: 12), the REC domain (residues 324 to 336; SEQ ID NO: 16) or the Lid domain (residues 1006 to 1018; SEQ ID NO: 20) compared to SEQ ID NO: 2; and/or
  ii) SEQ ID NO: 2, wherein said polypeptide sequence comprises at least one amino acid substitution in position 918, 1013, 1014, 1025 or 1028 of SEQ ID NO: 2.

The crRNA-Cpf1 complex comprises a mutant Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to:
  i) the sequence corresponding to residues 1 to 323, 337 to 1005, and 1019 to 1329 of SEQ ID NO: 2, wherein said polypeptide sequence further comprises:
    a. at least one amino acid mutation in the REC domain (residues 324 to 336; SEQ ID NO: 16) compared to SEQ ID NO: 2, wherein each mutation independently is an amino acid substitution or deletion; and/or
    b. at least two amino acid substitutions the Lid domain (residues 1006 to 1018; SEQ ID NO: 20) compared to SEQ ID NO: 2, wherein at least one of the residues at positions 917 and 1006 is a glutamic acid (E) or an aspartic acid (D);
and/or
  ii) SEQ ID NO: 2, wherein said polypeptide sequence comprises at least one amino acid substitution in position 918, 1013, 1014, 1025 or 1028 of SEQ ID NO: 2.

The crRNA-Cpf1 complex in other embodiments comprises a mutant Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 2, wherein said polypeptide sequence comprises at least one amino acid substitution in position 918, 1013, or 1014 of SEQ ID NO: 2, said mutant Cpf1 is described in detail herein above in the section "Mutant Cpf1".

In one embodiment the crRNA hybridises to the second target nucleic acid and the Cpf1 introduces a single strand break in a specific recognition nucleotide sequence of the first target nucleic acid.

In one embodiment the crRNA hybridises to the second target nucleic acid and the Cpf1 introduces a single strand break in a specific recognition nucleotide sequence of the first target nucleic acid, wherein the first and the second target nucleic acid are identical or overlapping. For example, the first and the second target nucleic acid may both comprise the same recognition sequence and the same PAM.

In one embodiment the crRNA hybridises to the second target nucleic acid and the Cpf1 introduces a single strand break in a specific recognition nucleotide sequence of the first target nucleic acid, wherein the first and the second target nucleic acid are the same nucleic acid.

The characteristics of the crRNA are described herein above in the section "Guide RNA (crRNA)".

Thus, the first and the second target nucleic may be identical or different. In one embodiment the first and the second target nucleic are identical. For example, the first and the second target nucleic are the same target nucleic acid.

In one embodiment the crRNA hybridises to the second target nucleic acid and the Cpf1 introduces a single strand break into one or more nonspecific nucleotide sequences of the first target nucleic acid.

In one embodiment, the first and the second target nucleic are different and the first target nucleic acid does not comprise a PAM sequence and thus is not recognized by the crRNA-Cpf1 complex, whereas the second target nucleic acid comprises a PAM sequence and is recognized by the crRNA-Cpf1 complex.

The mutant Cpf1 comprised in the crRNA-Cpf1 complex useful for introducing a single-stranded break in a nucleic acid sequence may be any of the mutants described herein. However, some mutants may be particularly advantageous. For example, a mutant Cpf1 having a Q1025G substitution, a mutant Cpf1 deleted for the REC domain as set out in SEQ ID NO: 34, a mutant Cpf1 wherein the REC domain has been entirely substituted (SEQ ID NO: 36), a mutant Cpf1 mutant in which the Lid domain has been entirely substituted are all capable of such non-specific DNA cleavage of a single stranded DNA, and are particularly useful for cleaving a second target nucleic acid which is different from the first target nucleic acid. Mutant Cpf1 having mutations at positions 1013 and 1014, or at positions 918 and 1013, may also be of interest.

In one embodiment the present disclosure relates to the use of a crRNA-Cpf1 complex for introducing a single strand break in a specific recognition nucleotide sequence of the first target nucleic acid, wherein the first target nucleic acid and the second target nucleic acid are identical, and wherein the Cpf1 endonuclease or orthologue thereof comprises an amino acid substitution at position 1025 of SEQ ID NO: 2.

In another embodiment the present disclosure relates to the use of a crRNA-Cpf1 complex for introducing a single strand break in a specific recognition nucleotide sequence of the first target nucleic acid, wherein the first target nucleic acid and the second target nucleic acid are identical, and wherein the Cpf1 endonuclease or orthologue thereof comprises a deletion of one or more amino acid residues of the REC domain defined by residues 298 to 309 of SEQ ID NO: 2.

In another embodiment the present disclosure relates to the use of a crRNA-Cpf1 complex for introducing a single strand break in a specific recognition nucleotide sequence of the first target nucleic acid, wherein the first target nucleic acid and the second target nucleic acid are identical, and wherein the Cpf1 endonuclease or orthologue thereof comprises a deletion of one or more amino acid residues of the Lid domain defined by residues 324 to 336 of SEQ ID NO: 2.

In another embodiment the present disclosure relates to the use of a crRNA-Cpf1 complex for introducing a single strand break in a specific recognition nucleotide sequence of the first target nucleic acid, wherein the first target nucleic acid and the second target nucleic acid are identical, and wherein the Cpf1 endonuclease or orthologue thereof comprises a mutation of two or more amino acid residues of the REC domain defined by residues 324 to 336 of SEQ ID NO: 2, wherein each mutation independently is an amino acid substitution or deletion.

In another embodiment the present disclosure relates to the use of a crRNA-Cpf1 complex for introducing a single strand break in a specific recognition nucleotide sequence of the first target nucleic acid, wherein the first target nucleic acid and the second target nucleic acid are identical, and wherein the Cpf1 endonuclease or orthologue thereof comprises a deletion of one or more amino acid residues of the Lid domain defined by residues 1006 to 1018 of SEQ ID NO: 2.

In another embodiment the present disclosure relates to the use of a crRNA-Cpf1 complex for introducing a single strand break in a specific recognition nucleotide sequence of the first target nucleic acid, wherein the first target nucleic acid and the second target nucleic acid are identical, and wherein the Cpf1 endonuclease or orthologue thereof comprises a substitution of two or more amino acid residues of the Lid domain defined by residues 1006 to 1018 of SEQ ID NO: 2.

In another embodiment the present disclosure relates to the use of a crRNA-Cpf1 complex for introducing a single strand break in a specific recognition nucleotide sequence of the first target nucleic acid, wherein the first target nucleic acid and the second target nucleic acid are identical, and wherein the Cpf1 endonuclease or orthologue thereof comprises an amino acid substitution at one or more of positions 918, 1013, 1014, 1025 and 1028 of SEQ ID NO: 2.

In one embodiment the present disclosure relates to use of a crRNA-Cpf1 complex for introducing a single strand break in a specific recognition nucleotide sequence of the first target nucleic acid, wherein the first target nucleic acid and the second target nucleic acid are identical, and wherein the Cpf1 endonuclease or orthologue thereof comprises amino acid substitutions at position 1013 and 1014 of SEQ ID NO: 2.

The substitution may in some embodiments be a substitution of an amino acid having a charged side chain to an amino acid having an uncharged side chain or a non-polar side chain. In some embodiments, the amino acid is substituted to an amino acid selected from the group consisting of glycine, alanine, valine, leucine, isoleucine, serine or threonine. In some embodiments, the amino acid is substituted to a glycine.

The deletion may in some embodiments be a deletion of one, more than one, or all the amino acid residues of the REC domain, the Lid domain or the finger domain. In some embodiments, some amino acids are substituted, while others are deleted. In some embodiments, the Cpf1 mutant comprises amino acid deletions and/or substitutions in more than one domain, e.g. in the REC domain and the Lid domain, in the REC domain and the finger domain, in the Lid domain and the finger domain, or in the REC domain, the Lid domain and the finger domain. The Cpf1 mutant may further comprise amino acid substitutions or deletions at one or more of positions 918, 1013, 1014, 1025 or 1028.

For example the crRNA-Cpf1 complex is used for introducing a single strand break in a specific recognition nucleotide sequence of the first target nucleic acid, wherein the first target nucleic acid and the second target nucleic acid are the same nucleic acid, and wherein the Cpf1 endonuclease or orthologue thereof comprises amino acid substitutions at position 1013 and 1014 of SEQ ID NO: 2.

In one embodiment the present disclosure relates to use of a crRNA-Cpf1 complex for introducing a single strand break in a specific recognition nucleotide sequence of the first target nucleic acid, wherein the first target nucleic acid and the second target nucleic acid are identical, and wherein the Cpf1 endonuclease or orthologue thereof comprises substitutions of an amino acid having a charged side chain to an amino acid having an uncharged side chain at position 1013 and 1014 of SEQ ID NO: 2.

In one embodiment the present disclosure relates to use of a crRNA-Cpf1 complex for introducing a single strand break in a specific recognition nucleotide sequence of the first target nucleic acid, wherein the first target nucleic acid and the second target nucleic acid are the same nucleic acid, and wherein the Cpf1 endonuclease or orthologue thereof comprises substitutions of an amino acid having a charged side chain to an amino acid having an uncharged side chain at position 1013 and 1014 of SEQ ID NO: 2.

In one embodiment the present disclosure relates to use of a crRNA-Cpf1 complex for introducing a single strand break in a specific recognition nucleotide sequence of the first target nucleic acid, wherein the first target nucleic acid and the second target nucleic acid are identical, and wherein the Cpf1 endonuclease or orthologue thereof comprises substitutions of an amino acid having a charged side chain to an amino acid having a non-polar side chain at position 1013 and 1014 of SEQ ID NO: 2.

In one embodiment the present disclosure relates to use of a crRNA-Cpf1 complex for introducing a single strand break in a specific recognition nucleotide sequence of the first target nucleic acid, wherein the first target nucleic acid and the second target nucleic acid are the same nucleic acid, and wherein the Cpf1 endonuclease or orthologue thereof comprises substitutions of an amino acid having a charged side chain to an amino acid having a non-polar side chain at position 1013 and 1014 of SEQ ID NO: 2.

In one embodiment the present disclosure relates to use of a crRNA-Cpf1 complex for introducing a single strand break in a specific recognition nucleotide sequence of the first target nucleic acid, wherein the first target nucleic acid and the second target nucleic acid are identical, and wherein the Cpf1 endonuclease or orthologue thereof comprises substitutions of an amino acid having a charged side chain to chain to a glycine, alanine, valine, leucine, isoleucine, serine or threonine in at position 1013 and 1014 of SEQ ID NO: 2.

In one embodiment the present disclosure relates to use of a crRNA-Cpf1 complex for introducing a single strand break in a specific recognition nucleotide sequence of the first target nucleic acid, wherein the first target nucleic acid and the second target nucleic acid are the same nucleic acid, and wherein the Cpf1 endonuclease or orthologue thereof comprises substitutions of an amino acid having a charged side chain to chain to a glycine, alanine, valine, leucine, isoleucine, serine or threonine at position 1013 and 1014 of SEQ ID NO: 2.

In one embodiment the present disclosure relates to use of a crRNA-Cpf1 complex for introducing a single strand break in a specific recognition nucleotide sequence of the first target nucleic acid, wherein the first target nucleic acid and the second target nucleic acid are identical, and wherein the Cpf1 endonuclease or orthologue thereof comprises substitutions of an amino acid having a charged side chain to chain to a glycine at position 1013 and 1014 of SEQ ID NO: 2.

In one embodiment the present disclosure relates to use of a crRNA-Cpf1 complex for introducing a single strand break in a specific recognition nucleotide sequence of the first target nucleic acid, wherein the first target nucleic acid and the second target nucleic acid are the same nucleic acid, and wherein the Cpf1 endonuclease or orthologue thereof comprises substitutions of an amino acid having a charged side chain to chain to a glycine at position 1013 and 1014 of SEQ ID NO: 2.

In one embodiment the present disclosure relates to use of a crRNA-Cpf1 complex for introducing a single strand break in a specific recognition nucleotide sequence of the first target nucleic acid, wherein the first target nucleic acid and the second target nucleic acid are identical, and wherein the Cpf1 endonuclease or orthologue thereof comprises substitutions of an amino acid having a charged side chain to chain to a glycine at position 1013 and 1014 of SEQ ID NO: 2.

In one embodiment the present disclosure relates to use of a crRNA-Cpf1 complex for introducing a single strand break in a specific recognition nucleotide sequence of the first target nucleic acid, wherein the first target nucleic acid and the second target nucleic acid are the same nucleic acid, and wherein the Cpf1 endonuclease or orthologue thereof comprises the substitutions K1013G and R1014G of SEQ ID NO: 2.

In one embodiment the present disclosure relates to use of a crRNA-Cpf1 complex for introducing a single strand break in a specific recognition nucleotide sequence of the first target nucleic acid, wherein the first target nucleic acid and the second target nucleic acid are identical, and wherein the Cpf1 endonuclease or orthologue thereof comprises or consists of a polypeptide having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity, such as 100% sequence identity to SEQ ID NO: 3.

In one embodiment the present disclosure relates to use of a crRNA-Cpf1 complex for introducing a single strand break in a specific recognition nucleotide sequence of the first target nucleic acid, wherein the first target nucleic acid and the second target nucleic acid are the same nucleic acid, and wherein the Cpf1 endonuclease or orthologue thereof comprises or consists of a polypeptide having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity, such as 100% sequence identity to SEQ ID NO: 3.

In one embodiment the present disclosure relates to use of a crRNA-Cpf1 complex for introducing a single strand break in a specific recognition nucleotide sequence of the first target nucleic acid, wherein the first target nucleic acid and the second target nucleic acid are identical, and wherein the Cpf1 endonuclease or orthologue thereof comprises or consists of SEQ ID NO: 3.

In one embodiment the present disclosure relates to use of a crRNA-Cpf1 complex for introducing a single strand break in a specific recognition nucleotide sequence of the first target nucleic acid, wherein the first target nucleic acid and the second target nucleic acid are the same nucleic acid, and wherein the Cpf1 endonuclease or orthologue thereof comprises or consists of SEQ ID NO: 3.

Some of the mutant Cpf1 endonucleases described herein are capable of introducing single strand breaks in a target nucleic acid, referred herein as the first target nucleic acid, which differs from the nucleic acid sequence recognized and hybridized by the crRNA, referred herein as the second target nucleic acid.

In some embodiments, the present disclosure relates to the use of a crRNA-Cpf1 complex for introducing a single strand break at one or more nonspecific nucleotide sequences of the first target nucleic acid, wherein the first target nucleic acid and the second target nucleic acid are different, and wherein the Cpf1 endonuclease or orthologue thereof has a mutation at position 1025 of SEQ ID NO: 2. In a particular embodiment, the mutation is a Q1025G mutation.

In other embodiments, the present disclosure relates to the use of a crRNA-Cpf1 complex for introducing a single strand break at one or more nonspecific nucleotide sequences of the first target nucleic acid, wherein the first target nucleic acid and the second target nucleic acid are different, and wherein the Cpf1 endonuclease or orthologue thereof has at least one amino acid substitution or deletion of the REC domain corresponding to residues 324 to 336 of SEQ ID NO: 2. For example, the mutant Cpf1 has a complete deletion of the REC domain, and has the sequence as set out in SEQ ID NO: 34. In a specific embodiment, the entire REC domain has been substituted and the mutant Cpf1 has for example the sequence set out in SEQ ID NO: 36.

In other embodiments, the present disclosure relates to the use of a crRNA-Cpf1 complex for introducing a single strand break at one or more nonspecific nucleotide sequences of the first target nucleic acid, wherein the first target nucleic acid and the second target nucleic acid are different, and wherein the Cpf1 endonuclease or orthologue thereof has at least one amino acid substitution or deletion of the Lid domain corresponding to residues 324 to 336 of SEQ ID NO: 2. For example, the entire Lid domain has been substituted and the mutant Cpf1 has the sequence set out in SEQ ID NO: 42.

In other embodiments, the present disclosure relates to the use of a crRNA-Cpf1 complex for introducing a single strand break at one or more nonspecific nucleotide sequences of the first target nucleic acid, wherein the first target nucleic acid and the second target nucleic acid are different, and wherein the Cpf1 endonuclease or orthologue thereof has at least one amino acid substitution or deletion of the Lid domain corresponding to residues 1006 to 1018 of SEQ ID NO: 2. For example, the entire Lid domain has been substituted and the mutant Cpf1 has the sequence set out in SEQ ID NO: 38.

In some embodiments, the crRNA-Cpf1 complex comprises amino acid substitutions or deletions in more than one of the REC, Lid or finger domain, for example in the REC domain and in the Lid domain; in the REC domain and in the finger domain; in the Lid domain and in the finger domain; or in the REC domain, the finger domain and the Lid domain. The mutant Cpf1 may further comprise amino acid substitutions or deletions at one or more of positions 918, 1013, 1014, 1025 or 1028 of SEQ ID NO: 2.

In one embodiment the present disclosure relates to use of a crRNA-Cpf1 complex for introducing a single strand break at one or more nonspecific nucleotide sequences of the first target nucleic acid, wherein the first target nucleic acid and the second target nucleic acid are different, and wherein the Cpf1 endonuclease or orthologue thereof comprises substitutions of an amino acid having a charged side chain to an amino acid having an uncharged side chain at position 918 and 1013 of SEQ ID NO: 2.

In one embodiment the present disclosure relates to use of a crRNA-Cpf1 complex for introducing a single strand break at one or more nonspecific nucleotide sequences of the first target nucleic acid, wherein the first target nucleic acid and the second target nucleic acid are the same nucleic acid, and wherein the Cpf1 endonuclease or orthologue thereof comprises substitutions of an amino acid having a charged side chain to an amino acid having an uncharged side chain at position 918 and 1013 of SEQ ID NO: 2.

In one embodiment the present disclosure relates to use of a crRNA-Cpf1 complex for introducing a single strand break at one or more nonspecific nucleotide sequences of the first target nucleic acid, wherein the first target nucleic acid and the second target nucleic acid are identical, and wherein the Cpf1 endonuclease or orthologue thereof comprises substitutions of an amino acid having a charged side chain to an amino acid having a non-polar side chain at position 918 and 1013 of SEQ ID NO: 2.

In one embodiment the present disclosure relates to use of a crRNA-Cpf1 complex for introducing a single strand break at one or more nonspecific nucleotide sequences of the first target nucleic acid, wherein the first target nucleic acid and the second target nucleic acid are the same nucleic acid, and wherein the Cpf1 endonuclease or orthologue thereof comprises substitutions of an amino acid having a charged side chain to an amino acid having a non-polar side chain at position 918 and 1013 of SEQ ID NO: 2.

In one embodiment the present disclosure relates to use of a crRNA-Cpf1 complex for introducing a single strand break at one or more nonspecific nucleotide sequences of the first target nucleic acid, wherein the first target nucleic acid and the second target nucleic acid are identical, and wherein the Cpf1 endonuclease or orthologue thereof comprises substitutions of an amino acid having a charged side chain to chain to a glycine, alanine, valine, leucine, isoleucine, serine or threonine in at position 918 and 1013 of SEQ ID NO: 2.

In one embodiment the present disclosure relates to use of a crRNA-Cpf1 complex for introducing a single strand break at one or more nonspecific nucleotide sequences of the first target nucleic acid, wherein the first target nucleic acid and the second target nucleic acid are the same nucleic acid, and wherein the Cpf1 endonuclease or orthologue thereof comprises substitutions of an amino acid having a charged side chain to chain to a glycine, alanine, valine, leucine, isoleucine, serine or threonine at position 918 and 1013 of SEQ ID NO: 2.

In one embodiment the present disclosure relates to use of a crRNA-Cpf1 complex for introducing a single strand break at one or more nonspecific nucleotide sequences of the first target nucleic acid, wherein the first target nucleic acid and the second target nucleic acid are identical, and wherein the Cpf1 endonuclease or orthologue thereof comprises substitutions of an amino acid having a charged side chain to chain to a glycine at position 918 and 1013 of SEQ ID NO: 2.

In one embodiment the present disclosure relates to use of a crRNA-Cpf1 complex for introducing a single strand break at one or more nonspecific nucleotide sequences of the first target nucleic acid, wherein the first target nucleic acid and the second target nucleic acid are the same nucleic acid, and wherein the Cpf1 endonuclease or orthologue thereof comprises substitutions of an amino acid having a charged side chain to chain to a glycine at position 918 and 1013 of SEQ ID NO: 2.

In one embodiment the present disclosure relates to use of a crRNA-Cpf1 complex for introducing a single strand break at one or more nonspecific nucleotide sequences of the first target nucleic acid, wherein the first target nucleic acid and the second target nucleic acid are identical, and wherein the Cpf1 endonuclease or orthologue thereof comprises substitutions of an amino acid having a charged side chain to chain to a glycine at position 918 and 1013 of SEQ ID NO: 2.

In one embodiment the present disclosure relates to use of a crRNA-Cpf1 complex for introducing a single strand break at one or more nonspecific nucleotide sequences of the first target nucleic acid, wherein the first target nucleic acid and the second target nucleic acid are the same nucleic acid, and wherein the Cpf1 endonuclease or orthologue thereof comprises the substitutions R918G and K1013G of SEQ ID NO: 2.

In one embodiment the present disclosure relates to use of a crRNA-Cpf1 complex for introducing a single strand break at one or more nonspecific nucleotide sequences of the first target nucleic acid, wherein the first target nucleic acid and the second target nucleic acid are identical, and wherein the Cpf1 endonuclease or orthologue thereof comprises or consists of a polypeptide having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity, such as about 100% sequence identity to SEQ ID NO: 4.

In one embodiment the present disclosure relates to use of a crRNA-Cpf1 complex for introducing a single strand break at one or more nonspecific nucleotide sequences of the first target nucleic acid, wherein the first target nucleic acid and the second target nucleic acid are the same nucleic acid, and wherein the Cpf1 endonuclease or orthologue thereof comprises or consists of a polypeptide having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity, such as about 100% sequence identity to SEQ ID NO: 4.

In one embodiment the present disclosure relates to use of a crRNA-Cpf1 complex for introducing a single strand break at one or more nonspecific nucleotide sequences of the first target nucleic acid, wherein the first target nucleic acid and the second target nucleic acid are identical, and wherein the Cpf1 endonuclease or orthologue thereof comprises or consists of SEQ ID NO: 4.

In one embodiment the present disclosure relates to use of a crRNA-Cpf1 complex for introducing a single strand break at one or more nonspecific nucleotide sequences of the first target nucleic acid, wherein the first target nucleic acid and the second target nucleic acid are the same nucleic acid, and wherein the Cpf1 endonuclease or orthologue thereof comprises or consists of SEQ ID NO: 4.

The mutants may further comprise additional mutations or deletions as described herein above in the section "Mutant Cpf1".

The crRNA-Cpf1 complex may be used for introducing single strand breaks in a first target nucleic acid in an ex-vivo method. The crRNA-Cpf1 complex may also be used for introducing single strand breaks in a first target nucleic acid in an in-vivo method.

In some embodiments, the efficiency of the introduction of single-strand breaks as described above is enhanced by the presence of activator DNA. The activator DNA may be single-stranded or double-stranded. In some embodiments, the activator DNA is the target DNA, corresponding to the second target nucleic acid.

Use of a crRNA-Cpf1 Endonuclease Complex for Genome Editing

Some of the mutant Cpf1 endonucleases of the present disclosure are capable of introducing single strand breaks only in the target sequence, which is hybridized by the crRNA of the crRNA-Cpf1 complex. Thus, in some embodiments when the crRNA of a crRNA-Cpf1 complex recognizes and hybridizes to a second target sequence, the DNAse activity of the Cpf1 of said complex will be activated and it will introduce single strand breaks specifically at specific sites of the second target nucleic acid sequence. Moreover, unspecific nucleic acid sequences will not be cleaved by the mutant Cpf1. This constitutes a great advantage over wild type Cpf1, which instead has non-specific ssDNA activity. In fact, single strand non-specific DNA cleavage is a dangerous activity for the cells since it targets the DNA that opens during normal cellular activity such as replication and transcription. The major outcome of this non-specific ssDNA activity is the production of random breaks that can results in unwanted mutagenesis and even cellular death.

The mutant Cpf1 endonucleases of the present disclosure may advantageously be used for genome editing in a safer manner compared to wild type Cpf1.

Hence, one aspect of the present disclosure relates to an in vitro method of introducing a site-specific, double-stranded break at a second target DNA sequence in a mammalian cell, the method comprising introducing into the mammalian cell a crRNA-Cpf1 complex, wherein the Cpf1 is a mutant Cpf1 endonuclease or orthologue thereof as described herein, and wherein the crRNA is specific for the second target nucleic acid.

In some embodiments, the mammalian cell is not a reproductive cell or an embryonic cell.

In some embodiments, the mutant Cpf1 endonuclease disclosed herein and used in an in vitro method of introducing a site-specific, double-stranded break at a second target DNA sequence in a mammalian cell, may be a Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 2, wherein said polypeptide sequence comprises at least two amino acid substitutions in position 1025 and 1028 of SEQ ID NO: 2.

In some embodiments, the mutant Cpf1 endonuclease disclosed herein and used in an in vitro method of introducing a site-specific, double-stranded break at a second target DNA sequence in a mammalian cell, may be a Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 2, wherein said polypeptide sequence comprises at least two amino acid substitutions of an amino acid having a charged side chain to an amino acid having an uncharged side chain in position 1025 and 1028 of SEQ ID NO: 2.

In some embodiments, the mutant Cpf1 endonuclease disclosed herein and used in an in vitro method of introducing a site-specific, double-stranded break at a second target DNA sequence in a mammalian cell, may be a Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 2, wherein said polypeptide sequence comprises at least two amino acid substitutions of an amino acid having a charged side chain to an amino acid having a non-polar side chain in position 1025 and 1028 of SEQ ID NO: 2.

In some embodiments, the mutant Cpf1 endonuclease disclosed herein and used in an in vitro method of introducing a site-specific, double-stranded break at a second target DNA sequence in a mammalian cell, may be a Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 2, wherein said polypeptide sequence comprises at least two amino acid substitutions of an amino acid having a charged side chain to a glycine, alanine, valine, leucine, isoleucine, serine or threonine in position 1025 and 1028 of SEQ ID NO: 2.

In some embodiments, the mutant Cpf1 endonuclease disclosed herein and used in an in vitro method of introducing a site-specific, double-stranded break at a second target DNA sequence in a mammalian cell, may be a Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 2, wherein said polypeptide sequence comprises at least two amino acid substitutions of an amino acid having a charged side chain to a glycine in position 1025 and 1028 of SEQ ID NO: 2.

For example mutant Cpf1 endonuclease used in the in vitro method of introducing a site-specific, double-stranded break at a second target DNA sequence in a mammalian cell, is a Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 2, wherein said polypeptide sequence comprises the amino acid substitutions Q1025G and E1028G.

For example mutant Cpf1 endonuclease used in the in vitro method of introducing a site-specific, double-stranded break at a second target DNA sequence in a mammalian cell, is a Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 32.

The mutants may further comprise additional mutations or deletions as described herein above in the section "Mutant Cpf1".

For example, mutant Cpf1 endonuclease used in the in vitro method of introducing a site-specific, double-stranded break at a second target DNA sequence in a mammalian cell, may be a Cpf1 endonuclease or orthologue thereof comprising at least two amino acid substitutions in the Lid domain as defined herein and one or more amino acid substitutions in any one of positions 918, 1013, 1014, 1025 or 1028 of SEQ ID NO: 2.

For example, mutant Cpf1 endonuclease used in the in vitro method of introducing a site-specific, double-stranded break at a second target DNA sequence in a mammalian cell, may be a Cpf1 endonuclease or orthologue thereof comprising at least two amino acid mutations in the REC domain as defined herein, wherein each mutation independently is an amino acid substitution or deletion, and one or more amino acid substitutions in any one of positions 918, 1013, 1014, 1025 or 1028 of SEQ ID NO: 2.

For example, mutant Cpf1 endonuclease used in the in vitro method of introducing a site-specific, double-stranded break at a second target DNA sequence in a mammalian cell, may be a Cpf1 endonuclease or orthologue thereof comprising at least two amino acid substitutions in the REC domain as defined herein and one or more amino acid substitutions in any one of positions 918, 1013, 1014, 1025 or 1028 of SEQ ID NO: 2.

For example, mutant Cpf1 endonuclease used in the in vitro method of introducing a site-specific, double-stranded break at a second target DNA sequence in a mammalian cell, may be a Cpf1 endonuclease or orthologue thereof comprising at least two amino acid deletions in the REC domain as defined herein and one or more amino acid substitutions in any one of positions 918, 1013, 1014, 1025 or 1028 of SEQ ID NO: 2.

Use of a crRNA-Cpf1 Endonuclease Complex for Detection and/or Quantification of a Target DNA Sequence Some of the mutant Cpf1 endonucleases of the present disclosure are capable of introducing single strand breaks only in a first target sequence, which is not hybridized by the crRNA of the crRNA-Cpf1 complex. Thus, in some embodiments when the crRNA of a crRNA-Cpf1 complex recognizes and hybridizes to a second target sequence, the DNAse activity of the Cpf1 of said complex will be activated and it will introduce single strand breaks unspecifically at random sites of a nucleic acid sequence, for example at random sites of the first target sequence. Moreover, the second target nucleic acid will not be cleaved by the Cpf1, which will therefore stay in an active state for a longer period of time and cleave more than one first target sequences. Provided that the first target sequence is labelled in a way that a signal will be released upon cleavage of said first target sequence, the described method will thus allow detection of the second target sequence.

These mutant Cpf1 endonucleases, when in a crRNA-Cpf1 complex, can be used to detect and quantify a second target sequence, with the help of a provided labelled first target sequence.

Hence, one aspect of the present disclosure relates to a method for detection of a second target nucleic acid in a sample, the method comprising:

a. Providing a crRNA-Cpf1 complex, wherein the Cpf1 is a Cpf1 endonuclease or orthologue thereof as described herein, and wherein the crRNA is specific for the second target nucleic acid;

b. Providing a labelled ssDNA, wherein the ssDNA is labelled with at least one set of interactive labels comprising at least one dye and at least one quencher;

c. Contacting the crRNA-Cpf1 complex and the ssDNA with the sample, wherein the sample comprises at least one second target nucleic acid; and d. Detecting cleavage of the ssDNA, by detecting a signal from the dye thereby detecting the presence of the second target nucleic acid in the sample.

In step c. the crRNA-Cpf1 complex and the ssDNA are contacted with at least one second target nucleic acid, and the recognition and binding of the crRNA with the second target nucleic acid results in activation of the crRNA-Cpf1 complex, which is then capable of introducing single strand breaks, such as cleaving, the ssDNA.

Hence, step c. may comprise activation of the crRNA-Cpf1 complex.

The method may further comprise the step of determining the level and/or concentration of the second target nucleic acid, wherein the level and/or concentration of the second target nucleic acid is correlated to the cleaved ssDNA.

As explained above, in some embodiments the mutant Cpf1 endonuclease disclosed herein will not cleave the second target nucleic acid and thus will stay active for a period of time sufficient for cleaving two or more first target nucleic acids, which in the method described herein may be the ssDNA or a fragment thereof. The more first target nucleic acid molecules are cleaved by the ccRNA-Cpf1 complex after hybridization of the ccRNA-Cpf1 complex to a second target nucleic acid, the higher the signal and thus the higher the sensitivity of the method. This is an advantage of the disclosed mutant Cpf1 over other Cpf1 endonucleases.

Hence, the method disclosed herein has high sensitivity and may allow detection of the second target nucleic acid at concentrations in the nanomolar range and below, such as at concentrations in the picomolar range and below, such as at concentrations in the femtomolar range or below. For example, the method disclosed herein allows detection of a second target nucleic acid at concentrations in the attomolar range.

In some embodiments, the mutant Cpf1 endonuclease disclosed herein will cleave the second target nucleic acid and thus will stay active only until the cleaved second target nucleic acid is released.

The ssDNA may be labelled in at least one base in any position along the chain. For example, the ssDNA is labelled in one base in any position along the chain, such as in at least two bases in any position along the chain, such as in at least three bases in any position along the chain, such as in at least four bases in any position along the chain.

The ssDNA may be labelled with at least one set of interactive labels comprising at least one dye and at least one quencher.

In one embodiment, the at least one dye is a fluorophore.

Thus, the cleavage of the ssDNA in step d. of the method comprises detecting a fluorescent signal resulting from cleavage of the ssDNA.

In one embodiment the at least one fluorophore is selected from the group comprising black hole quencher (BHQ) 1, BHQ2, and BHQ3, Cosmic Quencher (e.g. from Biosearch Technologies, Novato, USA), Excellent Bioneer Quencher (EBQ) (e.g. from Bioneer, Daejeon, Korea) or a combination hereof.

In one embodiment the at least one quencher is selected from the group comprising black hole quencher (BHQ) 1, BHQ2, and BHQ3 (from Biosearch Technologies, Novato, USA).

A fluorophore which may be useful in the present invention may include any fluorescent molecule known in the art. Examples of fluorophores are: Cy2™ Cfllfi), YO-PRn™-1 (509), YDYO™-1 (509), Calrein (517), FITC (518), FluorX™ (519), Alexa™ (520), Rhodamine 110 (520), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-I (533), TOTOI (533), JOE (548), 30 BODIPY530/550 (550), DiI (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 35 (615), Texas Red (615), Nile Red (628), YO-PRO™-3 (631), YOYO™-3 (631), RP3649PC00 phycocyanin (642), C-Phycocyanin (648), TO-PRO™-3 (660), TOT03 (660), DID DiIC(5) (665), Cy5™ (670), Thiadicarbocyanine (671), Cy5.5 (694), HEX (556), TET (536), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), 6-Carboxyfluorescein (6-FAM), Fluorescein (520), Fluorescein-C3 (520), Pulsar 650 (566), Quasar 570 (667), Quasar 670 (705) and Quasar 705 (610). The number in parenthesis is a maximum emission wavelength in nanometers.

It is noteworthy that a non-fluorescent black quencher molecule capable of quenching a fluorescence of a wide range of wavelengths or a specific wavelength may be used in the present invention.

Suitable pairs of fluorophores/quenchers are known in the art.

The method may be used to detect presence and levels of any nucleic acid and thus the sample may be any sample comprising nucleic acid and appropriately treated, for example to eliminate proteases. The sample may comprise DNA and/or RNA. The sample may be a sample suspected of comprising the second target nucleic acid. The sample may be culture extract of any prokaryotic or eukaryotic cell culture, body fluid of a mammal, such as of a human.

The second target nucleic acid may be a nucleic acid fragment of a viral genome, a microbial genome, a gene, such as an oncogene, or a genome of a pathogen.

The second target nucleic acid may also be a mutated nucleic acid sequence, for example a single nucleotide polymorphism (SNP).

The mutant Cpf1 endonuclease used in the method for detection of a second target nucleic acid in a sample may be any of the mutants described herein above, in particular in the section "Mutant Cpf1".

The mutant Cpf1 endonuclease used in the method for detection of a second target nucleic acid in a sample may be a Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 2, wherein said polypeptide sequence comprises at least two amino acid substitutions in position 918 and 1013 of SEQ ID NO: 2.

For example mutant Cpf1 endonuclease used in the method for detection of a second target nucleic acid in a sample is a Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 2, wherein said polypeptide sequence comprises at least two amino acid substitutions of an amino acid having a charged side chain to an amino acid having an uncharged side chain in position 918 and 1013 of SEQ ID NO: 2.

For example mutant Cpf1 endonuclease used in the method for detection of a second target nucleic acid in a sample is a Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 2, wherein said polypeptide sequence comprises at least two amino acid substitutions of an amino acid having a charged side chain to an amino acid having a non-polar side chain in position 918 and 1013 of SEQ ID NO: 2.

For example mutant Cpf1 endonuclease used in the method for detection of a second target nucleic acid in a sample is a Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 2, wherein said polypeptide sequence comprises at least two amino acid substitutions of an amino acid having a charged side chain to a glycine, alanine, valine, leucine, isoleucine, serine or threonine in position 918 and 1013 of SEQ ID NO: 2.

For example mutant Cpf1 endonuclease used in the method for detection of a second target nucleic acid in a sample is a Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 2, wherein said polypeptide sequence comprises at least two amino acid substitutions of an amino acid having a charged side chain to a glycine in position 918 and 1013 of SEQ ID NO: 2.

For example mutant Cpf1 endonuclease used in the method for detection of a second target nucleic acid in a sample is a Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 2, wherein said polypeptide sequence comprises the amino acid substitutions R918G and K1013G.

For example mutant Cpf1 endonuclease used in the method for detection of a second target nucleic acid in a sample is a Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity, such as about 100% sequence identity to SEQ ID NO: 4.

For example mutant Cpf1 endonuclease used in the method for detection of a second target nucleic acid in a sample is a Cpf1 endonuclease or orthologue thereof comprises or consists of SEQ ID NO: 4.

The mutant Cpf1 endonuclease used in the method for detection of a second target nucleic acid in a sample may also comprise other amino acid modifications.

Use of a crRNA-Cpf1 Endonuclease Complex for Diagnosis of a Disease

The present disclosure also relates to methods for diagnosis of any disease which is associated with increased/reduced gene expression and/or with the presence of exogenous genetic material.

One aspect of the present disclosure relates to an in vitro method for diagnosis of a disease in a subject, the method comprising:

a. Providing a crRNA-Cpf1 complex, wherein the Cpf1 is a mutant Cpf1 endonuclease or orthologue thereof as defined herein, and wherein the crRNA is specific for a second target nucleic acid;

b. Providing a labelled ssDNA, wherein the ssDNA is labelled with at least one set of interactive labels comprising at least one fluorophore and at least one quencher;

c. Providing a sample from the subject wherein said sample comprises or is suspected of comprising the second target nucleic acid; and d. Determining the level and/or concentration of the second target nucleic acid according to the method of detection described herein, wherein the second target nucleic acid is a nucleic acid fragment that correlates with the disease, thereby diagnosing a disease in a subject.

The method for diagnosis of a disease in a subject may further comprise the step treating said disease. For example, the method may further comprise treating said disease by administering a therapeutically effective agent.

The mutant Cpf1 endonuclease used in the method for detection of a second target nucleic acid in a sample may be any of the mutants described herein above, in particular in the section "Mutant Cpf1".

Use of a crRNA-Cpf1 Endonuclease Complex for Diagnosis of an Infectious Disease

One aspect of the present disclosure relates to an in vitro method for diagnosis of an infectious disease in a subject, the method comprising:

a. Providing a crRNA-Cpf1 complex, wherein the Cpf1 is a mutant Cpf1 endonuclease or orthologue thereof as defined herein, and wherein the crRNA is specific for a second target nucleic acid;

b. Providing a labelled ssDNA, wherein the ssDNA is labelled with at least one set of interactive labels and wherein said interactive label gives a signal upon cleavage of the ssDNA;

c. Providing a sample from the subject, wherein said sample comprises or is suspected of comprising the second target nucleic acid; and d. Determining the level and/or concentration of the second target nucleic acid according to the method of detection described herein, wherein the second target nucleic acid is a nucleic acid fragment of the genome of an infectious agent causing the disease, thereby diagnosing an infectious disease in a subject.

One aspect of the present disclosure relates to an in vitro method for diagnosis of an infectious disease in a subject, the method comprising:

a. Providing a crRNA-Cpf1 complex, wherein the Cpf1 is a mutant Cpf1 endonuclease or orthologue thereof as defined herein, and wherein the crRNA is specific for a second target nucleic acid;

b. Providing a labelled ssDNA, wherein the ssDNA is labelled with at least one set of interactive labels comprising at least one fluorophore and at least one quencher;

c. Providing a sample from the subject, wherein said sample comprises or is suspected of comprising the second target nucleic acid; and d. Determining the level and/or concentration of the second target nucleic acid according to the method of detection described herein, wherein the second target nucleic acid is a nucleic acid fragment of the genome of an infectious agent causing the disease, thereby diagnosing an infectious disease in a subject.

The interactive label may for example comprise a luminescent label.

The method for diagnosis of an infectious disease in a subject may further comprise the step treating said infectious disease. For example, the method may further comprise treating said infectious disease by administering a therapeutically effective agent.

The method for diagnosis of an infectious disease in a subject may further comprise the step of comparing the level and/or concentration of said second target nucleic acid with a cut-off value, wherein said cut-off value is determined from the concentration range of said second target nucleic acid in healthy subjects, such as subjects who do not present with the infectious disease, wherein a level and/or concentration that is greater than the cut-off value indicates the presence of the infectious disease.

An infectious disease is any disease caused by an infectious agent such as viruses, viroids, prions, bacteria, nematodes, parasitic roundworms, pinworms, arthropods, fungi, ringworm and macroparasites.

Thus, the second target nucleic acid may be a genome or fragment thereof of an infectious agent selected from the group consisting of viruses, viroids, prions, bacteria, nematodes, parasitic roundworms, pinworms, arthropods, fungi, ringworm and macroparasites.

The method disclosed herein may be used to diagnose an infection disease in a human.

Thus, the sample comprising the second target nucleic acid may by a sample taken from a human body. For example, the sample may be a human body fluid selected from the group consisting of blood, whole blood, plasma, serum, urine, saliva, tears, cerebrospinal fluid and semen.

The mutant Cpf1 endonuclease used in the method for detection of a second target nucleic acid in a sample may be any of the mutants described herein above, in particular in the section "Mutant Cpf1".

In one embodiment the present disclosure relates to the use of a crRNA-Cpf1 complex for introducing a single strand break in a specific recognition nucleotide sequence of the first target nucleic acid, wherein the first target nucleic acid and the second target nucleic acid are identical, and wherein the Cpf1 endonuclease or orthologue thereof comprises an amino acid substitution at position 1025 of SEQ ID NO: 2.

In another embodiment the present disclosure relates to the use of a crRNA-Cpf1 complex for introducing a single strand break in a specific recognition nucleotide sequence of the first target nucleic acid, wherein the first target nucleic acid and the second target nucleic acid are identical, and wherein the Cpf1 endonuclease or orthologue thereof comprises a deletion of one or more amino acid residues of the REC domain defined by residues 298 to 309 of SEQ ID NO: 2.

In another embodiment the present disclosure relates to the use of a crRNA-Cpf1 complex for introducing a single strand break in a specific recognition nucleotide sequence of the first target nucleic acid, wherein the first target nucleic acid and the second target nucleic acid are identical, and wherein the Cpf1 endonuclease or orthologue thereof comprises a deletion of one or more amino acid residues of the Lid domain defined by residues 324 to 336 of SEQ ID NO: 2.

In another embodiment the present disclosure relates to the use of a crRNA-Cpf1 complex for introducing a single strand break in a specific recognition nucleotide sequence of the first target nucleic acid, wherein the first target nucleic acid and the second target nucleic acid are identical, and wherein the Cpf1 endonuclease or orthologue thereof comprises a deletion of one or more amino acid residues of the Lid domain defined by residues 1006 to 1018 of SEQ ID NO: 2.

In another embodiment the present disclosure relates to the use of a crRNA-Cpf1 complex for introducing a single strand break in a specific recognition nucleotide sequence of the first target nucleic acid, wherein the first target nucleic acid and the second target nucleic acid are identical, and wherein the Cpf1 endonuclease or orthologue thereof comprises a substitution of two or more amino acid residues of the Lid domain defined by residues 1006 to 1018 of SEQ ID NO: 2.

In another embodiment the present disclosure relates to the use of a crRNA-Cpf1 complex for introducing a single strand break in a specific recognition nucleotide sequence of the first target nucleic acid, wherein the first target nucleic acid and the second target nucleic acid are identical, and wherein the Cpf1 endonuclease or orthologue thereof comprises an amino acid substitution at one or more of positions 918, 1013, 1014, 1025 and 1028 of SEQ ID NO: 2.

In another embodiment the present disclosure relates to the use of a crRNA-Cpf1 complex for introducing a single strand break in a specific recognition nucleotide sequence of the first target nucleic acid, wherein the first target nucleic acid and the second target nucleic acid are identical, and wherein the Cpf1 endonuclease or orthologue thereof comprises an amino acid substitution at two or more of positions 918, 1013, 1014, 1025 and 1028 of SEQ ID NO: 2.

The mutant Cpf1 endonuclease used in the method for diagnosis of an infectious disease is a Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 2, wherein said polypeptide sequence comprises at least two amino acid substitutions in position 918 and 1013 of SEQ ID NO: 2.

For example mutant Cpf1 endonuclease used in the method for diagnosis of an infectious disease is a Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 2, wherein said polypeptide sequence comprises at least two amino acid substitutions of an amino acid having a charged side chain to an amino acid having an uncharged side chain in position 918 and 1013 of SEQ ID NO: 2.

For example mutant Cpf1 endonuclease used in the method for diagnosis of an infectious disease is a Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 2, wherein said polypeptide sequence comprises at least two amino acid substitutions of an amino acid having a charged side chain to an amino acid having a non-polar side chain in position 918 and 1013 of SEQ ID NO: 2.

For example mutant Cpf1 endonuclease used in the method for diagnosis of an infectious disease is a Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 2, wherein said polypeptide sequence comprises at least two amino acid substitutions of an amino acid having a charged side chain to a glycine, alanine, valine, leucine, isoleucine, serine or threonine in position 918 and 1013 of SEQ ID NO: 2.

For example mutant Cpf1 endonuclease used in the method for diagnosis of an infectious disease in a sample is a Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 2, wherein said polypeptide sequence comprises at least two amino acid substitutions of an amino acid having a charged side chain to a glycine in position 918 and 1013 of SEQ ID NO: 2.

For example mutant Cpf1 endonuclease used in the method for diagnosis of an infectious disease is a Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity to SEQ ID NO: 2, wherein said polypeptide sequence comprises the amino acid substitutions R918G and K1013G.

For example mutant Cpf1 endonuclease used in the method for diagnosis of an infectious disease is a Cpf1 endonuclease or orthologue thereof comprising a polypeptide sequence having at least 80% sequence identity, such as at least 85% sequence identity, such as at least 90% sequence identity, such as at least 95% sequence identity, such as at least 96% sequence identity, such as at least 97% sequence identity, such as at least 98% sequence identity, such as at least 99% sequence identity, such as about 100% sequence identity to SEQ ID NO: 4.

For example mutant Cpf1 endonuclease used in the method for diagnosis of an infectious disease is a Cpf1 endonuclease or orthologue thereof comprises or consists of SEQ ID NO: 4.

The mutant Cpf1 endonuclease used in the method for diagnosis of an infectious disease may also comprise other amino acid modifications.

Items

1. A mutant Cpf1 endonuclease or orthologue thereof comprising a polypeptide sequence having at least 95% sequence identity to:
   i) the sequence corresponding to residues 1 to 297, 310 to 323, 337 to 1005, and 1019 to 1329 of SEQ ID NO: 2, wherein said polypeptide sequence further comprises at least one amino acid substitution or deletion in the finger domain (residues 298 to 309; SEQ ID NO: 12), the REC domain (residues 324 to 336; SEQ ID NO: 16) or the Lid domain (residues 1006 to 1018; SEQ ID NO: 20) compared to SEQ ID NO: 2; and/or
   ii) SEQ ID NO: 2, wherein said polypeptide sequence comprises at least one amino acid substitution in position 918, 1013, 1014, 1025 or 1028 of SEQ ID NO: 2.
2. A mutant Cpf1 endonuclease or orthologue thereof comprising a polypeptide sequence having at least 95% sequence identity to:
   i) the sequence corresponding to residues 1 to 323, 337 to 1005, and 1019 to 1329 of SEQ ID NO: 2, wherein said polypeptide sequence further comprises:
      a. at least two amino acid mutations in the REC domain (residues 324 to 336; SEQ ID NO: 16) compared to SEQ ID NO: 2, wherein each mutation independently is an amino acid substitution or deletion; and/or
      b. at least two amino acid substitutions in the Lid domain (residues 1006 to 1018; SEQ ID NO: 20) compared to SEQ ID NO: 2, wherein at least one of the residues at positions 917 and 1006 is a glutamic acid (E) or an aspartic acid (D);
   and/or
   ii) SEQ ID NO: 2, wherein said polypeptide sequence comprises at least two amino acid substitutions in two positions independently selected from the positions corresponding to residues 918, 1013, 1014, 1025 and 1028 of SEQ ID NO: 2.
3. The mutant Cpf1 endonuclease or orthologue thereof according to item 1, wherein the Cpf1 endonuclease is derived from *Francisella novicida*.
4. The mutant Cpf1 endonuclease or orthologue thereof according to any one of the preceding items, wherein said mutant Cpf1 comprises a polypeptide sequence having at least 95% sequence identity to the sequence corresponding to residues 1 to 323, 337 to 1005, and 1019 to 1329 of SEQ ID NO: 2, wherein said polypeptide sequence further comprises:
   a. at least two amino acid substitutions or deletions in the REC domain (residues 324 to 336; SEQ ID NO: 16) compared to SEQ ID NO: 2; and/or
   b. at least two amino acid substitutions in the Lid domain (residues 1006 to 1018; SEQ ID NO: 20) compared to SEQ ID NO: 2, with the proviso that at least one of the residues at positions 917 and 1006 of SEQ ID NO: 2 is a glutamic acid (E) or an aspartic acid (D);
   wherein said polypeptide sequence further comprises at least one amino acid substitution in position 918, 1013, 1014, 1025 or 1028 of SEQ ID NO: 2.
5. The mutant Cpf1 endonuclease or orthologue thereof according to any one of the preceding items, wherein one of the at least two amino acid substitutions is a substitution of an amino acid having a charged side chain to an amino acid having an uncharged side chain.
6. The mutant Cpf1 endonuclease or orthologue thereof according to any one of the preceding items, wherein the at least one amino acid substitution is a substitution of an amino acid having a charged side chain to an amino acid having an uncharged side chain.

7. The mutant Cpf1 endonuclease or orthologue thereof according to any one of the preceding items, wherein the at least one amino acid substitution is a substitution of an amino acid having a charged side chain to an amino acid residue having a non-polar side chain.
8. The mutant Cpf1 endonuclease or orthologue thereof according to any one of the preceding items, wherein one of the at least two amino acid substitutions is a substitution of an amino acid having a charged side chain to an amino acid residue having a non-polar side chain.
9. The mutant Cpf1 endonuclease or orthologue thereof according to any one of the preceding items, wherein one of the at least two amino acid substitutions is a substitution of an amino acid having a charged side chain to a glycine, alanine, valine, leucine, isoleucine, serine or threonine.
10. The mutant Cpf1 endonuclease or orthologue thereof according to any one of the preceding items, wherein the at least one amino acid substitution is a substitution of an amino acid having a charged side chain to a glycine, alanine, valine, leucine, isoleucine, serine or threonine.
11. The mutant Cpf1 endonuclease or orthologue thereof according to any one of the preceding items, wherein one of the at least two amino acid substitutions is a substitution of an amino acid having a charged side chain to a glycine.
12. The mutant Cpf1 endonuclease or orthologue thereof according to any one of the preceding items, wherein one of the at least two amino acid substitutions is a substitution of an amino acid having a charged side chain to a glycine.
13. The mutant Cpf1 endonuclease or orthologue thereof according to any one of the preceding items, wherein the at least one amino acid substitution or deletion is in the REC domain.
14. The mutant Cpf1 endonuclease or orthologue thereof according to any one of the preceding items, wherein the at least one amino acid substitution or deletion is a substitution or deletion of at least one residue in the REC domain, such as a substitution or deletion of at least 2 residues, such as a substitution or deletion of at least 3 residues, such as a substitution or deletion of at least 4 residues, such as a substitution or deletion of at least 5 residues, such as a substitution or deletion of at least 6 residues, such as a substitution or deletion of at least 7 residues, such as a substitution or deletion of at least 8 residues, such as a substitution or deletion of at least 9 residues, such as a substitution or deletion of at least 10 residues, such as a substitution or deletion of at least 11 residues, such as a substitution or deletion of at least 12 residues, such as a substitution or deletion of at least 13 residues of the REC domain.
15. The mutant Cpf1 endonuclease or orthologue thereof according to any one of the preceding items, wherein the at least two amino acid substitutions or deletions are a substitution or deletion of at least 2 residues in the REC domain, such as a substitution or deletion of at least 3 residues, such as a substitution or deletion of at least 4 residues, such as a substitution or deletion of at least 5 residues, such as a substitution or deletion of at least 6 residues, such as a substitution or deletion of at least 7 residues, such as a substitution or deletion of at least 8 residues, such as a substitution or deletion of at least 9 residues, such as a substitution or deletion of at least 10 residues, such as a substitution or deletion of at least 11 residues, such as a substitution or deletion of at least 12 residues, such as a substitution or deletion of at least 13 residues of the REC domain.
16. The mutant Cpf1 endonuclease or orthologue thereof according to any one of the preceding items, wherein the at least one substitution or deletion is a substitution or deletion of all the residues of the REC domain.
17. The mutant Cpf1 endonuclease or orthologue thereof according to any one of the preceding items, wherein the at least two substitutions or deletions are a substitution or deletion of all the residues of the REC domain.
18. The mutant Cpf1 endonuclease or orthologue thereof according to any one of the preceding items, wherein the at least one amino acid substitution or deletion is in the Lid domain.
19. The mutant Cpf1 endonuclease or orthologue thereof according to any one of the preceding items, wherein the at least two amino acid substitutions are in the Lid domain.
20. The mutant Cpf1 endonuclease or orthologue thereof according to any one of the preceding items, wherein the at least one amino acid substitution or deletion is a substitution or deletion of at least one residue in the Lid domain, such as a substitution or deletion of at least 2 residues, such as a substitution or deletion of at least 3 residues, such as a substitution or deletion of at least 4 residues, such as a substitution or deletion of at least 5 residues, such as a substitution or deletion of at least 6 residues, such as a substitution or deletion of at least 7 residues, such as a substitution or deletion of at least 8 residues, such as a substitution or deletion of at least 9 residues, such as a substitution or deletion of at least 10 residues, such as a substitution or deletion of at least 11 residues, such as a substitution or deletion of at least 12 residues, such as a substitution or deletion of at least 13 residues of the Lid domain.
21. The mutant Cpf1 endonuclease or orthologue thereof according to any one of the preceding items, wherein the at least two amino acid substitutions area substitution of at least two residues in the Lid domain, such as a substitution or deletion of at least 3 residues, such as a substitution or deletion of at least 4 residues, such as a substitution or deletion of at least 5 residues, such as a substitution or deletion of at least 6 residues, such as a substitution or deletion of at least 7 residues, such as a substitution or deletion of at least 8 residues, such as a substitution or deletion of at least 9 residues, such as a substitution or deletion of at least 10 residues, such as a substitution or deletion of at least 11 residues, such as a substitution or deletion of at least 12 residues, such as a substitution or deletion of at least 13 residues of the Lid domain.
22. The mutant Cpf1 endonuclease or orthologue thereof according to any one of the preceding items, wherein the at least one substitution or deletion is a substitution or deletion of all the residues of the Lid domain.
23. The mutant Cpf1 endonuclease or orthologue thereof according to any one of the preceding items, wherein the at least two substitutions are a substitution of all the residues of the Lid domain.
24. The mutant Cpf1 endonuclease or orthologue thereof according to any one of the preceding items, wherein the at least one amino acid substitution or deletion is in the finger domain.
25. The mutant Cpf1 endonuclease or orthologue thereof according to any one of the preceding items, wherein the at least one amino acid substitution or deletion is a substitution or deletion of at least one residue in the finger domain, such as a substitution or deletion of at least 2 residues, such as a substitution or deletion of at least 3 residues, such as a substitution or deletion of at least 4 residues, such as a substitution or deletion of at least 5 residues, such as a substitution or deletion of at least 6 residues, such as a substitution or deletion of at least 7 residues, such as a substitution or deletion of at least 8 residues, such as a substitution or deletion of at least 9 residues, such as a substitution or deletion of at least 10 residues, such as a substitution or deletion of at least 11 residues, such as a substitution or deletion of at least 12 residues of the finger domain.

26. The mutant Cpf1 endonuclease or orthologue thereof according to any one of the preceding items, wherein the at least one substitution or deletion is a substitution or deletion of all the residues of the finger domain.

27. The mutant Cpf1 endonuclease or orthologue thereof according to any one of the preceding items, wherein the at least one amino acid substitution is R918G, K1013G, R1014G, Q1025G or E1028G.

28. The mutant Cpf1 endonuclease or orthologue thereof according to any one of the preceding items, wherein the at least two amino acid substitutions are independently selected from R918G, K1013G, R1014G, Q1025G and E1028G.

29. The mutant Cpf1 endonuclease or orthologue thereof according to any one of the preceding items, wherein the Cpf1 endonuclease is a nicking endonuclease.

30. The mutant Cpf1 endonuclease or orthologue thereof according to any one of the preceding items, wherein said amino acid substitution is at position K1013.

31. The mutant Cpf1 endonuclease or orthologue thereof according to any one of the preceding items, comprising substitution at position corresponding to K1013 of SEQ ID NO: 2.

32. The mutant Cpf1 endonuclease or orthologue thereof according to any one of the preceding items, wherein said amino acid substitution is at positions R918 and K1013.

33. The mutant Cpf1 endonuclease or orthologue thereof according to any one of the preceding items, comprising substitutions at positions corresponding to R918 and K1013 of SEQ ID NO: 2.

34. The mutant Cpf1 endonuclease or orthologue thereof according to any one of the preceding items, wherein said amino acid substitution is at positions K1013 and R1014.

35. The mutant Cpf1 endonuclease or orthologue thereof according to any one of the preceding items, comprising substitutions at positions corresponding to K1013 and R1014 of SEQ ID NO: 2.

36. The mutant Cpf1 endonuclease or orthologue thereof according to any one of the preceding items, wherein said amino acid substitution is K1013G.

37. The mutant Cpf1 endonuclease or orthologue thereof according to any one of the preceding items, comprising substitution corresponding to K1013G of SEQ ID NO: 2.

38. The mutant Cpf1 endonuclease or orthologue thereof according to any one of the preceding items, wherein the Cpf1 endonuclease comprises the amino acid substitutions K1013G and R1014G.

39. The mutant Cpf1 endonuclease or orthologue thereof according to any one of the preceding items, comprising substitutions corresponding to K1013G and R1014G of SEQ ID NO: 2.

40. The mutant Cpf1 endonuclease or orthologue thereof according to any one of the preceding items, wherein said amino acid substitution is at position Q1025.

41. The mutant Cpf1 endonuclease or orthologue thereof according to any one of the preceding items, comprising substitution at position corresponding to Q1025 of SEQ ID NO: 2.

42. The mutant Cpf1 endonuclease or orthologue thereof according to any one of the preceding items, wherein said amino acid substitution is at position E1028.

43. The mutant Cpf1 endonuclease or orthologue thereof according to any one of the preceding items, comprising substitution at position corresponding to E1028 of SEQ ID NO: 2.

44. The mutant Cpf1 endonuclease or orthologue thereof according to any one of the preceding items, wherein said amino acid substitution is at positions Q1025 and E1028.

45. The mutant Cpf1 endonuclease or orthologue thereof according to any one of the preceding items, comprising substitutions at positions corresponding to Q1025 and E1028 of SEQ ID NO: 2.

46. The mutant Cpf1 endonuclease or orthologue thereof according to any one of the preceding items, wherein said amino acid substitution is Q1025G.

47. The mutant Cpf1 endonuclease or orthologue thereof according to any one of the preceding items, comprising substitution corresponding to Q1025G of SEQ ID NO: 2.

48. The mutant Cpf1 endonuclease or orthologue thereof according to any one of the preceding items, wherein said amino acid substitution is E1028G.

49. The mutant Cpf1 endonuclease or orthologue thereof according to any one of the preceding items, comprising substitution corresponding to E1028G of SEQ ID NO: 2.

50. The mutant Cpf1 endonuclease or orthologue thereof according to any one of the preceding items, wherein the Cpf1 endonuclease comprises the amino acid substitutions Q1025G and E1028G.

51. The mutant Cpf1 endonuclease or orthologue thereof according to any one of the preceding items, comprising substitutions corresponding to Q1025G and E1028G of SEQ ID NO: 2.

52. The mutant Cpf1 endonuclease or orthologue thereof according to any one of the preceding items, wherein the Cpf1 endonuclease comprises at least two amino acid substitutions or deletions in the REC domain (residues 324 to 336; SEQ ID NO: 16) compared to SEQ ID NO: 2, and at least one amino acid substitution in any one of positions 918, 1013, 1014, 1025 and 1028 of SEQ ID NO: 2.

53. The mutant Cpf1 endonuclease or orthologue thereof according to any one of the preceding items, wherein the Cpf1 endonuclease comprises at least two amino acid substitutions in the Lid domain (residues 1006 to 1018; SEQ ID NO: 20) compared to SEQ ID NO: 2, and at least one amino acid substitution in any one of positions 918, 1013, 1014, 1025 and 1028 of SEQ ID NO: 2.

54. The mutant Cpf1 endonuclease or orthologue thereof according to any one of the preceding items, wherein the Cpf1 endonuclease comprises at least two amino acid substitutions or deletions in the REC domain (residues 324 to 336; SEQ ID NO: 16) compared to SEQ ID NO: 2, and at least two amino acid substitutions in any one of positions 918, 1013, 1014, 1025 and 1028 of SEQ ID NO: 2.

55. The mutant Cpf1 endonuclease or orthologue thereof according to any one of the preceding items, wherein the Cpf1 endonuclease comprises at least two amino acid substitutions in the Lid domain (residues 1006 to 1018; SEQ ID NO: 20) compared to SEQ ID NO: 2, and at least two amino acid substitutions in any one of positions 918, 1013, 1014, 1025 and 1028 of SEQ ID NO: 2.

56. The mutant Cpf1 endonuclease or orthologue thereof according to any one of the preceding items, wherein the Cpf1 endonuclease comprises or consists of a polypeptide having at least 95% sequence identity to SEQ ID NO: 3 or SEQ ID NO: 4.

57. The mutant Cpf1 endonuclease or orthologue thereof according to any one of the preceding items, wherein the Cpf1 endonuclease comprises or consists of a polypeptide of SEQ ID NO: 3 or SEQ ID NO: 4.

58. The mutant Cpf1 endonuclease or orthologue thereof according to any one of the preceding items, wherein the REC domain of the mutant Cpf1 endonuclease comprises or consists of SEQ ID NO: 14.

59. The mutant Cpf1 endonuclease or orthologue thereof according to any one of the preceding items, wherein the Lid domain of the mutant Cpf1 endonuclease comprises or consists of SEQ ID NO: 18.

60. The mutant Cpf1 endonuclease or orthologue thereof according to any one of the preceding items, wherein the finger domain of the mutant Cpf1 endonuclease comprises or consists of SEQ ID NO: 22.

61. The mutant Cpf1 endonuclease or orthologue thereof according to any one of the preceding items, wherein the mutant Cpf1 has one or more altered activity compared to the wild-type Cpf1, said activity being selected from the group consisting of: double-stranded cleavage of a target or non-target nucleic acid; single-stranded cleavage of stranded target or non-target nucleic acid; single-stranded cleavage of a nucleic acid in a non-specific manner, optionally enhanced by single-stranded or double-stranded target DNA.

62. The mutant Cpf1 endonuclease or orthologue thereof according to any one of the preceding items, wherein the residue at position 917 of SEQ ID NO: 2 is a glutamic acid (E) or an aspartic acid (D).

63. The mutant Cpf1 endonuclease or orthologue thereof according to any one of the preceding items, wherein the residue at position 1006 of SEQ ID NO: 2 is a glutamic acid (E) or an aspartic acid (D).

64. A polynucleotide encoding the mutant Cpf1 endonuclease or orthologue thereof according to any one of the preceding items.

65. The polynucleotide according to item 64, wherein said polynucleotide is codon-optimized for expression in a host cell.

66. A recombinant vector comprising a polynucleotide according to any one of items 1 to 64, or a nucleic acid sequence encoding a mutant Cpf1 endonuclease or orthologue thereof according to any one of items 1 to 64.

67. The recombinant vector according to item 66, wherein said polynucleotide or nucleic acid sequence is operably linked to a promoter.

68. The recombinant vector according to any one of items 66 to 67, further comprising a nucleic acid sequence encoding a guide RNA (crRNA) operably linked to a promoter, wherein the crRNA binds the encoded Cpf1 endonuclease and a fragment with sufficient base pairs to hybridize to a target nucleic acid.

69. The recombinant vector according to any one of items 66 to 68, wherein the crRNA consists of a constant region of 19 or 20 nucleotides, and a variable region consisting of between 12 and 24 nucleotides, such that said crRNA is at least 40 nucleotides in length, such as 41 nucleotides in length, such as 42 nucleotides in length, such as 43 nucleotides in length, such as 44 nucleotides in length.

70. The recombinant vector according to any one of items 66 to 69, wherein the constant region of the crRNA is as set out in SEQ ID NO: 5.

71. A cell capable of expressing the mutant Cpf1 or orthologue thereof according to any one of items 1 to 63, the polynucleotide according to any one of items 64 to 65, or the recombinant vector according to any one of items 66 to 70.

72. A system for expression of a crRNA-Cpf1 complex comprising
    a. a polynucleotide according to any one of items 64 to 65, or a recombinant vector according to any one of items 66 to 70 comprising a polynucleotide encoding a mutant Cpf1 endonuclease or orthologue thereof;
    b. a polynucleotide or a recombinant vector comprising a polynucleotide encoding a guide RNA (crRNA), optionally operably linked to a promoter.

73. The system according to item 72, further comprising
    c. a cell for expression of the polynucleotide or the recombinant vector of a. and b. above.

74. The cell according to item 71 or the system according to any one of items 72 to 73, wherein said cell is a prokaryotic or a eukaryotic cell.

75. Use of a crRNA-Cpf1 complex for introducing a single strand break in a first target nucleic acid, wherein:
    a. a Cpf1 endonuclease or orthologue thereof is contacted with a guide RNA (crRNA), thereby obtaining a crRNA-Cpf1 complex capable of recognising a second target nucleic acid, the second target nucleic acid comprising a protospacer adjacent motif (PAM), and
    b. the crRNA-Cpf1 complex is contacted with the first target nucleic acid;
whereby a single strand break is made in the first target sequence.

76. The use according to item 75, wherein the Cpf1 endonuclease or orthologue thereof is according to any one of items 1 to 63, or encoded by a polynucleotide or a vector according to any one of items 64 to 70.

77. The use according to any one of items 75 to 76, wherein the crRNA hybridizes to the second target nucleic acid.

78. The use according to any one of items 75 to 77, wherein hybridization of the crRNA to the second target nucleic acid activates the crRNA-Cpf1 complex.

79. The use according to any one of items 75 to 78, wherein the single strand break is made in a specific recognition nucleotide sequence of the first target nucleic acid.

80. The use according to any one of items 75 to 79, wherein the single strand break is made at one or more nonspecific nucleotide sequences of the first target nucleic acid.

81. The use according to any one of items 75 to 80, wherein the crRNA is as defined in any one of the preceding items.
82. The use according to any one of items 75 to 81, wherein the molar ratio of Cpf1 to crRNA is between 0.5:3.0 and 1.0:1.0, such as 0.7:2.5, such as 0.8:2.0, such as 0.9:1.75, such as 0.95:1.5, such as 1.0:1.4, such as 1.0:1.3, such as 1.1:1.2.
83. The use according to any one of items 75 to 82, wherein the molar ratio of Cpf1:crRNA:second target nucleic acid is 0.5:3.0:5.0, such as 0.7:2.5:4.0, such as 0.8:2.0:3.5, such as 0.9:1.75:3.0, such as 0.95:1.5:2.0, such as 1.0:1.4:1.9, such as 1.0:1.3:1.7.
84. The use according to any one of items 75 to 83, wherein the second target nucleic acid comprises or consists of a recognition sequence comprising a sequence of at least 15 consecutive nucleotides, such as at least 16 consecutive nucleotides, such as at least 17 consecutive nucleotides, such as at least 18 consecutive nucleotides, such as at least 19 consecutive nucleotides, such as at least 20 consecutive nucleotides, such as at least 21 consecutive nucleotides, such as at least 22 consecutive nucleotides, such as at least 23 consecutive nucleotides, such as at least 24 consecutive nucleotides, such as at least 25 consecutive nucleotides, such as at least 26 consecutive nucleotides, such as at least 27 consecutive nucleotides, with the proviso that the 3 nucleic acids at the 5'-end consist of a PAM sequence.
85. The use according to any one of items 75 to 84, wherein the PAM comprises or consists of the sequence 5'-YRN-3' or 5'-RYN-3'.
86. The use according to any one of items 75 to 85, wherein the PAM comprises or consists of the sequence 5'-TTN-3'.
87. The use according to any one of items 75 to 86, wherein the first target nucleic acid and the second target nucleic acid are DNA or RNA.
88. The use according to any one of items 75 to 87, wherein the second target nucleic acid is double stranded DNA.
89. The use according to any one of items 75 to 88, wherein the second target nucleic acid is DNA selected from the group consisting of genomic DNA, chromatin, nucleosomes, plasmid DNA, methylated DNA, synthetic DNA, and DNA fragments.
90. The use according to any one of items 75 to 89, wherein the second target nucleic acid is RNA.
91. The use according to any one of items 75 to 90, wherein the first target nucleic acid and the second target nucleic acid are identical.
92. The use according to any one of items 75 to 91, wherein the first target nucleic acid and the second target nucleic acid are the same molecule, and wherein the Cpf1 endonuclease or orthologue thereof comprises amino acid substitutions at position 1013 and 1014 of SEQ ID NO: 2.
93. The use according to any one of items 75 to 92 wherein the first target nucleic acid and the second target nucleic acid are the same molecule, and wherein the Cpf1 endonuclease or orthologue thereof comprises or consists of SEQ ID NO: 3.
94. The use according to any one of items 75 to 93, wherein the single strand break is made in a specific recognition nucleotide sequence of the first target nucleic acid, and wherein the Cpf1 endonuclease or orthologue thereof comprises amino acid substitutions at position 1013 and 1014 of SEQ ID NO: 2.
95. The use according to any one of items 75 to 94, wherein the Cpf1 performs the single strand break in the first target nucleic acid specifically or non-specifically, and wherein the Cpf1 endonuclease or orthologue thereof comprises or consists of SEQ ID NO: 3.
96. The use according to any one of items 75 to 95, wherein the first target nucleic acid and the second target nucleic acid are different, and wherein the Cpf1 endonuclease or orthologue thereof comprises amino acid substitutions at position 918 and 1013 of SEQ ID NO: 2.
97. The use according to any one of items 75 to 96, wherein the first target nucleic acid and the second target nucleic acid are different, and wherein the Cpf1 endonuclease or orthologue thereof comprises or consists of SEQ ID NO: 4.
98. The use according to any one of items 75 to 97, wherein the Cpf1 performs the single strand break in the first target nucleic acid specifically or non-specifically, and wherein the Cpf1 endonuclease or orthologue thereof comprises amino acid substitutions at position 918 and 1013 of SEQ ID NO: 2.
99. The use according to any one of items 75 to 98, wherein the Cpf1 performs the single strand break in the first target nucleic acid specifically or non-specifically, and wherein the Cpf1 endonuclease or orthologue thereof comprises or consists of SEQ ID NO: 4.
100. The use according to any one of items 75 to 99, wherein the first target nucleic acid and the second target nucleic acid are different, and wherein the Cpf1 endonuclease or orthologue thereof comprises two or more amino acid substitutions or deletions at any one of positions 324 to 336 of SEQ ID NO: 2, such as wherein the Cpf1 endonuclease or orthologue thereof comprises amino acid substitutions at all of residues corresponding to positions 324 to 336 of SEQ ID NO: 2, such as wherein the Cpf1 endonuclease or orthologue thereof comprises amino acid deletions at all of residues corresponding to positions 324 to 336 of SEQ ID NO: 2.
101. The use according to any one of items 75 to 100, wherein the first target nucleic acid and the second target nucleic acid are different, and wherein the Cpf1 endonuclease or orthologue thereof comprises or consists of SEQ ID NO: 34 or SEQ ID NO: 36.
102. The use according to any one of items 75 to 101, wherein the Cpf1 performs the single strand break in the first target nucleic acid specifically or non-specifically, and wherein the Cpf1 endonuclease or orthologue thereof comprises two or more amino acid substitutions or deletions at any one of positions 324 to 336 of SEQ ID NO: 2, such as wherein the Cpf1 endonuclease or orthologue thereof comprises amino acid substitutions at all of residues corresponding to positions 324 to 336 of SEQ ID NO: 2, such as wherein the Cpf1 endonuclease or orthologue thereof comprises amino acid deletions at all of residues corresponding to positions 324 to 336 of SEQ ID NO: 2.
103. The use according to any one of items 75 to 102, wherein the Cpf1 performs the single strand break in the first target nucleic acid specifically or non-specifically, and wherein the Cpf1 endonuclease or orthologue thereof comprises or consists of SEQ ID NO: 34 or SEQ ID NO: 36.
104. The use according to any one of items 75 to 103, wherein the first target nucleic acid and the second target nucleic acid are different, and wherein the Cpf1 endonuclease or orthologue thereof comprises two or more amino acid substitutions at any one of positions 1006 to 1018 of SEQ ID NO: 2, such as wherein the Cpf1 endonuclease or orthologue thereof comprises amino acid substitutions at all of residues corresponding to positions 1006 to 1018 of SEQ ID NO: 2.
105. The use according to any one of items 75 to 104, wherein the first target nucleic acid and the second target nucleic acid are different, and wherein the Cpf1 endonuclease or orthologue thereof comprises or consists of SEQ ID NO: 38.
106. The use according to any one of items 75 to 105, wherein the Cpf1 performs the single strand break in the first target nucleic acid specifically or non-specifically, and wherein the Cpf1 endonuclease or orthologue thereof comprises two or more amino acid substitutions at any one of positions 1006 to 1018 of SEQ ID NO: 2, such as wherein the Cpf1 endonuclease or orthologue thereof comprises amino acid substitutions at all of residues corresponding to positions 1006 to 1018 of SEQ ID NO: 2.
107. The use according to any one of items 75 to 106, wherein the Cpf1 performs the single strand break in the first target nucleic acid specifically or non-specifically, and wherein the Cpf1 endonuclease or orthologue thereof comprises or consists of SEQ ID NO: 38.
108. The use according to any one of items 75 to 107, wherein the first target nucleic acid and the second target nucleic acid are identical or different, and wherein the Cpf1 endonuclease or orthologue thereof comprises amino acid substitutions at positions corresponding to 1025 and 1028 of SEQ ID NO: 2.
109. The use according to any one of items 75 to 108, wherein the first target nucleic acid and the second target nucleic acid are identical or different, and wherein the Cpf1 endonuclease or orthologue thereof comprises or consists of SEQ ID NO: 32.
110. The use according to any one of items 75 to 109, wherein the Cpf1 performs the single strand break in the first target nucleic acid specifically, wherein the target nucleic acid is in double stranded form, and wherein the Cpf1 endonuclease or orthologue thereof comprises two or more amino acid substitutions at positions corresponding to 1025 and 1028 of SEQ ID NO: 2.
111. The use according to any one of items 75 to 110, wherein the Cpf1 performs the single strand break in the first target nucleic acid specifically, and wherein the Cpf1 endonuclease or orthologue thereof comprises or consists of SEQ ID NO: 32.
112. The use according to any one of items 75 to 111, wherein said method is performed ex-vivo.
113. A method of introducing a single strand break in a first target nucleic acid, comprising the steps of:
  a. designing a guide-RNA (crRNA) capable of recognising a second target nucleic acid comprising a protospacer adjacent motif (PAM);
  b. contacting the crRNA of step a. with a Cpf1 endonuclease or orthologue thereof, thereby obtaining a crRNA-Cpf1 complex capable of binding to said second target nucleic acid, and
  c. contacting the crRNA and the Cpf1 with said first target nucleic acid, thereby introducing one or more single strand breaks in the first target nucleic acid.
114. The method according to item 113, wherein the Cpf1 endonuclease or orthologue thereof is according to any one of items 1 to 63, or encoded by a polynucleotide or a vector according to any one of items 64 to 70.
115. The method according to any one of items 113 to 114, wherein the steps b. and c. can occur simultaneously or one after the other.
116. The method according to any one of items 113 to 115, wherein the method is performed in a cell in vitro.
117. The method according to any one of items 113 to 116, wherein the single strand break is made in a specific recognition nucleotide sequence of the first target nucleic acid.
118. The method according to any one of items 113 to 117, wherein the single strand break is made specifically or non-specifically in the first target nucleic acid.
119. The method according to any one of items 113 to 118, wherein the first and the second target nucleic acids are as defined in any one of the preceding items.
120. An in vitro method of introducing a site-specific, double-stranded break at a second target nucleic acid in a mammalian cell, the method comprising introducing into the mammalian cell a crRNA-Cpf1 complex, wherein the Cpf1 is a mutant Cpf1 endonuclease or orthologue according to any one of items 1 to 63, and wherein the crRNA is specific for the second target nucleic acid.
121. A method for detection of a second target nucleic acid in a sample, the method comprising:
  a. Providing a crRNA-Cpf1 complex, wherein the Cpf1 is a Cpf1 endonuclease or orthologue thereof according to any one of items 1 to 63, and wherein the crRNA is specific for the second target nucleic acid;
  b. Providing a labelled ssDNA, wherein the ssDNA is labelled with at least one set of interactive labels comprising at least one dye and at least one quencher;
  c. Contacting the crRNA-Cpf1 complex and the ssDNA with the sample, wherein the sample comprises at least one second target nucleic acid; and
  d. Detecting cleavage of the ssDNA by detecting a fluorescent signal from the fluorophore,
  thereby detecting the presence of the second target nucleic acid in the sample.
122. The method according to item 121, wherein step c. comprises activation of the crRNA-Cpf1 complex, such as activation by single-stranded or double-stranded target DNA.
123. The method according to any one of items 121 to 122, further comprising:
  e. determining the level and/or concentration of the second target nucleic acid,
  wherein the level and/or concentration of the second target nucleic acid is correlated to the cleaved ssDNA.
124. The method according to any one of items 121 to 123, wherein the method can detect a second target nucleic acid at a concentration in the range of nanomolar or below, such as in a range of picomolar or below, such as in a range of femtomolar or below, such as in a range of attomolar or below.
125. The method according to any one of items 121 to 124, wherein the ssDNA is labelled in at least one base in any position along the chain.
126. The method according to any one of items 121 to 125, wherein the at least one dye is a fluorophore.

127. The method according to any one of items 121 to 126, wherein step d. comprises detecting a fluorescent signal resulting from cleavage of the ssDNA.
128. The method according to any one of items 121 to 127, wherein the sample comprises DNA and/or RNA.
129. The method according to any one of items 121 to 128, wherein the sample is suspected of comprising the second target nucleic acid.
130. The method according to any one of items 121 to 129, wherein the second target nucleic acid is a nucleic acid fragment of a viral genome, a microbial genome, a gene, or of a genome of a pathogen.
131. An in vitro method for diagnosis of an infectious disease in a subject, the method comprising:
    a. Providing a crRNA-Cpf1 complex, wherein the Cpf1 is a Cpf1 endonuclease or orthologue thereof according to any one of items 1 to 63, and wherein the crRNA is specific for a second target nucleic acid;
    b. Providing a labelled ssDNA, wherein the ssDNA is labelled with at least one set of interactive labels comprising at least one dye and at least one quencher;
    c. Providing a sample from the subject, wherein said sample comprises or is suspected of comprising the second target nucleic acid; and
    d. Determining the level and/or concentration of the second target nucleic acid as defined in any one of the preceding items,
wherein the second target nucleic acid is a nucleic acid of the genome of an infectious agent causing the disease or a fragment thereof, thereby diagnosing an infectious disease in a subject.
132. The method according to item 131, further comprising the step of treating said infectious disease.
133. The method according to item 132, further comprising treating said infectious disease by administration of a therapeutically effective compound.
134. The method according to any one of items 131 to 133, further comprising the step of comparing the level and/or concentration of said second target nucleic acid with a cut-off value, wherein said cut-off value is determined from the concentration range of said second target nucleic acid in healthy subjects, such as subjects who do not present with the infectious disease, wherein a level and/or concentration that is greater than the cut-off value indicates the presence of the infectious disease.
135. The method according to any one of items 131 to 134, wherein said infection disease is caused by an infectious agent and wherein the infectious agent comprises viruses, viroids, prions, bacteria, nematodes, parasitic roundworms, pinworms, arthropods, fungi, ringworm and macroparasites.
136. The method according to any one of items 131 to 135, wherein the subject is a human.
137. The method according to any one of items 131 to 136, wherein the sample body fluid selected from the group consisting of blood, whole blood, plasma, serum, urine, saliva, tears, cerebrospinal fluid and semen.
138. The methods according to any one of items 131 to 137, wherein the Cpf1 endonuclease or orthologue thereof comprises amino acid substitutions at position 918 and 1013 of SEQ ID NO: 2.
139. The methods according to any one of items 131 to 138, wherein the Cpf1 endonuclease or orthologue thereof comprises or consists of SEQ ID NO: 4.

EXAMPLES

Example 1. Cleavage Assay

The double strand DNA target was prepared by annealing: the target-strands (t-strand) 5'-atgcagtggccttat-taaatgacttctcTAA CG-3'-6FAM (SEQ ID NO: 6) and non-target stands (nt-strand) 6FAM-5'-cgTTAgagaagt-catttaataaggccactgcat-3' (SEQ ID NO: 7) for labelled DNA and the t-strands 5'-atgcagtggccttattaaatgacttctcTAACG-3' (SEQ ID NO: 8) and nt-target stands 5'-cgTTAgagaagt-catttaataaggccactgcat-3'(SEQ ID NO: 9) for non-labelled DNA target.

The cleavage assay was performed as follows:

4 pmoles of FnCpf1 protein (the wild type protein was used as control) and 5.2 pmoles of crRNA (rArArUrUrUr-CrUrArCrUrGrUrUrGrUrArGrArUrCrArCrCrGrArGrUr-GrCrArGrCrCrArCrUr CrGrGrCrGrCrU) (SEQ ID NO: 10) were mixed in in 20 mM Bicine-HCl pH8, 150 mM KCl, 0.5 mM TCPE pH8 and 5 mM MgCl at 25° C. for 30 min. Then 6 pmoles of double strand labelled DNA target was added to the mixture and incubate it for other 30 mins at 25° C. The reactions were stopped by adding equal volume of stop solution (8 M Urea and 100 mM EDTA at pH8) followed by incubation at 95° C. for 5 min. The samples were loaded on 15% Novex TBE-Urea Gels (Invitrogen) and run according to the manufacturer instructions. The gel was visualized using an Odyssey FC Imaging System (Li-Cor).

For the non-specific ssDNA the cleavage assay was performed as follows:

4 pmoles of FnCpf1 protein (the wild type protein was used as control) and 5.2 pmoles of crRNA were mixed in in 20 mM Bicine-HCl pH8, 150 mM KCl, 0.5 mM TCPE pH8 and mM MgCl at 25° C. for 30 min. Then 6 pmoles of double strand non-labelled DNA 5 target was added to the mixture and incubate it for other 30 mins at 25° C. Then labelled non-specific ssDNA (/5' 6-FAM/AGCATGCC-CAAATTGCTTACATATGTGTTACGACGGT) (SEQ ID NO: 23) was added and the mixture was incubated at 25° for 30 mins. The reactions were stopped by adding equal volume of stop solution (8 M Urea and 100 mM EDTA at pH8) followed by incubation at 95° C. for 5 min. The samples were loaded on 15% Novex TBE-Urea Gels (Invitrogen) and run according to the manufacture instructions. The gel was visualized using an Odyssey FC Imaging System (Li-Cor).

Endonuclease activity was calculated from the intensity (I) of the DNA bands. The intensity was quantified using ImageStudio. The intensity of the uncleaved DNA ($I_{uc}$) was used as reference. The % of cleavage of NTS (Non-Target Strand), TS (Target Strand) and SSDNA (non-specific single strand) was calculated using the following formula: $(100*I_n)/I_{uc}$ where $I_n$ is the intensity of the band of interested. The average of at least 3 independent experiments is used in the plot and the standard deviation is represented in the error bars.

Results:

In the DNA duplex contains a PAM sequence (5'-TTA-3') and a target sequence in the t-strand that is complementary to a part of the crRNA (FIG. 1).

Figure 2:
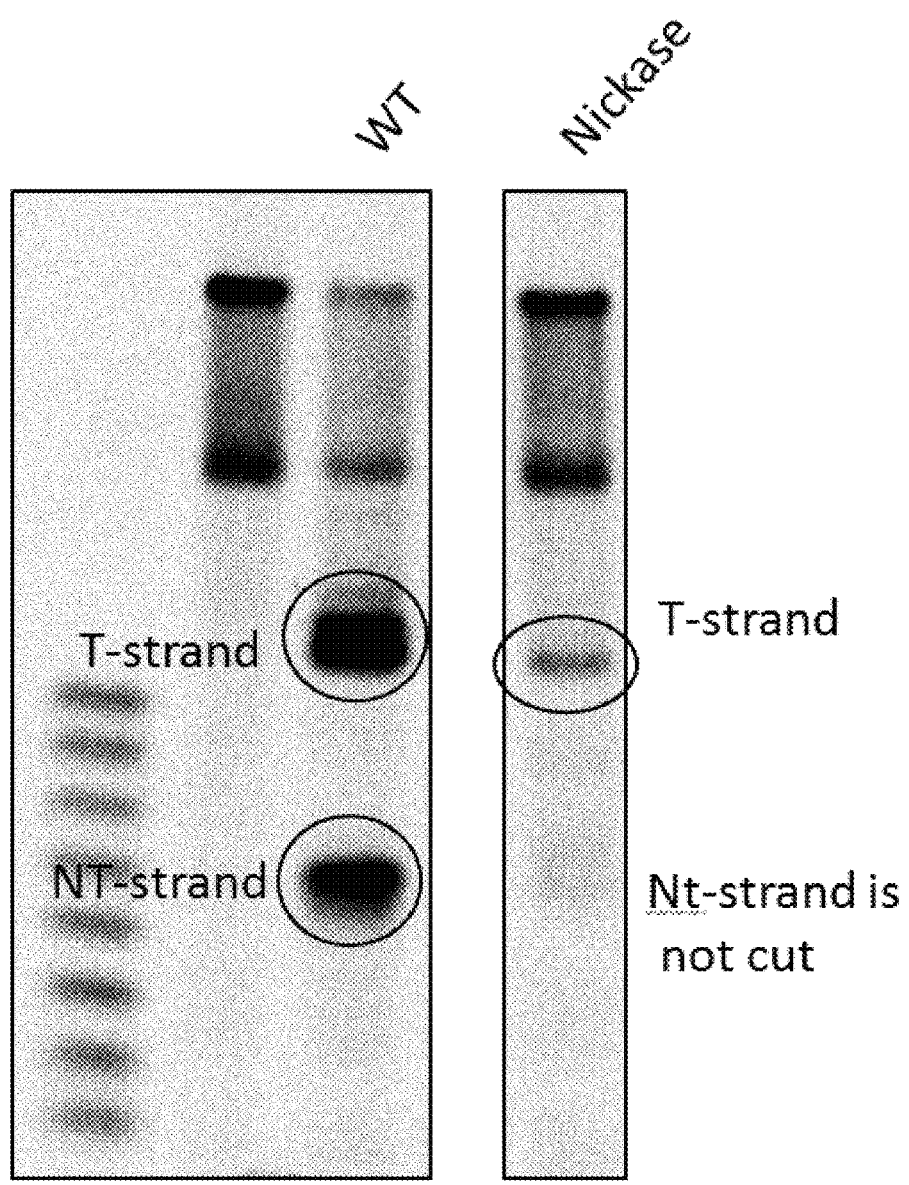
FIG. 2. Cleavage products of the double strand DNA target obtained by using wild type Cpf1 and mutant 1 (SEQ ID NO: 3).
Figure 3:
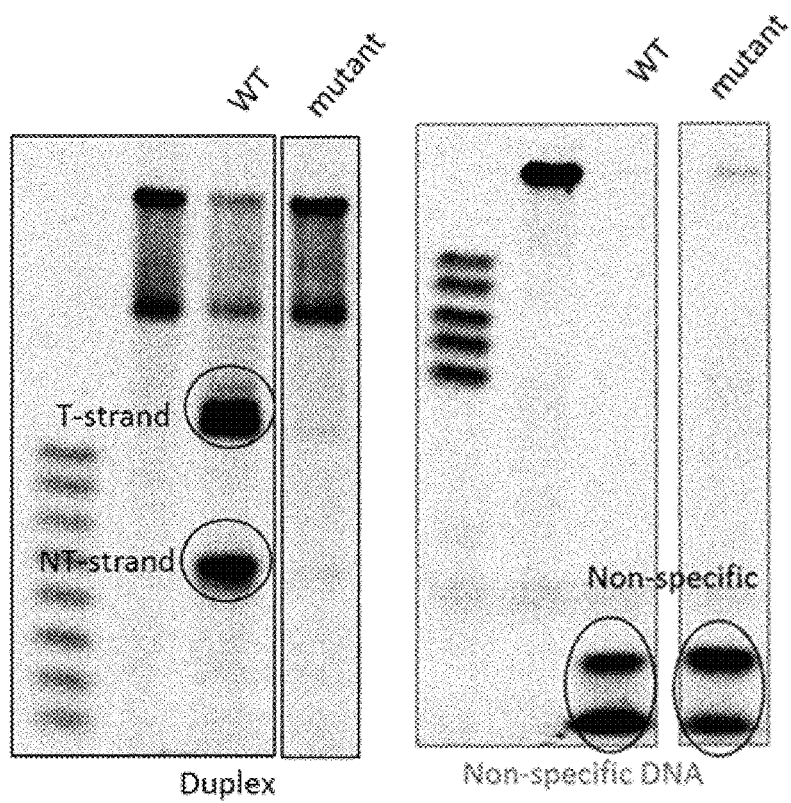
FIG. 3. Left panel: cleavage products of the double strand DNA target obtained by using wild type Cpf1 and mutant 1 (SEQ ID NO: 4, 918-1013 mutant) (black circles). Right panel: cleavage products of the non-specific ssDNA obtained by using wild type Cpf1 and mutant 2 (SEQ ID NO: 4, 918-1013 mutant) (black circle).
Figure 4:
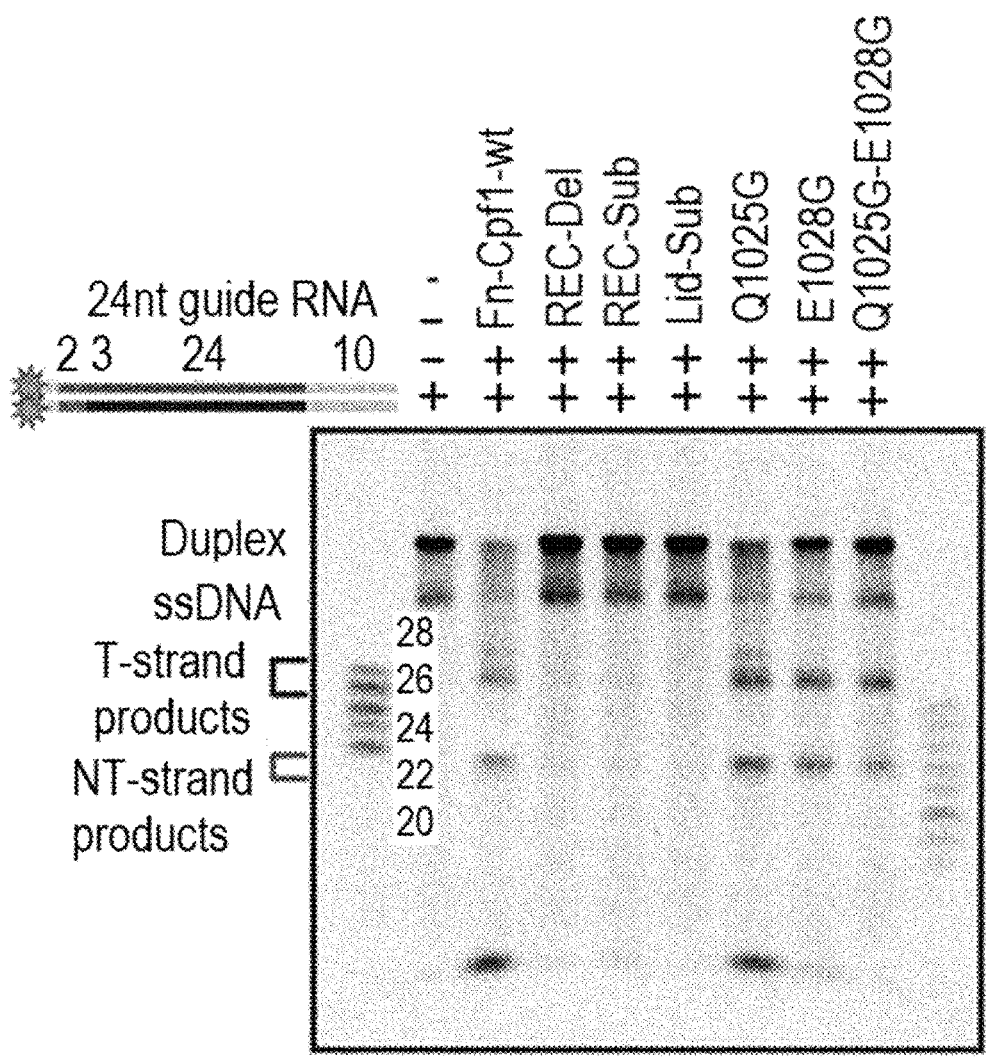
FIG. 4. (A) Cleavage activity assays with target DNA substrate for the REC-linker deletion and substitution (SEQ ID NO: 34 and 36), the lid substitution (SEQ ID NO: 38) and the Q1025G, E1028G and Q1025G-E1028G mutants (SEQ ID NO: 30 and 32). (B) Cleavage activity assays monitoring the cut of the t-strand complementary to crRNA for the REC-linker deletion and substitution, the lid substitution and the Q1025G, E1028G and Q1025G-E1028G mutants. (C) Cleavage activity assays upon activation with ssDNA complementary to crRNA using non-specific ssDNA as substrate for the REC-linker deletion and substitution, the lid substitution and the Q1025G, E1028G and Q1025G-E1028G mutants. (D) Cleavage activity assays monitoring the cut of the dsDNA substrate (t-strand, nt-strand and non-specific ssDNA for wild type Cpf1, (D917)Cpf1, (E1006-D917A)Cpf1 and (Lid substitution-D917A)Cpf1.
Figure 4:
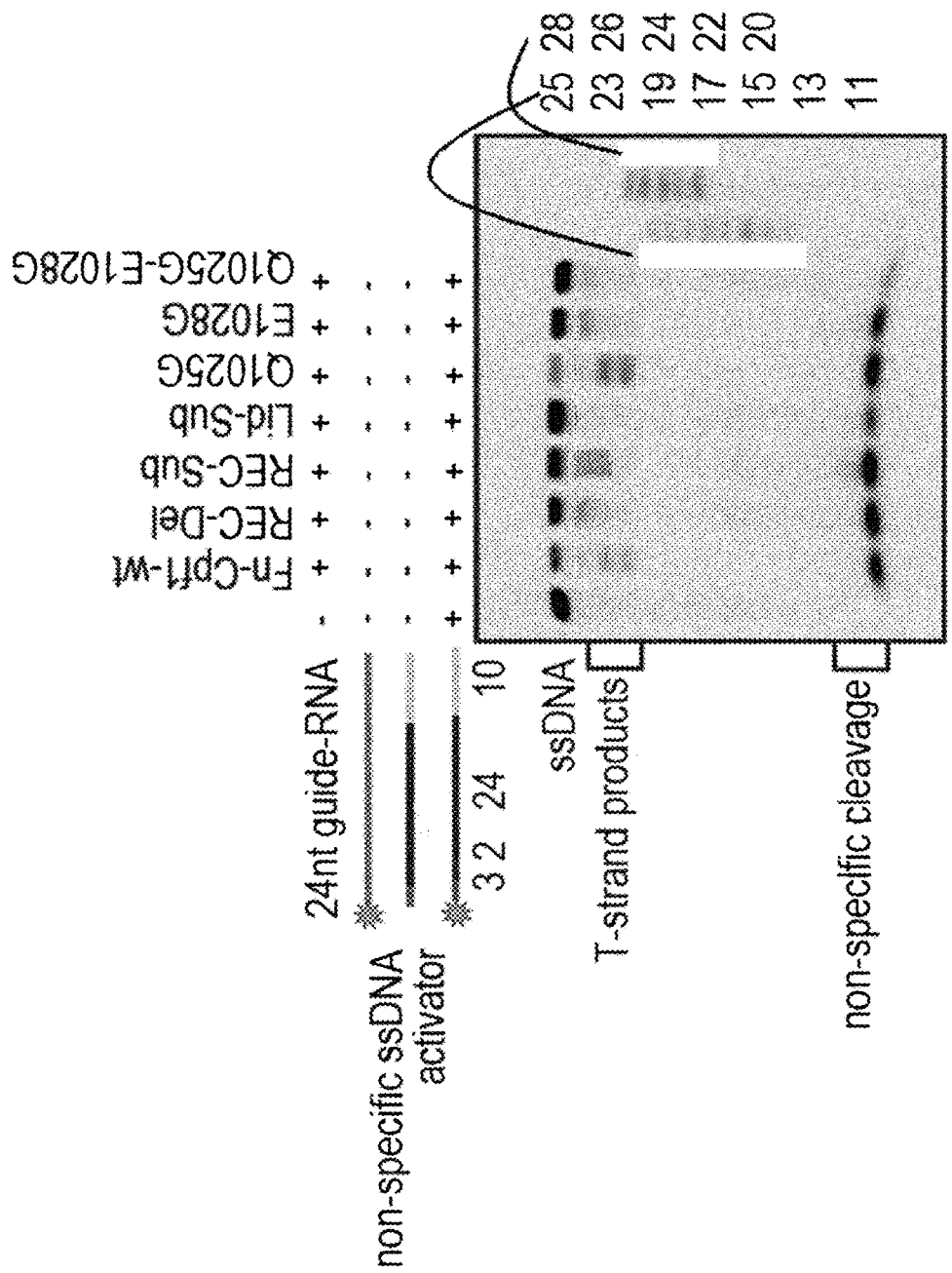
Figure 4:
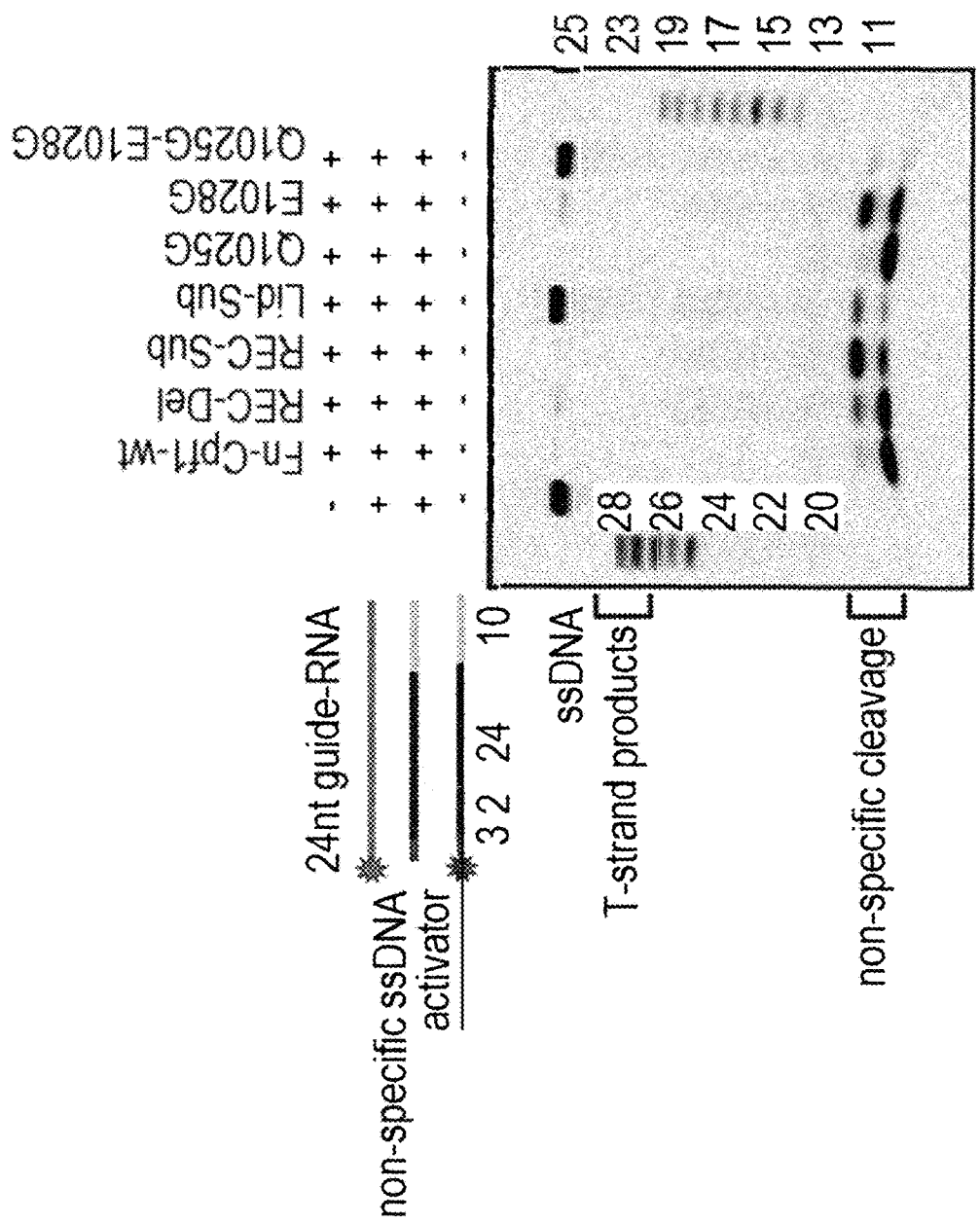
Figure 4:
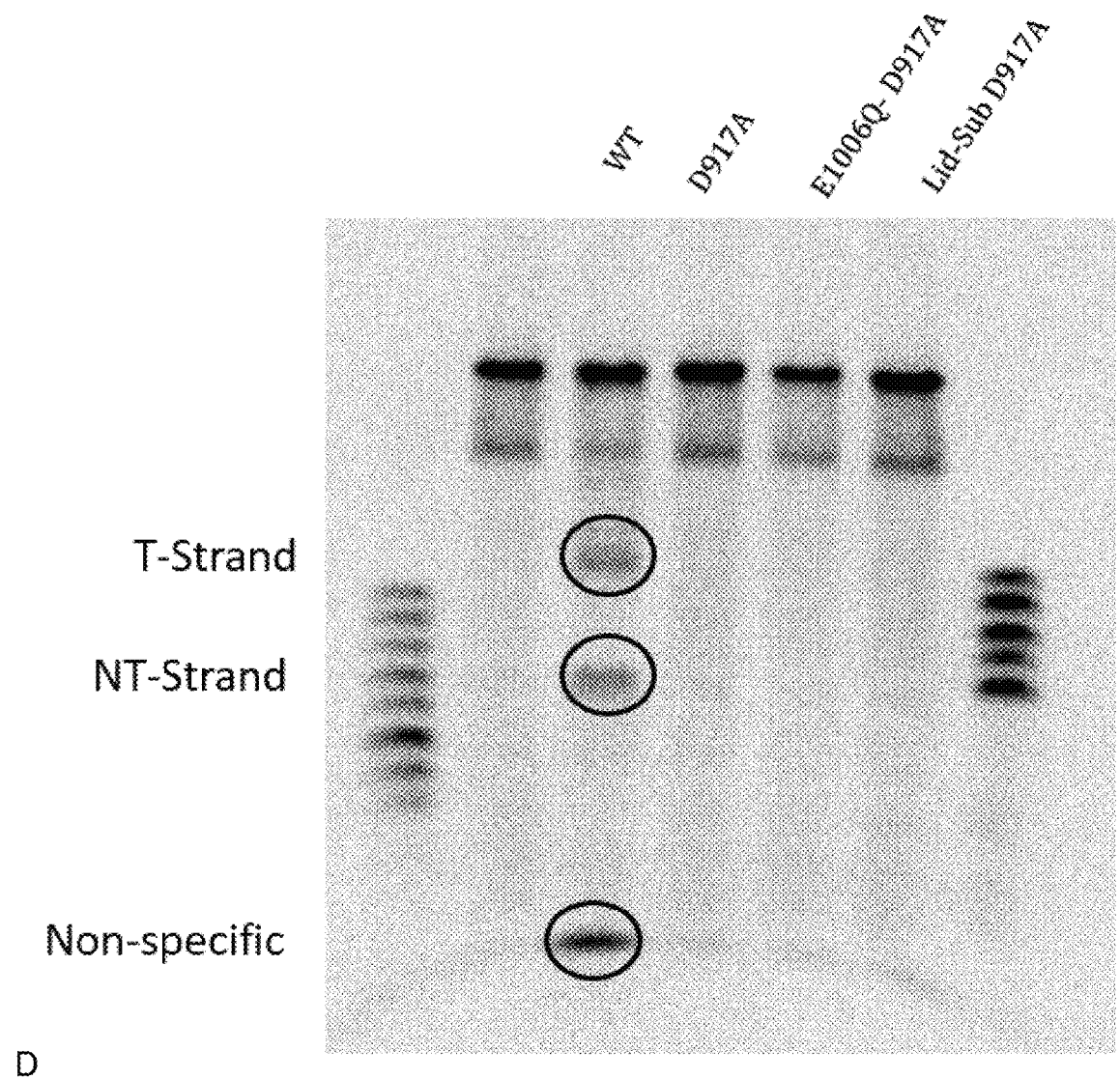
Figure 6:
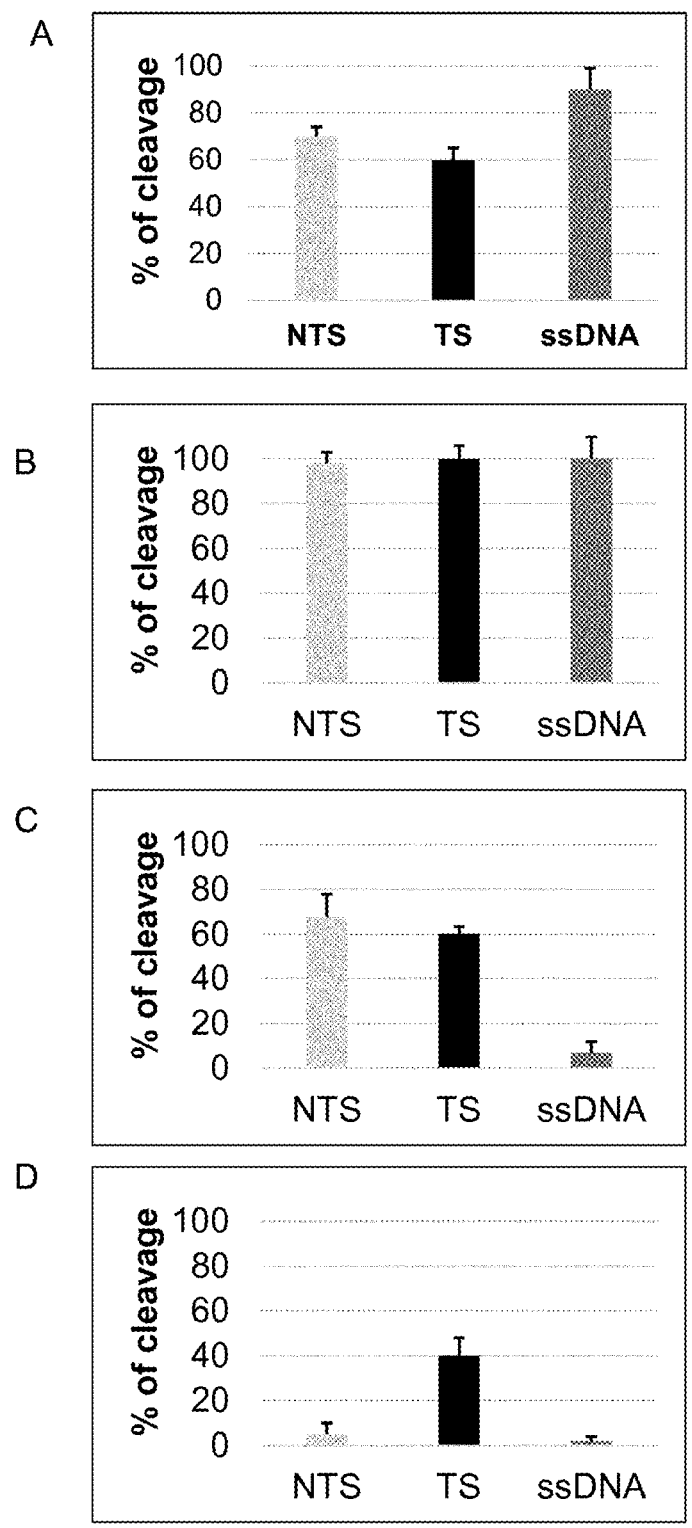
FIG. 6. A. Quantification of the cleavage activities: NTS (Non-Target Strand), TS (Target Strand) and ssDNA (non-specific single strand) of Cas12a wild type (cas12aWT); B. Cpf1 Q1025G (SEQ ID NO: 30); C. Cpf1 Q1025G-E1028G (SEQ ID NO: 32); D. nickase Cpf1 K1013G-R1014G (SEQ ID NO: 3). Each bar represents the average of at least 3 independent replicates and the standard deviation is shown.

The FnCpf1 wild type protein is able to cut both the t-strand and nt-strand (FIGS. 2-4 and 6). Mutant 1 (SEQ ID NO: 3; K1013-R1014Cpf1) is able to cut only the t-strand (FIGS. 2, 4 and 6D). This mutant is useful as a nickase.

The FnCpf1 wild type protein is able to cut non-specific ssDNA after activation with the double strand DNA-target (FIGS. 3, 4). Mutant 2 (SEQ ID NO: 4; R918G-K1013G) is not able to cut the specific DNA-target, neither as ssDNA nor as ddDNA, as well as the nt-strand, but is able to cut the non-specific ssDNA (FIGS. 3, 4).

The Cpf1 Q1025G mutant (SEQ ID NO: 30) is able to cut both the target-strand and the non-target strand when they are in the double strand DNA form more efficiently than the wild type. The mutant shows increased capacity for cutting the target-strand alone as single strand DNA (FIGS. 4A and B, and 6B). This mutant is able to cut non-specific ssDNA after activation with the double strand DNA-target and single-stranded DNA target. This mutant is useful for genome editing.

The Cpf1 Q1025G E1028G Mutant (SEQ ID NO: 32) is able to cut both the target-strand and non-target strand when they are in the double strand DNA form. The mutant shows a reduced capacity for cutting the target-strand alone as single strand DNA (FIG. 4A, B, and 6C). This mutant does not seem able to cut non-specific single-stranded DNA after activation with the double strand DNA-target. This mutant can be used for genome editing in a safer way because it does not have non-specific ssDNA activity that can be dangerous for the cells. The presence of non-specific nucleases that induce breaks in ssDNA can cut DNA during duplication, replication and transcription thus possibly generating random breaks in the genome of the cell and therefore inducing undesired mutations, genomic damage and cytotoxicity.

A Cpf1 mutant carrying a deletion of the entire REC domain (SEQ ID NO: 34) is NOT able to cut neither the target-strand nor the non-target strand. The mutant shows a reduced capacity for cutting the target strand alone as single strand DNA (FIG. 4A, B). This mutant is able to cut non-specific ssDNA after activation with the double strand DNA-target. It does not cut the activator so this protein will retain non-specific ssDNA activity longer compared to the wild type.

A Cpf1 mutant carrying a substituted REC domain (SEQ ID NO: 36) is NOT able to cut the target-strand or the non-target-strand when they are in the double strand DNA form. The mutant shows a reduced capacity for cutting the target-strand alone as single strand DNA. The mutant is able to cut non-specific ssDNA after activation with the double strand and single strand DNA-target. It does not cut the activator so this protein will retain non-specific ssDNA activity longer compared to the wild type.

A Cpf1 mutant carrying a substitution of the Lid domain (SEQ ID NO: 38) is NOT able to cut the target-strand and the non-target-strand when they are in the double strand DNA form. The mutant is not able to cut the target-strand alone as single strand DNA (FIG. 4A, B). The mutant is able to cut non-specific ssDNA although with a low activity. The entire Lid region seems to be important for the activity of the protein mutation in this region will induce changes in the activity of the protein. Interestingly, activity of this mutant carrying a substitution of the Lid domain is preserved despite substitution of the E1006. The present inventors have surprisingly found that if the entire Lid domain, including E1006, is substituted, activity is preserved provided that the residue corresponding to position 917 of the wild type FnCpf1 is non-substituted, or at the most substituted from an aspartate (D) to a glutamate (E).

A Cpf1 mutant carrying a deletion of the entire Lid domain (SEQ ID NO: 40) is not soluble (FIG. 5).

A Cpf1 mutant carrying a deletion of the entire finger domain (SEQ ID NO: 42) is not soluble (FIG. 5).

REFERENCES

Chen, J. S., Ma, E., Harrington, L. B., Da Costa, M., Tian, X., Palefsky, J. M., and Doudna, J. A. (2018). CRISPR-Cas12a target binding unleashes indiscriminate single-stranded DNase activity. Science. April 27; 360(6387): 436-439.

Fonfara, I., Richter, H., Bratovic, M., Le Rhun, A., and Charpentier, E. (2016). The CRISPR-associated DNA-cleaving enzyme Cpf1 also processes precursor CRISPR RNA. Nature 532, 517-521.

Makarova, K. S., Aravind, L., Wolf, Y. I., and Koonin, E. V. (2011). Unification of Cas protein families and a simple scenario for the origin and evolution of CRISPR-Cas systems. Biol Direct 6, 38.

Makarova, K. S., and Koonin, E. V. (2015). Annotation and Classification of CRISPR-Cas Systems. Methods Mol Biol 1311, 47-75.

Mojica, F. J., Diez-Villasenor, C., Garcia-Martinez, J., and Soria, E. (2005). Intervening sequences of regularly spaced prokaryotic repeats derive from foreign genetic elements. J Mol Evol 60, 174-182.

Vestergaard, G., Garrett, R. A., and Shah, S. A. (2014). CRISPR adaptive immune systems of Archaea. RNA Biol 11, 156-167.

Zetsche, B., Gootenberg, J. S., Abudayyeh, O. O., Slaymaker, I. M., Makarova, K. S., Essletzbichler, P., Volz, S. E., Joung, J., van der Oost, J., Regev, A., et al. (2015). Cpf1 Is a Single RNA-Guided Endonuclease of a Class 2 CRISPR-Cas System. Cell 163, 759-771.

Stella, S; Mesa, P; Thomsen, J; Paul, B; Alcón, P; Jensen, S B; Saligram, B; Moses, M E; Hatzakis, N S.; Montoya, G. (2018) Conformational Activation Promotes CRISPR-Cas12a Catalysis and Resetting of the Endonuclease Activity. Cell, 175(7) 1856-1871.

Sequence Overview

SEQ ID NO: 1 FnCpf1 DNA sequence
SEQ ID NO: 2 FnCpf1 amino acid sequence
SEQ ID NO: 3 Double mutant-Nickase, Cpf1 K1013G-R1014G
SEQ ID NO: 4 Double mutant-Nonspecific endonuclease, Cpf1 R918G-K1013G
SEQ ID NO: 5 crRNA constant region
SEQ ID NO: 6 t-strand
SEQ ID NO: 7 nt-strand
SEQ ID NO: 8 t-strand
SEQ ID NO: 9 nt-strand
SEQ ID NO: 10 crRNA
SEQ ID NO: 11 REC domain of FnCpf1, DNA sequence
SEQ ID NO: 12 REC domain of FnCpf1, amino acid sequence
SEQ ID NO: 13 mutated REC domain of FnCpf1, DNA sequence
SEQ ID NO: 14 mutated REC domain of FnCpf1, amino acid sequence
SEQ ID NO: 15 Lid domain of FnCpf1, DNA sequence
SEQ ID NO: 16 Lid domain of FnCpf1, amino acid sequence
SEQ ID NO: 17 mutated Lid domain of FnCpf1, DNA sequence
SEQ ID NO: 18 mutated Lid domain of FnCpf1, amino acid sequence
SEQ ID NO: 19 finger domain of FnCpf1, DNA sequence SEQ ID NO: 20 finger domain of FnCpf1, amino acid sequence
SEQ ID NO: 21 mutated finger domain of FnCpf1, DNA sequence
SEQ ID NO: 22 mutated finger domain of FnCpf1, amino acid sequence
SEQ ID NO: 23 labelled non-specific ssDNA
SEQ ID NO: 24 Cpf1 of *Acidaminococcus* sp. BV3L6
SEQ ID NO: 25 Cpf1 of *Lachnospiraceae bacterium* COE1
SEQ ID NO: 26 Cpf1 of *Succiniclasticum ruminis*
SEQ ID NO: 27 Cpf1 of *Butyrivibrio fibrisolvens*
SEQ ID NO: 28 non-specific ssDNA
SEQ ID NO: 29 FnCpf1 Q1025G mutant
SEQ ID NO: 30 FnCpf1 Q1025G mutant
SEQ ID NO: 31 FnCpf1 Q1025G E1028G mutant
SEQ ID NO: 32 FnCpf1 Q1025G E1028G mutant
SEQ ID NO: 33 Rec-deletion mutant FnCpf1
SEQ ID NO: 34 Rec-deletion mutant FnCpf1
SEQ ID NO: 35 Rec-substitution FnCpf1 mutant
SEQ ID NO: 36 Rec-substitution FnCpf1 mutant
SEQ ID NO: 37 LID-substitution FnCpf1 mutant
SEQ ID NO: 38 LID-substitution FnCpf1 mutant
SEQ ID NO: 39 LID-Deletion FnCpf1 mutant
SEQ ID NO: 40 LID-Deletion FnCpf1 mutant
SEQ ID NO: 41 Finger-deletion FnCpf1 mutant
SEQ ID NO: 42 Finger-deletion FnCpf1 mutant
SEQ ID NO: 43 Cpf1 of *Candidatus Methanoplasma termitum*
SEQ ID NO: 44 Cpf1 of uncultured *Clostridium* sp.

The invention claimed is:

1. A mutant Cpf1 comprising a polypeptide sequence that comprises at least two amino acid substitutions in two positions selected from the positions corresponding to residues 918, 1013, 1014, 1025, and 1028 of SEQ ID NO: 2, wherein the mutant Cpf1 exhibits endonuclease activity.

2. The mutant Cpf1 of claim 1, wherein the mutant Cpf1 endonuclease exhibits endonuclease activity upon a target dsDNA sequence to cleave both strands of the target dsDNA.

3. The mutant Cpf1 of claim 1, wherein the mutant Cpf1 exhibits nickase activity upon a target dsDNA sequence to cleave one strand of the target dsDNA.

4. The mutant Cpf1 of claim 1, wherein the polypeptide sequence comprises at least one amino acid substitution or deletion in the Lid domain sequence, or at least two amino acid substitutions or deletions in the Lid domain sequence.

5. The mutant Cpf1 of claim 1, wherein the polypeptide sequence comprises at least one amino acid substitution or deletion in the REC domain sequence, or at least two amino acid substitutions or deletions in the REC domain sequence.

6. The mutant Cpf1 of claim 1, wherein the polypeptide sequence comprises at least one amino acid substitution or deletion in the finger domain sequence.

7. The mutant Cpf1 of claim 4, wherein the Lid domain sequence of the wild type Cpf1 corresponds to the sequence at positions 1006-1018 of SEQ ID NO: 2.

8. The mutant Cpf1 of claim 7, wherein the mutant Cpf1 comprises a substitution or deletion of the amino acid residues corresponding to positions 1013 and/or 1014 of SEQ ID NO: 2.

9. The mutant Cpf1 of claim 6, wherein the finger domain sequence of the wild type Cpf1 corresponds to the sequence at positions 298-309 of SEQ ID NO: 2.

10. The mutant Cpf1 of claim 5, wherein the REC domain sequence of the wild type Cpf1 corresponds to the sequence at positions 324-336 of SEQ ID NO: 2.

11. A polynucleotide encoding the mutant Cpf1 of claim 1.

12. A recombinant vector comprising the polynucleotide of claim 11.

13. A cell comprising and/or expressing the polynucleotide of claim 11.

14. The recombinant vector of claim 12, further comprising a nucleic acid encoding a guide RNA, wherein the guide RNA binds the encoded mutant Cpf1.

15. The mutant Cpf1 of claim 10, wherein the polypeptide sequence of the mutant Cpf1 comprises a deletion of 13 contiguous amino acids corresponding to positions 324 to 336 of SEQ ID NO: 2.

16. The mutant Cpf1 of claim 1, wherein the mutant Cpf1 exhibits non-specific single stranded DNase activity, and exhibits reduced endonuclease activity on target DNA compared to said endonuclease activity of wild type Cpf1.

* * * * *

SEQUENCE LISTING

```
<160> NUMBER OF SEQ ID NOS: 44

<210> SEQ ID NO 1
<211> LENGTH: 3990
<212> TYPE: DNA
<213> ORGANISM: Francisella novicida

<400> SEQUENCE: 1
atgtcaattt atcaagaatt tgttaataaa tatagtttaa gtaaaactct aagatttgag      60
ttaatcccac agggtaaaac acttgaaaac ataaaagcaa gaggtttgat tttagatgat     120
gagaaaagag ctaaagacta caaaaaggct aaacaaataa ttgataaata tcatcagttt     180
tttatagagg agatattaag ttcggtttgt attagcgaag atttattaca aaactattct     240
gatgtttatt ttaaacttaa aagagtgat gatgataatc tacaaaaaga ttttaaaagt     300
gcaaaagata cgataaagaa acaaatatct gaatatataa aggactcaga gaaatttaag     360
aatttgttta atcaaaacct tatcgatgct aaaaaagggc aagagtcaga tttaattcta     420
tggctaaagc aatctaagga taatggtata gaactattta aagccaatag tgatatcaca     480
gatatagatg aggcgttaga aataatcaaa tcttttaaag gttggacaac ttattttaag     540
ggttttcatg aaaatagaaa aaatgtttat agtagcaatg atattcctac atctattatt     600
tataggatag tagatgataa tttgcctaaa tttctagaaa ataaagctaa gtatgagagt     660
ttaaaagaca aagctccaga agctataaac tatgaacaaa ttaaaaaaga tttggcagaa     720
gagctaacct ttgatattga ctacaaaaca tctgaagtta atcaaagagt tttttcactt     780
gatgaagttt ttgagatagc aaactttaat aattatctaa atcaagtgg tattactaaa     840 tttaatacta ttattggtgg taaatttgta aatggtgaaa atacaaagag aaaaggtata     900
aatgaatata taaatctata ctcacagcaa ataaatgata aacactcaa aaatataaa     960 atgagtgttt tatttaagca aattttaagt gatacagaat ctaaatcttt tgtaattgat    1020
aagttagaag atgatagtga tgtagttaca acgatgcaaa gttttttatga gcaaatagca    1080 gcttttaaaa cagtagaaga aaaatctatt aagaaacac tatctttatt atttgatgat    1140
ttaaaagctc aaaaacttga tttgagtaaa atttatttta aaaatgataa atctcttact    1200
gatctatcac aacaagtttt tgatgattat agtgttattg gtacagcggt actagaatat    1260
ataactcaac aaatagcacc taaaaatctt gataacccta gtaagaaaga gcaagaatta    1320
atagccaaaa aaactgaaaa agcaaaatac ttatctctag aaactataaa gcttgcctta    1380
gaagaattta ataagcatag agatatagat aaacagtgta ggtttgaaga atacttgca    1440 aactttgcgg ctattccgat gatatttgat gaaatagctc aaaacaaaga caatttggca    1500
```

```
cagatatcta tcaaatatca aaatcaaggt aaaaaagacc tacttcaagc tagtgcggaa      1560
gatgatgtta aagctatcaa ggatctttta gatcaaacta ataatctctt acataaacta      1620
aaaatatttc atattagtca gtcagaagat aaggcaaata ttttagacaa ggatgagcat      1680
ttttatctag tatttgagga gtgctacttt gagctagcga atatagtgcc tctttataac      1740
aaaattagaa actatataac tcaaaagcca tatagtgatg agaaatttaa gctcaatttt      1800
gagaactcga ctttggctaa tggttgggat aaaaataaag agcctgacaa tacggcaatt      1860
ttatttatca agatgataa atattatctg gtgtgatga ataagaaaaa taacaaaata      1920
tttgatgata aagctatcaa agaaaataaa ggcgagggtt ataaaaaaat tgtttataaa      1980
cttttacctg gcgcaaataa aatgttacct aaggttttct tttctgctaa atctataaaa      2040
ttttataatc ctagtgaaga tatacttaga ataagaaatc attccacaca tacaaaaaat      2100
ggtagtcctc aaaaaggata tgaaaaattt gagtttaata ttgaagattg ccgaaaattt      2160
atagattttt ataaacagtc tataagtaag catccggagt ggaaagattt tggatttaga      2220
ttttctgata ctcaaagata taattctata gatgaatttt atagagaagt tgaaaatcaa      2280
ggctacaaac taacttttga aaatatatca gagagctata ttgatagcgt agttaatcag      2340
ggtaaattgt acctattcca aatctataat aaagattttt cagcttatag caaagggcga      2400
ccaaatctac atactttata ttggaaagcg ctgtttgatg agagaaatct tcaagatgtg      2460
gtttataagc taaatggtga ggcagagctt ttttatcgta acaatcaat acctaaaaaa      2520 atcactcacc cagctaaaga ggcaaatagc taataaaaaca aagataatcc taaaaaagag      2580 agtgttttg aatatgattt aatcaaagat aaacgcttta ctgaagataa gtttttcttt      2640
cactgtccta ttacaatcaa ttttaaatct agtggagcta ataagtttaa tgatgaaatc      2700
aatttattgc taaagaaaa agcaaatgat gttcatatat taagtataga tagaggtgaa      2760
agacatttag cttactatac tttggtagat ggtaaaggca atatcatcaa acaagatact      2820
ttcaacatca ttggtaatga tagaatgaaa acaaactacc atgataagct tgctgcaata      2880
gagaaagata gggattcagc taggaaagac tggaaaaaga taaataacat caaagagatg      2940
aaagagggct atctatctca ggtagttcat gaaatagcta agctagttat agagtataat      3000
gctattgtgg tttttgagga tttaaatttt ggatttaaaa gagggcgttt caaggtagag      3060
aagcaggtct atcaaaagtt agaaaaaatg ctaattgaga aactaaacta tctagttttc      3120
aaagataatg agtttgataa aactggggga gtgcttagag cttatcagct aacagcacct      3180
tttgagactt ttaaaagat gggtaaacaa acaggtatta tctactatgt accagctggt      3240
tttacttcaa aaatttgtcc tgtaactggt tttgtaaatc agttatatcc taagtatgaa      3300
agtgtcagca atctcaaga gttctttagt aagtttgaca agatttgtta taaccttgat      3360
aagggctatt ttgagtttag ttttgattat aaaaactttg gtgacaaggc tgccaaaggc      3420
aagtggacta tagctagctt tgggagtaga ttgattaact ttagaaattc agataaaaat      3480
cataattggg atactcgaga agtttatcca actaaagagt ggagaaaatt gctaaaagat      3540
tattctatcg aatatgggca tggcgaatgt atcaaagcag ctatttgcgg tgagagcgac      3600
aaaaagtttt ttgctaagct aactagtgtc ctaaatacta tcttacaaat gcgtaactca      3660
aaaacaggta ctgagttaga ttatctaatt tcaccagtag cagatgtaaa tggcaatttc      3720
tttgattcgc gacaggcgcc aaaaaatatg cctcaagatg ctgatgccaa tggtgcttat      3780
catattgggc taaaaggtct gatgctacta ggtaggatca aaaataatca agagggcaaa      3840
```

```
aaactcaatt tggttatcaa aaatgaagag tattttgagt tcgtgcagaa taggaataac    3900
ggatccgaat tcgagctcga aaatctgtac tttcaaggcg agctccgtcg acaagcttct    3960
gctctggaac accaccatca tcatcactaa                                     3990
```

<210> SEQ ID NO 2
<211> LENGTH: 1329
<212> TYPE: PRT
<213> ORGANISM: Francisella novicida

<400> SEQUENCE: 2

```
Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
                20                  25                  30

Ala Arg Gly Leu Ile Leu Asp Asp Glu Lys Arg Ala Lys Asp Tyr Lys
            35                  40                  45

Lys Ala Lys Gln Ile Ile Asp Lys Tyr His Gln Phe Phe Ile Glu Glu
        50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350
```

```
Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
                420                 425                 430

Pro Ser Lys Lys Glu Gln Glu Leu Ile Ala Lys Lys Thr Glu Lys Ala
                435                 440                 445

Lys Tyr Leu Ser Leu Glu Thr Ile Lys Leu Ala Leu Glu Glu Phe Asn
                450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                    485                 490                 495

Asp Asn Leu Ala Gln Ile Ser Ile Lys Tyr Gln Asn Gly Lys Lys
                500                 505                 510

Asp Leu Leu Gln Ala Ser Ala Glu Asp Val Lys Ala Ile Lys Asp
                515                 520                 525

Leu Leu Asp Gln Thr Asn Asn Leu Leu His Lys Leu Lys Ile Phe His
                530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                    565                 570                 575

Pro Leu Tyr Asn Lys Ile Arg Asn Tyr Ile Thr Gln Lys Pro Tyr Ser
                580                 585                 590

Asp Glu Lys Phe Lys Leu Asn Phe Glu Asn Ser Thr Leu Ala Asn Gly
                595                 600                 605

Trp Asp Lys Asn Lys Glu Pro Asp Asn Thr Ala Ile Leu Phe Ile Lys
        610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                    645                 650                 655

Ile Val Tyr Lys Leu Leu Pro Gly Ala Asn Lys Met Leu Pro Lys Val
                660                 665                 670

Phe Phe Ser Ala Lys Ser Ile Lys Phe Tyr Asn Pro Ser Glu Asp Ile
                675                 680                 685

Leu Arg Ile Arg Asn His Ser Thr His Thr Lys Asn Gly Ser Pro Gln
        690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                    725                 730                 735

Phe Gly Phe Arg Phe Ser Asp Thr Gln Arg Tyr Asn Ser Ile Asp Glu
                    740                 745                 750

Phe Tyr Arg Glu Val Glu Asn Gln Gly Tyr Lys Leu Thr Phe Glu Asn
                755                 760                 765
```

```
Ile Ser Glu Ser Tyr Ile Asp Ser Val Val Asn Gln Gly Lys Leu Tyr
    770                 775                 780
Leu Phe Gln Ile Tyr Asn Lys Asp Phe Ser Ala Tyr Ser Lys Gly Arg
785                 790                 795                 800
Pro Asn Leu His Thr Leu Tyr Trp Lys Ala Leu Phe Asp Glu Arg Asn
                805                 810                 815
Leu Gln Asp Val Val Tyr Lys Leu Asn Gly Glu Ala Glu Leu Phe Tyr
                820                 825                 830
Arg Lys Gln Ser Ile Pro Lys Lys Ile Thr His Pro Ala Lys Glu Ala
                835                 840                 845
Ile Ala Asn Lys Asn Lys Asp Asn Pro Lys Lys Glu Ser Val Phe Glu
850                 855                 860
Tyr Asp Leu Ile Lys Asp Lys Arg Phe Thr Glu Asp Lys Phe Phe Phe
865                 870                 875                 880
His Cys Pro Ile Thr Ile Asn Phe Lys Ser Ser Gly Ala Asn Lys Phe
                885                 890                 895
Asn Asp Glu Ile Asn Leu Leu Leu Lys Glu Lys Ala Asn Asp Val His
                900                 905                 910
Ile Leu Ser Ile Asp Arg Gly Glu Arg His Leu Ala Tyr Tyr Thr Leu
                915                 920                 925
Val Asp Gly Lys Gly Asn Ile Ile Lys Gln Asp Thr Phe Asn Ile Ile
930                 935                 940
Gly Asn Asp Arg Met Lys Thr Asn Tyr His Asp Lys Leu Ala Ala Ile
945                 950                 955                 960
Glu Lys Asp Arg Asp Ser Ala Arg Lys Asp Trp Lys Lys Ile Asn Asn
                965                 970                 975
Ile Lys Glu Met Lys Glu Gly Tyr Leu Ser Gln Val Val His Glu Ile
                980                 985                 990
Ala Lys Leu Val Ile Glu Tyr Asn Ala Ile Val Val Phe Glu Asp Leu
                995                 1000                1005
Asn Phe Gly Phe Lys Arg Gly Arg Phe Lys Val Glu Lys Gln Val
            1010                1015                1020
Tyr Gln Lys Leu Glu Lys Met Leu Ile Glu Lys Leu Asn Tyr Leu
            1025                1030                1035
Val Phe Lys Asp Asn Glu Phe Asp Lys Thr Gly Gly Val Leu Arg
            1040                1045                1050
Ala Tyr Gln Leu Thr Ala Pro Phe Glu Thr Phe Lys Lys Met Gly
            1055                1060                1065
Lys Gln Thr Gly Ile Ile Tyr Tyr Val Pro Ala Gly Phe Thr Ser
            1070                1075                1080
Lys Ile Cys Pro Val Thr Gly Phe Val Asn Gln Leu Tyr Pro Lys
            1085                1090                1095
Tyr Glu Ser Val Ser Lys Ser Gln Glu Phe Phe Ser Lys Phe Asp
            1100                1105                1110
Lys Ile Cys Tyr Asn Leu Asp Lys Gly Tyr Phe Glu Phe Ser Phe
            1115                1120                1125
Asp Tyr Lys Asn Phe Gly Asp Lys Ala Ala Lys Gly Lys Trp Thr
            1130                1135                1140
Ile Ala Ser Phe Gly Ser Arg Leu Ile Asn Phe Arg Asn Ser Asp
            1145                1150                1155
Lys Asn His Asn Trp Asp Thr Arg Glu Val Tyr Pro Thr Lys Glu
            1160                1165                1170
Leu Glu Lys Leu Leu Lys Asp Tyr Ser Ile Glu Tyr Gly His Gly
```

```
                    1175                1180                1185
Glu Cys Ile Lys Ala Ala Ile Cys Gly Glu Ser Asp Lys Lys Phe
        1190                1195                1200
Phe Ala Lys Leu Thr Ser Val Leu Asn Thr Ile Leu Gln Met Arg
        1205                1210                1215
Asn Ser Lys Thr Gly Thr Glu Leu Asp Tyr Leu Ile Ser Pro Val
        1220                1225                1230
Ala Asp Val Asn Gly Asn Phe Phe Asp Ser Arg Gln Ala Pro Lys
        1235                1240                1245
Asn Met Pro Gln Asp Ala Asp Ala Asn Gly Ala Tyr His Ile Gly
        1250                1255                1260
Leu Lys Gly Leu Met Leu Leu Gly Arg Ile Lys Asn Asn Gln Glu
        1265                1270                1275
Gly Lys Lys Leu Asn Leu Val Ile Lys Asn Glu Glu Tyr Phe Glu
        1280                1285                1290
Phe Val Gln Asn Arg Asn Asn Gly Ser Glu Phe Glu Leu Glu Asn
        1295                1300                1305
Leu Tyr Phe Gln Gly Glu Leu Arg Arg Gln Ala Ser Ala Leu Glu
        1310                1315                1320
His His His His His His
        1325

<210> SEQ ID NO 3
<211> LENGTH: 1329
<212> TYPE: PRT
<213> ORGANISM: Artificial sequence
<220> FEATURE:
<223> OTHER INFORMATION: Double mutant - Nickase
<220> FEATURE:
<221> NAME/KEY: PEPTIDE
<222> LOCATION: (1)..(1329)
<223> OTHER INFORMATION: Double mutant - Nickase

<400> SEQUENCE: 3

Met Ser Ile Tyr Gln Glu Phe Val Asn Lys Tyr Ser Leu Ser Lys Thr
1               5                   10                  15
Leu Arg Phe Glu Leu Ile Pro Gln Gly Lys Thr Leu Glu Asn Ile Lys
            20                  25                  30
Ala Arg Gly Leu Ile Leu Asp Asp Glu Lys Arg Ala Lys Asp Tyr Lys
        35                  40                  45
Lys Ala Lys Gln Ile Ile Asp Lys Tyr His Gln Phe Phe Ile Glu Glu
    50                  55                  60
Ile Leu Ser Ser Val Cys Ile Ser Glu Asp Leu Leu Gln Asn Tyr Ser
65                  70                  75                  80
Asp Val Tyr Phe Lys Leu Lys Lys Ser Asp Asp Asn Leu Gln Lys
                85                  90                  95
Asp Phe Lys Ser Ala Lys Asp Thr Ile Lys Lys Gln Ile Ser Glu Tyr
            100                 105                 110
Ile Lys Asp Ser Glu Lys Phe Lys Asn Leu Phe Asn Gln Asn Leu Ile
        115                 120                 125
Asp Ala Lys Lys Gly Gln Glu Ser Asp Leu Ile Leu Trp Leu Lys Gln
    130                 135                 140
Ser Lys Asp Asn Gly Ile Glu Leu Phe Lys Ala Asn Ser Asp Ile Thr
145                 150                 155                 160
Asp Ile Asp Glu Ala Leu Glu Ile Ile Lys Ser Phe Lys Gly Trp Thr
                165                 170                 175
```

```
Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
            195                 200                 205

Pro Lys Phe Leu Glu Asn Lys Ala Lys Tyr Glu Ser Leu Lys Asp Lys
210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
            245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
            275                 280                 285

Phe Val Asn Gly Glu Asn Thr Lys Arg Lys Gly Ile Asn Glu Tyr Ile
            290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
            325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
            355                 360                 365

Ser Ile Lys Glu Thr Leu Ser Leu Leu Phe Asp Asp Leu Lys Ala Gln
            370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
            405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
            435                 440                 445

Lys Tyr Leu Ser Leu Glu Thr Ile Lys Leu Ala Leu Glu Glu Phe Asn
450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
            485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
            515                 520                 525

Leu Leu Asp Gln Thr Asn Asn Leu Leu His Lys Leu Lys Ile Phe His
            530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
            565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
```

```
            595                 600                 605

Trp Asp Lys Asn Lys Glu Pro Asp Asn Thr Ala Ile Leu Phe Ile Lys
610                 615                 620

Asp Asp Lys Tyr Tyr Leu Gly Val Met Asn Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
                660                 665                 670

Phe Phe Ser Ala Lys Ser Ile Lys Phe Tyr Asn Pro Ser Glu Asp Ile
                675                 680                 685

Leu Arg Ile Arg Asn His Ser Thr His Thr Lys Asn Gly Ser Pro Gln
690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
                740                 745                 750

Phe Tyr Arg Glu Val Glu Asn Gln Gly Tyr Lys Leu Thr Phe Glu Asn
                755                 760                 765

Ile Ser Glu Ser Tyr Ile Asp Ser Val Val Asn Gln Gly Lys Leu Tyr
770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
                820                 825                 830

Arg Lys Gln Ser Ile Pro Lys Lys Ile Thr His Pro Ala Lys Glu Ala
                835                 840                 845

Ile Ala Asn Lys Asn Lys Asp Asn Pro Lys Lys Glu Ser Val Phe Glu
850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
                900                 905                 910

Ile Leu Ser Ile Asp Arg Gly Glu Arg His Leu Ala Tyr Tyr Thr Leu
                915                 920                 925

Val Asp Gly Lys Gly Asn Ile Ile Lys Gln Asp Thr Phe Asn Ile Ile
                930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
                980                 985                 990

Ala Lys Leu Val Ile Glu Tyr Asn Ala Ile Val Val Phe Glu Asp Leu
                995                 1000                1005

Asn Phe Gly Phe Gly Gly Gly Arg Phe Lys Val Glu Lys Gln Val
        1010                1015                1020
```

```
Tyr Gln Lys Leu Glu Lys Met Leu Ile Glu Lys Leu Asn Tyr Leu
    1025                1030                1035

Val Phe Lys Asp Asn Glu Phe Asp Lys Thr Gly Gly Val Leu Arg
    1040                1045                1050

Ala Tyr Gln Leu Thr Ala Pro Phe Glu Thr Phe Lys Lys Met Gly
    1055                1060                1065

Lys Gln Thr Gly Ile Ile Tyr Tyr Val Pro Ala Gly Phe Thr Ser
    1070                1075                1080

Lys Ile Cys Pro Val Thr Gly Phe Val Asn Gln Leu Tyr Pro Lys
    1085                1090                1095

Tyr Glu Ser Val Ser Lys Ser Gln Glu Phe Phe Ser Lys Phe Asp
    1100                1105                1110

Lys Ile Cys Tyr Asn Leu Asp Lys Gly Tyr Phe Glu Phe Ser Phe
    1115                1120                1125

Asp Tyr Lys Asn Phe Gly Asp Lys Ala Ala Lys Gly Lys Trp Thr
    1130                1135                1140

Ile Ala Ser Phe Gly Ser Arg Leu Ile Asn Phe Arg Asn Ser Asp
    1145                1150                1155

Lys Asn His Asn Trp Asp Thr Arg Glu Val Tyr Pro Thr Lys Glu
    1160                1165                1170

Leu Glu Lys Leu Leu Lys Asp Tyr Ser Ile Glu Tyr Gly His Gly
    1175                1180                1185

Glu Cys Ile Lys Ala Ala Ile Cys Gly Glu Ser Asp Lys Lys Phe
    1190                1195                1200

Phe Ala Lys Leu Thr Ser Val Leu Asn Thr Ile Leu Gln Met Arg
    1205                1210                1215

Asn Ser Lys Thr Gly Thr Glu Leu Asp Tyr Leu Ile Ser Pro Val
    1220                1225                1230

Ala Asp Val Asn Gly Asn Phe Phe Asp Ser Arg Gln Ala Pro Lys
    1235                1240                1245

Asn Met Pro Gln Asp Ala Asp Ala Asn Gly Ala Tyr His Ile Gly
    1250                1255                1260

Leu Lys Gly Leu Met Leu Leu Gly Arg Ile Lys Asn Asn Gln Glu
    1265                1270                1275

Gly Lys Lys Leu Asn Leu Val Ile Lys Asn Glu Glu Tyr Phe Glu
    1280                1285                1290

Phe Val Gln Asn Arg Asn Asn Gly Ser Glu Phe Glu Leu Glu Asn
    1295                1300                1305

Leu Tyr Phe Gln Gly Glu Leu Arg Arg Gln Ala Ser Ala Leu Glu
    1310                1315                1320

His His His His His His
    1325

<210> SEQ ID NO 4
<211> LENGTH: 1329
<212> TYPE: PRT
<213> ORGANISM: Artificial sequence
<220> FEATURE:
<223> OTHER INFORMATION: Double mutant - Non specific endonuclease
<220> FEATURE:
<221> NAME/KEY: PEPTIDE
<222> LOCATION: (1)..(1329)
<223> OTHER INFORMATION: Double mutant - Non specific endonuclease

<400> SEQUENCE: 4

Met Ser Ile Tyr Gln Glu Phe Val Asn Lys Tyr Ser Leu Ser Lys Thr
```

```
            1               5                  10                 15
Leu Arg Phe Glu Leu Ile Pro Gln Gly Lys Thr Leu Glu Asn Ile Lys
                20                 25                 30
Ala Arg Gly Leu Ile Leu Asp Asp Glu Lys Arg Ala Lys Asp Tyr Lys
                35                 40                 45
Lys Ala Lys Gln Ile Ile Asp Lys Tyr His Gln Phe Phe Ile Glu Glu
 50                 55                 60
Ile Leu Ser Ser Val Cys Ile Ser Glu Asp Leu Leu Gln Asn Tyr Ser
 65                 70                 75                 80
Asp Val Tyr Phe Lys Leu Lys Lys Ser Asp Asp Asn Leu Gln Lys
                85                 90                 95
Asp Phe Lys Ser Ala Lys Asp Thr Ile Lys Lys Gln Ile Ser Glu Tyr
                100                105                110
Ile Lys Asp Ser Glu Lys Phe Lys Asn Leu Phe Asn Gln Asn Leu Ile
                115                120                125
Asp Ala Lys Lys Gly Gln Glu Ser Asp Leu Ile Leu Trp Leu Lys Gln
                130                135                140
Ser Lys Asp Asn Gly Ile Glu Leu Phe Lys Ala Asn Ser Asp Ile Thr
145                 150                155                160
Asp Ile Asp Glu Ala Leu Glu Ile Ile Lys Ser Phe Lys Gly Trp Thr
                165                170                175
Thr Tyr Phe Lys Gly Phe His Glu Asn Arg Lys Asn Val Tyr Ser Ser
                180                185                190
Asn Asp Ile Pro Thr Ser Ile Ile Tyr Arg Ile Val Asp Asp Asn Leu
                195                200                205
Pro Lys Phe Leu Glu Asn Lys Ala Lys Tyr Glu Ser Leu Lys Asp Lys
                210                215                220
Ala Pro Glu Ala Ile Asn Tyr Glu Gln Ile Lys Lys Asp Leu Ala Glu
225                 230                235                240
Glu Leu Thr Phe Asp Ile Asp Tyr Lys Thr Ser Glu Val Asn Gln Arg
                245                250                255
Val Phe Ser Leu Asp Glu Val Phe Glu Ile Ala Asn Phe Asn Asn Tyr
                260                265                270
Leu Asn Gln Ser Gly Ile Thr Lys Phe Asn Thr Ile Ile Gly Gly Lys
                275                280                285
Phe Val Asn Gly Glu Asn Thr Lys Arg Lys Gly Ile Asn Glu Tyr Ile
                290                295                300
Asn Leu Tyr Ser Gln Gln Ile Asn Asp Lys Thr Leu Lys Lys Tyr Lys
305                 310                315                320
Met Ser Val Leu Phe Lys Gln Ile Leu Ser Asp Thr Glu Ser Lys Ser
                325                330                335
Phe Val Ile Asp Lys Leu Glu Asp Ser Asp Val Val Thr Thr Met
                340                345                350
Gln Ser Phe Tyr Glu Gln Ile Ala Ala Phe Lys Thr Val Glu Glu Lys
                355                360                365
Ser Ile Lys Glu Thr Leu Ser Leu Leu Phe Asp Asp Leu Lys Ala Gln
                370                375                380
Lys Leu Asp Leu Ser Lys Ile Tyr Phe Lys Asn Asp Lys Ser Leu Thr
385                 390                395                400
Asp Leu Ser Gln Gln Val Phe Asp Asp Tyr Ser Val Ile Gly Thr Ala
                405                410                415
Val Leu Glu Tyr Ile Thr Gln Gln Ile Ala Pro Lys Asn Leu Asp Asn
                420                425                430
```

```
Pro Ser Lys Lys Glu Gln Glu Leu Ile Ala Lys Lys Thr Glu Lys Ala
            435                 440                 445
Lys Tyr Leu Ser Leu Glu Thr Ile Lys Leu Ala Leu Glu Glu Phe Asn
            450                 455                 460
Lys His Arg Asp Ile Asp Lys Gln Cys Arg Phe Glu Glu Ile Leu Ala
465                 470                 475                 480
Asn Phe Ala Ala Ile Pro Met Ile Phe Asp Glu Ile Ala Gln Asn Lys
                        485                 490                 495
Asp Asn Leu Ala Gln Ile Ser Ile Lys Tyr Gln Asn Gln Gly Lys Lys
                    500                 505                 510
Asp Leu Leu Gln Ala Ser Ala Glu Asp Val Lys Ala Ile Lys Asp
                515                 520                 525
Leu Leu Asp Gln Thr Asn Asn Leu Leu His Lys Leu Lys Ile Phe His
            530                 535                 540
Ile Ser Gln Ser Glu Asp Lys Ala Asn Ile Leu Asp Lys Asp Glu His
545                 550                 555                 560
Phe Tyr Leu Val Phe Glu Glu Cys Tyr Phe Glu Leu Ala Asn Ile Val
                        565                 570                 575
Pro Leu Tyr Asn Lys Ile Arg Asn Tyr Ile Thr Gln Lys Pro Tyr Ser
                580                 585                 590
Asp Glu Lys Phe Lys Leu Asn Phe Glu Asn Ser Thr Leu Ala Asn Gly
            595                 600                 605
Trp Asp Lys Asn Lys Glu Pro Asp Asn Thr Ala Ile Leu Phe Ile Lys
            610                 615                 620
Asp Asp Lys Tyr Tyr Leu Gly Val Met Asn Lys Lys Asn Asn Lys Ile
625                 630                 635                 640
Phe Asp Asp Lys Ala Ile Lys Glu Asn Lys Gly Glu Gly Tyr Lys Lys
                        645                 650                 655
Ile Val Tyr Lys Leu Leu Pro Gly Ala Asn Lys Met Leu Pro Lys Val
                660                 665                 670
Phe Phe Ser Ala Lys Ser Ile Lys Phe Tyr Asn Pro Ser Glu Asp Ile
            675                 680                 685
Leu Arg Ile Arg Asn His Ser Thr His Thr Lys Asn Gly Ser Pro Gln
            690                 695                 700
Lys Gly Tyr Glu Lys Phe Glu Phe Asn Ile Glu Asp Cys Arg Lys Phe
705                 710                 715                 720
Ile Asp Phe Tyr Lys Gln Ser Ile Ser Lys His Pro Glu Trp Lys Asp
                        725                 730                 735
Phe Gly Phe Arg Phe Ser Asp Thr Gln Arg Tyr Asn Ser Ile Asp Glu
                740                 745                 750
Phe Tyr Arg Glu Val Glu Asn Gln Gly Tyr Lys Leu Thr Phe Glu Asn
            755                 760                 765
Ile Ser Glu Ser Tyr Ile Asp Ser Val Val Asn Gln Gly Lys Leu Tyr
            770                 775                 780
Leu Phe Gln Ile Tyr Asn Lys Asp Phe Ser Ala Tyr Ser Lys Gly Arg
785                 790                 795                 800
Pro Asn Leu His Thr Leu Tyr Trp Lys Ala Leu Phe Asp Glu Arg Asn
                        805                 810                 815
Leu Gln Asp Val Val Tyr Lys Leu Asn Gly Glu Ala Glu Leu Phe Tyr
                820                 825                 830
Arg Lys Gln Ser Ile Pro Lys Lys Ile Thr His Pro Ala Lys Glu Ala
            835                 840                 845
```

-continued

```
Ile Ala Asn Lys Asn Lys Asp Asn Pro Lys Lys Glu Ser Val Phe Glu
    850             855             860

Tyr Asp Leu Ile Lys Asp Lys Arg Phe Thr Glu Asp Lys Phe Phe Phe
865             870             875             880

His Cys Pro Ile Thr Ile Asn Phe Lys Ser Ser Gly Ala Asn Lys Phe
                885             890             895

Asn Asp Glu Ile Asn Leu Leu Leu Lys Glu Lys Ala Asn Asp Val His
            900             905             910

Ile Leu Ser Ile Asp Gly Gly Glu Arg His Leu Ala Tyr Tyr Thr Leu
            915             920             925

Val Asp Gly Lys Gly Asn Ile Ile Lys Gln Asp Thr Phe Asn Ile Ile
    930             935             940

Gly Asn Asp Arg Met Lys Thr Asn Tyr His Asp Lys Leu Ala Ala Ile
945             950             955             960

Glu Lys Asp Arg Asp Ser Ala Arg Lys Asp Trp Lys Lys Ile Asn Asn
                965             970             975

Ile Lys Glu Met Lys Glu Gly Tyr Leu Ser Gln Val Val His Glu Ile
            980             985             990

Ala Lys Leu Val Ile Glu Tyr Asn  Ala Ile Val Val Phe  Glu Asp Leu
            995             1000            1005

Asn Phe  Gly Phe Gly Arg Gly  Arg Phe Lys Val Glu  Lys Gln Val
    1010            1015            1020

Tyr Gln  Lys Leu Glu Lys Met  Leu Ile Glu Lys Leu  Asn Tyr Leu
    1025            1030            1035

Val Phe  Lys Asp Asn Glu Phe  Asp Lys Thr Gly Gly  Val Leu Arg
    1040            1045            1050

Ala Tyr  Gln Leu Thr Ala Pro  Phe Glu Thr Phe Lys  Lys Met Gly
    1055            1060            1065

Lys Gln  Thr Gly Ile Ile Tyr  Tyr Val Pro Ala Gly  Phe Thr Ser
    1070            1075            1080

Lys Ile  Cys Pro Val Thr Gly  Phe Val Asn Gln Leu  Tyr Pro Lys
    1085            1090            1095

Tyr Glu  Ser Val Ser Lys Ser  Gln Glu Phe Phe Ser  Lys Phe Asp
    1100            1105            1110

Lys Ile  Cys Tyr Asn Leu Asp  Lys Gly Tyr Phe Glu  Phe Ser Phe
    1115            1120            1125

Asp Tyr  Lys Asn Phe Gly Asp  Lys Ala Ala Lys Gly  Lys Trp Thr
    1130            1135            1140

Ile Ala  Ser Phe Gly Ser Arg  Leu Ile Asn Phe Arg  Asn Ser Asp
    1145            1150            1155

Lys Asn  His Asn Trp Asp Thr  Arg Glu Val Tyr Pro  Thr Lys Glu
    1160            1165            1170

Leu Glu  Lys Leu Leu Lys Asp  Tyr Ser Ile Glu Tyr  Gly His Gly
    1175            1180            1185

Glu Cys  Ile Lys Ala Ala Ile  Cys Gly Glu Ser Asp  Lys Lys Phe
    1190            1195            1200

Phe Ala  Lys Leu Thr Ser Val  Leu Asn Thr Ile Leu  Gln Met Arg
    1205            1210            1215

Asn Ser  Lys Thr Gly Thr Glu  Leu Asp Tyr Leu Ile  Ser Pro Val
    1220            1225            1230

Ala Asp  Val Asn Gly Asn Phe  Phe Asp Ser Arg Gln  Ala Pro Lys
    1235            1240            1245

Asn Met  Pro Gln Asp Ala Asp  Ala Asn Gly Ala Tyr  His Ile Gly
```

```
              1250                1255                1260

Leu Lys  Gly Leu Met Leu Leu  Gly Arg Ile Lys  Asn Asn Gln Glu
   1265                1270                1275

Gly Lys  Lys Leu Asn Leu Val  Ile Lys Asn Glu  Glu Tyr Phe Glu
   1280                1285                1290

Phe Val  Gln Asn Arg Asn Asn  Gly Ser Glu Phe  Glu Leu Glu Asn
   1295                1300                1305

Leu Tyr  Phe Gln Gly Glu Leu  Arg Arg Gln Ala  Ser Ala Leu Glu
   1310                1315                1320

His His  His His His His
   1325

<210> SEQ ID NO 5
<211> LENGTH: 19
<212> TYPE: RNA
<213> ORGANISM: Artificial sequence
<220> FEATURE:
<223> OTHER INFORMATION: crRNA constant region
<220> FEATURE:
<221> NAME/KEY: misc_feature
<222> LOCATION: (1)..(19)
<223> OTHER INFORMATION: crRNA constant region

<400> SEQUENCE: 5
aauuucuacu guuguagau                                                   19

<210> SEQ ID NO 6
<211> LENGTH: 33
<212> TYPE: DNA
<213> ORGANISM: Artificial sequence
<220> FEATURE:
<223> OTHER INFORMATION: t-strand
<220> FEATURE:
<221> NAME/KEY: misc_feature
<222> LOCATION: (1)..(33)
<223> OTHER INFORMATION: t-strand

<400> SEQUENCE: 6
atgcagtggc cttattaaat gacttctcta acg                                   33

<210> SEQ ID NO 7
<211> LENGTH: 33
<212> TYPE: DNA
<213> ORGANISM: Artificial sequence
<220> FEATURE:
<223> OTHER INFORMATION: nt-strand
<220> FEATURE:
<221> NAME/KEY: misc_feature
<222> LOCATION: (1)..(33)
<223> OTHER INFORMATION: nt-strand

<400> SEQUENCE: 7
cgttagagaa gtcatttaat aaggccactg cat                                   33

<210> SEQ ID NO 8
<211> LENGTH: 33
<212> TYPE: DNA
<213> ORGANISM: Artificial sequence
<220> FEATURE:
<223> OTHER INFORMATION: t-strand
<220> FEATURE:
<221> NAME/KEY: misc_feature
<222> LOCATION: (1)..(1)
<223> OTHER INFORMATION: t-strand

<400> SEQUENCE: 8
```
atgcagtggc cttattaaat gacttctcta acg                              33

<210> SEQ ID NO 9
<211> LENGTH: 33
<212> TYPE: DNA
<213> ORGANISM: Artificial sequence
<220> FEATURE:
<223> OTHER INFORMATION: nt-strand
<220> FEATURE:
<221> NAME/KEY: misc_feature
<222> LOCATION: (1)..(33)
<223> OTHER INFORMATION: nt-strand

<400> SEQUENCE: 9
cgttagagaa gtcatttaat aaggccactg cat                              33

<210> SEQ ID NO 10
<211> LENGTH: 43
<212> TYPE: RNA
<213> ORGANISM: Artificial sequence
<220> FEATURE:
<223> OTHER INFORMATION: crRNA
<220> FEATURE:
<221> NAME/KEY: misc_feature
<222> LOCATION: (1)..(43)
<223> OTHER INFORMATION: crRNA

<400> SEQUENCE: 10
aauuucuacu guuguagauc accgagugca gccacucggc gcu                   43

<210> SEQ ID NO 11
<211> LENGTH: 39
<212> TYPE: DNA
<213> ORGANISM: Francisella novicida
<220> FEATURE:
<221> NAME/KEY: misc_feature
<222> LOCATION: (1)..(39)
<223> OTHER INFORMATION: DNA sequence of REC domain

<400> SEQUENCE: 11
ttatttaagc aaattttaag tgatacagaa tctaaatct                        39

<210> SEQ ID NO 12
<211> LENGTH: 13
<212> TYPE: PRT
<213> ORGANISM: Francisella novicida
<220> FEATURE:
<221> NAME/KEY: MISC_FEATURE
<222> LOCATION: (1)..(13)
<223> OTHER INFORMATION: amino acid sequence of REC domain

<400> SEQUENCE: 12

Leu Phe Lys Gln Ile Leu Ser Asp Thr Glu Ser Lys Ser
1               5                   10

<210> SEQ ID NO 13
<211> LENGTH: 39
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(39)
<223> OTHER INFORMATION: mutated REC domain, DNA sequence

<400> SEQUENCE: 13
ggtggtggag ccggtgcaag tgctggagga tctggatct                        39

```
<210> SEQ ID NO 14
<211> LENGTH: 13
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(13)
<223> OTHER INFORMATION: mutated REC domain, amino acid sequence

<400> SEQUENCE: 14

Gly Gly Gly Ala Gly Ala Ser Ala Gly Gly Ser Gly Ser
1               5                   10

<210> SEQ ID NO 15
<211> LENGTH: 39
<212> TYPE: DNA
<213> ORGANISM: Francisella novicida
<220> FEATURE:
<221> NAME/KEY: misc_feature
<222> LOCATION: (1)..(39)
<223> OTHER INFORMATION: Lid domain, DNA sequence

<400> SEQUENCE: 15
gaggatttaa attttggatt taaaagaggg cgtttcaag                              39

<210> SEQ ID NO 16
<211> LENGTH: 13
<212> TYPE: PRT
<213> ORGANISM: Francisella novicida
<220> FEATURE:
<221> NAME/KEY: MISC_FEATURE
<222> LOCATION: (1)..(13)
<223> OTHER INFORMATION: Lid domain, amino acid sequence

<400> SEQUENCE: 16

Glu Asp Leu Asn Phe Gly Phe Lys Arg Gly Arg Phe Lys
1               5                   10

<210> SEQ ID NO 17
<211> LENGTH: 39
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(39)
<223> OTHER INFORMATION: mutated Lid domain, DNA sequence

<400> SEQUENCE: 17
ggtggtggag ccggtggagc agctggaggg ggagccggt                              39

<210> SEQ ID NO 18
<211> LENGTH: 13
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(13)
<223> OTHER INFORMATION: Mutated Lid domain

<400> SEQUENCE: 18

Gly Gly Gly Ala Gly Gly Ala Ala Gly Gly Gly Ala Gly
1               5                   10
```

```
<210> SEQ ID NO 19
<211> LENGTH: 36
<212> TYPE: DNA
<213> ORGANISM: Francisella novicida
<220> FEATURE:
<221> NAME/KEY: misc_feature
<222> LOCATION: (1)..(36)
<223> OTHER INFORMATION: finger domain

<400> SEQUENCE: 19
aaaggtataa atgaatatat aaatctatac tcacag                                  36

<210> SEQ ID NO 20
<211> LENGTH: 12
<212> TYPE: PRT
<213> ORGANISM: Francisella novicida
<220> FEATURE:
<221> NAME/KEY: MISC_FEATURE
<222> LOCATION: (1)..(12)
<223> OTHER INFORMATION: Finger domain

<400> SEQUENCE: 20

Lys Gly Ile Asn Glu Tyr Ile Asn Leu Tyr Ser Gln
1               5                   10

<210> SEQ ID NO 21
<211> LENGTH: 36
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(36)
<223> OTHER INFORMATION: Mutated finger domain

<400> SEQUENCE: 21
ggtggtggag ccggtgcagc tggaggagct tcaggt                                  36

<210> SEQ ID NO 22
<211> LENGTH: 12
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(12)
<223> OTHER INFORMATION: mutated finger domain

<400> SEQUENCE: 22

Gly Gly Gly Ala Gly Ala Ala Gly Gly Ala Ser Gly
1               5                   10

<210> SEQ ID NO 23
<211> LENGTH: 37
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(33)
<223> OTHER INFORMATION: labelled non-specific ssDNA

<400> SEQUENCE: 23
agcatgccca aattgcttac atatgtgtta cgacggt                                 37
```

<210> SEQ ID NO 24
<211> LENGTH: 1307
<212> TYPE: PRT
<213> ORGANISM: Acidaminococcus sp. BV3L6

<400> SEQUENCE: 24

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

-continued

```
Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ser Ala Ala Gly Lys Glu Leu Ser
            420                 425                 430

Glu Ala Phe Lys Gln Lys Thr Ser Glu Ile Leu Ser His Ala His Ala
            435                 440                 445

Ala Leu Asp Gln Pro Leu Pro Thr Thr Leu Lys Lys Gln Glu Glu Lys
        450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
            515                 520                 525

Glu Lys Phe Lys Leu Asn Phe Gln Met Pro Thr Leu Ala Ser Gly Trp
530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
        770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
```

```
                805                 810                 815
Pro Ile Pro Asp Thr Leu Tyr Gln Glu Leu Tyr Asp Tyr Val Asn His
            820                 825                 830
Arg Leu Ser His Asp Leu Ser Asp Glu Ala Arg Ala Leu Leu Pro Asn
            835                 840                 845
Val Ile Thr Lys Glu Val Ser His Glu Ile Ile Lys Asp Arg Arg Phe
            850                 855                 860
Thr Ser Asp Lys Phe Phe Phe His Val Pro Ile Thr Leu Asn Tyr Gln
865                 870                 875                 880
Ala Ala Asn Ser Pro Ser Lys Phe Asn Gln Arg Val Asn Ala Tyr Leu
                885                 890                 895
Lys Glu His Pro Glu Thr Pro Ile Ile Gly Ile Asp Arg Gly Glu Arg
            900                 905                 910
Asn Leu Ile Tyr Ile Thr Val Ile Asp Ser Thr Gly Lys Ile Leu Glu
            915                 920                 925
Gln Arg Ser Leu Asn Thr Ile Gln Gln Phe Asp Tyr Gln Lys Lys Leu
            930                 935                 940
Asp Asn Arg Glu Lys Glu Arg Val Ala Ala Arg Gln Ala Trp Ser Val
945                 950                 955                 960
Val Gly Thr Ile Lys Asp Leu Lys Gln Gly Tyr Leu Ser Gln Val Ile
                965                 970                 975
His Glu Ile Val Asp Leu Met Ile His Tyr Gln Ala Val Val Val Leu
            980                 985                 990
Glu Asn Leu Asn Phe Gly Phe Lys  Ser Lys Arg Thr Gly  Ile Ala Glu
                995                 1000                1005
Lys Ala  Val Tyr Gln Gln Phe  Glu Lys Met Leu Ile  Asp Lys Leu
     1010                 1015                 1020
Asn Cys  Leu Val Leu Lys Asp  Tyr Pro Ala Glu Lys  Val Gly Gly
     1025                 1030                 1035
Val Leu  Asn Pro Tyr Gln Leu  Thr Asp Gln Phe Thr  Ser Phe Ala
     1040                 1045                 1050
Lys Met  Gly Thr Gln Ser Gly  Phe Leu Phe Tyr Val  Pro Ala Pro
     1055                 1060                 1065
Tyr Thr  Ser Lys Ile Asp Pro  Leu Thr Gly Phe Val  Asp Pro Phe
     1070                 1075                 1080
Val Trp  Lys Thr Ile Lys Asn  His Glu Ser Arg Lys  His Phe Leu
     1085                 1090                 1095
Glu Gly  Phe Asp Phe Leu His  Tyr Asp Val Lys Thr  Gly Asp Phe
     1100                 1105                 1110
Ile Leu  His Phe Lys Met Asn  Arg Asn Leu Ser Phe  Gln Arg Gly
     1115                 1120                 1125
Leu Pro  Gly Phe Met Pro Ala  Trp Asp Ile Val Phe  Glu Lys Asn
     1130                 1135                 1140
Glu Thr  Gln Phe Asp Ala Lys  Gly Thr Pro Phe Ile  Ala Gly Lys
     1145                 1150                 1155
Arg Ile  Val Pro Val Ile Glu  Asn His Arg Phe Thr  Gly Arg Tyr
     1160                 1165                 1170
Arg Asp  Leu Tyr Pro Ala Asn  Glu Leu Ile Ala Leu  Leu Glu Glu
     1175                 1180                 1185
Lys Gly  Ile Val Phe Arg Asp  Gly Ser Asn Ile Leu  Pro Lys Leu
     1190                 1195                 1200
Leu Glu  Asn Asp Asp Ser His  Ala Ile Asp Thr Met  Val Ala Leu
     1205                 1210                 1215
```

Ile Arg Ser Val Leu Gln Met Arg Asn Ser Asn Ala Ala Thr Gly
1220              1225              1230

Glu Asp Tyr Ile Asn Ser Pro Val Arg Asp Leu Asn Gly Val Cys
1235              1240              1245

Phe Asp Ser Arg Phe Gln Asn Pro Glu Trp Pro Met Asp Ala Asp
1250              1255              1260

Ala Asn Gly Ala Tyr His Ile Ala Leu Lys Gly Gln Leu Leu Leu
1265              1270              1275

Asn His Leu Lys Glu Ser Lys Asp Leu Lys Leu Gln Asn Gly Ile
1280              1285              1290

Ser Asn Gln Asp Trp Leu Ala Tyr Ile Gln Glu Leu Arg Asn
1295              1300              1305

<210> SEQ ID NO 25
<211> LENGTH: 1230
<212> TYPE: PRT
<213> ORGANISM: Lachnospiraceae bacterium COE1

<400> SEQUENCE: 25

Met His Glu Asn Asn Gly Lys Ile Ala Asp Asn Phe Ile Gly Ile Tyr
1               5                   10                  15

Pro Val Ser Lys Thr Leu Arg Phe Glu Leu Lys Pro Val Gly Lys Thr
                20                  25                  30

Gln Glu Tyr Ile Glu Lys His Gly Ile Leu Asp Glu Asp Leu Lys Arg
            35                  40                  45

Ala Gly Asp Tyr Lys Ser Val Lys Lys Ile Ile Asp Ala Tyr His Lys
        50                  55                  60

Tyr Phe Ile Asp Glu Ala Leu Asn Gly Ile Gln Leu Asp Gly Leu Lys
65                  70                  75                  80

Asn Tyr Tyr Glu Leu Tyr Glu Lys Lys Arg Asp Asn Asn Glu Glu Lys
                85                  90                  95

Glu Phe Gln Lys Ile Gln Met Ser Leu Arg Lys Gln Ile Val Lys Arg
            100                 105                 110

Phe Ser Glu His Pro Gln Tyr Lys Tyr Leu Phe Lys Lys Glu Leu Ile
        115                 120                 125

Lys Asn Val Leu Pro Glu Phe Thr Lys Asp Asn Ala Glu Glu Gln Thr
130                 135                 140

Leu Val Lys Ser Phe Gln Glu Phe Thr Thr Tyr Phe Glu Gly Phe His
145                 150                 155                 160

Gln Asn Arg Lys Asn Met Tyr Ser Asp Glu Glu Lys Ser Thr Ala Ile
                165                 170                 175

Ala Tyr Arg Val Val His Gln Asn Leu Pro Lys Tyr Ile Asp Asn Met
            180                 185                 190

Arg Ile Phe Ser Met Ile Leu Asn Thr Asp Ile Arg Ser Asp Leu Thr
        195                 200                 205

Glu Leu Phe Asn Asn Leu Lys Thr Lys Met Asp Ile Thr Ile Val Glu
    210                 215                 220

Glu Tyr Phe Ala Ile Asp Gly Phe Asn Lys Val Val Asn Gln Lys Gly
225                 230                 235                 240

Ile Asp Val Tyr Asn Thr Ile Leu Gly Ala Phe Ser Thr Asp Asp Asn
                245                 250                 255

Thr Lys Ile Lys Gly Leu Asn Glu Tyr Ile Asn Leu Tyr Asn Gln Lys
            260                 265                 270

Asn Lys Ala Lys Leu Pro Lys Leu Lys Pro Leu Phe Lys Gln Ile Leu

```
                275                 280                 285
Ser Asp Arg Asp Lys Ile Ser Phe Ile Pro Glu Gln Phe Asp Ser Asp
290                 295                 300
Thr Glu Val Leu Glu Ala Val Asp Met Phe Tyr Asn Arg Leu Leu Gln
305                 310                 315                 320
Phe Val Ile Glu Asn Glu Gly Gln Ile Thr Ile Ser Lys Leu Leu Thr
                325                 330                 335
Asn Phe Ser Ala Tyr Asp Leu Asn Lys Ile Tyr Val Lys Asn Asp Thr
                340                 345                 350
Thr Ile Ser Ala Ile Ser Asn Asp Leu Phe Asp Asp Trp Ser Tyr Ile
                355                 360                 365
Ser Lys Ala Val Arg Glu Asn Tyr Asp Ser Glu Asn Val Asp Lys Asn
370                 375                 380
Lys Arg Ala Ala Ala Tyr Glu Glu Lys Lys Glu Lys Ala Leu Ser Lys
385                 390                 395                 400
Ile Lys Met Tyr Ser Ile Glu Glu Leu Asn Phe Phe Val Lys Lys Tyr
                405                 410                 415
Ser Cys Asn Glu Cys His Ile Glu Gly Tyr Phe Glu Arg Arg Ile Leu
                420                 425                 430
Glu Ile Leu Asp Lys Met Arg Tyr Ala Tyr Glu Ser Cys Lys Ile Leu
                435                 440                 445
His Asp Lys Gly Leu Ile Asn Asn Ile Ser Leu Cys Gln Asp Arg Gln
                450                 455                 460
Ala Ile Ser Glu Leu Lys Asp Phe Leu Asp Ser Ile Lys Glu Val Gln
465                 470                 475                 480
Trp Leu Leu Lys Pro Leu Met Ile Gly Gln Glu Gln Ala Asp Lys Glu
                485                 490                 495
Glu Ala Phe Tyr Thr Glu Leu Leu Arg Ile Trp Glu Glu Leu Glu Pro
                500                 505                 510
Ile Thr Leu Leu Tyr Asn Lys Val Arg Asn Tyr Val Thr Lys Lys Pro
                515                 520                 525
Tyr Thr Leu Glu Lys Val Lys Leu Asn Phe Tyr Lys Ser Thr Leu Leu
                530                 535                 540
Asp Gly Trp Asp Lys Asn Lys Glu Lys Asp Asn Leu Gly Ile Ile Leu
545                 550                 555                 560
Leu Lys Asp Gly Gln Tyr Tyr Leu Gly Ile Met Asn Arg Arg Asn Asn
                565                 570                 575
Lys Ile Ala Asp Asp Ala Pro Leu Ala Lys Thr Asp Asn Val Tyr Arg
                580                 585                 590
Lys Met Glu Tyr Lys Leu Leu Thr Lys Val Ser Ala Asn Leu Pro Arg
                595                 600                 605
Ile Phe Leu Lys Asp Lys Tyr Asn Pro Ser Glu Glu Met Leu Glu Lys
                610                 615                 620
Tyr Glu Lys Gly Thr His Leu Lys Gly Glu Asn Phe Cys Ile Asp Asp
625                 630                 635                 640
Cys Arg Glu Leu Ile Asp Phe Phe Lys Gly Ile Lys Gln Tyr Glu
                645                 650                 655
Asp Trp Gly Gln Phe Asp Phe Lys Phe Ser Asp Thr Glu Ser Tyr Asp
                660                 665                 670
Asp Ile Ser Ala Phe Tyr Lys Glu Val Glu His Gln Gly Tyr Lys Ile
                675                 680                 685
Thr Phe Arg Asp Ile Asp Glu Thr Tyr Ile Asp Ser Leu Val Asn Glu
                690                 695                 700
```

```
Gly Lys Leu Tyr Leu Phe Gln Ile Tyr Asn Lys Asp Phe Ser Pro Tyr
705                 710                 715                 720

Ser Lys Gly Thr Lys Asn Leu His Thr Leu Tyr Trp Glu Met Leu Phe
            725                 730                 735

Ser Gln Gln Asn Leu Gln Asn Ile Val Tyr Lys Leu Asn Gly Asn Ala
            740                 745                 750

Glu Ile Phe Tyr Arg Lys Ala Ser Ile Asn Gln Lys Asp Val Val Val
            755                 760                 765

His Lys Ala Asp Leu Pro Ile Lys Asn Lys Asp Pro Gln Asn Ser Lys
770                 775                 780

Lys Glu Ser Met Phe Asp Tyr Asp Ile Ile Lys Asp Lys Arg Phe Thr
785                 790                 795                 800

Cys Asp Lys Tyr Gln Phe His Val Pro Ile Thr Met Asn Phe Lys Ala
                805                 810                 815

Leu Gly Glu Asn His Phe Asn Arg Lys Val Asn Arg Leu Ile His Asp
                820                 825                 830

Ala Glu Asn Met His Ile Ile Gly Ile Asp Arg Gly Glu Arg Asn Leu
                835                 840                 845

Ile Tyr Leu Cys Met Ile Asp Met Lys Gly Asn Ile Val Lys Gln Ile
    850                 855                 860

Ser Leu Asn Glu Ile Ile Ser Tyr Asp Lys Asn Lys Leu Glu His Lys
865                 870                 875                 880

Arg Asn Tyr His Gln Leu Leu Lys Thr Arg Glu Asp Glu Asn Lys Ser
                885                 890                 895

Ala Arg Gln Ser Trp Gln Thr Ile His Thr Ile Lys Glu Leu Lys Glu
                900                 905                 910

Gly Tyr Leu Ser Gln Val Ile His Val Ile Thr Asp Leu Met Val Glu
                915                 920                 925

Tyr Asn Ala Ile Val Val Leu Glu Asp Leu Asn Phe Gly Phe Lys Gln
    930                 935                 940

Gly Arg Gln Lys Phe Glu Arg Gln Val Tyr Gln Lys Phe Glu Lys Met
945                 950                 955                 960

Leu Ile Asp Lys Leu Asn Tyr Leu Val Asp Lys Ser Lys Gly Met Asp
                965                 970                 975

Glu Asp Gly Gly Leu Leu His Ala Tyr Gln Leu Thr Asp Glu Phe Lys
            980                 985                 990

Ser Phe Lys Gln Leu Gly Lys Gln Ser Gly Phe Leu Tyr Tyr Ile Pro
            995                 1000                1005

Ala Trp Asn Thr Ser Lys Leu Asp Pro Thr Thr Gly Phe Val Asn
    1010                1015                1020

Leu Phe Tyr Thr Lys Tyr Glu Ser Val Glu Lys Ser Lys Glu Phe
    1025                1030                1035

Ile Asn Asn Phe Thr Ser Ile Leu Tyr Asn Gln Glu Arg Glu Tyr
    1040                1045                1050

Phe Glu Phe Leu Phe Asp Tyr Ser Ala Phe Thr Ser Lys Ala Glu
    1055                1060                1065

Gly Ser Arg Leu Lys Trp Thr Val Cys Ser Lys Gly Glu Arg Val
    1070                1075                1080

Glu Thr Tyr Arg Asn Pro Lys Lys Asn Asn Glu Trp Asp Thr Gln
    1085                1090                1095

Lys Ile Asp Leu Thr Phe Glu Leu Lys Lys Leu Phe Asn Asp Tyr
    1100                1105                1110
```

```
Ser Ile Ser Leu Leu Asp Gly Asp Leu Arg Glu Gln Met Gly Lys
    1115                1120                1125

Ile Asp Lys Ala Asp Phe Tyr Lys Lys Phe Met Lys Leu Phe Ala
    1130                1135                1140

Leu Ile Val Gln Met Arg Asn Ser Asp Glu Arg Glu Asp Lys Leu
    1145                1150                1155

Ile Ser Pro Val Leu Asn Lys Tyr Gly Ala Phe Phe Glu Thr Gly
    1160                1165                1170

Lys Asn Glu Arg Met Pro Leu Asp Ala Asp Ala Asn Gly Ala Tyr
    1175                1180                1185

Asn Ile Ala Arg Lys Gly Leu Trp Ile Ile Glu Lys Ile Lys Asn
    1190                1195                1200

Thr Asp Val Glu Gln Leu Asp Lys Val Lys Leu Thr Ile Ser Asn
    1205                1210                1215

Lys Glu Trp Leu Gln Tyr Ala Gln Glu His Ile Leu
    1220                1225                1230

<210> SEQ ID NO 26
<211> LENGTH: 1307
<212> TYPE: PRT
<213> ORGANISM: Succiniclasticum ruminis

<400> SEQUENCE: 26

Met Gly Asn Phe Gly Glu Phe Thr His Lys Tyr Gln Val Ser Lys Thr
1               5                   10                  15

Leu Arg Phe Glu Leu Ile Pro Gln Gly Lys Thr Leu Glu Asn Val Ala
                20                  25                  30

Lys Tyr Gly Ile Val Asp Asp Lys Arg Arg Ser Glu Asn Tyr Lys
    35                  40                  45

Lys Leu Lys Pro Val Ile Asp Arg Ile Tyr Lys Tyr Phe Ile Asp Glu
50                  55                  60

Ser Leu Lys Asn Val Ser Ile Asp Trp Gln Pro Leu Tyr Glu Ala Ile
65                  70                  75                  80

Ile Ala Tyr Arg Lys Glu Gln Thr Thr Ala Asn Val Val Arg Leu Lys
                85                  90                  95

Glu Glu Gln Glu Ala Cys Arg Lys Ala Ile Ala Ala Trp Phe Glu Gly
                100                 105                 110

Lys Val Pro Asp Lys Gly Ser Lys Asp Leu Lys Glu Phe Asn Lys Thr
            115                 120                 125

Gln Ser Lys Leu Phe Lys Glu Leu Phe Gly Lys Glu Leu Phe Thr Glu
    130                 135                 140

Ser Val Thr Gln Leu Leu Pro Gly Leu Ser Leu Thr Glu Glu Glu Lys
145                 150                 155                 160

Glu Leu Leu Ala Ser Phe Asn Lys Phe Thr Ser Tyr Phe Lys Gly Phe
                165                 170                 175

Tyr Val Asn Arg Lys Asn Val Phe Ser Ala Asp Asp Ile Ser Thr Ser
            180                 185                 190

Ile Pro His Arg Leu Val Gln Glu Asn Phe Pro Lys Phe Met Asp Asn
    195                 200                 205

Cys Glu Ala Tyr Arg Arg Ile Val Glu Glu Tyr Pro Glu Leu Lys Ala
210                 215                 220

Lys Leu Glu Gly Thr Ala Gln Ala Thr Gly Ile Phe Ile Gly Phe Lys
225                 230                 235                 240

Leu Asp Asn Ile Phe Lys Val Ser Phe Tyr Asn His Leu Leu Gln Gln
                245                 250                 255
```

```
Ser Gln Ile Asp Leu Tyr Asn Gln Phe Leu Cys Gly Ile Ala Gly Glu
            260                 265                 270

Glu Gly Thr Met Arg Val Gln Gly Leu Asn Val Thr Leu Asn Leu Ala
            275                 280                 285

Met Lys Gln Asp Lys Val Leu Gly Gln Lys Leu Lys Ser Met Pro His
290                 295                 300

Arg Phe Ile Pro Leu Tyr Lys Gln Ile Leu Ser Asp Arg Thr Thr Leu
305                 310                 315                 320

Ser Phe Ile Pro Glu Ala Phe Gln Asn Asp Glu Val Leu Leu Thr
                325                 330                 335

Val Glu Glu Tyr Arg Lys Ser Leu Glu Ala Glu Arg Thr Thr Gly Ala
            340                 345                 350

Val Ser Asp Ile Phe Asn Ser Leu Gln Ala Ala Asp Leu Arg His Val
            355                 360                 365

Tyr Val Asn Pro Ala Lys Leu Thr Ala Phe Ser Gln Met Leu Phe Glu
            370                 375                 380

Asp Trp Ser Leu Cys Arg Glu Ser Leu Arg Asn Trp Lys Leu Arg Ser
385                 390                 395                 400

Tyr Gly Lys Ala Ala Thr Lys Lys Val Arg Glu Glu Ile Glu Ser Trp
                405                 410                 415

Leu Lys Glu Ser Ala Ile Ser Leu Asp Glu Leu Gln Ala Ala Leu Ala
            420                 425                 430

Asp Gly Thr Leu Ser Val Ile Ile Asn Gln Lys Val Gln Ser Val Ile
            435                 440                 445

Thr Thr Leu Glu Gln Glu Leu Ala Lys Pro Leu Pro Lys Lys Leu Lys
            450                 455                 460

Thr Ala Glu Glu Lys Glu Ser Leu Lys Ser Leu Leu Asp Ser Val Gln
465                 470                 475                 480

Glu Ala Cys His Ser Leu Glu Met Phe Ala Val Gly Glu Asn Met Asp
                485                 490                 495

Thr Asp Pro Cys Phe Tyr Val Pro Leu Arg Glu Ala Met Glu Ala Ile
            500                 505                 510

Gln Pro Ile Ile Pro Leu Tyr Asn Lys Val Arg Asn Phe Ala Thr Gln
            515                 520                 525

Lys Pro Tyr Ser Ile Glu Lys Phe Lys Leu Asn Phe Ser Asn Pro Ile
            530                 535                 540

Leu Ala Ser Gly Trp Asp Glu Asn Arg Glu Arg Gln Thr Cys Ala Ile
545                 550                 555                 560

Leu Phe Arg Lys Gly Glu Lys Tyr Tyr Leu Gly Ile Tyr Asn Ala Lys
                565                 570                 575

Val Lys Pro Asp Phe Ser Ile Ile Lys Ala Val Lys Gly Gly Asn Cys
            580                 585                 590

Phe Glu Lys Val Val Tyr Arg Gln Phe Pro Asp Phe Ser Lys Met Met
            595                 600                 605

Pro Lys Cys Thr Thr Gln Leu Lys Glu Val Gln Gln His Phe Ala Ser
            610                 615                 620

Ser Ser Glu Asp Tyr Val Leu Tyr Asn Lys Lys Phe Ile Lys Pro Leu
625                 630                 635                 640

Thr Ile Thr Lys Glu Ile Tyr Asp Leu Asn Asn Val Leu Phe Asp Gly
            645                 650                 655

Lys Lys Lys Phe Gln Ile Asp Tyr Leu Arg Lys Thr Lys Asp Glu Asp
            660                 665                 670
```

```
Gly Tyr Tyr His Ala Leu His Thr Trp Ile Asn Phe Ala Lys Glu Phe
            675                 680                 685

Val Ala Ser Tyr Glu Ser Thr Ser Ile Tyr Asp Thr Ser Thr Val Leu
    690                 695                 700

Ser Thr Glu Gln Tyr Val Lys Leu Asn Asp Phe Tyr Gly Asp Leu Asp
705                 710                 715                 720

Asn Leu Phe Tyr Arg Ile Lys Phe Glu Ser Val Ser Glu Glu Thr Ile
                725                 730                 735

Ser Glu Phe Val Asp Glu Gly Lys Leu Phe Leu Phe Gln Ile Tyr Asn
            740                 745                 750

Lys Asp Phe Ala Glu Gly Ala Thr Gly Ala Pro Asn Leu His Thr Ile
            755                 760                 765

Tyr Trp Lys Ala Val Phe Asp Pro Glu Asn Met Lys Asn Val Val Val
    770                 775                 780

Lys Leu Asn Gly Gln Ala Glu Leu Phe Tyr Arg Pro Lys Ser Ala Met
785                 790                 795                 800

Asp Ile Val Arg His Lys Val Gly Glu Lys Leu Val Asn Arg Arg Leu
                805                 810                 815

Lys Asp Gly Thr Ser Leu Thr Glu Glu Leu His Glu Glu Leu Tyr Leu
            820                 825                 830

Tyr Ala Asn Gly Lys Leu Lys Lys Leu Ser Glu Ala Ala Ala Ala
    835                 840                 845

Val Leu Pro Gln Ala Val Ile Tyr Asp Val His His Glu Ile Val Lys
    850                 855                 860

Asp Arg Arg Phe Thr Glu Asp Lys Phe Phe His Val Pro Leu Thr
865                 870                 875                 880

Leu Asn Tyr Lys Cys Asp Lys Asn Ala Val Gln Phe Asn Ala Ser Val
                885                 890                 895

Gln Glu Tyr Leu Lys Glu Asn Pro Asp Thr Tyr Ile Ile Gly Ile Asp
            900                 905                 910

Arg Gly Glu Arg Asn Leu Ile Tyr Ala Val Val Ile Asp Pro Gln Gly
            915                 920                 925

Asn Ile Val Glu Gln Lys Ser Phe Asn Val Ile Asn Gly Phe Asp Tyr
930                 935                 940

His Asn Lys Leu Glu Gln Arg Glu Lys Glu Arg Asn Lys Ala Arg Gln
945                 950                 955                 960

Asp Trp Thr Thr Val Gly Lys Ile Lys Glu Leu Lys Gln Gly Tyr Leu
                965                 970                 975

Ser Leu Val Val His Glu Ile Thr Ser Met Met Val Lys Tyr Asn Ala
            980                 985                 990

Ile Val Val Leu Glu Asn Leu Asn Val Gly Phe Lys Arg Ile Arg Ser
        995                 1000                1005

Gly Ile Ala Glu Lys Ala Val Tyr Gln Gln Phe Glu Lys Met Leu
    1010                1015                1020

Ile Asn Lys Leu Asn Tyr Leu Met Phe Lys Asp Val Glu Gly Ala
    1025                1030                1035

Lys Pro Gly Ser Val Leu Asn Ala Tyr Gln Leu Thr Asp Arg Phe
    1040                1045                1050

Glu Ser Phe Ala Ser Met Arg Asn Gln Thr Gly Phe Leu Phe Tyr
    1055                1060                1065

Ile Pro Ala Ala Phe Thr Ser Lys Ile Asp Pro Ala Thr Gly Phe
    1070                1075                1080

Val Asp Pro Phe Cys Trp Ser Ala Ile Lys Thr Leu Asp Asp Lys
```

```
              1085                1090                1095

Lys Thr Phe Ile Ser Gly Phe  Asp Thr Leu Lys Tyr  Asp Asn Val
    1100                1105                1110

Thr Gly Asn Phe Ile Leu His  Phe Glu Met Lys Lys  Asn Lys Asp
    1115                1120                1125

Phe Gln Lys Lys Leu Glu Gly  Phe Met Pro Glu Trp  Asp Ile Val
    1130                1135                1140

Val Glu Ala Asn Lys Asp Arg  Arg Asp Ala Glu Gly  Lys Thr Phe
    1145                1150                1155

Ile Ser Gly Lys Arg Ile Glu  Phe Val Arg Glu Asn  Asn Gly His
    1160                1165                1170

Gly His Tyr Glu Asp Tyr Leu  Pro Cys Lys Lys Leu  Val Glu Ile
    1175                1180                1185

Leu Arg Gln Tyr Asp Ile Leu  Phe Glu Asp Gly Lys  Asp Val Leu
    1190                1195                1200

Pro Leu Ile Met Lys Asn Gly  Asp Ser Lys Leu Ile  His Glu Val
    1205                1210                1215

Phe Lys Val Ile Arg Leu Ser  Leu Gln Met Arg Asn  Ser Asn Ala
    1220                1225                1230

Glu Ser Gly Glu Asp Phe Ile  Ser Ser Pro Val Glu  Asn Asn Glu
    1235                1240                1245

Gly Ile Cys Phe Asp Ser Arg  Leu Gly Val Glu Thr  Leu Pro Lys
    1250                1255                1260

Asp Ala Asp Ala Asn Gly Ala  Tyr His Ile Ala Leu  Lys Gly Leu
    1265                1270                1275

Leu Leu Leu Glu Lys Ile Arg  His Asp Glu Arg Lys  Leu Gly Ile
    1280                1285                1290

Ser Asn Ser Glu Trp Leu Asn  His Ile Gln Ser Leu  Arg Gly
    1295                1300                1305

<210> SEQ ID NO 27
<211> LENGTH: 1231
<212> TYPE: PRT
<213> ORGANISM: Butyrivibrio fibrisolvens

<400> SEQUENCE: 27

Met Tyr Tyr Glu Ser Leu Thr Lys Leu Tyr Pro Ile Lys Lys Thr Ile
1               5                   10                  15

Arg Asn Glu Leu Val Pro Ile Gly Lys Thr Leu Glu Asn Ile Lys Lys
            20                  25                  30

Asn Asn Ile Leu Glu Ala Asp Glu Asp Arg Lys Ile Ala Tyr Ile Arg
        35                  40                  45

Val Lys Ala Ile Met Asp Asp Tyr His Lys Arg Leu Ile Asn Glu Ala
    50                  55                  60

Leu Ser Gly Phe Ala Leu Ile Asp Leu Asp Lys Ala Ala Asn Leu Tyr
65                  70                  75                  80

Leu Ser Arg Ser Lys Ser Ala Asp Asp Ile Glu Ser Phe Ser Arg Phe
                85                  90                  95

Gln Asp Lys Leu Arg Lys Ala Ile Ala Lys Arg Leu Arg Glu His Glu
            100                 105                 110

Asn Phe Gly Lys Ile Gly Asn Lys Asp Ile Ile Pro Leu Leu Gln Lys
        115                 120                 125

Leu Ser Glu Asn Glu Asp Asp Tyr Asn Ala Leu Glu Ser Phe Lys Asn
    130                 135                 140
```

-continued

```
Phe Tyr Thr Tyr Phe Glu Ser Tyr Asn Asp Val Arg Leu Asn Leu Tyr
145                 150                 155                 160

Ser Asp Lys Glu Lys Ser Ser Thr Val Ala Tyr Arg Leu Ile Asn Glu
                165                 170                 175

Asn Leu Pro Arg Phe Leu Asp Asn Ile Arg Ala Tyr Asp Ala Val Gln
                180                 185                 190

Lys Ala Gly Ile Thr Ser Glu Glu Leu Ser Ser Glu Ala Gln Asp Gly
                195                 200                 205

Leu Phe Leu Val Asn Thr Phe Asn Asn Val Leu Ile Gln Asp Gly Ile
210                 215                 220

Asn Thr Tyr Asn Glu Asp Ile Gly Lys Leu Asn Val Ala Ile Asn Leu
225                 230                 235                 240

Tyr Asn Gln Lys Asn Ala Ser Val Gln Gly Phe Arg Lys Val Pro Lys
                245                 250                 255

Met Lys Val Leu Tyr Lys Gln Ile Leu Ser Asp Arg Glu Glu Ser Phe
                260                 265                 270

Ile Asp Glu Phe Glu Ser Asp Thr Glu Leu Leu Asp Ser Leu Glu Ser
                275                 280                 285

His Tyr Ala Asn Leu Ala Lys Tyr Phe Gly Ser Asn Lys Val Gln Leu
                290                 295                 300

Leu Phe Thr Ala Leu Arg Glu Ser Lys Gly Val Asn Val Tyr Val Lys
305                 310                 315                 320

Asn Asp Ile Ala Lys Thr Ser Phe Ser Asn Val Val Phe Gly Ser Trp
                325                 330                 335

Ser Arg Ile Asp Glu Leu Ile Asn Gly Glu Tyr Asp Asp Asn Asn Asn
                340                 345                 350

Arg Lys Lys Asp Glu Lys Tyr Tyr Asp Lys Arg Gln Lys Glu Leu Lys
                355                 360                 365

Lys Asn Lys Ser Tyr Thr Ile Glu Lys Ile Ile Thr Leu Ser Thr Glu
                370                 375                 380

Asp Val Asp Val Ile Gly Lys Tyr Ile Glu Lys Leu Glu Ser Asp Ile
385                 390                 395                 400

Asp Asp Ile Arg Phe Lys Gly Lys Asn Phe Tyr Glu Ala Val Leu Cys
                405                 410                 415

Gly His Asp Arg Ser Lys Lys Leu Ser Lys Asn Lys Gly Ala Val Glu
                420                 425                 430

Ala Ile Lys Gly Tyr Leu Asp Ser Val Lys Asp Phe Glu Arg Asp Leu
                435                 440                 445

Lys Leu Ile Asn Gly Ser Gly Gln Glu Leu Leu Lys Asn Leu Val Val
450                 455                 460

Tyr Gly Glu Gln Glu Ala Val Leu Ser Glu Leu Ser Gly Ile Asp Ser
465                 470                 475                 480

Leu Tyr Asn Met Thr Arg Asn Tyr Leu Thr Lys Lys Pro Phe Ser Thr
                485                 490                 495

Glu Lys Ile Lys Leu Asn Phe Asn Lys Pro Thr Phe Leu Asp Gly Trp
                500                 505                 510

Asp Tyr Gly Asn Glu Glu Ala Tyr Leu Gly Phe Phe Met Ile Lys Glu
                515                 520                 525

Gly Asn Tyr Phe Leu Ala Val Met Asp Ala Asn Trp Asn Lys Glu Phe
                530                 535                 540

Arg Asn Ile Pro Ser Val Asp Lys Ser Asp Cys Tyr Lys Lys Val Ile
545                 550                 555                 560

Tyr Lys Gln Ile Ser Ser Pro Glu Lys Ser Ile Gln Asn Leu Met Val
```

```
                565                 570                 575
Ile Asp Gly Lys Thr Val Lys Lys Asn Gly Arg Lys Glu Lys Glu Gly
            580                 585                 590
Ile His Ser Gly Glu Asn Leu Ile Leu Glu Glu Leu Lys Asn Thr Tyr
            595                 600                 605
Leu Pro Lys Lys Ile Asn Asp Ile Arg Lys Arg Ser Tyr Leu Asn
    610                 615                 620
Gly Asp Thr Phe Ser Lys Lys Asp Leu Thr Glu Phe Ile Gly Tyr Tyr
625                 630                 635                 640
Lys Gln Arg Val Ile Glu Tyr Tyr Asn Gly Tyr Ser Phe Tyr Phe Lys
                645                 650                 655
Ser Asp Asp Asp Tyr Ala Ser Phe Lys Glu Phe Gln Glu Asp Val Gly
                660                 665                 670
Arg Gln Ala Tyr Gln Ile Ser Tyr Val Asp Val Pro Val Ser Phe Val
                675                 680                 685
Asp Asp Leu Ile Asn Ser Gly Lys Leu Tyr Leu Phe Arg Val Tyr Asn
            690                 695                 700
Lys Asp Phe Ser Glu Tyr Ser Lys Gly Arg Leu Asn Leu His Thr Leu
705                 710                 715                 720
Tyr Phe Lys Met Leu Phe Asp Glu Arg Asn Leu Lys Asn Val Tyr
                725                 730                 735
Lys Leu Asn Gly Gln Ala Glu Val Phe Tyr Arg Pro Ser Ser Ile Lys
            740                 745                 750
Lys Glu Glu Leu Ile Val His Arg Ala Gly Glu Glu Ile Lys Asn Lys
            755                 760                 765
Asn Pro Lys Arg Ala Ala Gln Lys Pro Thr Arg Arg Leu Asp Tyr Asp
    770                 775                 780
Ile Val Lys Asp Arg Arg Tyr Ser Gln Asp Lys Phe Met Leu His Thr
785                 790                 795                 800
Ser Ile Ile Met Asn Phe Gly Ala Glu Glu Asn Val Ser Phe Asn Asp
                805                 810                 815
Ile Val Asn Gly Val Leu Arg Asn Glu Asp Lys Val Asn Val Ile Gly
            820                 825                 830
Ile Asp Arg Gly Glu Arg Asn Leu Leu Tyr Val Val Ile Asp Pro
            835                 840                 845
Glu Gly Lys Ile Leu Glu Gln Arg Ser Leu Asn Cys Ile Thr Asp Ser
    850                 855                 860
Asn Leu Asp Ile Glu Thr Asp Tyr His Arg Leu Leu Asp Glu Lys Glu
865                 870                 875                 880
Ser Asp Arg Lys Ile Ala Arg Arg Asp Trp Thr Thr Ile Glu Asn Ile
                885                 890                 895
Lys Glu Leu Lys Ala Gly Tyr Leu Ser Gln Val Val His Ile Val Ala
                900                 905                 910
Glu Leu Val Leu Lys Tyr Asn Ala Ile Ile Cys Leu Glu Asp Leu Asn
            915                 920                 925
Phe Gly Phe Lys Arg Gly Arg Gln Lys Val Glu Lys Gln Val Tyr Gln
    930                 935                 940
Lys Phe Glu Lys Met Leu Ile Asp Lys Leu Asn Tyr Leu Val Met Asp
945                 950                 955                 960
Lys Ser Arg Glu Gln Leu Ser Pro Glu Lys Ile Ser Gly Ala Leu Asn
                965                 970                 975
Ala Leu Gln Leu Thr Pro Asp Phe Lys Ser Phe Lys Val Leu Gly Lys
            980                 985                 990
```

Gln Thr Gly Ile Ile Tyr Tyr Val Pro Ala Tyr Leu Thr Ser Lys Ile
            995                 1000                1005

Asp Pro Met Thr Gly Phe Ala Asn Leu Phe Tyr Val Lys Tyr Glu
    1010                1015                1020

Asn Val Asp Lys Ala Lys Glu Phe Phe Ser Lys Phe Asp Ser Ile
    1025                1030                1035

Lys Tyr Asn Lys Asp Gly Lys Asn Trp Asn Thr Lys Gly Tyr Phe
    1040                1045                1050

Glu Phe Ala Phe Asp Tyr Lys Lys Phe Thr Asp Arg Ala Tyr Gly
    1055                1060                1065

Arg Val Ser Glu Trp Thr Val Cys Thr Val Gly Glu Arg Ile Ile
    1070                1075                1080

Lys Phe Lys Asn Lys Glu Lys Asn Asn Ser Tyr Asp Asp Lys Val
    1085                1090                1095

Ile Asp Leu Thr Asn Ser Leu Lys Glu Leu Phe Asp Ser Tyr Lys
    1100                1105                1110

Val Thr Tyr Glu Ser Glu Val Asp Leu Lys Asp Ala Ile Leu Ala
    1115                1120                1125

Ile Asp Asp Pro Ala Phe Tyr Arg Asp Leu Thr Arg Arg Leu Gln
    1130                1135                1140

Gln Thr Leu Gln Met Arg Asn Ser Ser Cys Asp Gly Ser Arg Asp
    1145                1150                1155

Tyr Ile Ile Ser Pro Val Lys Asn Ser Lys Gly Glu Phe Phe Cys
    1160                1165                1170

Ser Asp Asn Asn Asp Asp Thr Thr Pro Asn Asp Ala Asp Ala Asn
    1175                1180                1185

Gly Ala Phe Asn Ile Ala Arg Lys Gly Leu Trp Val Leu Asn Glu
    1190                1195                1200

Ile Arg Asn Ser Glu Glu Gly Ser Lys Ile Asn Leu Ala Met Ser
    1205                1210                1215

Asn Ala Gln Trp Leu Glu Tyr Ala Gln Asp Asn Thr Ile
    1220                1225                1230

<210> SEQ ID NO 28
<211> LENGTH: 37
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(37)
<223> OTHER INFORMATION: non-specific ssDNA

<400> SEQUENCE: 28
agcatgccca aattgcttac atatgtgtta cgacggt                              37

<210> SEQ ID NO 29
<211> LENGTH: 3900
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(3900)
<223> OTHER INFORMATION: FnCpf1 Q1025G mutant

<400> SEQUENCE: 29

```
atgtcaattt atcaagaatt tgttaataaa tatagtttaa gtaaaactct aagatttgag    60
ttaatcccac agggtaaaac acttgaaaac ataaaagcaa gaggtttgat tttagatgat   120
gagaaaagag ctaaagacta caaaaaggct aaacaaataa ttgataaata tcatcagttt   180
tttatagagg agatattaag ttcggtttgt attagcgaag atttattaca aaactattct   240
gatgtttatt ttaaacttaa aaagagtgat gatgataatc tacaaaaaga ttttaaaagt   300
gcaaaagata cgataaagaa acaaatatct gaatatataa aggactcaga gaaatttaag   360
aatttgttta atcaaaacct tatcgatgct aaaaaagggc aagagtcaga tttaattcta   420
tggctaaagc aatctaagga taatggtata gaactattta aagccaatag tgatatcaca   480
gatatagatg aggcgttaga aataatcaaa tcttttaaag gttggacaac ttattttaag   540
ggttttcatg aaaatagaaa aaatgtttat agtagcaatg atattcctac atctattatt   600
tataggatag tagatgataa tttgcctaaa tttctagaaa ataaagctaa gtatgagagt   660
ttaaaagaca aagctccaga agctataaac tatgaacaaa ttaaaaaaga tttggcagaa   720 gagctaaccct ttgatattga ctacaaaaca tctgaagtta atcaaagagt tttttcactt   780
gatgaagttt ttgagatagc aaactttaat aattatctaa atcaaagtgg tattactaaa   840
tttaatacta ttattggtgg taaatttgta aatggtgaaa atacaaagag aaaaggtata   900
aatgaatata taaatctata ctcacagcaa ataaatgata aaacactcaa aaatataaaa   960
atgagtgttt tatttaagca aattttaagt gatacagaat ctaaatcttt tgtaattgat  1020
aagttagaag atgatagtga tgtagttaca acgatgcaaa gtttttatga gcaaatagca  1080
gcttttaaaa cagtagaaga aaaatctatt aagaaacac tatctttatt atttgatgat  1140
ttaaaagctc aaaaacttga tttgagtaaa atttatttta aaaatgataa atctcttact  1200
gatctatcac aacaagtttt tgatgattat agtgttattg gtacagcggt actagaatat  1260
ataactcaac aaatagcacc taaaaatctt gataacccta gtaagaaaga gcaagaatta  1320
atagccaaaa aaactgaaaa agcaaaatac ttatctctag aaactataaa gcttgcctta  1380
gaagaattta ataagcatag agatatagat aaacagtgta ggtttgaaga atacttgca  1440 aactttgcgg ctattccgat gatatttgat gaaatagctc aaaacaaaga caatttggca  1500
cagatatcta tcaaatatca aaatcaaggt aaaaaagacc tacttcaagc tagtgcggaa  1560
gatgatgtta aagctatcaa ggatcttttta gatcaaacta ataatctctt acataaaacta  1620 aaaatatttc atattagtca gtcagaagat aaggcaaata ttttagacaa ggatgagcat  1680 tttatctag tatttgagga gtgctacttt gagctagcga atatagtgcc tctttataac  1740
aaaattagaa actatataac tcaaaagcca tatagtgatg agaaatttaa gctcaatttt  1800
gagaactcga cttttggctaa tggttgggat aaaaataaag agcctgacaa tacggcaatt  1860
ttatttatca aagatgataa atattatctg ggtgtgatga taagaaaaaa taacaaaata  1920
tttgatgata aagctatcaa agaaaataaa ggcgagggtt ataaaaaaat tgtttataaa  1980
cttttacctg gcgcaaataa aatgttacct aaggttttct tttctgctaa atctataaaa  2040
ttttataatc ctagtgaaga tatacttaga ataagaaatc attccacaca tacaaaaaat  2100
ggtagtcctc aaaaaggata tgaaaaattt gagtttaata ttgaagattg ccgaaaattt  2160 atagatttt ataaacagtc tataagtaag catccggagt ggaaagattt tggatttaga  2220
ttttctgata ctcaaagata taattctata gatgaattt atagagaagt tgaaaatcaa  2280
ggctacaaac taacttttga aaatatatca gagagctata ttgatagcgt agttaatcag  2340
ggtaaattgt acctattcca aatctataat aaagattttt cagcttatag caaagggcga  2400
```

```
ccaaatctac atactttata ttggaaagcg ctgtttgatg agagaaatct tcaagatgtg    2460
gtttataagc taaatggtga ggcagagctt ttttatcgta acaatcaat acctaaaaaa    2520 atcactcacc cagctaaaga ggcaatagct aataaaaaca aagataatcc taaaaaagag    2580 agtgttttg aatatgattt aatcaaagat aaacgcttta ctgaagataa gttttctttt    2640
cactgtccta ttacaatcaa ttttaaatct agtggagcta ataagtttaa tgatgaaatc    2700
aatttattgc taaagaaaaa agcaaatgat gttcatatat taagtataga tagaggtgaa    2760
agacatttag cttactatac tttggtagat ggtaaaggca atatcatcaa acaagatact    2820
ttcaacatca ttggtaatga tagaatgaaa acaaactacc atgataagct tgctgcaata    2880
gagaaagata gggattcagc taggaaagac tggaaaaaga taaataacat caaagagatg    2940
aaagagggct atctatctca ggtagttcat gaaatagcta agctagttat agagtataat    3000
gctattgtgg tttttgagga tttaaatttt ggatttaaaa gagggcgttt caaggtagag    3060
aagcaggtct atggaaagtt agaaaaaatg ctaattgaga aactaaacta tctagttttc    3120
aaagataatg agtttgataa aactggggga gtgcttagag cttatcagct aacagcacct    3180
tttgagactt ttaaaaagat gggtaaacaa acaggtatta tctactatgt accagctggt    3240
tttacttcaa aaatttgtcc tgtaactggt tttgtaaatc agttatatcc taagtatgaa    3300
agtgtcagca atctcaaga gttctttagt aagtttgaca agatttgtta taaccttgat    3360
aagggctatt ttgagtttag ttttgattat aaaaactttg gtgacaaggc tgccaaaggc    3420
aagtggacta tagctagctt tgggagtaga ttgattaact ttagaaattc agataaaaat    3480
cataattggg atactcgaga agttttatcca actaaagagt tggagaaatt gctaaaagat    3540
tattctatcg aatatgggca tggcgaatgt atcaaagcag ctatttgcgg tgagagcgac    3600
aaaaagtttt ttgctaagct aactagtgtc ctaaatacta tcttacaaat gcgtaactca    3660
aaaacaggta ctgagttaga ttatctaatt tcaccagtag cagatgtaaa tggcaatttc    3720
tttgattcgc gacaggcgcc aaaaaatatg cctcaagatg ctgatgccaa tggtgcttat    3780
catattgggc taaaaggtct gatgctacta ggtaggatca aaaataatca agagggcaaa    3840
aaactcaatt tggttatcaa aaatgaagag tattttgagt tcgtgcagaa taggaataac    3900
```

<210> SEQ ID NO 30  
<211> LENGTH: 1287  
<212> TYPE: PRT  
<213> ORGANISM: Artificial sequence  
<220> FEATURE:  
<223> OTHER INFORMATION: Synthetic sequence  
<220> FEATURE:  
<221> NAME/KEY: MISC_FEATURE  
<222> LOCATION: (1)..(1287)  
<223> OTHER INFORMATION: Q1025E Cpf1 mutant

<400> SEQUENCE: 30

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

```
Asp Val Tyr Phe Lys Leu Lys Lys Ser Asp Asp Asn Leu Gln Lys
             85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
            115                 120                 125

Asp Ala Lys Lys Gly Gln Glu Ser Asp Leu Ile Leu Trp Leu Lys Gln
        130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
            165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
            195                 200                 205

Pro Lys Phe Leu Glu Asn Lys Ala Lys Tyr Glu Ser Leu Lys Asp Lys
            210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
            275                 280                 285

Phe Val Asn Gly Glu Asn Thr Lys Arg Lys Gly Ile Asn Glu Tyr Ile
            290                 295                 300

Asn Leu Tyr Ser Gln Gln Ile Asn Asp Lys Thr Leu Lys Lys Tyr Lys
305                 310                 315                 320

Met Ser Val Phe Val Ile Asp Lys Leu Glu Asp Asp Ser Asp Val Val
                325                 330                 335

Thr Thr Met Gln Ser Phe Tyr Glu Gln Ile Ala Ala Phe Lys Thr Val
            340                 345                 350

Glu Glu Lys Ser Ile Lys Glu Thr Leu Ser Leu Leu Phe Asp Asp Leu
            355                 360                 365

Lys Ala Gln Lys Leu Asp Leu Ser Lys Ile Tyr Phe Lys Asn Asp Lys
        370                 375                 380

Ser Leu Thr Asp Leu Ser Gln Gln Val Phe Asp Asp Tyr Ser Val Ile
385                 390                 395                 400

Gly Thr Ala Val Leu Glu Tyr Ile Thr Gln Gln Ile Ala Pro Lys Asn
                405                 410                 415

Leu Asp Asn Pro Ser Lys Lys Glu Gln Glu Leu Ile Ala Lys Lys Thr
            420                 425                 430

Glu Lys Ala Lys Tyr Leu Ser Leu Glu Thr Ile Lys Leu Ala Leu Glu
        435                 440                 445

Glu Phe Asn Lys His Arg Asp Ile Asp Lys Gln Cys Arg Phe Glu Glu
            450                 455                 460

Ile Leu Ala Asn Phe Ala Ala Ile Pro Met Ile Phe Asp Glu Ile Ala
465                 470                 475                 480

Gln Asn Lys Asp Asn Leu Ala Gln Ile Ser Ile Lys Tyr Gln Asn Gln
            485                 490                 495
```

```
Gly Lys Lys Asp Leu Leu Gln Ala Ser Ala Glu Asp Val Lys Ala
            500                 505                 510

Ile Lys Asp Leu Leu Asp Gln Thr Asn Asn Leu Leu His Lys Leu Lys
            515                 520                 525

Ile Phe His Ile Ser Gln Ser Glu Asp Lys Ala Asn Ile Leu Asp Lys
            530                 535                 540

Asp Glu His Phe Tyr Leu Val Phe Glu Glu Cys Tyr Phe Glu Leu Ala
545                 550                 555                 560

Asn Ile Val Pro Leu Tyr Asn Lys Ile Arg Asn Tyr Ile Thr Gln Lys
                    565                 570                 575

Pro Tyr Ser Asp Glu Lys Phe Lys Leu Asn Phe Glu Asn Ser Thr Leu
                580                 585                 590

Ala Asn Gly Trp Asp Lys Asn Lys Glu Pro Asp Asn Thr Ala Ile Leu
            595                 600                 605

Phe Ile Lys Asp Asp Lys Tyr Tyr Leu Gly Val Met Asn Lys Lys Asn
            610                 615                 620

Asn Lys Ile Phe Asp Asp Lys Ala Ile Lys Glu Asn Lys Gly Glu Gly
625                 630                 635                 640

Tyr Lys Lys Ile Val Tyr Lys Leu Leu Pro Gly Ala Asn Lys Met Leu
                    645                 650                 655

Pro Lys Val Phe Phe Ser Ala Lys Ser Ile Lys Phe Tyr Asn Pro Ser
                660                 665                 670

Glu Asp Ile Leu Arg Ile Arg Asn His Ser Thr His Thr Lys Asn Gly
            675                 680                 685

Ser Pro Gln Lys Gly Tyr Glu Lys Phe Glu Phe Asn Ile Glu Asp Cys
690                 695                 700

Arg Lys Phe Ile Asp Phe Tyr Lys Gln Ser Ile Ser Lys His Pro Glu
705                 710                 715                 720

Trp Lys Asp Phe Gly Phe Arg Phe Ser Asp Thr Gln Arg Tyr Asn Ser
                    725                 730                 735

Ile Asp Glu Phe Tyr Arg Glu Val Glu Asn Gln Gly Tyr Lys Leu Thr
                740                 745                 750

Phe Glu Asn Ile Ser Glu Ser Tyr Ile Asp Ser Val Val Asn Gln Gly
            755                 760                 765

Lys Leu Tyr Leu Phe Gln Ile Tyr Asn Lys Asp Phe Ser Ala Tyr Ser
770                 775                 780

Lys Gly Arg Pro Asn Leu His Thr Leu Tyr Trp Lys Ala Leu Phe Asp
785                 790                 795                 800

Glu Arg Asn Leu Gln Asp Val Val Tyr Lys Leu Asn Gly Glu Ala Glu
                805                 810                 815

Leu Phe Tyr Arg Lys Gln Ser Ile Pro Lys Lys Ile Thr His Pro Ala
                820                 825                 830

Lys Glu Ala Ile Ala Asn Lys Asn Lys Asp Asn Pro Lys Lys Glu Ser
            835                 840                 845

Val Phe Glu Tyr Asp Leu Ile Lys Asp Lys Arg Phe Thr Glu Asp Lys
850                 855                 860

Phe Phe Phe His Cys Pro Ile Thr Ile Asn Phe Lys Ser Ser Gly Ala
865                 870                 875                 880

Asn Lys Phe Asn Asp Glu Ile Asn Leu Leu Lys Glu Lys Ala Asn
            885                 890                 895

Asp Val His Ile Leu Ser Ile Asp Arg Gly Glu Arg His Leu Ala Tyr
                900                 905                 910

Tyr Thr Leu Val Asp Gly Lys Gly Asn Ile Ile Lys Gln Asp Thr Phe
```

-continued

```
            915                 920                 925
Asn Ile Ile Gly Asn Asp Arg Met Lys Thr Asn Tyr His Asp Lys Leu
    930                 935                 940
Ala Ala Ile Glu Lys Asp Arg Asp Ser Ala Arg Lys Asp Trp Lys Lys
945                 950                 955                 960
Ile Asn Asn Ile Lys Glu Met Lys Glu Gly Tyr Leu Ser Gln Val Val
                965                 970                 975
His Glu Ile Ala Lys Leu Val Ile Glu Tyr Asn Ala Ile Val Val Phe
            980                 985                 990
Glu Asp Leu Asn Phe Gly Phe Lys Arg Gly Arg Phe Lys Val Glu Lys
        995                 1000                1005
Gln Val Tyr Gly Lys Leu Glu Lys Met Leu Ile Glu Lys Leu Asn
    1010                1015                1020
Tyr Leu Val Phe Lys Asp Asn Glu Phe Asp Lys Thr Gly Gly Val
    1025                1030                1035
Leu Arg Ala Tyr Gln Leu Thr Ala Pro Phe Glu Thr Phe Lys Lys
    1040                1045                1050
Met Gly Lys Gln Thr Gly Ile Ile Tyr Tyr Val Pro Ala Gly Phe
    1055                1060                1065
Thr Ser Lys Ile Cys Pro Val Thr Gly Phe Val Asn Gln Leu Tyr
    1070                1075                1080
Pro Lys Tyr Glu Ser Val Ser Lys Ser Gln Glu Phe Phe Ser Lys
    1085                1090                1095
Phe Asp Lys Ile Cys Tyr Asn Leu Asp Lys Gly Tyr Phe Glu Phe
    1100                1105                1110
Ser Phe Asp Tyr Lys Asn Phe Gly Asp Lys Ala Ala Lys Gly Lys
    1115                1120                1125
Trp Thr Ile Ala Ser Phe Gly Ser Arg Leu Ile Asn Phe Arg Asn
    1130                1135                1140
Ser Asp Lys Asn His Asn Trp Asp Thr Arg Glu Val Tyr Pro Thr
    1145                1150                1155
Lys Glu Leu Glu Lys Leu Leu Lys Asp Tyr Ser Ile Glu Tyr Gly
    1160                1165                1170
His Gly Glu Cys Ile Lys Ala Ala Ile Cys Gly Glu Ser Asp Lys
    1175                1180                1185
Lys Phe Phe Ala Lys Leu Thr Ser Val Leu Asn Thr Ile Leu Gln
    1190                1195                1200
Met Arg Asn Ser Lys Thr Gly Thr Glu Leu Asp Tyr Leu Ile Ser
    1205                1210                1215
Pro Val Ala Asp Val Asn Gly Asn Phe Phe Asp Ser Arg Gln Ala
    1220                1225                1230
Pro Lys Asn Met Pro Gln Asp Ala Asp Ala Asn Gly Ala Tyr His
    1235                1240                1245
Ile Gly Leu Lys Gly Leu Met Leu Leu Gly Arg Ile Lys Asn Asn
    1250                1255                1260
Gln Glu Gly Lys Lys Leu Asn Leu Val Ile Lys Asn Glu Glu Tyr
    1265                1270                1275
Phe Glu Phe Val Gln Asn Arg Asn Asn
    1280                1285
```

<210> SEQ ID NO 31
<211> LENGTH: 3900
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(3900)
<223> OTHER INFORMATION: Q1025G E1028G Cpf1 mutant

<400> SEQUENCE: 31

```
atgtcaattt atcaagaatt tgttaataaa tatagtttaa gtaaaactct aagatttgag      60
ttaatcccac agggtaaaac acttgaaaac ataaaagcaa gaggtttgat tttagatgat     120
gagaaaagag ctaaagacta caaaaaggct aaacaaataa ttgataaata tcatcagttt     180
tttatagagg agatattaag ttcggtttgt attagcgaag atttattaca aaactattct     240
gatgtttatt ttaaacttaa aaagagtgat gatgataatc tacaaaaaga ttttaaaagt     300
gcaaaagata cgataaagaa acaaatatct gaatatataa aggactcaga gaaatttaag     360
aatttgttta atcaaaacct tatcgatgct aaaaaagggc aagagtcaga tttaattcta     420
tggctaaagc aatctaagga taatggtata gaactatttta aagccaatag tgatatcaca     480
gatatagatg aggcgttaga ataatcaaa tcttttaaag gttggacaac ttattttaag     540
ggttttcatg aaaatagaaa aaatgtttat agtagcaatg atattcctac atctattatt     600
tataggatag tagatgataa tttgcctaaa tttctagaaa ataaagctaa gtatgagagt     660
ttaaaagaca aagctccaga agctataaac tatgaacaaa ttaaaaaaga tttggcagaa     720
gagctaacct ttgatattga ctacaaaaca tctgaagtta tcaaagagt tttttcactt     780
gatgaagttt ttgagatagc aaactttaat aattatctaa atcaaagtgg tattactaaa     840
tttaatacta ttattggtgg taaatttgta aatggtgaaa atacaaagag aaaaggtata     900
aatgaatata taaatctata ctcacagcaa ataaatgata aaacactcaa aaatataaaa     960
atgagtgttt tatttaagca aattttaagt gatacagaat ctaaatcttt tgtaattgat    1020
aagttagaag atgatagtga tgtagttaca acgatgcaaa gttttatga gcaaatagca    1080
gcttttaaaa cagtagaaga aaaatctatt aaagaaacac tatctttatt atttgatgat    1140
ttaaaagctc aaaaacttga tttgagtaaa atttatttta aaaatgataa atctcttact    1200
gatctatcac aacaagtttt tgatgattat agtgttattg gtacagcggt actagaatat    1260
ataactcaac aaatagcacc taaaaatctt gataaccta gtaagaaaga gcaagaatta    1320
atagccaaaa aaactgaaaa agcaaaatac ttatctctag aaactataaa gcttgcctta    1380
gaagaattta ataagcatag agatatagat aaacagtgta ggtttgaaga aatacttgca    1440
aactttgcgg ctattccgat gatatttgat gaaatagctc aaacaaaga caatttggca    1500
cagatatcta tcaaatatca aaatcaaggt aaaaagacc tacttcaagc tagtgcggaa    1560
gatgatgtta aagctatcaa ggatctttta gatcaaacta taatctctt acataaacta    1620
aaaatatttc atattagtca gtcagaagat aaggcaaata ttttagacaa ggatgagcat    1680
ttttatctag tatttgagga gtgctacttt gagctagcga atatagtgcc tctttataac    1740
aaaattagaa actatataac tcaaaagcca tatagtgatg agaaatttaa gctcaatttt    1800
gagaactcga ctttggctaa tggttgggat aaaaataaag agcctgacaa tacggcaatt    1860
ttatttatca aagatgataa atattatctg ggtgtgatga taagaaaaa taacaaaata    1920
tttgatgata aagctatcaa agaaaataaa ggcgagggtt ataaaaaaat tgtttataaa    1980
cttttacctg gcgcaaataa aatgttacct aaggttttct tttctgctaa atctataaaa    2040
ttttataatc ctagtgaaga tatacttaga ataagaaatc attccacaca tacaaaaaat    2100
```

```
ggtagtcctc aaaaaggata tgaaaaattt gagtttaata ttgaagattg ccgaaaattt    2160
atagattttt ataaacagtc tataagtaag catccggagt ggaaagattt tggatttaga    2220
ttttctgata ctcaaagata taattctata gatgaatttt atagagaagt tgaaaatcaa    2280
ggctacaaac taacttttga aaatatatca gagagctata ttgatagcgt agttaatcag    2340
ggtaaattgt acctattcca aatctataat aaagattttt cagcttatag caaagggcga    2400
ccaaatctac atactttata ttggaaagcg ctgtttgatg agagaaatct tcaagatgtg    2460
gtttataagc taaatggtga ggcagagctt ttttatcgta acaatcaat acctaaaaaa     2520 atcactcacc cagctaaaga ggcaatagct aataaaaaca aagataatcc taaaaaagag    2580 agtgttttg aatatgattt aatcaaagat aaacgcttta ctgaagataa gttttctttt     2640
cactgtccta ttacaatcaa ttttaaatct agtggagcta ataagtttaa tgatgaaatc    2700
aatttattgc taaagaaaa agcaaatgat gttcatatat aagtataga tagaggtgaa      2760 agacatttag cttactatac tttggtagat ggtaaaggca atatcatcaa acaagatact    2820
ttcaacatca ttggtaatga tagaatgaaa acaaactacc atgataagct tgctgcaata    2880
gagaaagata gggattcagc taggaaagac tggaaaaaga taaataacat caaagagatg    2940
aaagagggct atctatctca ggtagttcat gaaatagcta agctagttat agagtataat    3000
gctattgtgg tttttgagga tttaaatttt ggatttaaaa gagggcgttt caaggtagag    3060
aagcaggtct atggaaagtt aggaaaaatg ctaattgaga aactaaacta tctagttttc    3120
aaagataatg agtttgataa aactggggga gtgcttagag cttatcagct aacagcacct    3180
tttgagactt taaaaagat gggtaaacaa acaggtatta tctactatgt accagctggt    3240
tttacttcaa aaatttgtcc tgtaactggt tttgtaaatc agttatatcc taagtatgaa    3300
agtgtcagca atctcaaga gttctttagt aagtttgaca agatttgtta taaccttgat   3360
aagggctatt ttgagtttag ttttgattat aaaaactttg gtgacaaggc tgccaaaggc   3420
aagtggacta tagctagctt tgggagtaga ttgattaact ttagaaattc agataaaaat   3480
cataattggg atactcgaga agtttatcca actaaagagt tggagaaatt gctaaaagat   3540
tattctatcg aatatgggca tggcgaatgt atcaaagcag ctatttgcgg tgagagcgac   3600
aaaaagtttt ttgctaagct aactagtgtc ctaaatacta tcttacaaat gcgtaactca   3660
aaaacaggta ctgagttaga ttatctaatt tcaccagtag cagatgtaaa tggcaatttc   3720
tttgattcgc gacaggcgcc aaaaaatatg cctcaagatg ctgatgccaa tggtgcttat   3780
catattgggc taaaggtct gatgctacta ggtaggatca aaataatca agagggcaaa     3840 aaactcaatt tggttatcaa aaatgaagag tattttgagt tcgtgcagaa taggaataac   3900
```

<210> SEQ ID NO 32
<211> LENGTH: 1287
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1287)
<223> OTHER INFORMATION: Q1025G E1028G mutant

<400> SEQUENCE: 32

```
Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30
```

```
Ala Arg Gly Leu Ile Leu Asp Asp Glu Lys Arg Ala Lys Asp Tyr Lys
         35                  40                  45
Lys Ala Lys Gln Ile Ile Asp Lys Tyr His Gln Phe Phe Ile Glu Glu
 50                  55                  60
Ile Leu Ser Ser Val Cys Ile Ser Glu Asp Leu Leu Gln Asn Tyr Ser
 65                  70                  75                  80
Asp Val Tyr Phe Lys Leu Lys Lys Ser Asp Asp Asn Leu Gln Lys
             85                  90                  95
Asp Phe Lys Ser Ala Lys Asp Thr Ile Lys Lys Gln Ile Ser Glu Tyr
            100                 105                 110
Ile Lys Asp Ser Glu Lys Phe Lys Asn Leu Phe Asn Gln Asn Leu Ile
            115                 120                 125
Asp Ala Lys Lys Gly Gln Glu Ser Asp Leu Ile Leu Trp Leu Lys Gln
    130                 135                 140
Ser Lys Asp Asn Gly Ile Glu Leu Phe Lys Ala Asn Ser Asp Ile Thr
145                 150                 155                 160
Asp Ile Asp Glu Ala Leu Glu Ile Ile Lys Ser Phe Lys Gly Trp Thr
                165                 170                 175
Thr Tyr Phe Lys Gly Phe His Glu Asn Arg Lys Asn Val Tyr Ser Ser
            180                 185                 190
Asn Asp Ile Pro Thr Ser Ile Ile Tyr Arg Ile Val Asp Asp Asn Leu
            195                 200                 205
Pro Lys Phe Leu Glu Asn Lys Ala Lys Tyr Glu Ser Leu Lys Asp Lys
    210                 215                 220
Ala Pro Glu Ala Ile Asn Tyr Glu Gln Ile Lys Lys Asp Leu Ala Glu
225                 230                 235                 240
Glu Leu Thr Phe Asp Ile Asp Tyr Lys Thr Ser Glu Val Asn Gln Arg
                245                 250                 255
Val Phe Ser Leu Asp Glu Val Phe Glu Ile Ala Asn Phe Asn Asn Tyr
            260                 265                 270
Leu Asn Gln Ser Gly Ile Thr Lys Phe Asn Thr Ile Ile Gly Gly Lys
            275                 280                 285
Phe Val Asn Gly Glu Asn Thr Lys Arg Lys Gly Ile Asn Glu Tyr Ile
    290                 295                 300
Asn Leu Tyr Ser Gln Gln Ile Asn Asp Lys Thr Leu Lys Lys Tyr Lys
305                 310                 315                 320
Met Ser Val Phe Val Ile Asp Lys Leu Glu Asp Asp Ser Asp Val Val
                325                 330                 335
Thr Thr Met Gln Ser Phe Tyr Glu Gln Ile Ala Ala Phe Lys Thr Val
            340                 345                 350
Glu Glu Lys Ser Ile Lys Glu Thr Leu Ser Leu Leu Phe Asp Asp Leu
            355                 360                 365
Lys Ala Gln Lys Leu Asp Leu Ser Lys Ile Tyr Phe Lys Asn Asp Lys
    370                 375                 380
Ser Leu Thr Asp Leu Ser Gln Gln Val Phe Asp Tyr Ser Val Ile
385                 390                 395                 400
Gly Thr Ala Val Leu Glu Tyr Ile Thr Gln Gln Ile Ala Pro Lys Asn
                405                 410                 415
Leu Asp Asn Pro Ser Lys Lys Glu Gln Glu Leu Ile Ala Lys Lys Thr
            420                 425                 430
Glu Lys Ala Lys Tyr Leu Ser Leu Glu Thr Ile Lys Leu Ala Leu Glu
    435                 440                 445
```

-continued

```
Glu Phe Asn Lys His Arg Asp Ile Asp Lys Gln Cys Arg Phe Glu Glu
450                 455                 460
Ile Leu Ala Asn Phe Ala Ala Ile Pro Met Ile Phe Asp Glu Ile Ala
465                 470                 475                 480
Gln Asn Lys Asp Asn Leu Ala Gln Ile Ser Ile Lys Tyr Gln Asn Gln
                485                 490                 495
Gly Lys Lys Asp Leu Leu Gln Ala Ser Ala Glu Asp Val Lys Ala
            500                 505                 510
Ile Lys Asp Leu Leu Asp Gln Thr Asn Asn Leu Leu His Lys Leu Lys
            515                 520                 525
Ile Phe His Ile Ser Gln Ser Glu Asp Lys Ala Asn Ile Leu Asp Lys
            530                 535                 540
Asp Glu His Phe Tyr Leu Val Phe Glu Glu Cys Tyr Phe Glu Leu Ala
545                 550                 555                 560
Asn Ile Val Pro Leu Tyr Asn Lys Ile Arg Asn Tyr Ile Thr Gln Lys
                565                 570                 575
Pro Tyr Ser Asp Glu Lys Phe Lys Leu Asn Phe Glu Asn Ser Thr Leu
            580                 585                 590
Ala Asn Gly Trp Asp Lys Asn Lys Glu Pro Asp Asn Thr Ala Ile Leu
            595                 600                 605
Phe Ile Lys Asp Asp Lys Tyr Tyr Leu Gly Val Met Asn Lys Lys Asn
610                 615                 620
Asn Lys Ile Phe Asp Asp Lys Ala Ile Lys Glu Asn Lys Gly Glu Gly
625                 630                 635                 640
Tyr Lys Lys Ile Val Tyr Lys Leu Leu Pro Gly Ala Asn Lys Met Leu
                645                 650                 655
Pro Lys Val Phe Phe Ser Ala Lys Ser Ile Lys Phe Tyr Asn Pro Ser
            660                 665                 670
Glu Asp Ile Leu Arg Ile Arg Asn His Ser Thr His Thr Lys Asn Gly
            675                 680                 685
Ser Pro Gln Lys Gly Tyr Glu Lys Phe Glu Phe Asn Ile Glu Asp Cys
            690                 695                 700
Arg Lys Phe Ile Asp Phe Tyr Lys Gln Ser Ile Ser Lys His Pro Glu
705                 710                 715                 720
Trp Lys Asp Phe Gly Phe Arg Phe Ser Asp Thr Gln Arg Tyr Asn Ser
                725                 730                 735
Ile Asp Glu Phe Tyr Arg Glu Val Glu Asn Gln Gly Tyr Lys Leu Thr
                740                 745                 750
Phe Glu Asn Ile Ser Glu Ser Tyr Ile Asp Ser Val Val Asn Gln Gly
            755                 760                 765
Lys Leu Tyr Leu Phe Gln Ile Tyr Asn Lys Asp Phe Ser Ala Tyr Ser
770                 775                 780
Lys Gly Arg Pro Asn Leu His Thr Leu Tyr Trp Lys Ala Leu Phe Asp
785                 790                 795                 800
Glu Arg Asn Leu Gln Asp Val Val Tyr Lys Leu Asn Gly Glu Ala Glu
                805                 810                 815
Leu Phe Tyr Arg Lys Gln Ser Ile Pro Lys Lys Ile Thr His Pro Ala
            820                 825                 830
Lys Glu Ala Ile Ala Asn Lys Asn Lys Asp Asn Pro Lys Lys Glu Ser
            835                 840                 845
Val Phe Glu Tyr Asp Leu Ile Lys Asp Lys Arg Phe Thr Glu Asp Lys
850                 855                 860
Phe Phe Phe His Cys Pro Ile Thr Ile Asn Phe Lys Ser Ser Gly Ala
```

-continued

```
865                 870                 875                 880
Asn Lys Phe Asn Asp Glu Ile Asn Leu Leu Leu Lys Glu Lys Ala Asn
                885                 890                 895
Asp Val His Ile Leu Ser Ile Asp Arg Gly Glu Arg His Leu Ala Tyr
                900                 905                 910
Tyr Thr Leu Val Asp Gly Lys Gly Asn Ile Ile Lys Gln Asp Thr Phe
                915                 920                 925
Asn Ile Ile Gly Asn Asp Arg Met Lys Thr Asn Tyr His Asp Lys Leu
            930                 935                 940
Ala Ala Ile Glu Lys Asp Arg Asp Ser Ala Arg Lys Asp Trp Lys Lys
945                 950                 955                 960
Ile Asn Asn Ile Lys Glu Met Lys Glu Gly Tyr Leu Ser Gln Val Val
                965                 970                 975
His Glu Ile Ala Lys Leu Val Ile Glu Tyr Asn Ala Ile Val Val Phe
                980                 985                 990
Glu Asp Leu Asn Phe Gly Phe Lys Arg Gly Arg Phe Lys Val Glu Lys
                995                 1000                1005
Gln Val Tyr Gly Lys Leu Gly Lys Met Leu Ile Glu Lys Leu Asn
    1010                1015                1020
Tyr Leu Val Phe Lys Asp Asn Glu Phe Asp Lys Thr Gly Gly Val
    1025                1030                1035
Leu Arg Ala Tyr Gln Leu Thr Ala Pro Phe Glu Thr Phe Lys Lys
    1040                1045                1050
Met Gly Lys Gln Thr Gly Ile Ile Tyr Tyr Val Pro Ala Gly Phe
    1055                1060                1065
Thr Ser Lys Ile Cys Pro Val Thr Gly Phe Val Asn Gln Leu Tyr
    1070                1075                1080
Pro Lys Tyr Glu Ser Val Ser Lys Ser Gln Glu Phe Phe Ser Lys
    1085                1090                1095
Phe Asp Lys Ile Cys Tyr Asn Leu Asp Lys Gly Tyr Phe Glu Phe
    1100                1105                1110
Ser Phe Asp Tyr Lys Asn Phe Gly Asp Lys Ala Ala Lys Gly Lys
    1115                1120                1125
Trp Thr Ile Ala Ser Phe Gly Ser Arg Leu Ile Asn Phe Arg Asn
    1130                1135                1140
Ser Asp Lys Asn His Asn Trp Asp Thr Arg Glu Val Tyr Pro Thr
    1145                1150                1155
Lys Glu Leu Glu Lys Leu Leu Lys Asp Tyr Ser Ile Glu Tyr Gly
    1160                1165                1170
His Gly Glu Cys Ile Lys Ala Ala Ile Cys Gly Glu Ser Asp Lys
    1175                1180                1185
Lys Phe Phe Ala Lys Leu Thr Ser Val Leu Asn Thr Ile Leu Gln
    1190                1195                1200
Met Arg Asn Ser Lys Thr Gly Thr Glu Leu Asp Tyr Leu Ile Ser
    1205                1210                1215
Pro Val Ala Asp Val Asn Gly Asn Phe Phe Asp Ser Arg Gln Ala
    1220                1225                1230
Pro Lys Asn Met Pro Gln Asp Ala Asp Ala Asn Gly Ala Tyr His
    1235                1240                1245
Ile Gly Leu Lys Gly Leu Met Leu Leu Gly Arg Ile Lys Asn Asn
    1250                1255                1260
Gln Glu Gly Lys Lys Leu Asn Leu Val Ile Lys Asn Glu Glu Tyr
    1265                1270                1275
```

```
Phe Glu  Phe Val Gln Asn Arg  Asn Asn
    1280            1285
```

```
<210> SEQ ID NO 33
<211> LENGTH: 3861
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(3861)
<223> OTHER INFORMATION: Rec-deletion Cpf1 mutant

<400> SEQUENCE: 33
```

| | | | | |
|---|---|---|---|---|
| atgtcaattt | atcaagaatt | tgttaataaa | tatagtttaa gtaaaactct | aagatttgag | 60 |
| ttaatcccac | agggtaaaac | acttgaaaac | ataaaagcaa gaggtttgat | tttagatgat | 120 |
| gagaaaagag | ctaaagacta | caaaaaggct | aaacaaataa ttgataaata | tcatcagttt | 180 |
| tttatagagg | agatattaag | ttcggtttgt | attagcgaag atttattaca | aaactattct | 240 |
| gatgtttatt | ttaaacttaa | aaagagtgat | gatgataatc tacaaaaaga | ttttaaaagt | 300 |
| gcaaaagata | cgataaagaa | acaaatatct | gaatatataa aggactcaga | gaaatttaag | 360 |
| aatttgttta | atcaaaacct | tatcgatgct | aaaaaagggc aagagtcaga | tttaattcta | 420 |
| tggctaaagc | aatctaagga | taatggtata | gaactatttg aagccaatag | tgatatcaca | 480 |
| gatatagatg | aggcgttaga | aataatcaaa | tcttttaaag gttggacaac | ttattttaag | 540 |
| ggttttcatg | aaaatagaaa | aaatgtttat | agtagcaatg atattcctac | atctattatt | 600 |
| tataggatag | tagatgataa | tttgcctaaa | tttctagaaa ataaagctaa | gtatgagagt | 660 |
| ttaaaagaca | aagctccaga | agctataaac | tatgaacaaa ttaaaaaaga | tttggcagaa | 720 |
| gagctaacct | tgatattga | ctacaaaaca | tctgaagtta tcaaagagt | ttttcactt | 780 |
| gatgaagttt | ttgagatagc | aaactttaat | aattatctaa atcaaagtgg | tattactaaa | 840 |
| tttaatacta | ttattggtgg | taaatttgta | aatggtgaaa atacaaagag | aaaaggtata | 900 |
| aatgaatata | taaatctata | ctcacagcaa | ataaatgata aaacactcaa | aaaatataaa | 960 |
| atgagtgttt | ttgtaattga | taagttagaa | gatgatagtg atgtagttac | aacgatgcaa | 1020 |
| agttttatg | agcaaatagc | agcttttaaa | acagtagaag aaaaatctat | taagaaaaca | 1080 |
| ctatctttat | tatttgatga | tttaaaagct | caaaaacttg atttgagtaa | aatttatttt | 1140 |
| aaaaatgata | aatctcttac | tgatctatca | caacaagttt ttgatgatta | tagtgttatt | 1200 |
| ggtacagcgg | tactagaata | tataactcaa | caaatagcac ctaaaaatct | tgataaccct | 1260 |
| agtaagaaag | agcaagaatt | aatagccaaa | aaaactgaaa aagcaaaata | cttatctcta | 1320 |
| gaaactataa | agcttgcctt | agaagaattt | aataagcata gagatataga | taaacagtgt | 1380 |
| aggtttgaag | aaatacttgc | aaactttgcg | gctattccga tgatatttga | tgaaatagct | 1440 |
| caaaacaaag | acaatttggc | acagatatct | atcaaatatc aaaatcaagg | taaaaaagac | 1500 |
| ctacttcaag | ctagtgcgga | agatgatgtt | aaagctatca aggatctttt | agatcaaact | 1560 |
| aataatctct | tacataaact | aaaaatattt | catattagtc agtcagaaga | taaggcaaat | 1620 |
| attttagaca | aggatgagca | tttttatcta | gtatttgagg agtgctactt | tgagctagcg | 1680 |
| aatatagtgc | ctctttataa | caaaattaga | aactatataa ctcaaaagcc | atatagtgat | 1740 |
| gagaaattta | agctcaattt | tgagaactcg | actttggcta tggttgggga | taaaaataaa | 1800 |
| gagcctgaca | atacggcaat | tttatttatc | aaagatgata aatattatct | gggtgtgatg | 1860 |

```
aataagaaaa ataacaaaat atttgatgat aaagctatca aagaaaataa aggcgagggt   1920
tataaaaaaa ttgtttataa acttttacct ggcgcaaata aaatgttacc taaggttttc   1980
ttttctgcta aatctataaa attttataat cctagtgaag atatacttag aataagaaat   2040
cattccacac atacaaaaaa tggtagtcct caaaaaggat atgaaaaatt tgagtttaat   2100
attgaagatt gccgaaaatt tatagatttt tataaacagt ctataagtaa gcatccggag   2160
tggaaagatt ttggatttag attttctgat actcaaagat ataattctat agatgaattt   2220
tatagagaag ttgaaaatca aggctacaaa ctaactttg aaaatatatc agagagctat   2280
attgatagcg tagttaatca gggtaaattg tacctattcc aaatctataa taagatttt   2340 tcagcttata gcaagggcg accaaatcta catactttat attggaaagc gctgtttgat   2400
gagagaaatc ttcaagatgt ggtttataag ctaaatggtg aggcagagct ttttatcgt   2460 aaacaatcaa tacctaaaaa aatcactcac ccagctaaag aggcaatagc taataaaaac   2520
aaagataatc ctaaaaaga gagtgttttt gaatatgatt taatcaaaga taaacgcttt   2580
actgaagata agttttttctt tcactgtcct attacaatca attttaaatc tagtggagct   2640
aataagttta atgatgaaat caatttattg ctaaaagaaa aagcaaatga tgttcatata   2700
ttaagtatag atagaggtga aagacattta gcttactata ctttggtaga tggtaaaggc   2760
aatatcatca aacaagatac tttcaacatc attggtaatg atagaatgaa acaaactac   2820 catgataagc ttgctgcaat agagaaagat agggattcag ctaggaaaga ctggaaaaag   2880
ataaataaca tcaaagagat gaaagagggc tatctatctc aggtagttca tgaaatagct   2940
aagctagtta tagagtataa tgctattgtg gttttgagg atttaaatt tggatttaaa   3000 agagggcgtt tcaaggtaga gaagcaggtc tatggaaagt taggaaaaat gctaattgag   3060
aaactaaact atctagtttt caaagataat gagtttgata aaactggggg agtgcttaga   3120
gcttatcagc taacagcacc ttttgagact tttaaaaaga tgggtaaaca aacaggtatt   3180
atctactatg taccagctgg ttttacttca aaaatttgtc ctgtaactgg ttttgtaaat   3240
cagttatatc ctaagtatga aagtgtcagc aaatctcaag agttctttag taagtttgac   3300
aagatttgtt ataaccttga taagggctat tttgagttta gttttgatta taaaaacttt   3360
ggtgacaagg ctgccaaagg caagtggact atagctagct ttgggagtag attgattaac   3420
tttagaaatt cagataaaaa tcataattgg gatactcgag aagtttatcc aactaaagag   3480
ttggagaaat tgctaaaaga ttattctatc gaatatgggc atggcgaatg tatcaaagca   3540
gctatttgcg gtgagagcga caaaaagttt tttgctaagc taactagtgt cctaaatact   3600
atcttacaaa tgcgtaactc aaaaacaggt actgagttag attatctaat ttcaccagta   3660
gcagatgtaa atgcaatttt ctttgattcg cgacaggcgc caaaaatat gcctcaagat   3720 gctgatgcca atggtgctta tcatattggg ctaaaaggtc tgatgctact aggtaggatc   3780
aaaaataatc aagagggcaa aaaactcaat tggttatca aaaatgaaga gtatttgag    3840 ttcgtgcaga ataggaataa c                                            3861
```

<210> SEQ ID NO 34
<211> LENGTH: 1287
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1287)

<223> OTHER INFORMATION: Rec-deletion Cpf1 mutant

<400> SEQUENCE: 34

```
Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asn Leu Gln Lys
                85                  90                  95

Asp Phe Lys Ser Ala Lys Asp Thr Ile Lys Lys Gln Ile Ser Glu Tyr
                100                 105                 110

Ile Lys Asp Ser Glu Lys Phe Lys Asn Leu Phe Asn Gln Asn Leu Ile
            115                 120                 125

Asp Ala Lys Lys Gly Gln Glu Ser Asp Leu Ile Leu Trp Leu Lys Gln
        130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
                180                 185                 190

Asn Asp Ile Pro Thr Ser Ile Ile Tyr Arg Ile Val Asp Asp Asn Leu
            195                 200                 205

Pro Lys Phe Leu Glu Asn Lys Ala Lys Tyr Glu Ser Leu Lys Asp Lys
        210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
                260                 265                 270

Leu Asn Gln Ser Gly Ile Thr Lys Phe Asn Thr Ile Ile Gly Gly Lys
            275                 280                 285

Phe Val Asn Gly Glu Asn Thr Lys Arg Lys Gly Ile Asn Glu Tyr Ile
        290                 295                 300

Asn Leu Tyr Ser Gln Gln Ile Asn Asp Lys Thr Leu Lys Lys Tyr Lys
305                 310                 315                 320

Met Ser Val Phe Val Ile Asp Lys Leu Glu Asp Asp Ser Asp Val Val
                325                 330                 335

Thr Thr Met Gln Ser Phe Tyr Glu Gln Ile Ala Ala Phe Lys Thr Val
            340                 345                 350

Glu Glu Lys Ser Ile Lys Glu Thr Leu Ser Leu Leu Phe Asp Asp Leu
        355                 360                 365

Lys Ala Gln Lys Leu Asp Leu Ser Lys Ile Tyr Phe Lys Asn Asp Lys
        370                 375                 380

Ser Leu Thr Asp Leu Ser Gln Gln Val Phe Asp Asp Tyr Ser Val Ile
385                 390                 395                 400
```

```
Gly Thr Ala Val Leu Glu Tyr Ile Thr Gln Ile Ala Pro Lys Asn
                405                 410                 415

Leu Asp Asn Pro Ser Lys Lys Glu Gln Glu Leu Ile Ala Lys Lys Thr
            420                 425                 430

Glu Lys Ala Lys Tyr Leu Ser Leu Glu Thr Ile Lys Leu Ala Leu Glu
            435                 440                 445

Glu Phe Asn Lys His Arg Asp Ile Asp Lys Gln Cys Arg Phe Glu Glu
            450                 455                 460

Ile Leu Ala Asn Phe Ala Ala Ile Pro Met Ile Phe Asp Glu Ile Ala
465                 470                 475                 480

Gln Asn Lys Asp Asn Leu Ala Gln Ile Ser Ile Lys Tyr Gln Asn Gln
                485                 490                 495

Gly Lys Lys Asp Leu Leu Gln Ala Ser Ala Glu Asp Val Lys Ala
            500                 505                 510

Ile Lys Asp Leu Leu Asp Gln Thr Asn Asn Leu Leu His Lys Leu Lys
            515                 520                 525

Ile Phe His Ile Ser Gln Ser Glu Asp Lys Ala Asn Ile Leu Asp Lys
            530                 535                 540

Asp Glu His Phe Tyr Leu Val Phe Glu Glu Cys Tyr Phe Glu Leu Ala
545                 550                 555                 560

Asn Ile Val Pro Leu Tyr Asn Lys Ile Arg Asn Tyr Ile Thr Gln Lys
                565                 570                 575

Pro Tyr Ser Asp Glu Lys Phe Lys Leu Asn Phe Glu Asn Ser Thr Leu
            580                 585                 590

Ala Asn Gly Trp Asp Lys Asn Lys Glu Pro Asp Asn Thr Ala Ile Leu
            595                 600                 605

Phe Ile Lys Asp Asp Lys Tyr Tyr Leu Gly Val Met Asn Lys Lys Asn
            610                 615                 620

Asn Lys Ile Phe Asp Asp Lys Ala Ile Lys Glu Asn Lys Gly Glu Gly
625                 630                 635                 640

Tyr Lys Lys Ile Val Tyr Lys Leu Leu Pro Gly Ala Asn Lys Met Leu
                645                 650                 655

Pro Lys Val Phe Phe Ser Ala Lys Ser Ile Lys Phe Tyr Asn Pro Ser
            660                 665                 670

Glu Asp Ile Leu Arg Ile Arg Asn His Ser Thr His Thr Lys Asn Gly
            675                 680                 685

Ser Pro Gln Lys Gly Tyr Glu Lys Phe Glu Phe Asn Ile Glu Asp Cys
            690                 695                 700

Arg Lys Phe Ile Asp Phe Tyr Lys Gln Ser Ile Ser Lys His Pro Glu
705                 710                 715                 720

Trp Lys Asp Phe Gly Phe Arg Phe Ser Asp Thr Gln Arg Tyr Asn Ser
                725                 730                 735

Ile Asp Glu Phe Tyr Arg Glu Val Glu Asn Gln Gly Tyr Lys Leu Thr
            740                 745                 750

Phe Glu Asn Ile Ser Glu Ser Tyr Ile Asp Ser Val Val Asn Gln Gly
            755                 760                 765

Lys Leu Tyr Leu Phe Gln Ile Tyr Asn Lys Asp Phe Ser Ala Tyr Ser
            770                 775                 780

Lys Gly Arg Pro Asn Leu His Thr Leu Tyr Trp Lys Ala Leu Phe Asp
785                 790                 795                 800

Glu Arg Asn Leu Gln Asp Val Val Tyr Lys Leu Asn Gly Glu Ala Glu
                805                 810                 815

Leu Phe Tyr Arg Lys Gln Ser Ile Pro Lys Lys Ile Thr His Pro Ala
```

-continued

```
                820                 825                 830
Lys Glu Ala Ile Ala Asn Lys Asn Lys Asp Asn Pro Lys Lys Glu Ser
            835                 840                 845
Val Phe Glu Tyr Asp Leu Ile Lys Asp Lys Arg Phe Thr Glu Asp Lys
    850                 855                 860
Phe Phe Phe His Cys Pro Ile Thr Ile Asn Phe Lys Ser Ser Gly Ala
865                 870                 875                 880
Asn Lys Phe Asn Asp Glu Ile Asn Leu Leu Lys Glu Lys Ala Asn
                885                 890                 895
Asp Val His Ile Leu Ser Ile Asp Arg Gly Glu Arg His Leu Ala Tyr
            900                 905                 910
Tyr Thr Leu Val Asp Gly Lys Gly Asn Ile Ile Lys Gln Asp Thr Phe
    915                 920                 925
Asn Ile Ile Gly Asn Asp Arg Met Lys Thr Asn Tyr His Asp Lys Leu
        930                 935                 940
Ala Ala Ile Glu Lys Asp Arg Asp Ser Ala Arg Lys Asp Trp Lys Lys
945                 950                 955                 960
Ile Asn Asn Ile Lys Glu Met Lys Glu Gly Tyr Leu Ser Gln Val Val
                965                 970                 975
His Glu Ile Ala Lys Leu Val Ile Glu Tyr Asn Ala Ile Val Val Phe
            980                 985                 990
Glu Asp Leu Asn Phe Gly Phe Lys Arg Gly Arg Phe Lys Val Glu Lys
    995                 1000                1005
Gln Val Tyr Gly Lys Leu Gly Lys Met Leu Ile Glu Lys Leu Asn
    1010                1015                1020
Tyr Leu Val Phe Lys Asp Asn Glu Phe Asp Lys Thr Gly Gly Val
    1025                1030                1035
Leu Arg Ala Tyr Gln Leu Thr Ala Pro Phe Glu Thr Phe Lys Lys
    1040                1045                1050
Met Gly Lys Gln Thr Gly Ile Ile Tyr Tyr Val Pro Ala Gly Phe
    1055                1060                1065
Thr Ser Lys Ile Cys Pro Val Thr Gly Phe Val Asn Gln Leu Tyr
    1070                1075                1080
Pro Lys Tyr Glu Ser Val Ser Lys Ser Gln Glu Phe Phe Ser Lys
    1085                1090                1095
Phe Asp Lys Ile Cys Tyr Asn Leu Asp Lys Gly Tyr Phe Glu Phe
    1100                1105                1110
Ser Phe Asp Tyr Lys Asn Phe Gly Asp Lys Ala Ala Lys Gly Lys
    1115                1120                1125
Trp Thr Ile Ala Ser Phe Gly Ser Arg Leu Ile Asn Phe Arg Asn
    1130                1135                1140
Ser Asp Lys Asn His Asn Trp Asp Thr Arg Glu Val Tyr Pro Thr
    1145                1150                1155
Lys Glu Leu Glu Lys Leu Leu Lys Asp Tyr Ser Ile Glu Tyr Gly
    1160                1165                1170
His Gly Glu Cys Ile Lys Ala Ala Ile Cys Gly Glu Ser Asp Lys
    1175                1180                1185
Lys Phe Phe Ala Lys Leu Thr Ser Val Leu Asn Thr Ile Leu Gln
    1190                1195                1200
Met Arg Asn Ser Lys Thr Gly Thr Glu Leu Asp Tyr Leu Ile Ser
    1205                1210                1215
Pro Val Ala Asp Val Asn Gly Asn Phe Phe Asp Ser Arg Gln Ala
    1220                1225                1230
```

```
Pro Lys Asn Met Pro Gln Asp Ala Asp Ala Asn Gly Ala Tyr His
   1235            1240                1245

Ile Gly Leu Lys Gly Leu Met Leu Leu Gly Arg Ile Lys Asn Asn
   1250            1255                1260

Gln Glu Gly Lys Lys Leu Asn Leu Val Ile Lys Asn Glu Glu Tyr
   1265            1270                1275

Phe Glu Phe Val Gln Asn Arg Asn Asn
   1280            1285

<210> SEQ ID NO 35
<211> LENGTH: 3903
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(3903)
<223> OTHER INFORMATION: Rec-substitution Cpf1 mutant

<400> SEQUENCE: 35
atgtcaattt atcaagaatt tgttaataaa tatagtttaa gtaaaactct aagatttgag    60
ttaatcccac agggtaaaac acttgaaaac ataaaagcaa gaggtttgat tttagatgat   120
gagaaaagag ctaaagacta caaaaaggct aaacaaataa ttgataaata tcatcagttt   180
tttatagagg agatattaag ttcggtttgt attagcgaag atttattaca aaactattct   240
gatgtttatt ttaaacttaa aaagagtgat gatgataatc tacaaaaaga ttttaaaagt   300
gcaaaagata cgataaagaa acaaatatct gaatatataa aggactcaga gaaatttaag   360
aatttgttta tcaaaaccct tatcgatgct aaaaaaggc aagagtcaga tttaattcta   420
tggctaaagc aatctaagga taatggtata gaactattta agccaatag tgatatcaca   480 gatatagatg aggcgttaga aataatcaaa tcttttaaag gttggacaac ttatttaag   540 ggttttcatg aaaatagaaa aaatgtttat agtagcaatg atattcctac atctattatt   600
tataggatag tagtgataa tttgcctaaa tttctagaaa ataaagctaa gtatgagagt   660
ttaaaagaca agctccaga agctataaac tatgaacaaa ttaaaaaga tttggcagaa   720 gagctaacct tgatattga ctacaaaaca tctgaagtta tcaaagagt tttttcactt   780 gatgaagttt tgagatagc aaactttaat aattatctaa atcaaagtgg tattactaaa   840
tttaatacta ttattggtgg taaatttgta aatggtgaaa atacaaagag aaaaggtata   900
aatgaatata taaatctata ctcacagcaa ataaatgata aaacactcaa aaatatataaa   960 atgagtgttg gtggtggagc cggtgcaagt gctggaggat ctggatcttt gtaattgat  1020 aagttagaag atgatagtga tgtagttaca acgatgcaaa gttttttatga gcaaatagca  1080 gcttttaaaa cagtagaaga aaaatctatt aaagaaacac tatctttatt atttgatgat  1140
ttaaaagctc aaaaacttga tttgagtaaa atttattttta aaatgataaa atctcttact  1200
gatctatcac aacaagtttt tgatgattat agtgttattg gtacagcggt actagaatat  1260
ataactcaac aaatagcacc taaaaatctt gataaccta gtaagaaaga gcaagaatta  1320
atagccaaaa aaactgaaaa agcaaaatac ttatctctag aaactataaa gcttgccta  1380 gaagaattta ataagcatag agatatagat aaacagtgta ggtttgaaga atacttgca  1440 aactttgcgg ctattccgat gatatttgat gaaatagctc aaacaaaga caatttggca  1500 cagatatcta tcaaatatca aaatcaaggt aaaaagacc tacttcaagc tagtgcggaa  1560
```

```
gatgatgtta aagctatcaa ggatctttta gatcaaacta ataatctctt acataaacta   1620
aaaatatttc atattagtca gtcagaagat aaggcaaata ttttagacaa ggatgagcat   1680
ttttatctag tatttgagga gtgctacttt gagctagcga atatagtgcc tctttataac   1740
aaaattagaa actatataac tcaaaagcca tatagtgatg agaaatttaa gctcaatttt   1800
gagaactcga ctttggctaa tggttgggat aaaaataaag agcctgacaa tacggcaatt   1860
ttatttatca aagatgataa atattatctg ggtgtgatga ataagaaaaa taacaaaata   1920
tttgatgata aagctatcaa agaaaataaa ggcgagggtt ataaaaaaat tgtttataaa   1980
cttttacctg gcgcaaataa aatgttacct aaggttttct ttctgctaa atctataaaa    2040
ttttataatc ctagtgaaga tatacttaga ataagaaatc attccacaca tacaaaaaat   2100
ggtagtcctc aaaaaggata tgaaaaattt gagtttaata ttgaagattg ccgaaaattt   2160
atagattttt ataaacagtc tataagtaag catccggagt ggaaagattt tggatttaga   2220
ttttctgata ctcaaagata taattctata gatgaatttt atagaaagt tgaaaatcaa    2280
ggctacaaac taacttttga aaatatatca gagagctata ttgatagcgt agttaatcag   2340
ggtaaattgt acctattcca aatctataat aaagattttt cagcttatag caaagggcga   2400
ccaaatctac atactttata ttggaaagcg ctgtttgatg agaaaatct tcaagatgtg    2460
gtttataagc taaatggtga ggcagagctt ttttatcgta aacaatcaat acctaaaaaa   2520
atcactcacc cagctaaaga ggcaatagct aataaaaaca aagataatcc taaaaaagag   2580
agtgtttttg aatatgattt aatcaaagat aaacgcttta ctgaagataa gttttctttt   2640
cactgtccta ttacaatcaa ttttaaatct agtggagcta ataagtttaa tgatgaaatc   2700
aatttattgc taaagaaaa agcaaatgat gttcatatat taagtataga tagaggtgaa   2760
agacatttag cttactatac tttggtagat ggtaaaggca atatcatcaa acaagatact   2820
ttcaacatca ttggtaatga tagaatgaaa acaaactacc atgataagct tgctgcaata   2880
gagaaagata gggattcagc taggaaagac tggaaaaaga taaataacat caaagagatg   2940
aaagagggct atctatctca ggtagttcat gaaatagcta agctagttat agagtataat   3000
gctattgtgg ttttttgagga tttaaatttt ggatttaaaa gagggcgttt caaggtagag   3060
aagcaggtct atcaaaagtt agaaaaaatg ctaattgaga aactaaacta tctagttttc   3120
aaagataatg agtttgataa aactggggga gtgcttagag cttatcagct aacagcacct   3180
tttgagactt ttaaaaagat gggtaaacaa acaggtatta tctactatgt accagctggt   3240
tttacttcaa aaatttgtcc tgtaactggt tttgtaaatc agttatatcc taagtatgaa   3300
agtgtcagca atctcaaga gttctttagt aagtttgaca agatttgtta taaccttgat    3360
aagggctatt ttgagtttag ttttgattat aaaaactttg gtgacaaggc tgccaaaggc   3420
aagtggacta tagctagctt tgggagtaga ttgattaact ttagaaattc agataaaaat   3480
cataattggg atactcgaga agtttatcca actaaagagt tggagaaatt gctaaaagat   3540
tattctatcg aatatgggca tggcgaatgt atcaaagcag ctatttgcgg tgagagcgac   3600
aaaaagtttt ttgctaagct aactagtgtc ctaaatacta tcttacaaat gcgtaactca   3660
aaaacaggta ctgagttaga ttatctaatt tcaccagtag cagatgtaaa tggcaatttc   3720
tttgattcgc gacaggcgcc aaaaaatatg cctcaagatg ctgatgccaa tggtgcttat   3780
catattgggc taaaggtct gatgctacta ggtaggatca aaaataatca agagggcaaa    3840
aaactcaatt tggttatcaa aaatgaagag tattttgagt tcgtgcagaa taggaataac   3900
taa                                                                 3903
```

<210> SEQ ID NO 36
<211> LENGTH: 1300
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1300)
<223> OTHER INFORMATION: Rec-substitution Cpf1 mutant

<400> SEQUENCE: 36

```
Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Gly Gly Gly Ala Gly Ala Ser Ala Gly Ser Gly Ser
                325                 330                 335

Phe Val Ile Asp Lys Leu Glu Asp Asp Ser Asp Val Val Thr Thr Met
```

```
            340                 345                 350
Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765
```

-continued

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn Ala Ile Val Val Phe Glu Asp Leu
        995                 1000                1005

Asn Phe Gly Phe Lys Arg Gly Arg Phe Lys Val Glu Lys Gln Val
    1010                1015                1020

Tyr Gln Lys Leu Glu Lys Met Leu Ile Glu Lys Leu Asn Tyr Leu
    1025                1030                1035

Val Phe Lys Asp Asn Glu Phe Asp Lys Thr Gly Gly Val Leu Arg
    1040                1045                1050

Ala Tyr Gln Leu Thr Ala Pro Phe Glu Thr Phe Lys Lys Met Gly
    1055                1060                1065

Lys Gln Thr Gly Ile Ile Tyr Tyr Val Pro Ala Gly Phe Thr Ser
    1070                1075                1080

Lys Ile Cys Pro Val Thr Gly Phe Val Asn Gln Leu Tyr Pro Lys
    1085                1090                1095

Tyr Glu Ser Val Ser Lys Ser Gln Glu Phe Phe Ser Lys Phe Asp
    1100                1105                1110

Lys Ile Cys Tyr Asn Leu Asp Lys Gly Tyr Phe Glu Phe Ser Phe
    1115                1120                1125

Asp Tyr Lys Asn Phe Gly Asp Lys Ala Ala Lys Gly Lys Trp Thr
    1130                1135                1140

Ile Ala Ser Phe Gly Ser Arg Leu Ile Asn Phe Arg Asn Ser Asp
    1145                1150                1155

Lys Asn His Asn Trp Asp Thr Arg Glu Val Tyr Pro Thr Lys Glu
    1160                1165                1170

Leu Glu Lys Leu Leu Lys Asp Tyr Ser Ile Glu Tyr Gly His Gly
1175                 1180                1185

Glu Cys Ile Lys Ala Ala Ile Cys Gly Glu Ser Asp Lys Lys Phe
    1190                1195                1200

Phe Ala Lys Leu Thr Ser Val Leu Asn Thr Ile Leu Gln Met Arg
       1205                1210                1215

Asn Ser Lys Thr Gly Thr Glu Leu Asp Tyr Leu Ile Ser Pro Val
        1220                1225                1230

Ala Asp Val Asn Gly Asn Phe Phe Asp Ser Arg Gln Ala Pro Lys
   1235                1240                1245

Asn Met Pro Gln Asp Ala Asp Ala Asn Gly Ala Tyr His Ile Gly
   1250                1255                1260

Leu Lys Gly Leu Met Leu Leu Gly Arg Ile Lys Asn Asn Gln Glu
    1265                1270                1275

Gly Lys Lys Leu Asn Leu Val Ile Lys Asn Glu Glu Tyr Phe Glu
   1280                1285                1290

Phe Val Gln Asn Arg Asn Asn
   1295                1300

<210> SEQ ID NO 37
<211> LENGTH: 3903
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(3903)
<223> OTHER INFORMATION: LID-substitution Cpf1 mutant

<400> SEQUENCE: 37

```
atgtcaattt atcaagaatt tgttaataaa tatagtttaa gtaaaactct aagatttgag      60
ttaatcccac agggtaaaac acttgaaaac ataaaagcaa gaggtttgat tttagatgat     120
gagaaaagag ctaagactac aaaaaggct aaacaaataa ttgataaata tcatcagttt     180
tttatagagg agatattaag ttcggtttgt attagcgaag atttattaca aaactattct     240
gatgtttatt ttaaacttaa aaagagtgat gatgataatc tacaaaaaga ttttaaaagt     300
gcaaaagata cgataaagaa acaaatatct gaatatataa aggactcaga gaatttaaag     360
aatttgttta tcaaaaacct tatcgatgct aaaaaggc aagagtcaga tttaattcta     420
tggctaaagc aatctaagga taatggtata gaactattta agccaatag tgatatcaca     480 gatatagatg aggcgttaga aataatcaaa tcttttaaag gttggacaac ttattttaag     540
ggttttcatg aaaatagaaa aaatgtttat agtagcaatg atattcctac atctattatt     600
tataggatag tagatgataa tttgcctaaa tttctagaaa ataagctaa gtatgagagt     660 ttaaaagaca agctccaga agctataaac tatgaacaaa ttaaaaaaga tttggcagaa     720
gagctaacct tgatattga ctacaaaaca tctgaagtta tcaaagagt tttttcactt     780 gatgaagttt ttgagatagc aaactttaat aattatctaa atcaaagtgg tattactaaa     840
tttaatacta ttattggtgg taaatttgta aatggtgaaa atacaaagag aaaaggtata     900
aatgaatata taaatctata ctcacagcaa ataaatgata aacactcaa aaatataaa     960 atgagtgttt tatttaagca aattttaagt gatacagaat ctaaatcttt tgtaattgat    1020
aagttagaag atgatagtga tgtagttaca acgatgcaaa gttttatga gcaaatagca    1080 gcttttaaaa cagtagaaga aaaatctatt aaagaaacac tatctttat atttgatgat    1140
```

```
ttaaaagctc aaaaacttga tttgagtaaa atttatttta aaaatgataa atctcttact   1200
gatctatcac aacaagtttt tgatgattat agtgttattg gtacagcggt actagaatat   1260
ataactcaac aaatagcacc taaaaatctt gataaccta gtaagaaaga gcaagaatta   1320
atagccaaaa aaactgaaaa agcaaaatac ttatctctag aaactataaa gcttgcctta   1380
gaagaattta ataagcatag agatatagat aaacagtgta ggtttgaaga aatacttgca   1440
aactttgcgg ctattccgat gatatttgat gaaatagctc aaaacaaaga caatttggca   1500
cagatatcta tcaaatatca aaatcaaggt aaaaagacc tacttcaagc tagtgcggaa   1560
gatgatgtta aagctatcaa ggatctttta gatcaaacta ataatctctt acataaacta   1620
aaaatatttc atattagtca gtcagaagat aaggcaaata ttttagacaa ggatgagcat   1680
ttttatctag tatttgagga gtgctacttt gagctagcga atatagtgcc tctttataac   1740
aaaattagaa actatataac tcaaaagcca tatagtgatg agaaatttaa gctcaatttt   1800
gagaactcga ctttggctaa tggttgggat aaaaataaag agcctgacaa tacggcaatt   1860
ttatttatca aagatgataa atattatctg gtgtgatga ataagaaaaa taacaaaata   1920
tttgatgata aagctatcaa agaaaataaa ggcgagggtt ataaaaaaat tgtttataaa   1980
cttttacctg gcgcaaataa aatgttacct aaggttttct ttctgctaa atctataaaa   2040
ttttataatc ctagtgaaga tatacttaga ataagaaatc attccacaca tacaaaaaat   2100
ggtagtcctc aaaaaggata tgaaaaattt gagtttaata ttgaagattg ccgaaaattt   2160
atagattttt ataaacagtc tataagtaag catccggagt ggaaagattt tggatttaga   2220
ttttctgata ctcaaagata taattctata gatgaatttt atagagaagt tgaaaatcaa   2280
ggctacaaac taactttga aaatatatca gagagctata ttgatagcgt agttaatcag   2340
ggtaaattgt acctattcca aatctataat aaagattttt cagcttatag caaagggcga   2400
ccaaatctac atactttata ttggaaagcg ctgtttgatg agagaaatct tcaagatgtg   2460
gtttataagc taaatggtga ggcagagctt ttttatcgta acaatcaat acctaaaaaa   2520
atcactcacc cagctaaaga ggcaatagct aataaaaaca aagataatcc taaaaaagag   2580
agtgttttg aatatgattt aatcaaagat aaacgcttta ctgaagataa gttttctttt   2640
cactgtccta ttacaatcaa ttttaaatct agtggagcta ataagtttaa tgatgaaatc   2700
aatttattgc taaagaaaa agcaaatgat gttcatatat taagtataga tagaggtgaa   2760
agacatttag cttactatac tttggtagat ggtaaaggca atatcatcaa acaagatact   2820
ttcaacatca ttggtaatga tagaatgaaa acaaactacc atgataagct tgctgcaata   2880
gagaaagata gggattcagc taggaaagac tggaaaaaga taataacat caaagagatg   2940
aaagagggct atctatctca ggtagttcat gaaatagcta agctagttat agagtataat   3000
gctattgtgg ttttttggtgg tggagccggt ggagcagctg gaggggagc cggtgtagag   3060
aagcaggtct atcaaaagtt agaaaaaatg ctaattgaga aactaaacta tctagttttc   3120
aaagataatg agtttgataa aactggggga gtgcttagag cttatcagct aacagcacct   3180
tttgagactt ttaaaaagat gggtaaacaa acaggtatta tctactatgt accagctggt   3240
tttacttcaa aaatttgtcc tgtaactggt tttgtaaatc agttatatcc taagtatgaa   3300
agtgtcagca aatctcaaga gttctttagt aagtttgaca agatttgtta taaccttgat   3360
aagggctatt ttgagtttag ttttgattat aaaaactttg gtgacaaggc tgccaaaggc   3420
aagtggacta tagctagctt tgggagtaga ttgattaact ttagaaattc agataaaaat   3480
cataattggg atactcgaga agtttatcca actaaagagt tggagaaatt gctaaaagat   3540
```

-continued

```
tattctatcg aatatgggca tggcgaatgt atcaaagcag ctatttgcgg tgagagcgac   3600
aaaaagtttt ttgctaagct aactagtgtc ctaaatacta tcttacaaat gcgtaactca   3660
aaaacaggta ctgagttaga ttatctaatt tcaccagtag cagatgtaaa tggcaatttc   3720
tttgattcgc gacaggcgcc aaaaaatatg cctcaagatg ctgatgccaa tggtgcttat   3780
catattgggc taaaaggtct gatgctacta ggtaggatca aaaataatca agagggcaaa   3840
aaactcaatt tggttatcaa aaatgaagag tattttgagt tcgtgcagaa taggaataac   3900
taa                                                                 3903
```

```
<210> SEQ ID NO 38
<211> LENGTH: 1300
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1300)
<223> OTHER INFORMATION: LID-substitution Cpf1 mutant

<400> SEQUENCE: 38

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270
```

```
Leu Asn Gln Ser Gly Ile Thr Lys Phe Asn Thr Ile Ile Gly Gly Lys
            275                 280                 285

Phe Val Asn Gly Glu Asn Thr Lys Arg Lys Gly Ile Asn Glu Tyr Ile
290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
                340                 345                 350

Gln Ser Phe Tyr Glu Gln Ile Ala Ala Phe Lys Thr Val Glu Glu Lys
            355                 360                 365

Ser Ile Lys Glu Thr Leu Ser Leu Leu Phe Asp Asp Leu Lys Ala Gln
370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Thr Glu Lys Ala
                435                 440                 445

Lys Tyr Leu Ser Leu Glu Thr Ile Lys Leu Ala Leu Glu Glu Phe Asn
450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
                500                 505                 510

Asp Leu Leu Gln Ala Ser Ala Glu Asp Asp Val Lys Ala Ile Lys Asp
            515                 520                 525

Leu Leu Asp Gln Thr Asn Asn Leu Leu His Lys Leu Lys Ile Phe His
            530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
                580                 585                 590

Asp Glu Lys Phe Lys Leu Asn Phe Glu Asn Ser Thr Leu Ala Asn Gly
            595                 600                 605

Trp Asp Lys Asn Lys Glu Pro Asp Asn Thr Ala Ile Leu Phe Ile Lys
610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
            675                 680                 685
```

```
Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn Ala Ile Val Val Phe Gly Gly Gly
        995                 1000                1005

Ala Gly Gly Ala Ala Gly Gly Ala Gly Val Glu Lys Gln Val
    1010                1015                1020

Tyr Gln Lys Leu Glu Lys Met Leu Ile Glu Lys Leu Asn Tyr Leu
    1025                1030                1035

Val Phe Lys Asp Asn Glu Phe Asp Lys Thr Gly Gly Val Leu Arg
    1040                1045                1050

Ala Tyr Gln Leu Thr Ala Pro Phe Glu Thr Phe Lys Lys Met Gly
    1055                1060                1065

Lys Gln Thr Gly Ile Ile Tyr Tyr Val Pro Ala Gly Phe Thr Ser
    1070                1075                1080

Lys Ile Cys Pro Val Thr Gly Phe Val Asn Gln Leu Tyr Pro Lys
    1085                1090                1095

Tyr Glu Ser Val Ser Lys Ser Gln Glu Phe Phe Ser Lys Phe Asp
```

| | | | | | | | | | |
|---|---|---|---|---|---|---|---|---|---|
| | | 1100 | | | 1105 | | | 1110 | |
| Lys | Ile | Cys | Tyr | Asn | Leu | Asp | Lys | Gly | Tyr | Phe | Glu | Phe | Ser | Phe |
| | 1115 | | | | 1120 | | | | | 1125 | | | | |

Lys Ile Cys Tyr Asn Leu Asp Lys Gly Tyr Phe Glu Phe Ser Phe
    1115                1120                    1125

Asp Tyr Lys Asn Phe Gly Asp Lys Ala Ala Lys Gly Lys Trp Thr
    1130                1135                    1140

Ile Ala Ser Phe Gly Ser Arg Leu Ile Asn Phe Arg Asn Ser Asp
    1145                1150                    1155

Lys Asn His Asn Trp Asp Thr Arg Glu Val Tyr Pro Thr Lys Glu
    1160                1165                    1170

Leu Glu Lys Leu Leu Lys Asp Tyr Ser Ile Glu Tyr Gly His Gly
    1175                1180                    1185

Glu Cys Ile Lys Ala Ala Ile Cys Gly Glu Ser Asp Lys Lys Phe
    1190                1195                    1200

Phe Ala Lys Leu Thr Ser Val Leu Asn Thr Ile Leu Gln Met Arg
    1205                1210                    1215

Asn Ser Lys Thr Gly Thr Glu Leu Asp Tyr Leu Ile Ser Pro Val
    1220                1225                    1230

Ala Asp Val Asn Gly Asn Phe Phe Asp Ser Arg Gln Ala Pro Lys
    1235                1240                    1245

Asn Met Pro Gln Asp Ala Asp Ala Asn Gly Ala Tyr His Ile Gly
    1250                1255                    1260

Leu Lys Gly Leu Met Leu Leu Gly Arg Ile Lys Asn Asn Gln Glu
    1265                1270                    1275

Gly Lys Lys Leu Asn Leu Val Ile Lys Asn Glu Glu Tyr Phe Glu
    1280                1285                    1290

Phe Val Gln Asn Arg Asn Asn
    1295                1300

<210> SEQ ID NO 39
<211> LENGTH: 3814
<212> TYPE: DNA
<213> ORGANISM: Artificial sequence
<220> FEATURE:
<223> OTHER INFORMATION: Synthetic sequence

<400> SEQUENCE: 39
atgtcaattt atcaagaatt tgttaataaa tatagtttaa gtaaaactct aagatttgag    60
ttaatcccac agggtaaaac acttgaaaac ataaaagcaa gaggtttgat tttagatgat   120
gagaaaagag ctaaagacta caaaaaggct aaacaaataa ttgataaata tcatcagttt   180
tttatagagg agatattaag ttcggtttgt attagcgaag attttattaca aaactattct   240
gatgtttatt ttaaacttaa aaagagtgat gatgataatc tacaaaaaga ttttaaaagt   300
gcaaaagata cgataaagaa acaaatatct gaatatataa aggactcaga gaaatttaag   360
aatttgttta tcaaaaacct tatcgatgct aaaaaagggc aagagtcaga tttaattcta   420
tggctaaagc aatctaagga taatggtata gaactattta agccaatagt gatatcaca   480
gatatagatg aggcgttaga aataatcaaa tcttttaaag gttggacaac ttattttaag   540
ggttttcatg aaaatagaaa aaatgttat agtagcaatg atattcctac atctattatt   600
tataggatag tagatgataa tttgcctaaa tttctagaaa ataaagctaa gtatgagagt   660
ttaaaagaca agctccaga agctataaac tatgaacaaa ttaaaaaaga tttggcagaa   720
gagctaacct tgatattga ctacaaaaca tctgaagtta tcaaagagt ttttcactt   780
gatgaagttt tgagatagc aaactttaat aattatctaa atcaaagtgg tattactaaa   840

```
tttaatacta ttattggtgg taaatttgta aatggtgaaa atacaaagag aaaaggtata    900
aatgaatata taaatctata ctcacagcaa ataaatgata aaacactcaa aaaatataaa    960
atgagtgttt tatttaagca aattttaagt gatacagaat ctaaatcttt tgtaattgat   1020
aagttagaag atgatagtga tgtagttaca acgatgcaaa gttttttatga gcaaatagca   1080
gcttttaaaa cagtagaaga aaaatctatt aaagaaacac tatctttatt atttgatgat   1140
ttaaaagctc aaaaacttga tttgagtaaa atttattttta aaaatgataa atctcttact   1200
gatctatcac aacaagtttt tgatgattat agtgttattg gtacagcggt actagaatat   1260
ataactcaac aaatagcacc taaaaatctt gataaccta gtaagaaaga gcaagaatta   1320
atagccaaaa aaactgaaaa agcaaaatac ttatctctag aaactataaa gcttgcctta   1380
gaagaatttta ataagcatag agatatagat aaacagtgta ggtttgaaga atacttgca    1440
aactttgcgg ctattccgat gatatttgat gaaatagctc aaaacaaaga caatttggca    1500
cagatatcta tcaaatatca aaatcaaggt aaaaaagacc tacttcaagc tagtgcggaa   1560
gatgatgtta aagctatcaa ggatctttta gatcaaacta ataatctctt acataaacta   1620
aaaatatttc atattagtca gtcagaagat aaggcaaata ttttagacaa ggatgagcat   1680
ttttatctag tatttgagga gtgctacttt gagctagcga atatagtgcc tctttataac   1740
aaaattagaa actatataac tcaaaagcca tatagtgatg agaaattttaa gctcaatttt   1800
gagaactcga ctttggctaa tggttgggat aaaaataaag agcctgacaa tacggcaatt   1860
ttatttatca aagatgataa atattatctg gtgtgatga ataagaaaaa taacaaaata   1920
tttgatgata aagctatcaa agaaaataaa ggcgagggtt ataaaaaaat tgtttataaa   1980
cttttacctg gcgcaaataa aatgttacct aaggttttct tttctgctaa atctataaaa   2040
ttttataatc ctagtgaaga tatacttaga ataagaaatc attccacaca tacaaaaaat   2100
ggtagtcctc aaaaaggata tgaaaaattt gagtttaata ttgaagattg ccgaaaattt   2160
atagatttttt ataaacagtc tataagtaag catccggagt ggaaagattt tggatttaga   2220
ttttctgata ctcaaagata taattctata gatgaatttt atagagaagt tgaaaatcaa   2280
ggctacaaac taacttttga aaatatatca gagagctata ttgatagcgt agttaatcag   2340
ggtaaattgt acctattcca aatctataat aaagattttt cagcttatag caaagggcga   2400
ccaaatctac atactttata ttggaaagcg ctgtttgatg agagaaatct tcaagatgtg   2460
gtttataagc taaatggtga ggcagagctt ttttatcgta acaatcaat acctaaaaaa   2520
atcactcacc cagctaaaga ggcaatagct aataaaaaca aagataatcc taaaaaagag   2580
agtgtttttg aatatgattt aatcaaagat aaacgcttta ctgaagataa gttttttcttt   2640
cactgtccta ttacaatcaa ttttaaatct agtggagcta ataagtttaa tgatgaaatc   2700
aatttattgc taaaagaaaa agcaaatgat gttcatatat taagtataga tagaggtgaa   2760
agacatttag cttactatac tttggtagat ggtaaaggca atatcatcaa acaagatact   2820
ttcaacatca ttggtaatga tagaatgaaa acaaactacc atgataagct tgctgcaata   2880
gagaaagata gggattcagc taggaaagac tggaaaaaga taaataacat caaagagatg   2940
aaagagggct atctatctca ggtagttcat gaaatagcta agctagttat tagaaaaaat   3000
gctaattgag aaactaaact atctagtttt caaagataat gagtttgata aaactggggg   3060
agtgcttaga gctatcagc taacagcacc ttttgagact tttaaaaaga tgggtaaaca   3120
aacaggtatt atctactatg taccagctgg ttttacttca aaaatttgtc ctgtaactgg   3180
ttttgtaaat cagttatatc ctaagtatga aagtgtcagc aaatctcaag agttctttag   3240
```

```
taagtttgac aagatttgtt ataaccttga taagggctat tttgagttta gttttgatta    3300
taaaaacttt ggtgacaagg ctgccaaagg caagtggact atagctagct ttgggagtag    3360
attgattaac tttagaaatt cagataaaaa tcataattgg gatactcgag aagtttatcc    3420
aactaaagag ttggagaaat tgctaaaaga ttattctatc gaatatgggc atggcgaatg    3480
tatcaaagca gctatttgcg gtgagagcga caaaaagttt tttgctaagc taactagtgt    3540
cctaaatact atcttacaaa tgcgtaactc aaaaacaggt actgagttag attatctaat    3600
ttcaccagta gcagatgtaa atggcaattt ctttgattcg cgacaggcgc caaaaaatat    3660
gcctcaagat gctgatgcca atggtgctta tcatattggg ctaaaaggtc tgatgctact    3720
aggtaggatc aaaaataatc aagagggcaa aaaactcaat ttggttatca aaaatgaaga    3780
gtattttgag ttcgtgcaga ataggaataa ctaa                               3814

<210> SEQ ID NO 40
<211> LENGTH: 1287
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1287)
<223> OTHER INFORMATION: LID-deletion Cpf1 mutant

<400> SEQUENCE: 40

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240
```

-continued

```
Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655
```

-continued

```
Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
            675                 680                 685

Leu Arg Ile Arg Asn His Ser Thr His Thr Lys Asn Gly Ser Pro Gln
            690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
            755                 760                 765

Ile Ser Glu Ser Tyr Ile Asp Ser Val Val Asn Gln Gly Lys Leu Tyr
            770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
            805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
            835                 840                 845

Ile Ala Asn Lys Asn Lys Asp Asn Pro Lys Lys Glu Ser Val Phe Glu
850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
            885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
            915                 920                 925

Val Asp Gly Lys Gly Asn Ile Ile Lys Gln Asp Thr Phe Asn Ile Ile
930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
            965                 970                 975

Ile Lys Glu Met Lys Glu Gly Tyr Leu Ser Gln Val Val His Glu Ile
            980                 985                 990

Ala Lys Leu Val Ile Glu Tyr Asn Ala Ile Val Val Phe Val Glu Lys
            995                 1000                1005

Gln Val Tyr Gln Lys Leu Glu Lys Met Leu Ile Glu Lys Leu Asn
            1010                1015                1020

Tyr Leu Val Phe Lys Asp Asn Glu Phe Asp Lys Thr Gly Gly Val
            1025                1030                1035

Leu Arg Ala Tyr Gln Leu Thr Ala Pro Phe Glu Thr Phe Lys Lys
            1040                1045                1050

Met Gly Lys Gln Thr Gly Ile Ile Tyr Tyr Val Pro Ala Gly Phe
            1055                1060                1065

Thr Ser Lys Ile Cys Pro Val Thr Gly Phe Val Asn Gln Leu Tyr
```

Pro Lys Tyr Glu Ser Val Ser Lys Ser Gln Glu Phe Phe Ser Lys
1085                1090                1095

Phe Asp Lys Ile Cys Tyr Asn Leu Asp Lys Gly Tyr Phe Glu Phe
1100                1105                1110

Ser Phe Asp Tyr Lys Asn Phe Gly Asp Lys Ala Ala Lys Gly Lys
1115                1120                1125

Trp Thr Ile Ala Ser Phe Gly Ser Arg Leu Ile Asn Phe Arg Asn
1130                1135                1140

Ser Asp Lys Asn His Asn Trp Asp Thr Arg Glu Val Tyr Pro Thr
1145                1150                1155

Lys Glu Leu Glu Lys Leu Leu Lys Asp Tyr Ser Ile Glu Tyr Gly
1160                1165                1170

His Gly Glu Cys Ile Lys Ala Ala Ile Cys Gly Glu Ser Asp Lys
1175                1180                1185

Lys Phe Phe Ala Lys Leu Thr Ser Val Leu Asn Thr Ile Leu Gln
1190                1195                1200

Met Arg Asn Ser Lys Thr Gly Thr Glu Leu Asp Tyr Leu Ile Ser
1205                1210                1215

Pro Val Ala Asp Val Asn Gly Asn Phe Phe Asp Ser Arg Gln Ala
1220                1225                1230

Pro Lys Asn Met Pro Gln Asp Ala Asp Ala Asn Gly Ala Tyr His
1235                1240                1245

Ile Gly Leu Lys Gly Leu Met Leu Leu Gly Arg Ile Lys Asn Asn
1250                1255                1260

Gln Glu Gly Lys Lys Leu Asn Leu Val Ile Lys Asn Glu Glu Tyr
1265                1270                1275

Phe Glu Phe Val Gln Asn Arg Asn Asn
1280                1285

<210> SEQ ID NO 41
<211> LENGTH: 3867
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(3867)
<223> OTHER INFORMATION: Finger-deletion Cpf1 mutant

<400> SEQUENCE: 41
atgtcaattt atcaagaatt tgttaataaa tatagtttaa gtaaaactct aagatttgag      60
ttaatcccac agggtaaaac acttgaaaac ataaaagcaa gaggtttgat tttagatgat     120
gagaaaagag ctaaagacta caaaaaggct aaacaaataa ttgataaata tcatcagttt     180
tttatagagg agatattaag ttcggtttgt attagcgaag atttattaca aaactattct     240
gatgtttatt ttaaacttaa aaagagtgat gatgataatc tacaaaaaga ttttaaaagt     300
gcaaaagata cgataaagaa acaaatatct gaatatataa aggactcaga gaaatttaag     360
aatttgttta atcaaaacct tatcgatgct aaaaaaggc aagagtcaga tttaattcta     420
tggctaaagc aatctaagga taatggtata gaactattta agccaatag tgatatcaca     480 gatatagatg aggcgttaga aataatcaaa tctttttaaag gttggacaac ttattttaag     540
ggttttcatg aaaatagaaa aaatgttat agtagcaatg atattcctac atctattatt     600
tataggatag tagatgataa tttgcctaaa tttctagaaa ataaagctaa gtatgagagt     660

```
ttaaaagaca aagctccaga agctataaac tatgaacaaa ttaaaaaaga tttggcagaa      720
gagctaacct ttgatattga ctacaaaaca tctgaagtta atcaaagagt tttttcactt      780
gatgaagttt ttgagatagc aaactttaat aattatctaa atcaaagtgg tattactaaa      840
tttaatacta ttattggtgg taaatttgta aatggtgaaa atacaaagag acaaataaat      900
gataaaacac tcaaaaaata taaaatgagt gttttattta agcaaatttt aagtgataca      960
gaatctaaat cttttgtaat tgataagtta aagatgata gtgatgtagt tacaacgatg      1020
caaagttttt atgagcaaat agcagctttt aaaacagtag aagaaaaatc tattaaagaa      1080
acactatctt tattatttga tgatttaaaa gctcaaaaac ttgatttgag taaaatttat      1140
tttaaaaatg ataaatctct tactgatcta tcacaacaag ttttttgatga ttatagtgtt      1200 attggtacag cggtactaga atatataact caacaaatag cacctaaaaa tcttgataac      1260
cctagtaaga aagagcaaga attaatagcc aaaaaaactg aaaaagcaaa atacttatct      1320
ctagaaacta taaagcttgc cttagaagaa tttaataagc atagagatat agataaacag      1380
tgtaggtttg aagaaatact tgcaaacttt gcggctattc cgatgatatt tgatgaaata      1440
gctcaaaaca aagacaattt ggcacagata tctatcaaat atcaaaatca aggtaaaaaa      1500
gacctacttc aagctagtgc ggaagatgat gttaaagcta tcaaggatct tttagatcaa      1560
actaataatc tcttacataa actaaaaata tttcatatta gtcagtcaga agataaggca      1620
aatattttag acaaggatga gcattttat ctagtatttg aggagtgcta ctttgagcta      1680
gcgaatatag tgcctctttta taacaaaatt agaaactata taactcaaaa gccatatagt      1740
gatgagaaat ttaagctcaa ttttgagaac tcgactttgg ctaatggttg ggataaaaat      1800
aaagagcctg acaatacggc aatttttattt atcaaagatg ataaatatta tctgggtgtg      1860
atgaataaga aaaataacaa atatttgat gataaagcta tcaaagaaaa taaggcgag      1920 ggttataaaa aaattgttta taaactttta cctggcgcaa ataaaatgtt acctaaggtt      1980 ttctttctg ctaaatctat aaaatttat aatcctagtg aagatatact tagaataaga      2040
aatcattcca cacatacaaa aaatggtagt cctcaaaaag gatatgaaaa atttgagttt      2100
aatattgaag attgccgaaa atttatagat ttttataaac agtctataag taagcatccg      2160
gagtggaaag atttttggatt tagattttct gatactcaaa gatataattc tatagatgaa      2220
ttttatagag aagttgaaaa tcaaggctac aaactaactt ttgaaaatat atcagagagc      2280
tatattgata gcgtagttaa tcagggtaaa ttgtacctat tccaaatcta taataaagat      2340
ttttcagctt atagcaaagg gcgaccaaat ctacatactt tatattggaa agcgctgttt      2400
gatgagagaa atcttcaaga tgtggtttat aagctaaatg gtgaggcaga gctttttttat      2460 cgtaaacaat caatacctaa aaaaatcact cacccagcta aagaggcaat agctaataaa      2520
aacaaagata atcctaaaaa agagagtgtt tttgaatatg atttaatcaa agataaacgc      2580
tttactgaag ataagttttt ctttcactgt cctattacaa tcaattttaa atctagtgga      2640
gctaataagt ttaatgatga aatcaattta ttgctaaaag aaaaagcaaa tgatgttcat      2700
atattaagta tagatagagg tgaaagacat ttagcttact atactttggt agatggtaaa      2760
ggcaatatca tcaaacaaga tactttcaac atcattggta atgatagaat gaaaacaaac      2820
taccatgata agcttgctgc aatagagaaa gatagggatt cagctaggaa agactggaaa      2880
aagataaata acatcaaaga gatgaaagag ggctatctat ctcaggtagt tcatgaaata      2940
gctaagctag ttatagagta taatgctatt gtggtttttg aggatttaaa ttttggatttt      3000
```

-continued

```
aaaagagggc gtttcaaggt agagaagcag gtctatcaaa agttagaaaa aatgctaatt    3060
gagaaactaa actatctagt tttcaaagat aatgagtttg ataaaactgg gggagtgctt    3120
agagcttatc agctaacagc accttttgag acttttaaaa agatgggtaa acaaacaggt    3180
attatctact atgtaccagc tggttttact tcaaaaattt gtcctgtaac tggttttgta    3240
aatcagttat atcctaagta tgaaagtgtc agcaaatctc aagagttctt tagtaagttt    3300
gacaagattt gttataacct tgataagggc tattttgagt ttagttttga ttataaaaac    3360
tttggtgaca aggctgccaa aggcaagtgg actatagcta gctttgggag tagattgatt    3420
aactttagaa attcagataa aaatcataat tgggatactc gagaagttta tccaactaaa    3480
gagttggaga aattgctaaa agattattct atcgaatatg ggcatggcga atgtatcaaa    3540
gcagctattt gcggtgagag cgacaaaaag ttttttgcta agctaactag tgtcctaaat    3600
actatcttac aaatgcgtaa ctcaaaaaca ggtactgagt tagattatct aatttcacca    3660
gtagcagatg taaatggcaa tttctttgat tcgcgacagg cgccaaaaaa tatgcctcaa    3720
gatgctgatg ccaatggtgc ttatcatatt gggctaaaag gtctgatgct actaggtagg    3780
atcaaaaata atcaagaggg caaaaaactc aatttggtta tcaaaaatga agagtatttt    3840
gagttcgtgc agaataggaa taactaa                                       3867
```

<210> SEQ ID NO 42
<211> LENGTH: 1288
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1288)
<223> OTHER INFORMATION: Finger-deletion Cpf1 mutant

<400> SEQUENCE: 42

```
Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190
```

```
Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
            245                 250                 255

Val Phe Ser Leu Asp Glu Val Phe Glu Ile Ala Asn Phe Asn Asn Tyr
                260                 265                 270

Leu Asn Gln Ser Gly Ile Thr Lys Phe Asn Thr Ile Gly Gly Lys
        275                 280                 285

Phe Val Asn Gly Glu Asn Thr Lys Arg Gln Ile Asn Asp Lys Thr Leu
    290                 295                 300

Lys Lys Tyr Lys Met Ser Val Leu Phe Lys Gln Ile Leu Ser Asp Thr
305                 310                 315                 320

Glu Ser Lys Ser Phe Val Ile Asp Lys Leu Glu Asp Ser Asp Val
            325                 330                 335

Val Thr Thr Met Gln Ser Phe Tyr Glu Gln Ile Ala Ala Phe Lys Thr
                340                 345                 350

Val Glu Glu Lys Ser Ile Lys Glu Thr Leu Ser Leu Leu Phe Asp Asp
        355                 360                 365

Leu Lys Ala Gln Lys Leu Asp Leu Ser Lys Ile Tyr Phe Lys Asn Asp
    370                 375                 380

Lys Ser Leu Thr Asp Leu Ser Gln Gln Val Phe Asp Tyr Ser Val
385                 390                 395                 400

Ile Gly Thr Ala Val Leu Glu Tyr Ile Thr Gln Gln Ile Ala Pro Lys
            405                 410                 415

Asn Leu Asp Asn Pro Ser Lys Lys Glu Gln Glu Leu Ile Ala Lys Lys
                420                 425                 430

Thr Glu Lys Ala Lys Tyr Leu Ser Leu Glu Thr Ile Lys Leu Ala Leu
        435                 440                 445

Glu Glu Phe Asn Lys His Arg Asp Ile Asp Lys Gln Cys Arg Phe Glu
    450                 455                 460

Glu Ile Leu Ala Asn Phe Ala Ala Ile Pro Met Ile Phe Asp Glu Ile
465                 470                 475                 480

Ala Gln Asn Lys Asp Asn Leu Ala Gln Ile Ser Ile Lys Tyr Gln Asn
            485                 490                 495

Gln Gly Lys Lys Asp Leu Leu Gln Ala Ser Ala Glu Asp Val Lys
                500                 505                 510

Ala Ile Lys Asp Leu Leu Asp Gln Thr Asn Asn Leu Leu His Lys Leu
        515                 520                 525

Lys Ile Phe His Ile Ser Gln Ser Glu Asp Lys Ala Asn Ile Leu Asp
    530                 535                 540

Lys Asp Glu His Phe Tyr Leu Val Phe Glu Glu Cys Tyr Phe Glu Leu
545                 550                 555                 560

Ala Asn Ile Val Pro Leu Tyr Asn Lys Ile Arg Asn Tyr Ile Thr Gln
            565                 570                 575

Lys Pro Tyr Ser Asp Glu Lys Phe Lys Leu Asn Phe Glu Asn Ser Thr
                580                 585                 590

Leu Ala Asn Gly Trp Asp Lys Asn Lys Glu Pro Asp Asn Thr Ala Ile
        595                 600                 605
```

```
Leu Phe Ile Lys Asp Asp Lys Tyr Tyr Leu Gly Val Met Asn Lys Lys
    610                 615                 620

Asn Asn Lys Ile Phe Asp Asp Lys Ala Ile Lys Glu Asn Lys Gly Glu
625                 630                 635                 640

Gly Tyr Lys Lys Ile Val Tyr Lys Leu Leu Pro Gly Ala Asn Lys Met
                645                 650                 655

Leu Pro Lys Val Phe Phe Ser Ala Lys Ser Ile Lys Phe Tyr Asn Pro
        660                 665                 670

Ser Glu Asp Ile Leu Arg Ile Arg Asn His Ser Thr His Thr Lys Asn
    675                 680                 685

Gly Ser Pro Gln Lys Gly Tyr Glu Lys Phe Glu Phe Asn Ile Glu Asp
    690                 695                 700

Cys Arg Lys Phe Ile Asp Phe Tyr Lys Gln Ser Ile Ser Lys His Pro
705                 710                 715                 720

Glu Trp Lys Asp Phe Gly Phe Arg Phe Ser Asp Thr Gln Arg Tyr Asn
                725                 730                 735

Ser Ile Asp Glu Phe Tyr Arg Glu Val Glu Asn Gln Gly Tyr Lys Leu
        740                 745                 750

Thr Phe Glu Asn Ile Ser Glu Ser Tyr Ile Asp Ser Val Val Asn Gln
    755                 760                 765

Gly Lys Leu Tyr Leu Phe Gln Ile Tyr Asn Lys Asp Phe Ser Ala Tyr
770                 775                 780

Ser Lys Gly Arg Pro Asn Leu His Thr Leu Tyr Trp Lys Ala Leu Phe
785                 790                 795                 800

Asp Glu Arg Asn Leu Gln Asp Val Val Tyr Lys Leu Asn Gly Glu Ala
                805                 810                 815

Glu Leu Phe Tyr Arg Lys Gln Ser Ile Pro Lys Lys Ile Thr His Pro
        820                 825                 830

Ala Lys Glu Ala Ile Ala Asn Lys Asn Lys Asp Asn Pro Lys Lys Glu
    835                 840                 845

Ser Val Phe Glu Tyr Asp Leu Ile Lys Asp Lys Arg Phe Thr Glu Asp
    850                 855                 860

Lys Phe Phe Phe His Cys Pro Ile Thr Ile Asn Phe Lys Ser Ser Gly
865                 870                 875                 880

Ala Asn Lys Phe Asn Asp Glu Ile Asn Leu Leu Leu Lys Glu Lys Ala
                885                 890                 895

Asn Asp Val His Ile Leu Ser Ile Asp Arg Gly Glu Arg His Leu Ala
        900                 905                 910

Tyr Tyr Thr Leu Val Asp Gly Lys Gly Asn Ile Ile Lys Gln Asp Thr
    915                 920                 925

Phe Asn Ile Ile Gly Asn Asp Arg Met Lys Thr Asn Tyr His Asp Lys
    930                 935                 940

Leu Ala Ala Ile Glu Lys Asp Arg Asp Ser Ala Arg Lys Asp Trp Lys
945                 950                 955                 960

Lys Ile Asn Asn Ile Lys Glu Met Lys Glu Gly Tyr Leu Ser Gln Val
                965                 970                 975

Val His Glu Ile Ala Lys Leu Val Ile Glu Tyr Asn Ala Ile Val Val
        980                 985                 990

Phe Glu Asp Leu Asn Phe Gly Phe Lys Arg Gly Arg Phe Lys Val Glu
    995                 1000                1005

Lys Gln Val Tyr Gln Lys Leu Glu Lys Met Leu Ile Glu Lys Leu
    1010                1015                1020

Asn Tyr Leu Val Phe Lys Asp Asn Glu Phe Asp Lys Thr Gly Gly
```

```
            1025                1030                1035

Val Leu Arg Ala Tyr Gln Leu Thr Ala Pro Phe Glu Thr Phe Lys
        1040                1045                1050

Lys Met Gly Lys Gln Thr Gly Ile Ile Tyr Tyr Val Pro Ala Gly
        1055                1060                1065

Phe Thr Ser Lys Ile Cys Pro Val Thr Gly Phe Val Asn Gln Leu
        1070                1075                1080

Tyr Pro Lys Tyr Glu Ser Val Ser Lys Ser Gln Glu Phe Phe Ser
        1085                1090                1095

Lys Phe Asp Lys Ile Cys Tyr Asn Leu Asp Lys Gly Tyr Phe Glu
        1100                1105                1110

Phe Ser Phe Asp Tyr Lys Asn Phe Gly Asp Lys Ala Ala Lys Gly
        1115                1120                1125

Lys Trp Thr Ile Ala Ser Phe Gly Ser Arg Leu Ile Asn Phe Arg
        1130                1135                1140

Asn Ser Asp Lys Asn His Asn Trp Asp Thr Arg Glu Val Tyr Pro
        1145                1150                1155

Thr Lys Glu Leu Glu Lys Leu Leu Lys Asp Tyr Ser Ile Glu Tyr
        1160                1165                1170

Gly His Gly Glu Cys Ile Lys Ala Ala Ile Cys Gly Glu Ser Asp
        1175                1180                1185

Lys Lys Phe Phe Ala Lys Leu Thr Ser Val Leu Asn Thr Ile Leu
        1190                1195                1200

Gln Met Arg Asn Ser Lys Thr Gly Thr Glu Leu Asp Tyr Leu Ile
        1205                1210                1215

Ser Pro Val Ala Asp Val Asn Gly Asn Phe Phe Asp Ser Arg Gln
        1220                1225                1230

Ala Pro Lys Asn Met Pro Gln Asp Ala Asp Ala Asn Gly Ala Tyr
        1235                1240                1245

His Ile Gly Leu Lys Gly Leu Met Leu Leu Gly Arg Ile Lys Asn
        1250                1255                1260

Asn Gln Glu Gly Lys Lys Leu Asn Leu Val Ile Lys Asn Glu Glu
        1265                1270                1275

Tyr Phe Glu Phe Val Gln Asn Arg Asn Asn
        1280                1285

<210> SEQ ID NO 43
<211> LENGTH: 1238
<212> TYPE: PRT
<213> ORGANISM: Candidatus Methanoplasma termitum

<400> SEQUENCE: 43

Met Asn Asn Tyr Asp Glu Phe Thr Lys Leu Tyr Pro Ile Gln Lys Thr
1               5                   10                  15

Ile Arg Phe Glu Leu Lys Pro Gln Gly Arg Thr Met Glu His Leu Glu
                20                  25                  30

Thr Phe Asn Phe Phe Glu Glu Asp Arg Asp Arg Ala Glu Lys Tyr Lys
            35                  40                  45

Ile Leu Lys Glu Ala Ile Asp Glu Tyr His Lys Lys Phe Ile Asp Glu
        50                  55                  60

His Leu Thr Asn Met Ser Leu Asp Trp Asn Ser Leu Lys Gln Ile Ser
65                  70                  75                  80

Glu Lys Tyr Tyr Lys Ser Arg Glu Glu Lys Asp Lys Lys Val Phe Leu
                85                  90                  95
```

```
Ser Glu Gln Lys Arg Met Arg Gln Glu Ile Val Ser Glu Phe Lys Lys
            100                 105                 110

Asp Asp Arg Phe Lys Asp Leu Phe Ser Lys Lys Leu Phe Ser Glu Leu
        115                 120                 125

Leu Lys Glu Glu Ile Tyr Lys Lys Gly Asn His Gln Glu Ile Asp Ala
    130                 135                 140

Leu Lys Ser Phe Asp Lys Phe Ser Gly Tyr Phe Ile Gly Leu His Glu
145                 150                 155                 160

Asn Arg Lys Asn Met Tyr Ser Asp Gly Asp Glu Ile Thr Ala Ile Ser
                165                 170                 175

Asn Arg Ile Val Asn Glu Asn Phe Pro Lys Phe Leu Asp Asn Leu Gln
            180                 185                 190

Lys Tyr Gln Glu Ala Arg Lys Lys Tyr Pro Glu Trp Ile Ile Lys Ala
        195                 200                 205

Glu Ser Ala Leu Val Ala His Asn Ile Lys Met Asp Glu Val Phe Ser
    210                 215                 220

Leu Glu Tyr Phe Asn Lys Val Leu Asn Gln Glu Gly Ile Gln Arg Tyr
225                 230                 235                 240

Asn Leu Ala Leu Gly Gly Tyr Val Thr Lys Ser Gly Glu Lys Met Met
                245                 250                 255

Gly Leu Asn Asp Ala Leu Asn Leu Ala His Gln Ser Glu Lys Ser Ser
            260                 265                 270

Lys Gly Arg Ile His Met Thr Pro Leu Phe Lys Gln Ile Leu Ser Glu
        275                 280                 285

Lys Glu Ser Phe Ser Tyr Ile Pro Asp Val Phe Thr Glu Asp Ser Gln
    290                 295                 300

Leu Leu Pro Ser Ile Gly Gly Phe Phe Ala Gln Ile Glu Asn Asp Lys
305                 310                 315                 320

Asp Gly Asn Ile Phe Asp Arg Ala Leu Glu Leu Ile Ser Ser Tyr Ala
                325                 330                 335

Glu Tyr Asp Thr Glu Arg Ile Tyr Ile Arg Gln Ala Asp Ile Asn Arg
            340                 345                 350

Val Ser Asn Val Ile Phe Gly Glu Trp Gly Thr Leu Gly Gly Leu Met
        355                 360                 365

Arg Glu Tyr Lys Ala Asp Ser Ile Asn Asp Ile Asn Leu Glu Arg Thr
    370                 375                 380

Cys Lys Lys Val Asp Lys Trp Leu Asp Ser Lys Glu Phe Ala Leu Ser
385                 390                 395                 400

Asp Val Leu Glu Ala Ile Lys Arg Thr Gly Asn Asn Asp Ala Phe Asn
                405                 410                 415

Glu Tyr Ile Ser Lys Met Arg Thr Ala Arg Glu Lys Ile Asp Ala Ala
            420                 425                 430

Arg Lys Glu Met Lys Phe Ile Ser Glu Lys Ile Ser Gly Asp Glu Glu
        435                 440                 445

Ser Ile His Ile Ile Lys Thr Leu Leu Asp Ser Val Gln Gln Phe Leu
    450                 455                 460

His Phe Phe Asn Leu Phe Lys Ala Arg Gln Asp Ile Pro Leu Asp Gly
465                 470                 475                 480

Ala Phe Tyr Ala Glu Phe Asp Glu Val His Ser Lys Leu Phe Ala Ile
                485                 490                 495

Val Pro Leu Tyr Asn Lys Val Arg Asn Tyr Leu Thr Lys Asn Asn Leu
            500                 505                 510

Asn Thr Lys Lys Ile Lys Leu Asn Phe Lys Asn Pro Thr Leu Ala Asn
```

-continued

```
            515                 520                 525
Gly Trp Asp Gln Asn Lys Val Tyr Asp Tyr Ala Ser Leu Ile Phe Leu
530                 535                 540

Arg Asp Gly Asn Tyr Tyr Leu Gly Ile Ile Asn Pro Lys Arg Lys Lys
545                 550                 555                 560

Asn Ile Lys Phe Glu Gln Gly Ser Gly Asn Gly Pro Phe Tyr Arg Lys
                565                 570                 575

Met Val Tyr Lys Gln Ile Pro Gly Pro Asn Lys Asn Leu Pro Arg Val
                580                 585                 590

Phe Leu Thr Ser Thr Lys Gly Lys Lys Glu Tyr Lys Pro Ser Lys Glu
                595                 600                 605

Ile Ile Glu Gly Tyr Glu Ala Asp Lys His Ile Arg Gly Asp Lys Phe
610                 615                 620

Asp Leu Asp Phe Cys His Lys Leu Ile Asp Phe Phe Lys Glu Ser Ile
625                 630                 635                 640

Glu Lys His Lys Asp Trp Ser Lys Phe Asn Phe Tyr Phe Ser Pro Thr
                645                 650                 655

Glu Ser Tyr Gly Asp Ile Ser Glu Phe Tyr Leu Asp Val Glu Lys Gln
                660                 665                 670

Gly Tyr Arg Met His Phe Glu Asn Ile Ser Ala Glu Thr Ile Asp Glu
                675                 680                 685

Tyr Val Glu Lys Gly Asp Leu Phe Leu Phe Gln Ile Tyr Asn Lys Asp
690                 695                 700

Phe Val Lys Ala Ala Thr Gly Lys Lys Asp Met His Thr Ile Tyr Trp
705                 710                 715                 720

Asn Ala Ala Phe Ser Pro Glu Asn Leu Gln Asp Val Val Lys Leu
                725                 730                 735

Asn Gly Glu Ala Glu Leu Phe Tyr Arg Asp Lys Ser Asp Ile Lys Glu
                740                 745                 750

Ile Val His Arg Glu Gly Glu Ile Leu Val Asn Arg Thr Tyr Asn Gly
                755                 760                 765

Arg Thr Pro Val Pro Asp Lys Ile His Lys Lys Leu Thr Asp Tyr His
770                 775                 780

Asn Gly Arg Thr Lys Asp Leu Gly Glu Ala Lys Glu Tyr Leu Asp Lys
785                 790                 795                 800

Val Arg Tyr Phe Lys Ala His Tyr Asp Ile Thr Lys Asp Arg Arg Tyr
                805                 810                 815

Leu Asn Asp Lys Ile Tyr Phe His Val Pro Leu Thr Leu Asn Phe Lys
                820                 825                 830

Ala Asn Gly Lys Lys Asn Leu Asn Lys Met Val Ile Glu Lys Phe Leu
                835                 840                 845

Ser Asp Glu Lys Ala His Ile Ile Gly Ile Asp Arg Gly Glu Arg Asn
                850                 855                 860

Leu Leu Tyr Tyr Ser Ile Ile Asp Arg Ser Gly Lys Ile Ile Asp Gln
865                 870                 875                 880

Gln Ser Leu Asn Val Ile Asp Gly Phe Asp Tyr Arg Glu Lys Leu Asn
                885                 890                 895

Gln Arg Glu Ile Glu Met Lys Asp Ala Arg Gln Ser Trp Asn Ala Ile
                900                 905                 910

Gly Lys Ile Lys Asp Leu Lys Glu Gly Tyr Leu Ser Lys Ala Val His
                915                 920                 925

Glu Ile Thr Lys Met Ala Ile Gln Tyr Asn Ala Ile Val Val Met Glu
930                 935                 940
```

Glu Leu Asn Tyr Gly Phe Lys Arg Gly Arg Phe Lys Val Glu Lys Gln
945                 950                 955                 960

Ile Tyr Gln Lys Phe Glu Asn Met Leu Ile Asp Lys Met Asn Tyr Leu
            965                 970                 975

Val Phe Lys Asp Ala Pro Asp Glu Ser Pro Gly Gly Val Leu Asn Ala
        980                 985                 990

Tyr Gln Leu Thr Asn Pro Leu Glu Ser Phe Ala Lys Leu Gly Lys Gln
            995                 1000                1005

Thr Gly Ile Leu Phe Tyr Val Pro Ala Ala Tyr Thr Ser Lys Ile
    1010                1015                1020

Asp Pro Thr Thr Gly Phe Val Asn Leu Phe Asn Thr Ser Ser Lys
    1025                1030                1035

Thr Asn Ala Gln Glu Arg Lys Glu Phe Leu Gln Lys Phe Glu Ser
    1040                1045                1050

Ile Ser Tyr Ser Ala Lys Asp Gly Gly Ile Phe Ala Phe Ala Phe
    1055                1060                1065

Asp Tyr Arg Lys Phe Gly Thr Ser Lys Thr Asp His Lys Asn Val
    1070                1075                1080

Trp Thr Ala Tyr Thr Asn Gly Glu Arg Met Arg Tyr Ile Lys Glu
    1085                1090                1095

Lys Lys Arg Asn Glu Leu Phe Asp Pro Ser Lys Glu Ile Lys Glu
    1100                1105                1110

Ala Leu Thr Ser Ser Gly Ile Lys Tyr Asp Gly Gly Gln Asn Ile
    1115                1120                1125

Leu Pro Asp Ile Leu Arg Ser Asn Asn Asn Gly Leu Ile Tyr Thr
    1130                1135                1140

Met Tyr Ser Ser Phe Ile Ala Ala Ile Gln Met Arg Val Tyr Asp
    1145                1150                1155

Gly Lys Glu Asp Tyr Ile Ile Ser Pro Ile Lys Asn Ser Lys Gly
    1160                1165                1170

Glu Phe Phe Arg Thr Asp Pro Lys Arg Arg Glu Leu Pro Ile Asp
    1175                1180                1185

Ala Asp Ala Asn Gly Ala Tyr Asn Ile Ala Leu Arg Gly Glu Leu
    1190                1195                1200

Thr Met Arg Ala Ile Ala Glu Lys Phe Asp Pro Asp Ser Glu Lys
    1205                1210                1215

Met Ala Lys Leu Glu Leu Lys His Lys Asp Trp Phe Glu Phe Met
    1220                1225                1230

Gln Thr Arg Gly Asp
    1235

<210> SEQ ID NO 44
<211> LENGTH: 1272
<212> TYPE: PRT
<213> ORGANISM: uncultured Clostridium sp.

<400> SEQUENCE: 44

Met Glu Asp Lys Gln Phe Leu Glu Arg Tyr Lys Glu Phe Ile Gly Leu
1               5                   10                  15

Asn Ser Leu Ser Lys Thr Leu Arg Asn Ser Leu Ile Pro Val Gly Ser
            20                  25                  30

Thr Leu Lys His Ile Gln Glu Tyr Gly Ile Leu Glu Glu Asp Ser Leu
        35                  40                  45

Arg Ala Gln Lys Arg Glu Glu Leu Lys Gly Ile Met Asp Asp Tyr Tyr

```
            50                  55                  60
Arg Asn Tyr Ile Glu Met His Leu Arg Asp Val His Asp Ile Asp Trp
 65                  70                  75                  80

Asn Glu Leu Phe Glu Ala Leu Thr Glu Val Lys Lys Asn Gln Thr Asp
                 85                  90                  95

Asp Ala Lys Lys Cys Leu Glu Lys Ile Gln Glu Lys Lys Arg Lys Glu
            100                 105                 110

Ile Tyr Gln Tyr Leu Ser Asp Asp Ala Val Phe Ser Glu Met Phe Lys
        115                 120                 125

Glu Lys Met Ile Ser Gly Ile Leu Pro Asp Phe Ile Arg Cys Asn Glu
    130                 135                 140

Glu Tyr Ser Glu Glu Glu Lys Glu Glu Lys Leu Lys Thr Val Ala Leu
145                 150                 155                 160

Phe His Arg Phe Thr Ser Ser Phe Asn Asp Phe Leu Asn Arg Lys
                165                 170                 175

Asn Val Phe Thr Lys Glu Ala Ile Ala Thr Ala Ile Gly Tyr Arg Val
            180                 185                 190

Val His Glu Asn Ala Glu Ile Phe Leu Glu Asn Met Val Ala Phe Gln
        195                 200                 205

Asn Ile Gln Lys Ser Ala Glu Ser Gln Ile Ser Ile Glu Arg Lys
    210                 215                 220

Asn Glu His Tyr Phe Met Glu Trp Lys Leu Ser His Ile Phe Thr Ala
225                 230                 235                 240

Asp Tyr Tyr Met Met Leu Met Thr Gln Lys Ala Ile Glu His Tyr Asn
                245                 250                 255

Glu Met Cys Gly Val Val Asn Gln His Met Lys Glu Tyr Cys Gln Lys
            260                 265                 270

Glu Lys Lys Asn Trp Asn Leu Tyr Arg Met Lys Arg Leu His Lys Gln
        275                 280                 285

Ile Leu Ser Asn Ala Ser Thr Ser Phe Lys Ile Pro Glu Lys Tyr Glu
    290                 295                 300

Asn Asp Ala Glu Val Tyr Glu Ser Val Asn Ser Phe Leu Gln Asn Val
305                 310                 315                 320

Met Glu Lys Thr Val Met Glu Arg Ile Ala Val Leu Lys Asn Asn Thr
                325                 330                 335

Asp Asn Phe Asp Leu Ser Lys Ile Tyr Ile Thr Ala Pro Tyr Tyr Glu
            340                 345                 350

Lys Ile Ser Asn Tyr Leu Cys Gly Ser Trp Asn Thr Ile Ala Asp Cys
        355                 360                 365

Leu Thr His Tyr Tyr Glu Gln Gln Ile Ala Gly Lys Gly Ala Arg Lys
    370                 375                 380

Asp Gln Lys Val Lys Ala Val Lys Ala Asp Lys Trp Lys Ser Leu
385                 390                 395                 400

Ser Glu Ile Glu Gln Leu Leu Lys Glu Tyr Ala Arg Ala Glu Val
                405                 410                 415

Lys Arg Lys Pro Glu Glu Tyr Ile Ala Glu Ile Glu Asn Ile Val Ser
            420                 425                 430

Leu Lys Glu Val His Leu Leu Glu Tyr His Pro Glu Val Asn Leu Ile
        435                 440                 445

Glu Asn Glu Lys Tyr Ala Thr Glu Ile Lys Asp Val Leu Asp Asn Tyr
    450                 455                 460

Met Glu Leu Phe His Trp Met Lys Trp Phe Tyr Ile Glu Glu Ala Val
465                 470                 475                 480
```

```
Glu Lys Glu Val Asn Phe Tyr Gly Glu Leu Asp Asp Leu Tyr Glu Glu
                485                 490                 495

Ile Arg Asp Ile Val Pro Leu Tyr Asn Lys Val Arg Asn Tyr Val Thr
                500                 505                 510

Gln Lys Pro Tyr Ser Asp Thr Lys Ile Lys Leu Asn Phe Gly Thr Pro
                515                 520                 525

Thr Leu Ala Asn Gly Trp Ser Lys Ser Lys Glu Tyr Asp Tyr Asn Ala
            530                 535                 540

Ile Leu Leu Gln Lys Asp Gly Lys Tyr Tyr Met Gly Ile Phe Asn Pro
545                 550                 555                 560

Val Gln Lys Pro Glu Lys Glu Ile Ile Glu Gly His Ser His Pro Leu
                565                 570                 575

Glu Gly Asn Glu Tyr Lys Lys Met Val Tyr Tyr Leu Pro Ser Ala
                580                 585                 590

Asn Lys Met Leu Pro Lys Val Leu Leu Ser Lys Gly Met Glu Ile
            595                 600                 605

Tyr Gln Pro Ser Glu Tyr Ile Ile Asn Gly Tyr Lys Glu Arg His
            610                 615                 620

Ile Lys Ser Glu Glu Lys Phe Asp Leu Gln Phe Cys His Asp Leu Ile
625                 630                 635                 640

Asp Tyr Phe Lys Ser Gly Ile Glu Arg Asn Pro Asp Trp Lys Val Phe
                645                 650                 655

Gly Phe His Phe Ser Asp Thr Asp Thr Tyr Gln Asp Ile Ser Gly Phe
                660                 665                 670

Tyr Arg Glu Val Glu Asp Gln Gly Tyr Lys Ile Asp Trp Thr Tyr Ile
            675                 680                 685

Lys Glu Ala Asp Ile Asp Arg Leu Asn Glu Gly Lys Leu Tyr Leu
            690                 695                 700

Phe Gln Ile Tyr Asn Lys Asp Phe Ser Glu Lys Ser Thr Gly Arg Glu
705                 710                 715                 720

Asn Leu His Thr Met Tyr Leu Lys Asn Leu Phe Ser Glu Glu Asn Ile
                725                 730                 735

Arg Glu Gln Val Leu Lys Leu Asn Gly Glu Ala Glu Ile Phe Phe Arg
                740                 745                 750

Lys Ser Ser Val Lys Lys Pro Ile Ile His Lys Lys Gly Thr Met Leu
            755                 760                 765

Val Asn Arg Thr Tyr Met Glu Glu Met His Gly Glu Ser Val Lys Lys
            770                 775                 780

Asn Ile Pro Glu Lys Glu Tyr Gln Glu Ile Tyr Asn Tyr Met Asn His
785                 790                 795                 800

Arg Trp Lys Gly Glu Leu Ser Ala Glu Ala Lys Glu Tyr Leu Lys Lys
                805                 810                 815

Ala Val Cys His Glu Thr Lys Lys Asp Ile Val Lys Asp Tyr Arg Tyr
                820                 825                 830

Ser Val Asp Lys Phe Phe Ile His Leu Pro Ile Thr Ile Asn Tyr Arg
            835                 840                 845

Ala Ser Gly Lys Glu Ala Leu Asn Ser Val Ala Gln Arg Tyr Ile Ala
            850                 855                 860

His Gln Asn Asp Met His Val Ile Gly Ile Asp Arg Gly Glu Arg Asn
865                 870                 875                 880

Leu Ile Tyr Val Ser Val Ile Asn Met Gln Gly Glu Ile Ile Glu Gln
                885                 890                 895
```

```
Lys Ser Phe Asn Val Val Asn Lys Tyr Asn Tyr Lys Glu Lys Leu Lys
            900                 905                 910

Glu Arg Glu Gln Asn Arg Asp Glu Ala Arg Lys Asn Trp Lys Glu Ile
            915                 920                 925

Gly Gln Ile Lys Asp Leu Lys Glu Gly Tyr Leu Ser Gly Val Ile His
            930                 935                 940

Glu Ile Ala Lys Met Met Ile Lys Tyr His Ala Ile Val Ala Met Glu
945                 950                 955                 960

Asp Leu Asn Tyr Gly Phe Lys Arg Gly Arg Phe Lys Val Glu Arg Gln
            965                 970                 975

Val Tyr Gln Lys Phe Glu Asn Met Leu Ile Gln Lys Leu Asn Tyr Leu
            980                 985                 990

Val Phe Lys Asp Arg Ser Ala Asp Glu Asp Gly Gly Val Leu Arg Gly
            995                 1000                1005

Tyr Gln Leu Ala Tyr Ile Pro Asp Ser Val Lys Lys Leu Gly Arg
        1010                1015                1020

Gln Cys Gly Met Ile Phe Tyr Val Pro Ala Ala Phe Thr Ser Lys
        1025                1030                1035

Ile Asp Pro Ala Thr Gly Phe Val Asp Ile Phe Asn His Lys Ala
        1040                1045                1050

Tyr Thr Thr Asp Gln Ala Lys Arg Glu Phe Ile Leu Ser Phe Asp
        1055                1060                1065

Glu Ile Cys Tyr Asp Val Glu Arg Gln Leu Phe Arg Phe Thr Phe
        1070                1075                1080

Asp Tyr Ala Asn Phe Ala Thr His Asn Val Thr Leu Ala Arg Asn
        1085                1090                1095

Asn Trp Thr Ile Tyr Thr Asn Gly Thr Arg Thr Gln Lys Glu Phe
        1100                1105                1110

Val Asn Arg Arg Val Arg Asp Lys Lys Glu Val Phe Asp Pro Thr
        1115                1120                1125

Glu Lys Met Leu Lys Leu Leu Glu Leu Glu Gly Val Glu Tyr Gln
        1130                1135                1140

Ser Gly Ala Asn Leu Leu Pro Lys Leu Glu Lys Ile Ser Asp Pro
        1145                1150                1155

His Leu Phe His Glu Leu Gln Arg Ile Val Arg Phe Thr Val Gln
        1160                1165                1170

Leu Arg Asn Ser Lys Asn Glu Glu Asn Asp Val Asp Tyr Asp His
        1175                1180                1185

Val Ile Ser Pro Val Leu Asn Glu Glu Gly Lys Phe Phe Asp Ser
        1190                1195                1200

Ser Lys Tyr Glu Asn Lys Glu Lys Lys Glu Ser Leu Leu Pro
        1205                1210                1215

Val Asp Ala Asp Ala Asn Gly Ala Tyr Cys Ile Ala Leu Lys Gly
        1220                1225                1230

Leu Tyr Ile Met Gln Ala Ile Gln Lys Asn Trp Ser Glu Glu Lys
        1235                1240                1245

Ala Leu Ser Pro Asp Val Leu Arg Leu Asn Asn Asn Asp Trp Phe
        1250                1255                1260

Asp Tyr Ile Gln Asn Lys Arg Tyr Arg
        1265                1270
```